(12) United States Patent
Petrie et al.

(10) Patent No.: US 12,195,739 B2
(45) Date of Patent: *Jan. 14, 2025

(54) ENZYMES AND METHODS FOR PRODUCING OMEGA-3 FATTY ACIDS

(71) Applicants: Commonwealth Scientific and Industrial Research Organisation, Acton (AU); GRAINS RESEARCH AND DEVELOPMENT CORPORATION, Barton (AU)

(72) Inventors: James Robertson Petrie, Bywong (AU); Anne Maree Mackenzie, Hawker (AU); Qing Liu, Giralang (AU); Pushkar Shrestha, Lawson (AU); Peter David Nichols, West Hobart (AU); Susan Irene Ellis Blackburn, Battery Point (AU); Maged Peter Mansour, Gladstone Park (AU); Stanley Suresh Robert, Oyster Cove (AU); Dion Matthew Frederick Frampton, Bonnet Hill (AU); Xue-Rong Zhou, Harrison (AU); Surinder Pal Singh, Downer (AU); Craig Christopher Wood, Dickson (AU)

(73) Assignees: COMMONWEALTH SCIENTIFIC AND INDUSTRIAL RESEARCH ORGANISATION, Acton (AU); GRAINS RESEARCH AND DEVELOPMENT CORPORATION, Barton (AU)

(*) Notice: Subject to any disclaimer, the term of this patent is extended or adjusted under 35 U.S.C. 154(b) by 0 days.

This patent is subject to a terminal disclaimer.

(21) Appl. No.: 18/409,591

(22) Filed: Jan. 10, 2024

(65) Prior Publication Data
US 2024/0150779 A1 May 9, 2024

Related U.S. Application Data

(63) Continuation of application No. 16/860,936, filed on Apr. 28, 2020, now Pat. No. 11,976,287, which is a continuation of application No. 15/642,223, filed on Jul. 5, 2017, now Pat. No. 10,648,046, which is a continuation of application No. 14/332,202, filed on Jul. 15, 2014, now Pat. No. 9,938,486, which is a continuation of application No. 13/129,940, filed as application No. PCT/AU2009/001488 on Nov. 17, 2009, now Pat. No. 8,809,559.

(60) Provisional application No. 61/270,710, filed on Jul. 9, 2009, provisional application No. 61/119,669, filed on Nov. 18, 2008.

(51) Int. Cl.
C12N 15/82 (2006.01)
C12P 7/6427 (2022.01)
C12P 7/6432 (2022.01)
C12P 7/6434 (2022.01)
C12P 7/6472 (2022.01)

(52) U.S. Cl.
CPC ........ *C12N 15/8247* (2013.01); *C12P 7/6427* (2013.01); *C12P 7/6432* (2022.01); *C12P 7/6434* (2022.01); *C12P 7/6472* (2013.01); *C12Y 602/01003* (2013.01)

(58) Field of Classification Search
None
See application file for complete search history.

(56) References Cited

U.S. PATENT DOCUMENTS

| | | |
|---|---|---|
| 5,004,863 A | 4/1991 | Umbeck |
| 5,159,135 A | 10/1992 | Umbeck |
| 5,177,010 A | 1/1993 | Goldman |
| 5,362,865 A | 11/1994 | Austin |
| 5,416,011 A | 5/1995 | Hinchee |
| 5,451,513 A | 9/1995 | Maliga |
| 5,463,174 A | 10/1995 | Moloney |

(Continued)

FOREIGN PATENT DOCUMENTS

| | | |
|---|---|---|
| AU | 667939 | 1/1994 |
| AU | 776417 | 9/2004 |

(Continued)

OTHER PUBLICATIONS

Experimental data relating to EPA production in different plants by BASF with Aug. 23, 2017 Appeal Brief, filed by BASF in connection with Opposition to European Patent No. EP1756280 (Year: 2017).*

(Continued)

*Primary Examiner* — Matthew R Keogh
(74) *Attorney, Agent, or Firm* — Gary J. Gershik

(57) ABSTRACT

The present invention relates to methods of synthesizing long-chain polyunsaturated fatty acids, especially eicosapentaenoic acid, docosapentaenoic acid and docosahexaenoic acid, in recombinant cells such as yeast or plant cells. Also provided are recombinant cells or plants which produce long-chain polyunsaturated fatty acids. Furthermore, the present invention relates to a group of new enzymes which possess desaturase or elongase activity that can be used in methods of synthesizing long-chain polyunsaturated fatty acids. In particular, the present invention provides ω3 desaturases, Δ5 elongases and Δ6 desaturases with novel activities. Also provided are methods and DNA constructs for transiently and/or stably transforming cells, particularly plant cells, with multiple genes.

Figure 1:
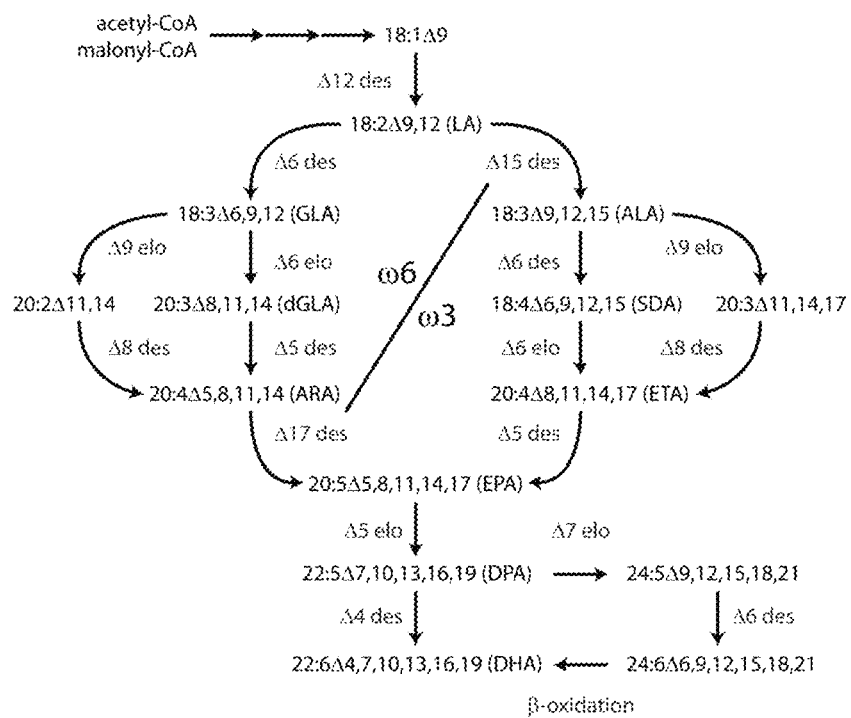

17 Claims, 15 Drawing Sheets
Specification includes a Sequence Listing.

(56) References Cited

U.S. PATENT DOCUMENTS

| | | |
|---|---|---|
| 5,504,200 A | 4/1996 | Hall |
| 5,518,908 A | 5/1996 | Corbin |
| 5,545,818 A | 8/1996 | McBride |
| 5,569,834 A | 10/1996 | Hinchee |
| 5,589,617 A | 12/1996 | Nehra |
| 5,608,152 A | 3/1997 | Kridl |
| 5,859,347 A | 1/1999 | Brown |
| 5,877,402 A | 3/1999 | Maliga |
| 5,932,479 A | 8/1999 | Daniell |
| 6,100,447 A | 8/2000 | Wu |
| 6,541,257 B2 | 4/2003 | Lemaux |
| 7,208,297 B2 | 4/2007 | Mukerji |
| 7,211,656 B2 | 5/2007 | Mukerji |
| 7,214,853 B2 | 5/2007 | Facciotti |
| 7,220,897 B2 | 5/2007 | Mukerji |
| 7,241,619 B2 | 7/2007 | Mukerji |
| 7,247,461 B2 | 7/2007 | Metz |
| 7,589,253 B2 | 9/2009 | Green |
| 7,619,105 B2 | 11/2009 | Green |
| 7,709,239 B2 | 5/2010 | Damude |
| 7,714,185 B2 | 5/2010 | Napier |
| 7,736,884 B2 | 6/2010 | Gunnarsson |
| 7,807,849 B2 | 10/2010 | Singh |
| 7,834,248 B2 | 11/2010 | Green |
| 7,834,250 B2 | 11/2010 | Singh |
| 7,838,651 B2 | 11/2010 | Picataggio |
| 7,901,928 B2 | 3/2011 | Yadav |
| 7,932,438 B2 | 4/2011 | Singh |
| 8,013,216 B2 | 9/2011 | Napier |
| 8,071,341 B2 | 12/2011 | Singh |
| 8,106,226 B2 | 1/2012 | Singh |
| 8,119,861 B2 | 2/2012 | Napier |
| 8,134,046 B2 | 3/2012 | Cirpus |
| 8,158,392 B1 | 4/2012 | Singh |
| 8,288,572 B2 | 10/2012 | Singh |
| 8,318,914 B2 | 11/2012 | Bauer |
| 8,455,035 B2 | 6/2013 | Rein |
| 8,535,917 B2 | 9/2013 | Singh |
| 8,575,377 B2 | 11/2013 | Singh |
| 8,716,555 B2 | 5/2014 | Liu |
| 8,778,644 B2 | 7/2014 | Singh |
| 8,785,163 B2 | 7/2014 | Senger |
| 8,785,727 B2 | 7/2014 | Bauer |
| 8,809,559 B2 * | 8/2014 | Petrie ........................ A61P 9/06 554/9 |
| 8,816,106 B2 | 8/2014 | Damcevski |
| 8,816,111 B2 | 8/2014 | Petrie |
| 8,822,662 B2 | 9/2014 | Senger |
| 8,853,383 B2 | 10/2014 | Bauer |
| 8,853,432 B2 | 10/2014 | Singh |
| 8,901,374 B2 | 12/2014 | Bauer |
| 8,921,652 B2 | 12/2014 | Liu |
| 8,946,460 B2 | 2/2015 | Petrie |
| 9,090,902 B2 | 7/2015 | Bauer |
| 9,212,371 B2 | 12/2015 | Senger |
| 9,428,757 B2 | 8/2016 | Senger |
| 9,453,183 B2 | 9/2016 | Singh |
| 9,458,410 B2 | 10/2016 | Singh |
| 9,493,520 B2 | 11/2016 | Bauer |
| 9,550,718 B2 | 1/2017 | Petrie |
| 9,556,102 B2 | 1/2017 | Petrie |
| 9,718,759 B2 | 8/2017 | Petrie |
| 9,725,399 B2 | 8/2017 | Petrie |
| 9,926,579 B2 | 3/2018 | Singh |
| 9,932,289 B2 | 4/2018 | Petrie |
| 9,932,290 B2 | 4/2018 | Petrie |
| 9,932,541 B2 | 4/2018 | Petrie |
| 9,938,486 B2 * | 4/2018 | Petrie ........................ A61P 29/00 |
| 9,951,357 B2 | 4/2018 | Singh |
| 9,963,723 B2 | 5/2018 | Singh |
| 9,969,954 B2 | 5/2018 | Petrie |
| 9,970,033 B2 | 5/2018 | Singh |
| 9,976,107 B2 | 5/2018 | Petrie |
| 9,994,792 B2 | 6/2018 | Petrie |
| 9,994,880 B2 | 6/2018 | Singh |
| 9,999,607 B2 | 6/2018 | Petrie |
| 10,005,713 B2 | 6/2018 | Petrie |
| 10,125,084 B2 | 11/2018 | Petrie |
| 10,190,073 B2 | 1/2019 | Petrie |
| 10,335,386 B2 | 7/2019 | Petrie |
| 10,443,079 B2 | 10/2019 | Singh |
| 10,648,046 B2 * | 5/2020 | Petrie ........................ A61P 9/10 |
| 2003/0033633 A1 | 2/2003 | Lightner |
| 2003/0159173 A1 | 8/2003 | Wolter |
| 2003/0163844 A1 | 8/2003 | Lightner |
| 2005/0273885 A1 | 12/2005 | Singh |
| 2007/0118929 A1 | 5/2007 | Damude |
| 2007/0192902 A1 | 8/2007 | Qiu |
| 2007/0220634 A1 | 9/2007 | Metz |
| 2007/0238648 A1 | 10/2007 | Brownlie |
| 2007/0244192 A1 | 10/2007 | Metz |
| 2007/0245431 A1 | 10/2007 | Metz |
| 2007/0261138 A1 | 11/2007 | Graham |
| 2007/0270494 A1 | 11/2007 | Metz |
| 2008/0005811 A1 | 1/2008 | Metz |
| 2008/0022422 A1 | 1/2008 | Weaver |
| 2008/0076166 A1 | 3/2008 | Cirpus |
| 2008/0155705 A1 | 6/2008 | Zank |
| 2008/0214667 A1 | 9/2008 | Das |
| 2008/0254191 A1 | 10/2008 | Damude |
| 2008/0254195 A1 | 10/2008 | Damude |
| 2009/0222951 A1 | 9/2009 | Cirpus |
| 2009/0253188 A1 | 10/2009 | Zhu |
| 2009/0320161 A1 | 12/2009 | McGonigle |
| 2010/0092640 A1 | 4/2010 | Ursin |
| 2010/0189868 A1 | 7/2010 | Damude |
| 2010/0227924 A1 | 9/2010 | Cirpus |
| 2011/0016585 A1 | 1/2011 | Pereira |
| 2011/0039010 A1 | 2/2011 | Rein |
| 2011/0218348 A1 | 9/2011 | Zhou |
| 2011/0314725 A1 | 12/2011 | Petrie |
| 2016/0369290 A1 | 12/2016 | Cirpus |
| 2018/0010141 A1 | 1/2018 | Petrie |
| 2018/0354888 A1 | 12/2018 | Petrie |
| 2019/0194572 A1 | 6/2019 | Petrie |
| 2020/0385822 A1 | 12/2020 | Petrie |

FOREIGN PATENT DOCUMENTS

| | | |
|---|---|---|
| AU | 2005901673 | 4/2005 |
| AU | 2007276257 | 1/2008 |
| CA | 2092588 | 9/1994 |
| EP | 256223 | 2/1988 |
| EP | 275957 | 7/1988 |
| WO | WO 1984/02913 | 8/1984 |
| WO | WO 1987/005327 | 9/1987 |
| WO | WO 1991/002071 | 2/1991 |
| WO | WO 1991/013980 | 9/1991 |
| WO | WO 1995/015389 | 6/1995 |
| WO | WO 1997/006269 | 2/1997 |
| WO | WO 1997/48814 | 12/1997 |
| WO | WO 1998/045461 | 10/1998 |
| WO | WO 1999/005265 | 2/1999 |
| WO | WO 1999/14314 | 3/1999 |
| WO | WO 1999/016890 | 4/1999 |
| WO | WO 1999/49050 A2 | 9/1999 |
| WO | WO 2000/052183 | 9/2000 |
| WO | WO 2001/014538 | 3/2001 |
| WO | WO 2001/038512 A2 | 5/2001 |
| WO | WO 2001/70777 | 9/2001 |
| WO | WO 2001/96363 | 12/2001 |
| WO | WO 2002/081668 | 10/2002 |
| WO | WO 2002/90493 A2 | 11/2002 |
| WO | WO 2002/092540 A1 | 11/2002 |
| WO | WO 2004/057001 | 7/2004 |
| WO | WO 2004/71467 A2 | 8/2004 |
| WO | WO 2004/101757 | 11/2004 |
| WO | WO 2005/012316 | 2/2005 |
| WO | WO 2005/83093 A2 | 9/2005 |
| WO | WO 2005/97982 A2 | 10/2005 |
| WO | WO 2005/98033 A1 | 10/2005 |
| WO | WO 2005/103253 | 11/2005 |
| WO | WO 2006/052870 A2 | 5/2006 |
| WO | WO 2006/052871 | 5/2006 |

(56) References Cited

FOREIGN PATENT DOCUMENTS

| WO | WO 2006/064317 A1 | 6/2006 |
|---|---|---|
| WO | WO 2006/069936 | 7/2006 |
| WO | WO 2005/80578 A2 | 9/2006 |
| WO | WO 2007/005882 A2 | 1/2007 |
| WO | WO 2007/042510 | 4/2007 |
| WO | WO 2007/092460 A2 | 8/2007 |
| WO | WO 2007/096387 | 8/2007 |
| WO | WO 2007/127381 | 11/2007 |
| WO | WO 2007/137788 | 12/2007 |
| WO | WO 2008/009600 A1 | 1/2008 |
| WO | WO 2008/022963 | 2/2008 |
| WO | WO 2008/040787 A2 | 4/2008 |
| WO | WO 2008/104559 A1 | 9/2008 |
| WO | WO 2008/128241 | 10/2008 |
| WO | WO 2013/185184 | 12/2013 |
| WO | WO 2015/089587 | 7/2015 |

OTHER PUBLICATIONS

Dubois et al 2007 (Eur. J. Lipid Sci. Technol. 109: p. 710-732) (Year: 2017).*
Abdullah, R., Cocking, E. C., & Thompson, J. A. (Dec. 1986). Efficient plant regeneration from rice protoplasts through somatic embryogenesis. *Biotechnology*, 4, 1087-1090.
Al-Mariri et al. (2002) "Yersinia enterocolitica as a Vehicle for a Naked DNA Vaccine Encoding Brucella abortus Bacterioferritin or P39 Antigen" Infect. Immun. 70:1915- 1923.
Alvarez et al. (2000) "Silencing of HMW glutenins in transgenic wheat expressing extra HMW subunits" Theor Appl Genet 100:319-327.
Bates et al. (2007) "Incorporation of Newly Synthesized Fatty Acids into Cytosolic Glycerolipids in Pea Leaves Occurs via Acyl Editing" J. Biol. Chem. 282:31206-31216.
Baumberger et al. (2007) "The Polerovirus Silencing Suppressor P0Targets Argonaute Proteins for Degradation" Curr. Biol. 17:1609-1614.
Beclin et al. (2002) "A Branched Pathway for Transgene-Induced RNA Silencing in Plants" Curr. Biol. 12:684-688.
Bligh and Dyer (1959) "Orange-red Flesh in Cod and Haddock", Canadian J. Biochem 37:911-917.
Bortolamiol et al. (2007) The Polerovirus F box protein P0 targets Argonaute1 to suppress RNA silencing. Curr. Biol. 17(18): 1615-162.
Bouvier (2000) "Identification of neoxanthin synthase as a carotenoid" Eur J. Biochem. 267:6346-6352.
Brodersen et al. (2008) "Widespread Translational Inhibition by Plant miRNAs and siRNAs" Science 320:1185-1190.
Brosnan et al. (2007) "Nuclear gene silencing directs reception of long-distance mRNA silencing in *Arabidopsis*" Proc. Natl. Acad. Sci U.S.A. 104:14741-14746.
Capecchi (1980) "High Efficiency Transformation by Direct Microinjection of DNA into Cultured Mammalian Cells" Cell 22:479-488.
Chapman et al. (2004) Transgenic Cotton Plants with Increased Seed Oleic Acid Content. Gen. Dev. 18:1179-1186.
Chen et al. (2004) "Introgression of Salt-Tolerance From Somatic Hybrids Between common Wheat and Thinopyrum Ponticum" Plant Science 167:773-779.
Cheng, M., Jarret, R. L., Li, Z., Xing, A., & Demski, J. W. (1996). Production of fertile transgenic peanut (*Arachis hypogaea* L.) plants using *Agrobacterium tumefaciens*. *Plant Cell Reports*, 15, 653-657.
Certik M. and Shimizu S., Biosynthesis and regulation of microbial polyunsaturated fatty acid production. J. Biosci Bioeng, 1999; 87(1):1-14.
Chikwamba et al. (2003) "Localization of a bacterial protein in starch granules of transgenic maize kernels" Proc. Natl. Acad. Sci. U.S.A. 100:11127-11132.
Chung et al. (2006) "Effect of 5'UTR introns on gene expression in *Arabidopsis thaliana*" BMC Genomics 7:120.
Clapp, Clin. Perinatol, 1993, 20:155-168.

Coutu et al. (2007) "pORE: a modular binary vector series suited for both monocot and dicot plant transformation" Transgenic Res. 16: 771-781.
Curiel et al. (1992) "High-Efficiency Gene Transfer Mediated by Adenovirus Coupled to DNA-Polylysine Complexes" Hum. Gen. Ther. 3:147-154.
Damude et al., (2007) "Engineering Oilseed Plants for a Sustainable, Land-Based Source of Long Chain Polyunsaturated Fatty Acids", Lipids, 42:179-185.
Darji et al. (1997) "Oral Somatic Transgene Vaccination Using Attenuated S. typhimurium" Cell 91:765-775.
Denic and Weissman (2007) A molecular caliper mechanism for determining very long-chain fatty acid length, Cell 130:663-677.
Ding and Voinett (2007) "Antiviral Immunity Directed by Small RNAs" Cell 130:413-426.
Dunoyer et al. (2004) "Probing the MicroRNA and Small Interfering RNA Pathways with Virus-Encoded Suppressors of RNA Silencing" The Plant Cell 16:1235-1250.
Eglitis et al. (1988) "Retroviral Vectors for Introduction of Genes into Mammalian Cells" Biotechniques 6:608-614.
Eigenheer et al (2002) "Isolation and molecular characterization of Musca domestica delta-9 desaturase sequences" Insect Molecular Biology 11(6):533-542.
Fennelly et al. (1999) "Mucosal DNA Vaccine Immunization Against Measles with a Highly Attenuated Shigella flexneri Vector" J. Immunol. 162:1603-1610.
Fraser et al. (2004) "Expression of the Isochrysis C18-Δ9 Polyunsaturated Fatty Acid Specific Elongase Component Alters *Arabidopsis* Glycerolipid Profiles" Plant Physiol. 135:859-866.
Fuji et al. (2007) "*Arabidopsis* Vacuolar Sorting Mutants (green fluorescent seed) Can Be Identified Efficiently by Secretion of Vacuole-Targeted Green Fluorescent Protein in Their Seeds" Plant Cell 19:597-609.
Fujimura et al. (1985) "Regeneration of Rice Plants from Protoplasts" Plant Tissue Culture Lett. 2:74.
Gleave (1992) "A versatile binary vector system with a T-DNA organisational structure conducive to efficient integration of cloned DNA into the plant genome" Plant Mol. Biol. 20:1203-1207.
Glevin et al (2003) "Agrobacterium-Mediated Plant Transformation: the Biology behind the 'Gene-Jockeying' Tool" Microbiol. Mol. Biol. Rev. 67:16-37.
Glick et al. (2008) "Interaction with host SGS3 is required for suppression of RNA silencing by tomato yellow leaf curl virus V2 protein" Proc. Natl. Acad. Sci U.S.A. 105:157-161.
Graham et al. (1973) "Transformation of Rat Cells by DNA of Human Adenovirus 5" Virology 54:536-539.
Grant, J. E., Cooper, P. A., McAra, A. E., & Frew, T. J. (1995). Transformation of peas (*Pisum sativum* L.) using immature cotyledons. *Plant Cell Reports*, 15, 254-258.
Grillot-Courvalin (1999) "Bacteria as gene delivery vectors for mammalian cells" Curr. Opin. Biotech. 10:477-481.
Hamilton and Baulcombe (1999) "A Species of Small Antisense RNA in Posttranscriptional Gene Silencing in Plants" Science 286:950-952.
Harayama, S. (1998). Artificial evolution by DNA shuffling. *Trends in Biotechnology*, 16(2), 76-82.
Hense et al. (2001) "Eukaryotic expression plasmid transfer from the intracellular bacterium Listeria monocytogenes to host cells" Cell Microbiol. 3:599-609.
Hoffman et al (2007) "A Small Membrane-peripheral Region Close to the Active Center Determines Regioselectivity of Membrane-bound Fatty Acid Desaturases from Aspergillus nidulans" J. Biol. Chem. 282:26666-26674.
Horvath et al. (2000) "The production of recombinant proteins in transgenic barley grains" Proc. Natl. Acad. Sci. U.S.A. 97:1914-1919.
Huang et al. (2004) "How Insulin Binds: the B-Chain a-Helix Contacts the L1 b-Helix of the Insulin Receptor" J. Mol. Biol. 341:529-550.
Johansen and Carrington (2001) "Silencing on the Spot. Induction and Suppression of RNA Silencing in the Agrobacterium-Mediated Transient Expression System" Plant Physiol. 126-930-938.

(56) References Cited

OTHER PUBLICATIONS

Kajikawa et al. (2006) Isolation and functional characterization of fatty acid delta5-elongase gene from the liverwort Marchantia polymorpha L, Febs Lett 580:149-154.
Kasschau et al. (2003) "P1/HC-Pro, a Viral Suppressor of RNA Silencing, Interferes with *Arabidopsis* Development and miRNA Function" Devel. Cell 4:205-217.
Khozin et al. (1997) "Elucidation of the Biosynthesis of Eicosapentaenoic Acid in the Microalga Porphyridium cruentum" Plant Physiol. 114:223-230.
Koziel et al. (1996) "Optimizing expression of transgenes with an emphasis on post-transcriptional events" Plant Mol. Biol. 32:393-405.
Kunik et al. (2001) "Genetic transformation of HeLa cells by Agrobacterium" Proc. Natl. Acad. Sci. U.S.A. 98:1871-1876.
Lacroix et al. (2008) "Association of the Agrobacterium T-DNA-protein complex with plant nucleosomes" Proc. Natl. Acad. Sci. U.S.A. 105: 15429-15434.
Lechtenberg et al. (2003) "Neither inverted repeat T-DNA configurations nor arrangements of tandemly repeated transgenes are sufficient to trigger transgene silencing" Plant J. 507-517.
Lewsey et al. (2007) "Selective targeting of miRNA-regulated plant development by a viral counter-silencing protein" Plant J. 50:240-252.
Lindbo et al. (1993) "Induction of a Highly Specific Antiviral State in Transgenic Plants: Implications for Regulation of Gene Expression and Virus Resistance" Plant Cell 5:1749-1759.
Lu et al. (1993) "High Efficiency Retroviral Mediated Gene Transduction into Single Isolated Immature and Replatable CD343+ Hematopoietic Stem/Progenitor Cells from Human Umbilical Cord Blood" J. Exp. Med. 178:2089-2096.
Mallory et al.(2002) "The amplicon-plus system for high-level expression of transgenes in plants" Nat. Biotech. 20:622-625.
Matzke et al. (2001) "RNA: Guiding Gene Silencing" Science 293:1080-1083.
Meng et al. (2008) "Hibiscus chlorotic ringspot virus coat protein inhibits trans-acting small interfering RNA biogenesis in *Arabidopsis*" J. Gen. Virol. 89:2349-2358.
Moreau et al. (1998) "Lipid Trafficking in Plant Cells" Progress Lip. Res. 37:371-391.
Napier (2007) "The Production of Unusual Fatty Acids in Transgenic Plants" Ann. Rev. Plant. Biol. 58:295-319.
Needleman, S. B., & Wunsch, C. D. (1970). A general method applicable to the search for similarities in the amino acid sequence of two proteins. *J. Mol. Biol.*, 48, 443-453.
Niedz et al (1995) "Green fluorescent protein: an in vivo reporter of plant gene expression" Plant Cell Reports 14:403-406.
Nishizawa et al. (2003) "A C-terminal sequence of soybean b-conglycinin a' subunit acts as a vacuolar sorting determinant in seed cells" Plant J. 34:647-659.
Ohlrogge and Jaworski (1997) Regulation of Fatty Acid Synthesis. Annu Rev Plant Physiol Plant Mol Biol. 48:109-136.
Ow et al. (1986) "Transient and Stable Expression of the Firefly Luciferase Gene in Plant Cells and Transgenic Plants" Science 234:856-859.
Park and Jeong (2005) "Cloning and Functional Expression of cDNA Encoding Pheromone Δ9 Acyl-CoA Desaturase of the Tobacco Cutworm, Spodoptera litura (Lepidoptera: Noctuidae)" Entomological Research, 35(4):253-263.
Passorn et al.(1999) "Heterologous Expression of Mucor rouxii Δ12-Desaturase Gene in *Saccharomyces cerevisiae*" Biochemical and Biophysical Research Communications 263, 47-51.
Pereira et al. (2004b) Identification of two novel microalgal enzymes involved in the conversion of the omega3-fatty acid, eicosapentaenoic acid, into docosahexaenoic acid, Biochem. J. 384:357-366.
Potenza et al. (2004) "Targeting Transgene Expression in Research, Agricultural, and Environmental Applications: Promoters Used in Plant Transformation" In Vitro Cell Dev Biol—Plant 40:1-22.

Riddervold et al.(2002) "Biochemical and molecular characterizaton of house cricket (Acheta domesticus, Orthoptera: Gryllidae) Δ9 desaturase" Insect Biochemistry and Molecular Biology 32, 1731-1740.
Rose et al. (1998) "Consensus-degenerate hybrid oligonucleotide primers for amplification of distantly related sequences" Nucleic Acids Res. 26:1628-1635.
Ruiz-Lopez et al. (2012) "Enhancing the accumulation of omega-3 long chain polyunsaturated fatty acids in transgenic *Arabidopsis thaliana* via iterative metabolic engineering and genetic crossing" Transgenic Res, 21:1233-1243.
Saha et al. (2006) "Cytosolic Triacylglycerol Biosynthetic Pathway in Oilseeds. Molecular Cloning and Expression of Peanut Cytosolic Diacylglycerol Acyltransferase" Plant Physiol. 141:1533-1543.
Sayanova et al. (2006) Identification of Primula "front-end" desaturases with distinct n-6 or n-3 substrate preferences, Planta 224:1269-1277.
Sayanova, O., Haslam, R., Caleron, M. V., & Napier, J. A. (May 2007). Cloning and characterization of unusual fatty acid desaturases from Anemone leveillei: identification of an acyl-coenzyme A C20 Δ5-desaturase responsible for the synthesis of sciadonic acid. Plant Physiology, 144, 455-467.
Schubert et al. (2004) "Silencing in *Arabidopsis* T-DNA Transformants: The Predominant Role of a Gene-Specific RNA Sensing Mechanism versus Position Effects" Plant Cell 16:2561-2572.
Simopoulus, A. P. (2000). Human requirement for N-3 polyunsaturated fatty acids. *Poultry Science*, 79(7), 961-970.
Stalker et al (1988) "Purification and Properties of a Nitrilase Specific for the Herbicide Bromoxynil and Corresponding Nucleotide Sequence Analysis of the bxn Gene" J. Biol. Chem. 263:6310-6314.
Suiyun et al. (2004) "Introgression of salt-tolerance from somatic hybrids between common wheat and Thinopyrum ponticum" Plant Science 773-779.
Thillet et al.(1988) "Site-directed Mutagenesis of Mouse Dihydrofolate Reductase" J. Biol. Chem 263:12500-12508.
Toriyama et al., Haploid and diploid plant regeneration from protoplasts of anther callus in rice. Theor Appl Genet, 1986, 73:16-19.
Truksa et al., (2006) "Metabolic Engineering of Plants to Produce Very Long-Chain Polyunsaturated Fatty Acids", Transgenic Research, 15:131-137.
Tzfira & Citovsky (2006) "Agrobacterium-mediated genetic transformation of plants: biology and biotechnology" Curr. Opin. Biotech. 17:147-154.
Voinnet et al., (2003) "An enhanced transient expression system in plants based on suppression of gene silencing by the p19 protein of tomato bushy stunt virus" Plant J. 33:949-956.
Wada et al.(1993) "The desA Gene of the *Cyanobacterium Synechocystis* sp. Strain PCC6803 Is the Structural Gene for Δ12 Desaturase" Journal of Bacteriology 175(18):6056-6058.
Wagner et al. (1992) "Coupling of adenovirus to transferrin-polylysine/DNA complexes greatly enhances receptor-mediated gene delivery and expression of transfected genes" Proc. Natl. Acad. Sci. USA 89:6099-6103.
Wang and Hildebrand (1988) "Biosynthesis and Regulation of Linolenic Acid in Higher Plants" Plant Physiol. Biochem. 26(6), 777-792.
Watts, L., and Browse, J. "A palmitoyl-CoA-specific Δ9 fatty acid desaturase from Caenorhabditis elegans." Biochemical and biophysical research communications 272, No. 1 (2000): 263-269.
Wood (2009) A leaf-based assay using interchangeable design principles to rapidly assemble multistep recombinant pathways, Plant Biotechnol J. 7:914-24.
Yang et al. (2003) "Expression and localization of human lysozyme in the endosperm of transgenic rice" Planta 216:597-603.
Zhang et al. (2006) "Cucumber mosaic virus-encoded 2b suppressor inhibits *Arabidopsis* Argonaute1 cleavage activity to counter plant defense" Genes & Development 20:3255-3268.
Zhang et al. (2008) Identification and characterization of a novel yeast omega3-fatty acid desaturase acting on long-chain n-6 fatty acid substrates from Pichia pastoris, Yeast 25: 21-27.

(56) References Cited

OTHER PUBLICATIONS

Zipfel et al. (2006) "Perception of the Bacterial PAMP EF-Tu by the Receptor EFR Restricts Agrobacterium-Mediated Transformation" Cell 125:749-760.
GenBank accession AAV67797, Meyer et al. (2004).
Genbank accession AAF19262, Benveniste (1998).
Genbank accession AAL37626, Qi et al. (2001).
GenBank accession AAM09687, Qiu et al. (2001).
GenBank accession AAR20444, Periera et al. (2003).
GenBank accession AAT85661, Kajikawa et al. (2004).
GenBank accession AAV67799, Meyer et al. (2004).
GenBank accession AAV67800, Meyer et al. (2004).
GenBank accession AAW70157, Domergue and Heinz (2004).
GenBank accession AAW70159, Domergue and Heinz (2004).
GenBank accession AAX14505, Tonon et al. (2004).
GenBank accession AAY15135, Zhou et al. (2005).
GenBank accession AAY15136, Zhou et al. (2005).
GenBank accession ABC18313, Huang and Jiang (2005).
GenBank accession ABC18314, Huang and Jiang (2005).
GenBank accession ABL63813, Zhang et al. (2006).
GenBank accession ABL96295, Zhou et al. (2006).
Genbank accession ABL96296, Zhou et al. (2006).
GenBank accession ABO94747, Grigoriev et al. (2007).
GenBank accession ABP49078, Li et al. (2007).
GenBank accession ABR67690, Niu et al. (2007).
GenBank accession BAD11952, Oura and Kajiwara (2003).
Genbank accession BAD91495, Sakuradani et al. (2004).
GenBank accession CAD58540, Napier et al. (2002).
GenBank accession CAI58897, Zank et al. (2005).
GenBank accession CAJ30869, Cirpus et al. (2005).
GenBank accession CAL23339, Cirpus et al. (2006).
GenBank accession CAM55882, Cirpus (2006).
GenBank accession EDQ92231, Kuo et al. (2007).
GenBank accession XP_001416454, Grigoriev et al. (2007).
GenBank accession XP_001421073 Grigoriev et al. (2007).
U.S. Appl. No. 60/564,627, filed Apr. 22, 2004, Singh.
U.S. Appl. No. 60/613,861, filed Sep. 27, 2004, Singh.
U.S. Appl. No. 60/668,705, filed Aug. 30, 2005, Singh.
International Search Report issued Apr. 1, 2010 for PCT International Application Publication No. PCT/AU2009/001488.
International Preliminary Report on Patentability, issued May 24, 2011 in connection with PCT International Application Publication No. PCT/AU2009/001488.
Written Opinion of the International Search Authority, issued Apr. 1, 2010 in connection with PCT International Application Publication No. PCT/AU2009/001488.
Jun. 8, 2012 Australian Examination Report issued in connection with Australian Patent Application No. 2009317860.
Dec. 9, 2013 Response filed in connection with Australian Patent Application No. 2009317860.
Jan. 15, 2014 Office Action issued in connection with Australian Patent Application No. 2009317860.
Feb. 7, 2014 Response filed in connection with Australian Patent Application No. 2009317860.
Feb. 24, 2014 Office Action issued in connection with Australian Patent Application No. 2009317860.
Mar. 4, 2014 Response filed in connection with Australian Patent Application No. 2009317860.
Jan. 22, 2014 Office Action, issued in connection with Australian Patent Application No. 2013204270.
Mar. 19, 2015 Response to First Examination Report filed in connection with Australian Patent Application No. 2013204270.
Jan. 22, 2014 Office Action, issued in connection with Australian Patent Application No. 2013204254.
Apr. 22, 2015 Response filed in connection with Australian Patent Application No. 2013204254.
First Examination Report issued Sep. 1, 2016 in connection with Australian Patent Application 2015224521.
Response to Sep. 1, 2016 Examination Report No. 1, filed Aug. 22, 2017 in connection with Australian Patent Application No. AU 2015224521.
Aug. 28, 2017 Examination Report No. 2, issued in connection with Australian Patent Application No. AU 2015224521.
Response to Aug. 28, 2017 Examination Report No. 2, filed Aug. 30, 2017 in connection with Australian Patent Application No. AU 2015224521.
Nov. 25, 2015 Office Action, issued in connection with Canadian Patent Application 2,743,880.
Dec. 12, 2016 Examination Report, issued in connection with Canadian Patent Application 2,743,880.
May 25, 2016 Response to Examiner's Report, filed in connection with Canadian Patent Application 2,743,880.
Jun. 12, 2017 Response to Dec. 12, 2016 Office Action filed in connection with Canadian Patent Application No. 2,743,880.
Sep. 10, 2013 Office Action issued in connection with Chilean Patent Application No. 1162-2011.
Dec. 19, 2013 Response filed in connection with Chilean Patent Application No. 1162-2011, including English Language Copy of the Claims.
Jul. 22, 2014 Office Action, issued in connection with Chilean Patent Application No. 1162-2011, including English language translation.
Jan. 14, 2013 Chinese First Office Action issued in connection with Chinese Patent Application No. 200980154876.9.
Sep. 16, 2013 Office Action issued in connection with Chinese Patent Application No. 200980154876.9.
May 21, 2014 Chinese Third Office Action, issued in connection with Chinese Patent Application No. 200980154876.9.
Mar. 9, 2015 Response to Office Action filed in connection with Chinese Patent Application 200980154876.9, including English language translation.
Jul. 6, 2015 Chinese Fifth Office Action issued in connection with Chinese Patent Application No. 200980154876.9, including English language translation;.
Jan. 6, 2017 Notification of Re-examination, issued in connection with Chinese Patent Application No. 200980154876.9, including English language translation.
Jan. 27, 2017 Decision of Rejection, issued in connection with Chinese Patent Application No. 200980154876.9, including English Language Translation.
English translation of response to the Notification of Re-examination as filed in relation to Chinese Patent Application No. 200980154876.9.
Jun. 19, 2017 Decision of Re-examination and its English translation which issued in relation to Chinese Patent Application No. 200980154876.9.
Mar. 29, 2012 Extended European Search Report and Search Opinion issued in connection with European Patent Application No. 09827035.8.
Oct. 29, 2012 Response to European Search Opinion filed in connection with European Patent Application No. 09827035.8.
Apr. 11, 2014 Response to Examination Report, filed in connection with European Patent Application No. 09827035.8.
Jul. 10, 2014 Third Party Observations, filed in connection with European Patent Application No. 09827035.8.
Apr. 7, 2015 Response to the Oct. 13, 2014 Office Action filed in connection with European patent application 09827035.8.
Aug. 13, 2015 Third Examination Report European Patent Application No. 09827035.8.
Jan. 21, 2016 Response to Aug. 13, 2015 Third Examination Report, filed in connection with European Patent Application No. EP09827035.8.
Jun. 16, 2016 Summons to Oral Proceedings, issued in connection with European Patent Application No. 09827035.8.
Jan. 13, 2017 Written Submissions Pursuant to Rule 116 EPC, filed in connection with European Patent Application No. 09827035.8.
Feb. 1, 2017 Result of Consultation with the Examiner; issued in connection with European Patent Application No. 09827035.8.
Feb. 2, 2017 Letter to European Patent Office, filed in connection with European Patent Application No. 09827035.8.

(56) References Cited

OTHER PUBLICATIONS

Feb. 2, 2017 New Main Request, filed in connection with European Patent Application No. 09827035.8.
Feb. 2, 2017 Amended Description, filed in connection with European Patent Application No. 09827035.8.
May 13, 2014 First Japanese Office Action, issued in connection with Japanese Patent Application No. 2011-535839.
Aug. 13, 2014 Response to First Japanese Office Action, filed in connection with Japanese Patent Application No. 2011-535839.
Mar. 3, 2015 Decision of Refusal, issued in connection with Japanese application 2011-535839, including English language translation.
Nov. 2, 2015 Pretrial reexamination report, issued in connection with Japanese Patent Application No. 2011-535839, including English language translation.
Jul. 12, 2016 Office Action, issued in connection with Japanese application 2011-535839, including English language translation.
Response to Office Action filed Oct. 24, 2016 in connection with Japanese Patent Application No. 2011-535839, including English Language Translation.
May 9, 2017 Office Action, issued in connection with Japanese application No. 2015-134711.
Jun. 22, 2011 New Zealand Examination Report issued in connection with New Zealand Patent Application No. 593097.
Dec. 11, 2012 Response to New Zealand Examination Report filed in connection with New Zealand Patent Application No. 593097.
Jan. 3, 2013 New Zealand Examination Report issued in connection with New Zealand Patent Application No. 593097.
Jan. 8, 2013 Response to New Zealand Examination Report filed in connection with New Zealand Patent Application No. 593097.
Dafny-Yelin et al., Delivery of Multiple Transgenes to Plant Cells, Plant Physiology, Dec. 2007, vol. 145, pp. 1118-1128.
Halpin, Gene stacking in transgenic plants—the challenge for 21st century plant biotechnology, Plant Biotechnology Journal (2005, 3, pp. 141-155).
Jiang et al. (2014) Isolation and Characterization of the Diatom Phaeodactylum Δ5-Elongase Gene for Transgenic LC-PUFA Production in Pichia pastoris. Mar. Drugs, 12, 1317-1334.
Jøstensen et al. (2002) Molecular-phylogenetic, structural and biochemical features of a cold-adapted marine ichtyosporean near the animal-fungal divergence, described from in vitro cultures. Europ. J. Protistol., 38, 93-104.
Kang et al. (2008) "Coexpression of Elo-like Enzyme and Δ4-Desaturases Derived from Thraustochytrium aureum ATCC 34304 and the Production of DHA and DPA in Pichia pastoris" 13:483-490.
Meyer, A., et al., (2004) "Novel Fatty Acid Elongases and Their Use For the Reconstitution of Docosahexaenoic Acid Biosynthesis," Journal of Lipid Research, 45(10): 1899-1909.
Petrie et al. (2010) "Isolation and Characterisation of a High-Efficiency Desaturase and Elongases from Microalgae for Transgenic LC-PUFA Production" Mar Biotechnol 12:430-438.
Robert et al., Metabolic engineering of *Arabidopsis* to produce nutritionally important DHA in seed oil, Functional Plant Biology, 2005, vol. 32, p. 473-479.
Robert et al. (2009) Isolation and characterisation of a delta5-fatty acid elongase from the marine microalga Pavlova salina, Marine Biotech 11:410-418.
Ruiz-López et al., (2012) Metabolic engineering of the omega-3 long chain polyunsaturated fatty acid biosynthetic pathway into transgenic plants. Journal of Experimental Botany, 63(7):2397-2410.
Slater et al., Metabolic engineering of *Arabidopsis* and Brassica for poly(3-hydroxybutyrate-co-3-hydroxyvalerate) copolymer production, Nature Biotechnology, Oct. 1999, vol. 12, 1011-1016.
Vrinten et al. (2013) Biosynthesis of Long Chain Polyunsaturated Fatty Acids in the Marine Ichthyosporean Sphaeroforma arctica. Lipids, 48:263-274.

Zank et al. (2000) "Cloning and functional expression of the first plant fatty acid elongase specific for Δ6-polyunsaturated fatty acids", Biochemical Society Transactions 28(6):654-658.
Apr. 13, 2017 Complaint for Declaratory Judgment, filed by BASF in connection with U.S. Pat. No. 7,807,849, issued Oct. 5, 2010 (Singh et al.); U.S. Pat. No. 7,834,250, issued Nov. 16, 2010 (Singh et al.); U.S. Pat. No. 8,106,226, issued Jan. 31, 2012 (Singh et al.); U.S. Pat. No. 8,288,572, issued Oct. 16, 2012 (Singh et al.); U.S. Pat. No. 8,575,377, issued Nov. 5, 2013 (Singh et al.); U.S. Pat. No. 8,809,559, issued Aug. 19, 2014 (Petrie et al.); U.S. Pat. No. 8,853,432, issued Oct. 7, 2014 (Singh et al.); and U.S. Pat. No. 9,458,410, issued Oct. 4, 2016 (Singh et al.), In the United States District Court of the District of Delaware, Civil Action No. 17-421.
Opsahl-Ferstad et al. (2003) "Biotechnological approaches to modify rapeseed oil composition for applications in aquaculture" Plant Science 165: 349-357.
Aug. 22, 2017 Memorandum granting Nuseed America's Motion to Dismiss the Complaint for Declaratory Judgment, filed by BASF in connection with U.S. Pat. No. 7,807,849, issued Oct. 5, 2010 (Singh et al.); U.S. Pat. No. 7,834,250, issued Nov. 16, 2010 (Singh et al.); U.S. Pat. No. 8,106,226, issued Jan. 31, 2012 (Singh et al.); U.S. Pat. No. 8,288,572, issued Oct. 16, 2012 (Singh et al.); U.S. Pat. No. 8,575,377, issued Nov. 5, 2013 (Singh et al.); U.S. Pat. No. 8,809,559, issued Aug. 19, 2014 (Petrie et al.); U.S. Pat. No. 8,853,432, issued Oct. 7, 2014 (Singh et al.); and U.S. Pat. No. 9,458,410, issued Oct. 4, 2016 (Singh et al.), In the United States District Court of the District of Delaware, Civil Action No. 17-421, Cite ID No. NP1-073.
Sep. 28, 2017 Extended European Search Report issued in connection with patent application 17182502.9.
Aug. 20, 2015 Communication of a Notice of Opposition, issued in connection with Opposition to European Patent No. EP1756280, including a list of documents cited by the Opponent.
Domergue et al., (2003), Acyl Carriers Used as Substrates by the Desaturases and Elongases Involved in Very Long-chian Polyunsaturated Fatty Acids Biosynthesis Reconstituted in Yeast, J. Biol. Chem. 278; 35115-35126.
Beaudoin, et al., (2000) "Production of C20 polyunsaturated fatty acids (PUFAs) by pathway engineering: identification of a PUFA elongase component from Caenorhabditis elegans", Biochemical Society Transactions, vol. 28, Part 6, p. 661-663.
Hastings, N., et al., (2001) "A Vertebrate Fatty Acid Desaturase With Δ5 and Δ6 Activities," Proceedings of the National Academy of Sciences of the United States of America, 98(25): 14304-14309.
Domergue, et al. (2005) "In vivo characterization of the first acyl-CoA Δ6 desaturase from a member of the plant kingdom, the microalga Ostreococcus tauri" Biochem. J., vol. 389, p. 483-490.
Kajikawa, M., et al., (2004) "Isolation and Characterization of Δ6-Desaturase, An ELO-Like Enzyme and Δ5-Desaturase From The Liverwort Marchantia polymorpha and Production of Arachidonic and Eicosapentaenoic Acids in the Methylotrophic Yeast Pichia pastoris," Plant Molecular Biology, 54: 335-352.
Sayanova, O.V. and Napier, J.A., (2004) "Eicosapentaenoic Acid: Biosynthetic Routes and the Potential for Synthesis in Transgenic Plants," Phytochemistry, 65(2): 147-158.
Abbadi, A., et al., (2001) "Transgenic Oilseeds as Sustainable Source of Nutritionally Relevant C20 and C22 Polyunsaturated Fatty Acids?" European Journal of Lipid Science and Technology, 103(2): 106-113.
Beaudoin, F., et al., (2000) "Heterologous Reconstitution in Yeast of the Polyunsaturated Fatty Acid Biosynthetic Pathway," Proceedings of the National Academy of Sciences of the United States of America, 97(12): 6421-6426.
Ohlrogge and Browse (1995) "Lipid Biosynthesis" Plant Cell 7:957-970.
Sequence alignment demonstrating that the amino acid sequence of GenBank accession No. AY055117 was found to have the same length as protein Seq Id No. 64 of WO 2005/103253, filed as "D18" in connection with Opposition to European Patent No. EP1756280 (Application No. EP05733657.0).
Sequence alignment demonstrating that the amino acid sequence of GenBank accession No. AY055118 was found to have the same length as protein Seq Id No. 64 of WO 2005/103253, filed as "D19"

(56) References Cited

OTHER PUBLICATIONS in connection with Opposition to European Patent No. EP1756280 (Application No. EP05733657.0).
Reference formula used for the calculation of the melting temperature as regards sequences hybridizing under high stringency conditions, filed as "D20" in connection with Opposition to European Patent No. EP1756280 (Application No. EP05733657.0).
Abbadi, A., et al., (2004) "Biosynthesis of Very-Long-Chain Polyunsaturated Fatty Acids in Transgenic Oilseeds: Constraints on Their Accumulation," The Plant Cell, 16(10): 2734-2748.
Mar. 29, 2016 Response to the Notice of Opposition, filed by CSIRO in connection with Opposition to European Patent No. EP1756280 (Application No. EP05733657.0).
Jul. 18, 2016 EPO Communication providing Summons to attend Oral Proceedings and Preliminary Opinion, issued in connection with Opposition to European Patent No. EP1756280 (Application No. EP05733657.0).
Jan. 9, 2017 Written Submissions under Rule 116 EPC filed in response to the Summons to Oral Proceedings, filed by CSIRO in connection with Opposition to European Patent No. EP1756280 (Application No. EP05733657.0).
Auxiliary Request I claims, filed with Jan. 9, 2017 Written Submissions under Rule 116 EPC, in response to the Summons to Oral Proceedings, in connection with Opposition to European Patent No. EP1756280 (Application No. EP05733657.0).
Jan. 9, 2017 Written Submissions under Rule 116 EPC filed in response to the Summons to Oral Proceedings, filed by BASF in connection with European Patent Application No. EP05733657.0.
Huang Y. S., Pereira S. L., Leonard A. E. (2004) "Enzymes for transgenic biosynthesis of long-chain polyunsaturated fatty acids" Biochimie, vol. 86, No. 11, p. 793-798.
Graham, et al. (2004) "The use of very long chain polyunsaturated fatty acids to ameliorate metabolic syndrome: transgenic plants as an alternative sustainable source to fish oils" Nutrition Bulletin, vol. 29, p. 228-233.
Napier JA, Beaudoin F, Michaelson LV, Sayanova O. (2004) "The production of long chain polyunsaturated fatty acids in transgenic plants by reverse-engineering." Biochimie. Nov. 86, 2004(11):785-92.
Napier JA, Beaudoin F, Sayanova O. (2005) "Reverse engineering of long-chain polyunsaturated fatty acid biosynthesis into transgenic plants" European Journal of Lipid Science and Technology 107(4):249-255.
Cahoon, E. B., Marillia, E., Stecca, K. L., Hall, S. E., Taylor, D. C., & Kinney, A. J. (2000). Production of fatty acid components of meadowfoam oil in somatic soybean embryos. *Plant Physiology*, 124, 243-251.
Kinney AJ, Cahoon EB, Hitz WD. "Manipulating desaturase activities in transgenic crop plants." Biochem Soc Trans. Nov. 30, 2002(Pt 6):1099-103.
Voelker Tl, Kinney Aj. "Variations in the Biosynthesis of Seed-Storage Lipids." Annu Rev Plant Physiol Plant Mol Biol. Jun. 52, 2001:335-361.
Surinder Singh (2010) "Engineering Complex Fatty Acid Pathways in Seeds: The EPA/DHA Example", submitted as "D31" subsequently renumbered as "D34" in connection with Opposition to European Patent No. EP1756280 (Application No. EP05733657.0). Materials and methods, results and conclusions for experimental data provided by the Opponent. The Opponent's experiments repeated and expanded on the experiment described in Example 5 of the opposed patent EP 1756280 (Annex A); Data table depicting the fatty acid composition of segregating T2 or T1 seeds from *Arabidopsis* or *Brassica napus* (canola) (Annex B); Media used in *Brassica napus* transformation (Annex C), filed by BASF in connection with Opposition to European Patent No. EP1756280 (Application No. EP05733657.0).
Feb. 21, 2017 Additional Submissions, including list of all documents cited to date and documents "D36", "D37" and "D38" filed in connection with Opposition to European Patent No. EP1756280 (Application No. EP05733657.0).

Mar. 9, 2017 Information about the result of Oral Proceedings, filed in connection with Opposition to European Patent No. EP1756280 (Application No. EP05733657.0).
List of documents cited by CSIRO and BASF as of Jan. 16, 2017, in connection Opposition to European Patent No. EP1756280 (Application No. EP05733657.0).
Aug. 23, 2017 Appeal Brief, filed by BASF in connection with Opposition to European Patent No. EP1756280.
Aug. 30, 2017 Correction to Aug. 23, 2017 Appeal Brief, filed by BASF in connection with Opposition to European Patent No. EP1756280.
Feature-structured claim 1, submitted as "D39" by BASF with Aug. 23, 2017 Appeal Brief, filed by BASF in connection with Opposition to European Patent No. EP1756280.
Heinz (2002). "Docosahexaenoic acid (DHA) in transgenic oilseeds: which approach will be successful first?" European Journal of Lipid Science and Technology 2002, 104:1-2.
Das et al. (2000) "Polyunsaturated fatty acid-specific elongation enzymes", Biochemical Society Transactions 28(6):658-660.
Domergue, F., et al., (2002) "Cloning and Functional Characterization of Phaeodactylum Tricornutum Front-End Desaturases Involved In Eicosapentaenoic Acid Biosynthesis," European Journal Of Biochemistry, 269(16):4105-4113.
Presentation "Engineering of LCPUFA biosynthesis" presented by Prof. Heinz at the 1st European Symposium on Plant Lipids held Sep. 10-13, 2003 in Aachen, submitted as "D44" by BASF with Aug. 23, 2017 Appeal Brief, filed by BASF in connection with Opposition to European Patent No. EP1756280.
Qi, et al., (2004) "Production of Very Long Chain Polyunsaturated Omega-3 and Omega-6 Fatty Acids in Plants", Nature Biotechnology 22:739-745 (published online May 16, 2004).
Evidence of the publication date of D44, submitted as "D44a" by BASF with Aug. 23, 2017 Appeal Brief, filed by BASF in connection with Opposition to European Patent No. EP1756280.
Hoffman et al., (2008) "Metabolic Engineering of ω3-Very Long Chain Polyunsaturated Fatty Acid Production by an Exclusively Acyl-CoA-dependent Pathway", The Journal of Biological Chemistry, 283:22352-22362.
Expert declaration from Dr. Domergue, submitted as "D47" by BASF with Aug. 23, 2017 Appeal Brief, filed by BASF in connection with Opposition to European Patent No. EP1756280.
Leonard et al. (2004) "Elongation of long-chain fatty acids", Progress in Lipid Research 43:36-54.
Experimental data relating to EPA production in different plants, including experimental details, results, a discussion and conclusion, submitted as "D49" by BASF with Aug. 23, 2017 Appeal Brief, filed by BASF in connection with Opposition to European Patent No. EP1756280 including Attachment 1 of D49 ("D52").
Media used in Brassica transformation described in D49, submitted as "D49a" by BASF with Aug. 23, 2017 Appeal Brief, filed by BASF in connection with Opposition to European Patent No. EP1756280.
Experimental data on EPA production of segregating seeds, submitted as "D50" by BASF with Aug. 23, 2017 Appeal Brief, filed by BASF in connection with Opposition to European Patent No. EP1756280.
Experimental data on EPA production of homozygous seeds, submitted as "D51" by BASF with Aug. 23, 2017 Appeal Brief, filed by BASF in connection with Opposition to European Patent No. EP1756280.
Dec. 28, 2018 Examination Report, issued in connection with Canadian Patent Application No. 2,743,880.
Jan. 4, 2018 Response of Commonwealth Scientific and Industrial Research Organisation (Patentee) to Statement of Appeal by BASF SE (Opponent) in connection with Opposition to European Patent No. EP1756280, including copies of Argument, Main Request and six Auxiliary Requests.
Jan. 4, 2018 Response of BASF SE to Grounds of Appeal filed by Commonwealth Scientific and Industrial Research Organisation on Aug. 22, 2017 in connection with Opposition to European Patent No. EP1756280.

(56) References Cited

OTHER PUBLICATIONS

Sayanova et al., The role of delta (6)-desaturase acyl-carrier specificity in the efficient synthesis of long-chain polyunsaturated fatty acids in transgenic plants. Plant Biotechnology Journal, (2012) 10:195-206.
Connor, W. E. (2000). Importance of n-3 fatty acids in health and disease. The American journal of clinical nutrition, 71(1), 171S-175S.
Apr. 20, 2018 Amended Complaint for Declaratory Judgment filed by BASF Plant Science, LP in connection with U.S. Pat. No. 7,807,849, issued Oct. 5, 2010 (Singh et al.); U.S. Pat. No. 8,106,226, issued Jan. 31, 2012 (Singh et al.); U.S. Pat. No. 8,288,572, issued Oct. 16, 2012 (Singh et al.); U.S. Pat. No. 8,575,377, issued Nov. 5, 2013 (Singh et al.); U.S. Pat. No. 8,853,432, issued Oct. 7, 2014 (Singh et al.); and U.S. Pat. No. 9,458,410, issued Oct. 4, 2016 (Singh et al.), In the United States District Court for the Eastern District of Virginia Norfolk Division, Civil Action No. 2:17-cv-00503-HCM-LRL.
Response to Examination Report filed Apr. 23, 2018 in connection with counterpart Indian Patent Application No. 3829/CHENP/2011.
May 16, 2018 Office Action issued in connection with Argentinian Patent Application No. 20090104445 and its English translation.
May 8, 2018 Office Action issued in connection with Japanese Application No. 2015-134711 and its English translation.
Jun. 27, 2018 Response to Examination Report dated Dec. 28, 2017, issued in connection with Canadian Patent Application No. 2,743,880.
Jun. 26, 2018 Response to Communication under Rule 69 and Invitation under Rule 70a(1) EPC dated Jan. 4, 2018, issued in connection with European Patent Application No. 17182502.9.
Oct. 9, 2018 First Examination Report issued in connection with Canadian Patent Application No. 3,015,426.
Nov. 12, 2018 Office Action issued in connection with Argentine Patent Application No. 20090104445 including English language translation thereof.
Nov. 21, 2018 First Examination Report issued in connection with European Patent Application No. 17182502.9.
Jan. 8, 2019 Response to the Oct. 9, 2018 First Examination Report filed in connection with Canadian Patent Application No. 3015426.
Dec. 19, 2018 Fourth Examination Report issued in connection with Canadian Patent Application No. 2,743,880.
Feb. 25, 2019 Second Examination Report issued in connection with Canadian Patent Application No. 3015426.
Mar. 25, 2019 Office Action issued in connection with Argentine Patent Application No. 20090104445 including English language translation thereof.
May 24, 2019 Response to the Feb. 25, 2019 Second Examination Report filed in connection with Canadian Patent Application No. 3015426.
May 31, 2019 Response to the Nov. 21, 2018 First Examination Report filed in connection with European Patent Application No. 17182502.9.
Jan. 3, 2019 First Amended Counterclaims filed by Commonwealth Scientific and Industrial Research Corporation, Grains Research and Development Corporation, and Nuseed Pty. Ltd. in the United States District Court for the Eastern District of Virginia Norfolk Division, Civil Action No. 2:17-cv-00503-HCM-LRL.
Jan. 11, 2019 BASF Plant Science, LP's Answer and Amended Affirmative Defenses to Counterclaimants' Amended Counterclaims and BASF Plant Science, LP and BASF Plant Science GMBH's Amended Counterclaims Against Counterclaimants (Public Redacted Version), in the United States District Court for the Eastern District of Virginia Norfolk Division, Civil Action No. 2:17-cv-00503-HCM-LRL.
Feb. 27, 2019 Opening Claim Construction Brief Of Cargill, Incorporated, in the United States District Court for the Eastern District of Virginia Norfolk Division, Civil Action No. 2:17-cv-00503-HCM-LRL.
Feb. 27, 2019 BASF Plant Science, LP's and BASF Plant Science GMBH's Opening Claim Construction Brief, in the United States District Court for the Eastern District of Virginia Norfolk Division, Civil Action No. 2:17-cv-00503-HCM-LRL.
Feb. 27, 2019 Counterclaimants Commonwealth Scientific and Industrial Research Organisation, Grains Research and Development Corp., and Nuseed Pty Ltd.'s Initial Markman Brief, in the United States District Court for the Eastern District of Virginia Norfolk Division, Civil Action No. 2:17-cv-00503-HCM-LRL.
Mar. 13, 2019 Responsive Claim Construction Brief of Cargill, Incorporated, in the United States District Court for the Eastern District of Virginia Norfolk Division, Civil Action No. 2:17-cv-00503-HCM-LRL.
Mar. 13, 2019 BASF Plant Science, LP's and BASF Plant Science GMBH's Responsive Claim Construction Brief, in the United States District Court for the Eastern District of Virginia Norfolk Division, Civil Action No. 2:17-cv-00503-HCM-LRL.
Mar. 13, 2019 Counterclaimants Commonwealth Scientific and Industrial Research Organisation, Grains Research and Development Corp., and Nuseed Pty Ltd.'s Rebuttal Markman Brief, in the United States District Court for the Eastern District of Virginia Norfolk Division, Civil Action No. 2:17-cv-00503-HCM-LRL.
Apr. 17, 2019 Counterclaimants Commonwealth Scientific and Industrial Research Organisation, Grains Research and Development Corp., and Nuseed Pty Ltd.'s Supplemental Brief on Term 9, in the United States District Court for the Eastern District of Virginia Norfolk Division, Civil Action No. 2:17-cv-00503-HCM-LRL.
Apr. 17, 2019 Cargill, Incorporated's Supplemental Claim Construction Brief Regarding The "Acyl-Coa Substrate" Claim Term, in the United States District Court for the Eastern District of Virginia Norfolk Division, Civil Action No. 2:17-cv-00503-HCM-LRL.
Apr. 30, 2019 Claim Construction Order and Opinion, in the United States District Court for the Eastern District of Virginia Norfolk Division, Civil Action No. 2:17-cv-00503-HCM-LRL.
May 15, 2019 Supplemental Claim Construction Opinion and Order, in the United States District Court for the Eastern District of Virginia Norfolk Division, Civil Action No. 2:17-cv-00503-HCM-LRL.
Jun. 19, 2019 Response to the Dec. 19, 2018 Fourth Examination Report filed in connection with Canadian Patent Application No. 2,743,880, Cite ID No. NP1-280.
Oct. 4, 2018 Plaintiff BASF Plant Science, LP's Objections and Responses to Commonwealth Scientific and Industrial Research Organisation's First Set of Interrogatories (Excerpted for Interrogatory Nos. 5 and 7), in the United States District Court for the Eastern District of Virginia Norfolk Division, Civil Action No. 2:17-cv-00503-HCM-LRL.
Oct. 31, 2018 Cargill Incorporated's Responses to Counterclaimant Commonwealth Scientific and Industrial Research Organisation's First Set of Interrogatories (Excerpted for Interrogatory Nos. 5 and 7), in the United States District Court for the Eastern District of Virginia Norfolk Division, Civil Action No. 2:17-cv-00503-HCM-LRL.
Jan. 18, 2019 Plaintiff BASF Plant Science, LP's Supplemental Responses to Commonwealth Scientific and Industrial Research Organisation's Interrogatory Nos. 5 and 7, in the United States District Court for the Eastern District of Virginia Norfolk Division, Civil Action No. 2:17-cv-00503-HCM-LRL.
Feb. 25, 2019 Cargill Incorporated's Supplemental Responses to Counterclaimant Commonwealth Scientific and Industrial Research Organisation's First Set of Interrogatories (Excerpted for Interrogatory Nos. 5 and 7), in the United States District Court for the Eastern District of Virginia Norfolk Division, Civil Action No. 2:17-cv-00503-HCM-LRL.
May 13, 2019 BASF Plant Science, LP's Second Supplemental Response to Commonwealth Scientific and Industrial Research Organisation's Interrogatory Nos. 5 and 7, in the United States District Court for the Eastern District of Virginia Norfolk Division, Civil Action No. 2:17-cv-00503-HCM-LRL.
May 13, 2019 Cargill Incorporated's Second Supplemental Responses to Counterclaimant Commonwealth Scientific and Industrial Research Organisation's First Set of Interrogatories, in the United States District Court for the Eastern District of Virginia Norfolk Division, Civil Action No. 2:17-cv-00503-HCM-LRL.

(56) References Cited

OTHER PUBLICATIONS

May 13, 2019 BASF Plant Science, LP's and BASF Plant Science Gmbh's Objections and Responses to Commonwealth Scientific and Industrial Organisation's Second Set of Interrogatories (Request Nos. 14-25) (Excerpted), in the United States District Court for the Eastern District of Virginia Norfolk Division, Civil Action No. 2:17-cv-00503-HCM-LRL.
May 29, 2019 Expert Report of Denis J. Murphy, Ph.D. (redacted version), in the United States District Court for the Eastern District of Virginia Norfolk Division, Civil Action No. 2:17-cv-00503-HCM-LRL.
Jul. 1, 2019 Rebuttal Validity Expert Report of Ljerka Kunst, Ph.D., in the United States District Court for the Eastern District of Virginia Norfolk Division, Civil Action No. 2:17-cv-00503-HCM-LRL.
Aug. 6, 2019 Office Action issued in connection with Japanese Patent Application No. JP 2018-167852 and its English translation.
Aug. 6, 2019 Office Action issued in connection with Japanese Patent Application No. JP 2018-167853 and its English translation.
Aug. 20, 2019 First Examination Report issued in connection with Australian Patent Application No. 2017276232.
Sep. 12, 2019 Response to Jun. 17, 2019 Examination Report issued in connection with Canadian Patent Application No. 3,015,426.
Sep. 30, 2019 Notice of Hearing issued in connection with corresponding Indian patent application 3829/CHENP/2011 and its English translation.
Nov. 6, 2018 Protective Order Signed by District Judge Henry C. Morgan, Jr in the United States District Court for the Eastern District of Virginia Norfolk Division, Civil Action No. 2:17-cv-00503-HCM-LRL.
Nov. 1, 2019 Jury Verdict Form in United States District Court for the Eastern District of Virginia Norfolk Division, Civil Action No. 2:17-cv-00503-HCM-LRL.
Dec. 23, 2019 Judgment in a Civil Case issued in United States District Court for the Eastern District of Virginia Norfolk Division, Civil Action No. 2:17-cv-00503-HCM-LRL.
Dec. 23, 2019 Opinion and Order Regarding Remedies issued in United States District Court for the Eastern District of Virginia Norfolk Division, Civil Action No. 2:17-cv-00503-HCM-LRL.
Aug. 23, 2019 Counterclaimants' Answer to BASF Plant Science, LP and BASF Plant Science Gmbh's Amended Counterclaims Against Counterclaimants (Public Redacted Version), filed in the United States District Court for the Eastern District of Virginia Norfolk Division, Civil Action No. 2:17-cv-00503-HCM-LRL.
Sep. 4, 2019 BASF/Cargill's Brief in Support of Their Daubert Motion to Exclude Portions of the Testimony of Dr. Ljerka Kunst and Mr. John C. Jarosz (Public Redacted Version), filed in the United States District Court for the Eastern District of Virginia Norfolk Division, Civil Action No. 2:17-cv-00503-HCM-LRL.
Sep. 4, 2019 Counterclaimants' Memorandum in Support of Motion to Exclude Certain Opinions and Preclude Certain Testimony By Defendants' Experts Brian Napper and Dr. Denis Murphy (Public Redacted Version), filed in the United States District Court for the Eastern District of Virginia Norfolk Division, Civil Action No. 2:17-cv-00503-HCM-LRL.
Sep. 4, 2019 Counterclaimants' Memorandum in Support of Motion for Summary Judgment (Public Redacted Version), filed in the United States District Court for the Eastern District of Virginia Norfolk Division, Civil Action No. 2:17-cv-00503-HCM-LRL.
Sep. 6, 2019 Counterclaimants' Memorandum in Support of Motions in Limine (Nos. 1-13) (Public Redacted Version), filed in the United States District Court for the Eastern District of Virginia Norfolk Division, Civil Action No. 2:17-cv-00503-HCM-LRL.
Sep. 6, 2019 BASF's and Cargill's Motions In Limine (Public Redacted Version), filed in the United States District Court for the Eastern District of Virginia Norfolk Division, Civil Action No. 2:17-cv-00503-HCM-LRL.
Sep. 13, 2019 Counterclaimants' Opposition to BASF and Cargill's Daubert Motion to Exclude Portions of The Testimony of Dr. Ljerka Kunst and Mr. John Jarosz (Public Redacted Version), filed in the United States District Court for the Eastern District of Virginia Norfolk Division, Civil Action No. 2:17-cv-00503-HCM-LRL.
Sep. 14, 2019 BASF/Cargill's Memorandum in Opposition to Counterclaimants' Motion for Summary Judgment (Public Redacted Version), filed in the United States District Court for the Eastern District of Virginia Norfolk Division, Civil Action No. 2:17-cv-00503-HCM-LRL.
Sep. 14, 2019 BASF/Cargill's Memorandum in Opposition to Counterclaimants' Daubert Motion (Public Redacted Version), filed in the United States District Court for the Eastern District of Virginia Norfolk Division, Civil Action No. 2:17-cv-00503-HCM-LRL.
Sep. 19, 2019 Counterclaimants' Opposition to BASF's and Cargill's Motions In Limine (Public Redacted Version), filed in the United States District Court for the Eastern District of Virginia Norfolk Division, Civil Action No. 2:17-cv-00503-HCM-LRL.
Sep. 19, 2019 Counterclaimants' Reply in Support of Motion to Exclude Certain Opinions and Preclude Certain Testimony by Defendants' Experts Brian Napper and Dr. Denis Murphy (Public Redacted Version), filed in the United States District Court for the Eastern District of Virginia Norfolk Division, Civil Action No. 2:17-cv-00503-HCM-LRL.
Sep. 19, 2019 BASF/Cargill's Reply Brief in Support of Their Daubert Motion to Exclude Portions of the Testimony of Dr. Ljerka Kunst and Mr. John C. Jarosz (Public Redacted Version), filed in the United States District Court for the Eastern District of Virginia Norfolk Division, Civil Action No. 2:17-cv-00503-HCM-LRL.
Sep. 19, 2019 Counterclaimants' Reply in Support of Motion for Summary Judgment (Public Redacted Version), filed in the United States District Court for the Eastern District of Virginia Norfolk Division, Civil Action No. 2:17-cv-00503-HCM-LRL.
Sep. 30, 2019 BASF/Cargill's Memorandum in Opposition to Counterclaimants' Motions In Limine (Public Redacted Version), filed in the United States District Court for the Eastern District of Virginia Norfolk Division, Civil Action No. 2:17-cv-00503-HCM-LRL.
Sep. 27, 2019 Transcript of Proceedings (Motions Hearing) in the United States District Court for the Eastern District of Virginia Norfolk Division, Civil Action No. 2:17- CV-00503-HCM-LRL.
Oct. 3, 2019 Proposed Final Pretrial Order in the United States District Court for the Eastern District of Virginia Norfolk Division, Civil Action No. 2:17-cv-00503-HCM-LRL.
Oct. 8, 2019 BASF's Brief Supporting Trial by Jury of BASF's MTEA-Based Claims and Defenses (Public Redacted Version), filed in the United States District Court for the Eastern District of Virginia Norfolk Division, Civil Action No. 2:17-cv-00503-HCM-LRL.
Oct. 8, 2019 CSIRO, Nuseed, and GRDC's Memorandum in Support of Excluding BASF's MTEA Counterclaims and Related Defenses from Trial (Public Redacted Version), filed in the United States District Court for the Eastern District of Virginia Norfolk Division, Civil Action No. 2:17-cv-00503-HCM-LRL.
Oct. 28, 2019 Proponents' Motion Seeking Dismissal of Opponents' Unclean Hands Defense (Public Redacted Version), filed in the United States District Court for the Eastern District of Virginia Norfolk Division, Civil Action No. 2:17-cv-00503-HCM-LRL.
Oct. 28, 2019 BASF/Cargill's Proposed Final Jury Instructions, filed in the United States District Court for the Eastern District of Virginia Norfolk Division, Civil Action No. 2:17-cv-00503-HCM-LRL.
Oct. 28, 2019 Counterclaimants' Final Proposed Jury Instructions—Liability Phase, filed in the United States District Court for the Eastern District of Virginia Norfolk Division, Civil Action No. 2:17-cv-00503-HCM-LRL.
Oct. 29, 2019 Proponents' Trial Brief in Support of Jury Instructions Regarding Continuation Patent Applications, Corroborating Evidence of Conception, and Willful Infringement, filed in the United States District Court for the Eastern District of Virginia Norfolk Division, Civil Action No. 2:17-cv-00503-HCM-LRL.
Oct. 30, 2019 Counterclaimants' Final Proposed Jury Instructions—Liability Phase, filed in the United States District Court for the Eastern District of Virginia Norfolk Division, Civil Action No. 2:17-cv-00503-HCM-LRL.

(56) References Cited

OTHER PUBLICATIONS

Oct. 30, 2019 Proponents' Memorandum Regarding a Jury Instruction Concerning Written Description, filed in the United States District Court for the Eastern District of Virginia Norfolk Division, Civil Action No. 2:17-cv-00503-HCM-LRL.
Oct. 30, 2019 Proponents' Brief in Support of Motion Under Fed. R. Civ. P. 50(A), filed in the United States District Court for the Eastern District of Virginia Norfolk Division, Civil Action No. 2:17-cv-00503-HCM-LRL.
Oct. 31, 2019 Opponents' Brief in Support of Motion Under Fed. R. Civ. P. 50(A) Concerning Co-Ownership Under Mtea, Lack of Written Description, and Obviousness, filed in the United States District Court for the Eastern District of Virginia Norfolk Division, Civil Action No. 2:17-cv-00503-HCM-LRL.
Oct. 31, 2019 Proponents' Proposed Jury Instruction on MTEA, filed in the United States District Court for the Eastern District of Virginia Norfolk Division, Civil Action No. 2:17-cv-00503-HCM-LRL.
Oct. 31, 2019 Proponents' Supplemental Memorandum in Support of its Motion for Judgment as a Matter of Law to Address Additional Bases for Relief Under Fed. R. Civ. Proc. 50, filed in the United States District Court for the Eastern District of Virginia Norfolk Division, Civil Action No. 2:17-cv-00503-HCM-LRL.
Dec. 2, 2019 Proponents' Memorandum in Support of Motions for Judgment as a Matter of Law and a New Trial as to Jury Issues Not Decided by Verdict Under Fed. R. Civ. P. 50(B) and 59, filed in the United States District Court for the Eastern District of Virginia Norfolk Division, Civil Action No. 2:17-cv-00503-HCM-LRL.
Dec. 16, 2019 Opponents' Brief in Opposition to Proponents' Motions for Judgment as a Matter of Law and a New Trial as to Jury Issues Not Decided by Verdict Under Fed. R. Civ. P. 50(B) and 59, filed in the United States District Court for the Eastern District of Virginia Norfolk Division, Civil Action No. 2:17-cv-00503-HCM-LRL.
Dec. 23, 2019 Proponents' Reply Brief in Support of Their Motion for Judgment as a Matter of Law and Motion for a New Trial as to Jury Issues Not Decided by Verdict, filed in the United States District Court for the Eastern District of Virginia Norfolk Division, Civil Action No. 2:17-cv-00503-HCM-LRL.
Aug. 15, 2019 Opinion and Order on Motions to Seal issued in the United States District Court for the Eastern District of Virginia Norfolk Division, Civil Action No. 2:17-cv-00503-HCM-LRL.
Jan. 11, 2019 BASF Plant Science, LP's Answer and Amended Affirmative Defenses to Counterclaimants' Amended Counterclaims and BASF Plant Science, LP and BASF Plant Science GMBH's Amended Counterclaims Against Counterclaimants (Public Redacted Version filed Aug. 25, 2019), in the United States District Court for the Eastern District of Virginia Norfolk Division, Civil Action No. 2:17-cv-00503-HCM-LRL.
Translation of Office Action which issued in connection with corresponding Argentinian Patent Application No. AR2009010445.
Jan. 13, 2020 Written Submission filed in connection with Indian Patent Application No. 3829/CHENP/2011.
May 13, 2020 First Office Action and its English translation issued in connection with corresponding Chinese patent Application No. 201710929893.
Sep. 29, 2020 Appeal Brief filed in connection with Indian Patent Application No. 3829/CHENP/2011.
Nov. 19, 2020 Office Action issued in connection with Brazilian Patent Application No. PI0921467-4 including English translation thereof.
Jan. 15, 2021 Third Communication pursuant to Article 94(3) EPC issued in connection with European Patent Application No. 17182502.9 (Divisional of EP 2358882).
Jan. 20, 2021 Second Office Action issued in connection with Chinese Patent Application No. 201710929893.1 including English translation thereof.
Apr. 23, 2021 Written Opinion issued in connection with Brazilian Patent Application No. PI0921467-4 including English translation thereof.
Apr. 23, 2021 Written Opinion issued in connection with Brazilian Patent Application No. BR122021003836-8 including English translation thereof.
Apr. 23, 2021 Written Opinion issued in connection with Brazilian Patent Application No. BR122021003835-0 including English translation thereof.
Apr. 23, 2021 Written Opinion issued in connection with Brazilian Patent Application No. BR122021003871-6 including English translation thereof.
Jul. 7, 2021 First Examination Report issued in connection with Canadian Patent Application No. 3082380.
Oct. 26, 2021 Response to Jan. 15, 2021 Examination Report filed in connection with European Patent Application No. 17182502.9 (Divisional of EP 2358882).
Nov. 8, 2021 Response to Jul. 7, 2021 First Examination Report filed in connection with Canadian Patent Application No. 3082380.
Jan. 21, 2022 First Examination Report issued in connection with Indian Patent Application 201948054509 (Divisional of IN 3829/CHENP/2011).
May 13, 2022 Fourth Examination Report issued in connection with European Patent Application 17182502.9 (Divisional of EP 2358882).
Jun. 28, 2022 First Examination Report issued in connection with Australian Patent Application No. 2020277266 (Divisional of AU 2017276232).
Jul. 18, 2022 Response to Jan. 21, 2022 First Examination Report filed in connection with Indian Patent Application 201948054509 (Divisional of IN 3829/CHENP/2011).
Jul. 4, 2022 Second Examination Report issued in connection with Canadian Patent Application No. 3082380.
Aug. 9, 2022 Response to First Examination Report in connection with Australian Patent Application No. 2020277266 (Divisional of AU 2017276232).
Sep. 6, 2022 Second Examination Report issued in connection with Australian Patent Application No. 2020277266 (Divisional of AU 2017276232).
Mar. 31, 2023 Fifth examination report issued in connection with European Patent Application 17182502.9.
May 1, 2023 Response to First Examination Report filed in connection with Indian Patent Application 201948054536.
Jun. 16, 2023 Response to Sep. 6, 2022 Second Examination Report filed in connection with Australian Patent Application No. 2020277266 (Divisional of AU 2017276232).
Nov. 4, 2022 Response to Jul. 4, 2022 Second Examination Report in connection with Canadian Patent Application No. 3,082,380 (Divisional of CA 2743880).
Jun. 16, 2023 Third Examination Report in connection with Canadian Patent Application No. 3,082,380 (Divisional of CA 2743880).
Nov. 22, 2023 Office Action issued in connection with Argentine Patent Application No. P190102274 including English language translation thereof.
Nov. 15, 2023 Office Action issued in connection with Chinese Patent Application No. 202111172412.X (Divisional of CN ZL201710929893.1), including English translation thereof.
Oct. 10, 2022 First Examination Report issued in connection with Indian Patent Application 201948054536.
Aug. 10, 2023 Response to Mar. 31, 2023 Fifth Examination Report filed in connection with European Patent Application No. 17182502.9 (Divisional of EP 2358882).
Dec. 15, 2023 Office Action issued in connection with Chinese Patent Application No. 202111171358.7 (Divisional of CN ZL201710929893.1) including English language translation thereof.
Mar. 26, 2024 Hearing Notice issued in connection with Indian Patent Application No. 201948054509.
Mar. 27, 2024 Hearing Notice issued in connection with Indian Patent Application No. 201948054536.
Feb. 19, 2024 Office Action issued in connection with Chinese Patent Application No. 202111172382.2 (Divisional of CN 200980154876.9) including English language translation thereof.
Aug. 14, 2024 Office Action issued in connection with Chinese Patent Application 202111171358.7 (Divisional of CN ZL201710929893.1) and English language translation thereof.

* cited by examiner

Figure 9

ENZYMES AND METHODS FOR PRODUCING OMEGA-3 FATTY ACIDS

CROSS-REFERENCE TO RELATED APPLICATIONS

This application is a continuation of U.S. application Ser. No. 16/860,936, filed Apr. 28, 2020, which is a continuation of U.S. application Ser. No. 15/642,223, filed Jul. 5, 2017, now U.S. Pat. No. 10,648,046, issued May 12, 2020, which is a continuation of U.S. application Ser. No. 14/332,202, filed Jul. 15, 2014, now U.S. Pat. No. 9,938,486, issued Apr. 10, 2018, which is a continuation of U.S. application Ser. No. 13/129,940, filed Sep. 30, 2011, now U.S. Pat. No. 8,809,559, a § 371 national stage of PCT International Application No. PCT/AU2009/001488, filed Nov. 17, 2009, which claims the benefit of U.S. Provisional Applications Nos. 61/270,710, filed Jul. 9, 2009; and 61/199,669, filed Nov. 18, 2008, the content of each of which are hereby incorporated by reference into the subject application.

REFERENCE TO SEQUENCE LISTING

This application incorporates-by-reference nucleotide and/or amino acid sequences which are present in the file named "240126_79998-A5A-PCT-US_Sequence_Listing_DH.xml", which is 198,621 bytes in size, and which was created Jan. 24, 2024 in the IBM-PC machine format, having an operating system compatibility with MS-Windows, which is contained in the xml file filed Jan. 26, 2024 as part of this application.

FIELD OF THE INVENTION

The present invention relates to methods of synthesizing long-chain polyunsaturated fatty acids, especially eicosapentaenoic acid, docosapentaenoic acid and docosahexaenoic acid, in recombinant cells such as yeast or plant cells. Also provided are recombinant cells or plants which produce long-chain polyunsaturated fatty acids. Furthermore, the present invention relates to a group of new enzymes which possess desaturase or elongase activity that can be used in methods of synthesizing long-chain polyunsaturated fatty acids. In particular, the present invention provides ω3 desaturases, Δ5 elongases and Δ6 desaturases with novel activities. Also provided are methods and DNA constructs for transiently and/or stably transforming cells, particularly plant cells, with multiple genes.

BACKGROUND OF THE INVENTION

Omega-3 long-chain polyunsaturated fatty acids (LC-PUFA and VLC-PUFA) are now widely recognized as important compounds for human and animal health.

These fatty acids may be obtained from dietary sources or by conversion of linoleic (LA, 18:2ω6) or α-linolenic (ALA, 18:3ω3) fatty acids, both of which are regarded as essential fatty acids in the human diet. While humans and many other vertebrate animals are able to convert LA or ALA, obtained from plant sources, to VLC-PUFA, they carry out this conversion at a very low rate. Moreover, most modern societies have imbalanced diets in which at least 90% of polyunsaturated fatty acids (PUFA) are of the ω6 fatty acids, instead of the 4:1 ratio or less for ω6:ω3 fatty acids that is regarded as ideal (Trautwein, 2001). The immediate dietary source of VLC-PUFAs such as eicosapentaenoic acid (EPA, 20:5ω3) and docosahexaenoic acid (DHA, 22:6ω3) for humans is mostly from fish or fish oil. Health professionals have therefore recommended the regular inclusion of fish containing significant levels of VLC-PUFA into the human diet. Increasingly, fish-derived VLC-PUFA oils are being incorporated into food products and in infant formula, for example. However, due to a decline in global and national fisheries, alternative sources of these beneficial health-enhancing oils are needed.

Higher plants, in contrast to animals, lack the capacity to synthesise polyunsaturated fatty acids with chain lengths longer than 18 carbons. In particular, crop and horticultural plants along with other angiosperms do not have the enzymes needed to synthesize the longer chain ω3 fatty acids such as EPA, docosapentaenoic acid (DPA, 22:5ω3) and DHA that are derived from ALA. An important goal in plant biotechnology is therefore the engineering of crop plants which produce substantial quantities of VLC-PUFA, thus providing an alternative source of these compounds.

VLC-PUFA Biosynthesis Pathways

Biosynthesis of VLC-PUFAs in organisms such as microalgae, mosses and fungi usually occurs as a series of oxygen-dependent desaturation and elongation reactions (FIG. 1). The most common paplantthway that produces EPA in these organisms includes a Δ6-desaturation, Δ6-elongation and Δ5-desaturation (termed the Δ6-desaturation pathway) whilst a less common pathway uses a Δ9-elongation, Δ8-desaturation and Δ5-desaturation (termed the Δ9-desaturation pathway). These consecutive desaturation and elongation reactions can begin with either the ω6 fatty acid substrate LA, shown schematically as the upper left part of FIG. 1 (ω6) or the ω3 substrate ALA, shown as the lower right part of FIG. 1 (ω3). If the initial Δ6-desaturation is performed on the ω6 substrate LA, the VLC-PUFA product of the series of three enzymes will be the ω6 fatty acid ARA. VLC-PUFA synthesising organisms may convert ω6 fatty acids to ω3 fatty acids using an ω3-desaturase, shown as the Δ17-desaturase step in FIG. 1 for conversion of arachidonic acid (ARA, 20:4ω6) to EPA. Some members of the ω3-desaturase family can act on a variety of substrates ranging from LA to ARA. Plant ω3-desaturases often specifically catalyse the Δ15-desaturation of LA to ALA, while fungal and yeast ω3-desaturases may be specific for the Δ17-desaturation of ARA to EPA (Pereira et al., 2004a; Zank et al., 2005). Some reports suggest that non-specific ω3-desaturases may exist which can convert a wide variety of ω6 substrates to their corresponding ω3 products (Zhang et al., 2007). Other ω3-desaturases may have a preference for ω3 substrates (Sayanova et al., 2003).

The conversion of EPA to DHA in these organisms is relatively simple, and consists of a Δ5-elongation of EPA to produce DPA, followed by a Δ4-desaturation to produce DHA (FIG. 1). In contrast, mammals use the so-called "Sprecher" pathway which converts DPA to DHA by three separate reactions that are independent of a Δ4 desaturase (Sprecher et al., 1995).

The front-end desaturases generally found in plants, mosses, microalgae, and lower animals such as *Caenorhabditis elegans* predominantly accept fatty acid substrates esterified to the sn-2 position of a phosphatidylcholine (PC) substrate. These desaturases are therefore known as acyl-PC, lipid-linked, front-end desaturases (Domergue et al., 2003). In contrast, higher animal front-end desaturases generally accept acyl-CoA substrates where the fatty acid substrate is linked to CoA rather than PC (Domergue et al., 2005).

Each PUFA and VLC-PUFA elongation reaction consists of four steps catalysed by a multi-component protein complex: first, a condensation reaction results in the addition of a 2C unit from malonyl-CoA to the fatty acid, resulting in the formation of a β-ketoacyl intermediate. This is then reduced by NADPH, followed by a dehydration to yield an enoyl intermediate. This intermediate is finally reduced a second time to produce the elongated fatty acid. It is generally thought that the condensation step of these four reactions is substrate specific whilst the other steps are not. In practice, this means that native plant elongation machinery is capable of elongating VLC-PUFA providing that the condensation enzyme (typically called an 'elongase') specific to the VLC-PUFA is introduced, although the efficiency of the native plant elongation machinery in elongating the non-native VLC-PUFA substrates may be low. In 2007 the identification and characterisation of the yeast elongation cycle dehydratase was published (Denic and Weissman, 2007).

VLC-PUFA desaturation in plants, mosses and microalgae naturally occurs to fatty acid substrates predominantly in the acyl-PC pool whilst elongation occurs to substrates in the acyl-CoA pool. Transfer of fatty acids from acyl-PC molecules to a CoA carrier is performed by phospholipases (PLAs) whilst the transfer of acyl-CoA fatty acids to a PC carrier is performed by lysophosphatidyl-choline acyltransferases (LPCATs) (FIG. 2) (Singh et al., 2005). The reduction in flux due to an acyl-exchange having to occur before desaturation can follow elongation, or vice-versa, may be overcome by using a desaturase that has specificity for acyl-CoA substrates (Hoffmann et al., 2008).

Engineered Production of VLC-PUFA

Most VLC-PUFA metabolic engineering has been performed using the aerobic Δ6-desaturation/elongation pathway. The biosynthesis of γ-linolenic acid (GLA, 18:3ω6) in tobacco was first reported in 1996 using a Δ6-desaturase from the cyanobacterium *Synechocystis* (Reddy and Thomas, 1996). More recently, GLA has been produced in crop plants such as safflower (73% GLA; Knauf et al., 2006) and soybean (28% GLA; Sato et al., 2004). The production of VLC-PUFA such as EPA and DHA involves more complicated engineering due to the increased number of desaturation and elongation steps involved. EPA production in a land plant was first reported by Qi et al. (2004) who introduced genes encoding a Δ9-elongase from *Isochrysis galbana*, a Δ8-desaturase from *Euglena gracilis* and a Δ5-desaturase from *Mortierella alpina* into *Arabidopsis* yielding up to 3% EPA. This work was followed by Abbadi et al. (2004) who reported the production of up to 0.8% EPA in flax seed using genes encoding a Δ6-desaturase and Δ6-elongase from *Physcomitrella patens* and a Δ5-desaturase from *Phaeodactylum tricornutum*.

The first report of DHA production, and to date the highest levels of VLC-PUFA production reported, was in WO 04/017467 where the production of 3% DHA in soybean embryos is described, but not seed, by introducing genes encoding the *Saprolegnia diclina* Δ6-desaturase, *Mortierella alpina* Δ6-desaturase, *Mortierella alpina* Δ5-desaturase, *Saprolegnia diclina* Δ4-desaturase, *Saprolegnia diclina* Δ17-desaturase, *Mortierella alpina* Δ6-elongase and *Pavlova lutheri* Δ5-elongase. The maximal EPA level in embryos also producing DHA was 19.6%, indicating that the efficiency of conversion of EPA to DHA was poor (WO 2004/071467). This finding was similar to that published by Robert et al. (2005), where the flux from EPA to DHA was low, with the production of 3% EPA and 0.5% DHA in *Arabidopsis* using the *Danio rerio* Δ5/6-desaturase, the *Caenorhabditis elegans* Δ6-elongase, and the *Pavlova salina* Δ5-elongase and Δ4-desaturase. Also in 2005, Wu et al. published the production of 25% ARA, 15% EPA, and 1.5% DHA in *Brassica juncea* using the *Pythium irregulare* Δ6-desaturase, a Thraustochytrid Δ5-desaturase, the *Physcomitrella patens* Δ6-elongase, the *Calendula officianalis* Δ12-desaturase, a Thraustochytrid Δ5-elongase, the *Phytophthora infestans* Δ17-desaturase, the *Oncorhyncus mykiss* VLC-PUFA elongase, a Thraustochytrid Δ4-desaturase and a Thraustochytrid LPCAT (Wu et al., 2005).

There therefore remains a need for more efficient production of LC-PUFA in recombinant cells, in particular in seeds of oil-seed plants.

SUMMARY OF THE INVENTION

The present inventors have identified for the first time a Δ5 elongase which efficiently converts EPA to DPA in a recombinant cell.

Accordingly, the present invention further provides a recombinant cell, preferably a plant cell and more preferably a plant seed cell, comprising an exogenous polynucleotide encoding a fatty acid elongase with Δ5 elongase activity, wherein the elongase has activity on EPA to produce DPA with an efficiency of at least 60%, at least 65%, at least 70% or at least 75% when the elongase is expressed from the exogenous polynucleotide in the cell, preferably in a plant cell.

In one embodiment, the elongase comprises amino acids having a sequence as provided in SEQ ID NO:6, a biologically active fragment thereof, or an amino acid sequence which is at least 47% identical to SEQ ID NO:6.

In another embodiment, the cell further comprises exogenous polynucleotides encoding;
 i) a Δ8 desaturase and/or a Δ6 desaturase,
 ii) a Δ9 elongase and/or a Δ6 elongase,
 iii) a Δ5 desaturase, and
 iv) optionally a Δ4 desaturase and/or an ω3 desaturase,
wherein each polynucleotide is operably linked to one or more promoters that are capable of directing expression of said polynucleotides in the cell.

The present inventors have also identified an ω3 desaturase with novel properties. The ω3 desaturase is useful in recombinant pathways designed to yield EPA, the downstream fatty acids DPA and DHA, and other ω3 VLC-PUFA.

Accordingly, the present invention provides a recombinant cell, preferably a plant cell and more preferably a plant seed cell, comprising an exogenous polynucleotide encoding a fatty acid desaturase with ω3 desaturase activity, wherein the desaturase is capable of desaturating at least one of ARA to EPA, DGLA to ETA, GLA to SDA, both ARA to EPA and DGLA to ETA, both ARA to EPA and GLA to SDA, or all three of these when the desaturase is expressed from the exogenous polynucleotide in the cell.

The desaturase is preferably a front-end desaturase.

In another embodiment, the desaturase has Δ17 desaturase activity on a C20 fatty acid which has at least three carbon-carbon double bonds in its acyl chain, preferably ARA.

In another embodiment, the desaturase has Δ15 desaturase activity on a C18 fatty acid which has three carbon-carbon double bonds in its acyl chain, preferably GLA.

The desaturase preferably has greater activity on an acyl-CoA substrate than a corresponding acyl-PC substrate.

In one embodiment, the acyl-CoA substrate is ARA-CoA and the acyl-PC substrate comprises ARA at the sn-2 position of PC.

In yet another embodiment, the cell is a plant cell and the desaturase has activity on ARA to produce EPA with an efficiency of at least 40% when expressed from the exogenous polynucleotide in the cell.

In one particular embodiment, the desaturase comprises amino acids having a sequence as provided in SEQ ID NO:15, 17 or 20, a biologically active fragment thereof, or an amino acid sequence which is at least 35% identical to SEQ ID NO:15, at least 60% identical to SEQ ID NO:17 and/or at least 60% identical to SEQ ID NO:20.

In addition, the present inventors have identified a gene encoding a Δ6 desaturase which has greater conversion efficiency for ω3 fatty acid substrates than for the corresponding ω6 fatty acid substrate in plants and/or in yeast. This Δ6 desaturase also exhibits Δ8 desaturase activity. The use of this Δ6 desaturase or other desaturases with high specificity for ω3 desaturated fatty acid substrates in recombinant LC-PUFA pathways in plants increases levels of EPA, DPA and DHA relative to the use of desaturases without preference for ω3 desaturated fatty acid substrates.

Accordingly, the present invention further provides a recombinant cell, preferably a plant cell and more preferably a plant seed cell, comprising an exogenous polynucleotide encoding a fatty acid desaturase with Δ6 desaturase activity, wherein the desaturase is further characterised by having at least two, preferably all three, of the following;
  i) greater Δ6 desaturase activity on ALA than LA as fatty acid substrate, preferably in a plant cell,
  ii) greater Δ6 desaturase activity on ALA-CoA as fatty acid substrate than on ALA joined to the sn-2 position of PC as fatty acid substrate, preferably in a plant cell, and
  iii) Δ8 desaturase activity on ETrA, preferably in a plant cell.

The present invention further provides a recombinant cell, preferably a plant cell and more preferably a plant seed cell, comprising an exogenous polynucleotide encoding a fatty acid desaturase with Δ6 desaturase activity, wherein the desaturase has greater activity on an ω3 substrate than the corresponding ω6 substrate, and wherein the desaturase has activity on ALA to produce SDA with an efficiency of at least 5%, at least 7.5%, or at least 10% when the desaturase is expressed from the exogenous polynucleotide in the cell, or at least 35% when expressed in a yeast cell.

In one embodiment, the desaturase has greater Δ6 desaturase activity on ALA than LA as fatty acid substrate, preferably in a plant cell.

The Δ6 desaturase preferably has at least about a 2-fold greater Δ6 desaturase activity, at least 3-fold greater activity, at least 4-fold greater activity, or at least 5-fold greater activity, on ALA as a substrate compared to LA, preferably in a plant cell.

In another embodiment, the Δ6 desaturase has greater activity on ALA-CoA as fatty acid substrate than on ALA joined to the sn-2 position of PC as fatty acid substrate, preferably in a plant cell.

The Δ6 desaturase preferably has at least about a 5-fold greater Δ6 desaturase activity or at least 10-fold greater activity, on ALA-CoA as fatty acid substrate than on ALA joined to the sn-2 position of PC as fatty acid substrate, preferably in a plant cell.

The Δ6 desaturase preferably is a front-end desaturase.

In yet another embodiment, the cell according to the invention further comprises exogenous polynucleotides encoding;
  i) a Δ6 elongase,
  ii) a Δ5 desaturase,
  iii) a Δ5 elongase, and
  iv) optionally a Δ4 desaturase and/or an ω3 desaturase,
wherein each polynucleotide is operably linked to one or more promoters that are capable of directing expression of said polynucleotides in the cell.

The Δ6 desaturase in the cell of the invention preferably has no detectable Δ5 desaturase activity on ETA.

The Δ6 desaturase preferably comprises amino acids having a sequence as provided in SEQ ID NO:10, a biologically active fragment thereof, or an amino acid sequence which is at least 77% identical to SEQ ID NO:10.

In another embodiment, the Δ6 desaturase comprises amino acids having a sequence as provided in SEQ ID NO:8, a biologically active fragment thereof, or an amino acid sequence which is at least 67% identical to SEQ ID NO:8 and has Δ8 desaturase activity.

The present inventors have also found that recombinant cells expressing Δ9 elongase, Δ8 desaturase and Δ5 desaturase are able to more efficiently convert fatty acid substrates to EPA, DPA and DHA.

Accordingly, the present invention further provides a recombinant cell, preferably a plant cell and more preferably a plant seed cell, comprising exogenous polynucleotides encoding;
  i) a Δ9 elongase,
  ii) a Δ8 desaturase,
  iii) a Δ5 desaturase,
  iv) optionally a Δ5 elongase, and
  v) if the Δ5 elongase is present, optionally a Δ4 desaturase,
wherein each polynucleotide is operably linked to one or more promoters that are capable of directing expression of said polynucleotides in the cell, and wherein at least 15%, at least 20%, or at least 25%, of the total fatty acids in the cell comprise at least carbons and at least 3 carbon-carbon double bonds in their acyl chains.

In one embodiment, the sum total of ARA, EPA, DPA and DHA in the fatty acids in the cell of the invention comprises at least 15%, at least 20%, or at least 25% of the total fatty acids in the cell.

In a further embodiment, the cell according to the invention has reduced ability to convert oleic acid to eicosenoic acid (C20:1) when compared to a wild-type plant, and/or less than 5% of the oleic acid is converted to eicosenoic acid in the cell.

In one particular embodiment, the total fatty acid in the cell has less than 1% C20:1.

In a further embodiment, the cell according to the invention has reduced endogenous Δ15 desaturase activity when compared to a wild-type cell, and/or less than 10% of the LA is converted to ALA in the cell.

In one particular embodiment, the endogenous Δ15 desaturase has greater activity on an acyl-PC substrate than on the corresponding acyl-CoA substrate, preferably where the acyl group is LA.

In a further embodiment, the cell of the invention further comprises an increased conversion of GLA to SDA and/or ARA to EPA relative to the corresponding cell lacking the exogenous polynucleotides.

In one embodiment, the amount of DHA in the fatty acids in the cell of the invention is at least 3%, at least 5%, or at least 10%, of the total fatty acids in the cell.

In another embodiment, the efficiency of conversion of LA to ARA and/or ALA to EPA in the cell of the invention is at least 80% or at least 90%.

In one embodiment, the Δ9 elongase comprises amino acids having a sequence as provided in SEQ ID NO:22, a biologically active fragment thereof, or an amino acid sequence which is at least 80% identical to SEQ ID NO:22.

In a further embodiment, the Δ8 desaturase comprises amino acids having a sequence as provided in SEQ ID NO:24, a biologically active fragment thereof, or an amino acid sequence which is at least 80% identical to SEQ ID NO:24.

In yet another embodiment, the Δ5 desaturase comprises amino acids having a sequence as provided in SEQ ID NO:26 or SEQ ID NO:13, a biologically active fragment thereof, or an amino acid sequence which is at least 80% identical to SEQ ID NO:26 and/or SEQ ID NO:13.

The present inventors have obtained results which indicate that a set of genes expressing the Δ6-desaturase, Δ6 elongase, Δ5 desaturase, Δ5 elongase, and Δ4 desaturase, or a similar set of genes in particular where the desaturases are active on acyl-CoA substrates, can be used to synthesise substantial levels of EPA, DPA and DHA.

Accordingly, the present invention further provides a recombinant cell, preferably a plant cell and more preferably a plant seed cell, comprising exogenous polynucleotides encoding;
  i) a Δ6 elongase and/or a Δ9 elongase,
  ii) a Δ6 desaturase and/or a Δ8 desaturase,
  iii) a Δ5 desaturase,
  iv) a Δ5 elongase,
  v) a Δ4 desaturase, and
  vi) optionally a diacylglycerol acyltransferase
wherein each polynucleotide is operably linked to one or more promoters that are capable of directing expression of said polynucleotides in the cell, characterised by one or more or all of the following properties:
  a) the efficiency of conversion of ALA to EPA, DPA or DHA is at least 17.3%, or at least 23%,
  b) the efficiency of conversion of ALA to DPA or DHA is at least 15.4%, or at least 21%,
  c) the efficiency of conversion of ALA to DHA is at least 9.5%, or at least 10.8%, and
  d) the efficiency of conversion of EPA to DHA is at least 45%, or at least 50%, and preferably further characterised in that at least 4% of the total fatty acid in the cell is DHA.

Preferably, at least 6%, at least 11% or at least 15% of the total fatty acid incorporated in triacylglycerol in the cell is DHA.

In an embodiment, DHA constitutes 20-65%, preferably, 40-65%, of the total of SDA, ETA, EPA, DPA and DHA in the cell.

Preferably, of the ω3 fatty acids in the cell 0.1-25% is SDA, 0.1-10% is ETA, 0.1-60% is EPA, 0.1-50% is DPA and 30-95% is DHA, more preferably of the ω3 fatty acids in the cell 0.1-25% is SDA, 0.1-10% is ETA, 0.1-50% is EPA, 0.1-50% is DPA and 40-95% is DHA.

The Δ4 desaturase preferably comprises amino acids having a sequence as provided in SEQ ID NO:73, a biologically active fragment thereof, or an amino acid sequence which is at least 80% identical to SEQ ID NO:73.

In another aspect, the present invention provides a recombinant cell, preferably a plant cell and more preferably a plant seed cell, comprising exogenous polynucleotides encoding;
  i) a Δ6 elongase and/or a Δ9 elongase,
  ii) a Δ6 desaturase and/or a Δ8 desaturase,
  iii) a Δ5 desaturase,
  iv) a Δ5 elongase, and
  v) optionally a diacylglycerol acyltransferase
wherein each polynucleotide is operably linked to one or more promoters that are capable of directing expression of said polynucleotides in the cell, characterised by one or more or all of the following properties:
  a) the efficiency of conversion of ALA to EPA or DPA is at least 17.3%, or at least 23%, and
  b) the efficiency of conversion of ALA to DPA is at least 15.4%, or at least 21%,
and preferably further characterised in that at least 4% of the total fatty acid in the cell is DPA.

Preferably, at least 6%, at least 11% or at least 15% of the total fatty acids incorporated in triacylglycerol in the cell is DPA.

The DPA preferably constitutes 20-65%, more preferably 40-65%, of the total of SDA, ETA, EPA and DPA in the cell.

Preferably, of the ω3 fatty acids in the cell 0.1-35% is SDA, 0.1-15% is ETA, 0.1-60% is EPA and 30-75% is DPA, more preferably of the ω3 fatty acids in the cell 0.1-35% is SDA, 0.1-15% is ETA, 0.1-50% is EPA and 40-75% is DPA.

In one embodiment, the Δ6 elongase comprises amino acids having a sequence as provided in SEQ ID NO:4, a biologically active fragment thereof, or an amino acid sequence which is at least 55% identical to SEQ ID NO:4.

In another embodiment, the Δ6 desaturase comprises amino acids having a sequence as provided in SEQ ID NO:8, a biologically active fragment thereof, or an amino acid sequence which is at least 67% identical to SEQ ID NO:8.

In one embodiment, the Δ5 desaturase comprises amino acids having a sequence as provided in SEQ ID NO:26, a biologically active fragment thereof, or an amino acid sequence which is at least 80% identical to SEQ ID NO:26.

In yet another embodiment, the Δ5 elongase comprises amino acids having a sequence as provided in SEQ ID NO:6, a biologically active fragment thereof, or an amino acid sequence which is at least 47% identical to SEQ ID NO:6.

In one embodiment, the diacylglycerol acyltransferase comprises amino acids having a sequence as provided in SEQ ID NO:75 or SEQ ID NO:108, a biologically active fragment thereof, or an amino acid sequence which is at least 80% identical to SEQ ID NO:75 and/or SEQ ID NO:108.

Combinations of any two, three, four or all of the above enzymes are clearly encompassed by the invention.

In yet another embodiment, the cell, preferably a plant cell and more preferably a plant seed cell, of the invention further comprises exogenous polynucleotides encoding;
  i) a Δ17 desaturase,
  ii) a Δ15 desaturase, and/or
  iii) a Δ12 desaturase
wherein each polynucleotide is operably linked to one or more promoters that are capable of directing expression of said polynucleotides in the cell, In a further embodiment, one or more or all of the desaturases expressed from exogenous polynucleotides in the cell of the invention have greater activity on an acyl-CoA substrate than the corresponding acyl-PC substrate. In a particular embodiment, the Δ6 desaturase and the Δ5 desaturase, the Δ5 desaturase and the Δ4 desaturase, the Δ6 desaturase and the Δ4 desaturase, or all three of the Δ6 desaturase, Δ5 desaturase and Δ4 desaturases, or additionally to each of these combinations any of Δ17 desaturase, Δ15 desaturase and/or Δ12 desaturases have greater activity on their acyl-CoA substrates than the corresponding acyl-PC substrates. In this embodiment, the other desaturases expressed from exogenous polynucleotides in the cell may or may not have greater activity on an acyl-CoA substrate than the corresponding acyl-PC substrate. As would be appreciated, the preferred acyl-CoA substrate for each enzyme is different.

The present invention further provides a recombinant cell, preferably a plant cell and more preferably a plant seed cell, comprising an exogenous polynucleotide encoding a fatty acid elongase with Δ6 elongase and Δ9 elongase activity, wherein the elongase has greater Δ6 elongase activity than Δ9 elongase activity.

In one embodiment, the elongase has an efficiency of conversion on SDA to produce ETA which is at least 50% or at least 60%, and/or an efficiency of conversion on ALA to produce ETrA which is at least 6% or at least 9%.

Preferably, the elongase has at least about 6.5 fold greater Δ6 elongase activity than Δ9 elongase activity.

In yet another embodiment, the elongase has no detectable Δ5 elongase activity.

The elongase preferably comprises amino acids having a sequence as provided in SEQ ID NO:4, a biologically active fragment thereof, or an amino acid sequence which is at least 55% identical to SEQ ID NO:4.

In yet another embodiment, the cell further comprises exogenous polynucleotides encoding;
  i) a Δ8 desaturase and/or a Δ6 desaturase,
  ii) a Δ5 desaturase,
  iii) a Δ5 elongase, and
  iv) optionally a Δ4 desaturase and/or an ω3 desaturase,
wherein each polynucleotide is operably linked to one or more promoters that are capable of directing expression of said polynucleotides in the cell.

The present invention further provides a recombinant cell, preferably a plant cell and more preferably a plant seed cell, comprising an exogenous polynucleotide encoding a fatty acid desaturase with Δ5 desaturase activity, wherein the desaturase comprises amino acids having a sequence as provided in SEQ ID NO:13, a biologically active fragment thereof, or an amino acid sequence which is at least 53% identical to SEQ ID NO:13.

The present invention further provides a recombinant cell, preferably a plant cell and more preferably a plant seed cell, comprising an exogenous polynucleotide encoding a fatty acid elongase with Δ9 elongase activity, wherein the elongase comprises amino acids having a sequence as provided in any one of SEQ ID NOs:28, 94 and 96, a biologically active fragment thereof, an amino acid sequence which is at least 81% identical to SEQ ID NO:28, or an amino acid sequence which is at least 50% identical to SEQ ID NO:94 and/or SEQ ID NO:96.

In an embodiment, the Δ9 elongase comprises amino acids having a sequence as provided in SEQ ID NO:94 or SEQ ID NO:96, a biologically active fragment thereof, or an amino acid sequence which is at least 50% identical to SEQ ID NO:94 and/or SEQ ID NO:96, and wherein the elongase has greater activity on an ω6 substrate than the corresponding ω3 substrate More preferably, the Δ9 elongase has at least a 2 fold, more preferably at least a 4 fold greater activity on an ω6 substrate (for example LA) than the corresponding ω3 substrate (for example ALA).

In another aspect, the present invention provides a recombinant cell comprising an exogenous polynucleotide encoding a diacylglycerol acyltransferase, wherein the diacylglycerol acyltransferase comprises amino acids having a sequence as provided in SEQ ID NO:108, a biologically active fragment thereof, or an amino acid sequence which is at least 54% identical to SEQ ID NO:108.

In one embodiment of the cell according to the invention, the desaturase and/or elongase, or multiple desaturases and/or elongases, can purified from microalga. Preferred microalgae are *Pavlova* spp, *Pyramimonas* spp and *Micromonas* spp.

In a preferred embodiment, the cell according to the invention is a eukaryotic cell. For example the cell may be a plant cell, a mammalian cell, an insect cell, a fungal cell or a yeast cell. The cell may be a cell in tissue culture, in vitro and/or isolated.

In one embodiment, the cell is in a plant and/or is a mature plant seed cell. The plant may be in the field or harvested as a plant part, or the seed may be harvested seed.

In one particular embodiment, the plant or plant seed is an oilseed plant or an oilseed respectively.

As the skilled addressee will appreciate, one of more of the defined elongases and/or desaturases can be co-expressed in the same cell.

In a further embodiment, the cell of the invention is capable of synthesising long chain polyunsaturated fatty acids (LC-PUFA), wherein the cell is derived from a cell that is not capable of synthesising said LC-PUFA.

The present inventors have also found that co-expression of a silencing suppressor can enhance the levels of fatty acid biosynthesis enzymes in plant cells, particularly over repeated generations from the initially transformed plant. Thus, in a preferred embodiment, a cell of the invention, preferably a plant cell and more preferably a plant storage organ cell or seed cell, comprises an exogenous polynucleotide encoding a silencing suppressor.

Preferably, the exogenous polynucleotide encoding the silencing suppressor is operably linked to a plant storage organ specific promoter. In an embodiment, the plant storage organ specific promoter is a seed specific promoter, or a cotyledon-specific promoter or an endosperm-specific promoter that is preferentially expressed in the developing seed.

The present invention further provides a method of obtaining a cell, preferably a plant cell and more preferably a plant seed cell, capable of synthesising one or more long chain polyunsaturated fatty acids (LC-PUFAs), the method comprising
  a) introducing into a cell, preferably a cell which is not capable of synthesising said LC-PUFA, an exogenous polynucleotide encoding a fatty acid ω3 desaturase activity, wherein the polynucleotide is operably linked to a promoter that is capable of directing expression of said polynucleotide in the cell,
  b) expressing the exogenous polynucleotides in the cell,
  c) analysing the fatty acid composition of the cell, and
  d) selecting a cell capable of desaturating at least one of ARA to EPA, DGLA to ETA, GLA to SDA, both ARA to EPA and DGLA to ETA, both ARA to EPA and GLA to SDA, or all three of these.

In one embodiment, the selected cell is a cell according to the invention. In particular, the cell may further comprise a combination of desaturases and elongases as described herein.

The present invention further provides a method of obtaining a cell, preferably a plant cell and more preferably a plant seed cell, capable of synthesising one or more long chain polyunsaturated fatty acids (LC-PUFAs), the method comprising
  a) introducing into a cell, preferably a cell which is not capable of synthesising said LC-PUFA, an exogenous polynucleotide encoding a fatty acid Δ5 elongase wherein the polynucleotide is operably linked to a promoter that is capable of directing expression of said polynucleotide in the cell,
  b) expressing the exogenous polynucleotide in the cell,
  c) analysing the fatty acid composition of the cell, and d) selecting a cell wherein the Δ5 elongase has activity on EPA to produce DPA with an efficiency of at least 60%, at least 65%, at least 70% or at least 75%.

In one embodiment of the method of the invention, the selected cell is a cell according to the invention. In particular, the cell may further comprise a combination of desaturases and elongases as described herein.

The present invention further provides a method of obtaining a cell, preferably a plant cell and more preferably a plant seed cell, capable of synthesising one or more long chain polyunsaturated fatty acids (LC-PUFAs), the method comprising
  a) introducing into a cell, preferably a cell which is not capable of synthesising said LC-PUFA, an exogenous polynucleotide encoding a fatty acid Δ6 desaturase, wherein the polynucleotide is operably linked to a promoter that is capable of directing expression of said polynucleotide in the cell,
  b) expressing the exogenous polynucleotide in the cell,
  c) analysing the fatty acid composition of the cell, and
  d) selecting a cell having at least two, preferably all three, of the following
    i) greater Δ6 desaturase activity on ALA than LA as fatty acid substrate, preferably in a plant cell,
    ii) greater Δ6 desaturase activity on ALA-CoA as fatty acid substrate than on ALA joined to the sn-2 position of PC as fatty acid substrate, preferably in a plant cell, and
    iii) Δ6 desaturase activity on ALA and Δ8 desaturase on ETrA, preferably in a plant cell.

The present invention further provides a method of obtaining a cell, preferably a plant cell and more preferably a plant seed cell, capable of synthesising one or more long chain polyunsaturated fatty acids (LC-PUFAs), the method comprising
  a) introducing into a cell, preferably a cell which is not capable of synthesising said LC-PUFA, an exogenous polynucleotide encoding a fatty acid Δ6 desaturase, wherein the polynucleotide is operably linked to a promoter that is capable of directing expression of said polynucleotide in the cell,
  b) expressing the exogenous polynucleotide in the cell,
  c) analysing the fatty acid composition of the cell, and
  d) selecting a cell with Δ6 desaturase activity which has greater activity on an ω3 substrate than the corresponding ω6 substrate, and with activity on ALA to produce SDA with an efficiency of at least 5%, at least 7.5%, or at least 10%, or at least 35% when expressed in a yeast cell.

In one embodiment, the selected cell is a cell according to the invention. In particular, the cell may further comprise a combination of desaturases and elongases as described herein.

The present invention further provides a method of obtaining a cell, preferably a plant cell and more preferably a plant seed cell, capable of synthesising one or more long chain polyunsaturated fatty acids (LC-PUFAs), the method comprising
  a) introducing into a cell, preferably a cell which is not capable of synthesising said LC-PUFA, exogenous polynucleotides encoding;
    i) a Δ9 elongase,
    ii) a Δ8 desaturase,
    iii) a Δ5 desaturase,
    iv) optionally a Δ5 elongase, and
    v) if the Δ5 elongase is present, optionally a Δ4 desaturase, wherein each polynucleotide is operably linked to one or more promoters that are capable of directing expression of said polynucleotides in the cell,
  b) expressing the exogenous polynucleotides in the cell;
  c) analysing the fatty acid composition of the cell, and
  d) selecting a cell where at least 15%, at least 20% or at least 25% of the total fatty acids comprise at least 20 carbons and at least 3 carbon-carbon double bonds in their acyl chains.

In one embodiment, the selected cell is a cell according to the invention.

The present invention further provides a method of obtaining a cell, preferably a plant cell and more preferably a plant seed cell, capable of synthesising one or more long chain polyunsaturated fatty acids (LC-PUFAs), the method comprising
  a) introducing into the cell, preferably a cell which is not capable of synthesising said LC-PUFA, exogenous polynucleotides encoding;
    i) a Δ6 elongase and/or a Δ9 elongase,
    ii) a Δ6 desaturase and/or a Δ8 desaturase,
    iii) a Δ5 desaturase,
    iv) a Δ5 elongase,
    v) a Δ4 desaturase, and
    vi) optionally a diacylglycerol acyltransferase, wherein each polynucleotide is operably linked to one or more promoters that are capable of directing expression of said polynucleotides in the cell,
  b) expressing the exogenous polynucleotides in the cell;
  c) analysing the fatty acid composition of the cell, and
  d) selecting a cell characterised by one or more or all of the following properties:
    1) the efficiency of conversion of ALA to EPA, DPA or DHA is at least 17.3%, or at least 23%;
    2) the efficiency of conversion of ALA to DPA or DHA is at least 15.4%, or at least $2^1$%;
    3) the efficiency of conversion of ALA to DHA is at least 9.5%, or at least 10.8%; and
    4) the efficiency of conversion of EPA to DHA is at least 45%, or at least 50%;
and preferably further characterised in that at least 4% of the total fatty acid in the cell is DHA.

In a further aspect, the present invention provides a method of obtaining a cell, preferably a plant cell and more preferably a plant seed cell, capable of synthesising one or more long chain polyunsaturated fatty acids (LC-PUFAs), the method comprising
  a) introducing into the cell, preferably a cell which is not capable of synthesising said LC-PUFA, exogenous polynucleotides encoding;
    i) a Δ6 elongase and/or a Δ9 elongase,
    ii) a Δ6 desaturase and/or a Δ8 desaturase,
    iii) a Δ5 desaturase,
    iv) a Δ5 elongase, and
    v) optionally a diacylglycerol acyltransferase wherein each polynucleotide is operably linked to one or more promoters that are capable of directing expression of said polynucleotides in the cell,
  b) expressing the exogenous polynucleotides in the cell;
  c) analysing the fatty acid composition of the cell, and
  d) selecting a cell characterised by one or more or all of the following properties:
    a) the efficiency of conversion of ALA to EPA or DPA is at least 17.3%, or at least 23%, and
    b) the efficiency of conversion of ALA to DPA is at least 15.4%, or at least 21%,
and preferably further characterised in that at least 4% of the total fatty acid in the cell is DPA.

In one embodiment of the method according to the invention, the exogenous polynucleotides become stably integrated into the genome of the cell.

In another embodiment, the method further comprises the step of regenerating a transformed plant from the cell of step a).

In a further embodiment, the exogenous polynucleotide(s) are expressed transiently in the cell.

In one embodiment, the cell is a leaf cell in a plant.

The present invention further provides a process for selecting a nucleic acid molecule involved in fatty acid desaturation comprising:
  i) obtaining a nucleic acid molecule operably linked to a promoter, the nucleic acid molecule encoding a polypeptide which may be a fatty acid desaturase;
  ii) introducing the nucleic acid molecule into a cell in which the promoter is active;
  iii) expressing the nucleic acid molecule in the cell;
  iv) analysing the fatty acid composition of the cell; and
  v) selecting the nucleic acid molecule involved in fatty acid desaturation on the basis that the polypeptide has ω3 desaturase activity and is capable of desaturating at least one of ARA to EPA, DGLA to ETA, GLA to SDA, both ARA to EPA and DGLA to ETA, both ARA to EPA and GLA to SDA, or all three of these.

In one embodiment of the process, the amino acid sequence of the polypeptide is at least 35% identical to SEQ ID NO:15, at least 60% identical to SEQ ID NO:17 and/or at least 60% identical to SEQ ID NO:20.

The present invention further provides a process for selecting a nucleic acid molecule involved in fatty acid elongation comprising:
  i) obtaining a nucleic acid molecule operably linked to a promoter, the nucleic acid molecule encoding a polypeptide which may be a fatty acid elongase,
  ii) introducing the nucleic acid molecule into a cell in which the promoter is active,
  iii) expressing the nucleic acid molecule in the cell;
  iv) analysing the fatty acid composition of the cell; and
  v) selecting the nucleic acid molecule involved in fatty acid elongation on the basis that the polypeptide has Δ5 elongase activity and an efficiency of conversion on EPA to produce DPA which is at least 60%, at least 65%, at least 70% or at least 75%.

In one embodiment, the amino acid sequence of the polypeptide is at least 47% identical to SEQ ID NO:6.

The present invention further provides a process for selecting a nucleic acid molecule involved in fatty acid desaturation comprising:
  i) obtaining a nucleic acid molecule operably linked to a promoter, the nucleic acid molecule encoding a polypeptide which may be a fatty acid desaturase,
  ii) introducing the nucleic acid molecule into a cell in which the promoter is active,
  iii) expressing the nucleic acid molecule in the cell;
  iv) analysing the fatty acid composition of the cell; and
  v) selecting a nucleic acid molecule involved in fatty acid desaturation on the basis that the polypeptide has Δ6 desaturase activity and at least two, preferably all three, of the following:
  a) greater Δ6 desaturase activity on ALA than LA as fatty acid substrate, preferably in a plant cell,
  b) greater Δ6 desaturase activity on ALA-CoA as fatty acid substrate than on ALA joined to the sn-2 position of PC as fatty acid substrate, preferably in a plant cell, and
  c) Δ8 desaturase activity on ALA, preferably in a plant cell.

In one embodiment of the process, the amino acid sequence of the polypeptide is at least 77% identical to SEQ ID NO:10 and/or is at least 67% identical to SEQ ID NO:8.

The present invention further provides a process for selecting a nucleic acid molecule involved in fatty acid desaturation comprising:
  i) obtaining a nucleic acid molecule operably linked to a promoter, the nucleic acid molecule encoding a polypeptide which may be a fatty acid desaturase,
  ii) introducing the nucleic acid molecule into a cell in which the promoter is active,
  iii) expressing the nucleic acid molecule in the cell;
  iv) analysing the fatty acid composition of the cell; and
  v) selecting a nucleic acid molecule involved fatty acid desaturation on the basis that the polypeptide has both Δ6 desaturase and Δ8 desaturase activities.

In one embodiment, the amino acid sequence of the polypeptide is at least 67% identical to SEQ ID NO:8.

In a further embodiment, step (v) of the process of the invention comprises selecting a nucleic acid molecule encoding a desaturase active on acyl-CoA substrates or a front-end desaturase.

The present invention further provides a combination of exogenous polynucleotides as defined herein when used to produce a recombinant cell, express a combination of at least two fatty acid desaturases and two fatty acid elongases in a recombinant cell, and/or to produce LC-PUFA in a recombinant cell.

The present invention further provides a substantially purified and/or recombinant fatty acid Δ5 elongase, wherein the elongase has activity on EPA to produce DPA with an efficiency of at least 60%, at least 65%, at least 70% or at least 75% when expressed from an exogenous polynucleotide in a cell.

In one embodiment, the Δ5 elongase of is characterised by any one or more of the properties as defined herein.

The present invention further provides a substantially purified and/or recombinant fatty acid ω3 desaturase which is capable of desaturating at least one of ARA to EPA, DGLA to ETA, GLA to SDA, both ARA to EPA and DGLA to ETA, both ARA to EPA and GLA to SDA, or all three of these when expressed from an exogenous polynucleotide in a cell.

In one embodiment, the ω3 desaturase of the invention is characterised by any one or more of the properties as defined herein.

The present invention further provides a substantially purified and/or recombinant fatty acid Δ6 desaturase, wherein the desaturase is further characterised by having at least two, preferably all three, of the following;
  i) greater Δ6 desaturase activity on ALA than LA as fatty acid substrate, preferably in a plant cell,
  ii) greater Δ6 desaturase activity on ALA-CoA as fatty acid substrate than on ALA joined to the sn-2 position of PC as fatty acid substrate, preferably in a plant cell, and
  iii) Δ8 desaturase activity on ETrA, preferably in a plant cell.

The present invention further provides a substantially purified and/or recombinant fatty acid Δ6 desaturase, wherein the desaturase has greater activity on an ω3 substrate than the corresponding ω6 substrate, and wherein the desaturase has activity on ALA to produce SDA with an efficiency of at least 5%, at least 7.5%, or at least 10% when the desaturase is expressed from an exogenous polynucleotide in a cell, or at least 35% when expressed in a yeast cell.

In one embodiment, the Δ6 desaturase of the invention is characterised by any one or more of the properties as defined herein.

The present invention further provides a substantially purified and/or recombinant fatty acid Δ6 elongase and Δ9 elongase, wherein the elongase has greater Δ6 elongase activity than Δ9 elongase activity.

In one embodiment, the Δ6 elongase and Δ9 elongase of the invention is characterised by any one or more of the properties as defined herein.

The present invention further provides a substantially purified and/or recombinant fatty acid Δ5 desaturase which comprises amino acids having a sequence as provided in SEQ ID NO:13, a biologically active fragment thereof, or an amino acid sequence which is at least 53% identical to SEQ ID NO:13.

The present invention further provides a substantially purified and/or recombinant fatty acid Δ9 elongase which comprises amino acids having a sequence as provided in any one of SEQ ID NOs: 28, 94 and 96, a biologically active fragment thereof, an amino acid sequence which is at least 81% identical to SEQ ID NO:28, or an amino acid sequence which is at least 50% identical to SEQ ID NO:94 and/or SEQ ID NO:96.

In an embodiment, the Δ9 elongase comprises amino acids having a sequence as provided in SEQ ID NO:94 or SEQ ID NO:96, a biologically active fragment thereof, or an amino acid sequence which is at least 50% identical to SEQ ID NO:94 and/or SEQ ID NO:96, and wherein the elongase has greater activity on an ω6 substrate than the corresponding ω3 substrate.

In another aspect, the present invention provides a substantially purified and/or recombinant diacylglycerol acyltransferase which comprises amino acids having a sequence as provided in SEQ ID NO:108, a biologically active fragment thereof, or an amino acid sequence which is at least 54% identical to SEQ ID NO:108.

In an embodiment, the desaturase or elongase according to the invention can purified from microalga. Preferred microalgae are *Pavlova* spp, *Pyramimonas* spp and *Micromonas* spp.

The present invention further provides an isolated and/or exogenous polynucleotide comprising:
 i) a sequence of nucleotides selected from any one of SEQ ID NOs:3, 5, 7, 9, 11, 12, 14, 16, 18, 19, 27, 29, 93, 95, 107 or 125 to 129,
 ii) a sequence of nucleotides encoding a desaturase or an elongase according to the invention,
 iii) a sequence of nucleotides which are at least 50% identical to one or more of the sequences set forth in SEQ ID NOs: 3, 5, 7, 9, 11, 12, 14, 16, 18, 19, 27, 29, 93, 95, 107 or 125 to 129 and/or
 iv) a sequence which hybridises to any one of i) to iii) under stringent conditions.

In one embodiment, the isolated and/or exogenous polynucleotide comprises a sequence of nucleotides which is at least 57% identical to SEQ ID NO:3 and/or SEQ ID NO:126, and encodes a Δ6 elongase.

In another embodiment, the isolated and/or exogenous polynucleotide comprises a sequence of nucleotides which is at least 50% identical to SEQ ID NO: 14, SEQ ID NO:16, SEQ ID NO:18 and/or SEQ ID NO:19, and encodes a ω3 desaturase.

In another embodiment, the isolated and/or exogenous polynucleotide comprises a sequence of nucleotides which is at least 50% identical to SEQ ID NO:5 and/or SEQ ID NO:128, and encodes a Δ5 elongase.

In one embodiment, the isolated and/or exogenous polynucleotide comprises a sequence of nucleotides which is at least 75% identical to SEQ ID NO:7, SEQ ID NO:9, SEQ ID NO:11 and/or SEQ ID NO:125, and encodes a Δ6 desaturase.

In yet another embodiment, the isolated and/or exogenous polynucleotide comprises a sequence of nucleotides which is at least 60% identical to SEQ ID NO:12, and encodes a Δ5 desaturase.

In another embodiment, the isolated and/or exogenous polynucleotide comprises a sequence of nucleotides which is at least 50% identical to SEQ ID NO:27, SEQ ID NO:29, SEQ ID NO:93 and/or SEQ ID NO:96, and encodes a Δ9 elongase.

In yet another embodiment, the isolated and/or exogenous polynucleotide comprises a sequence of nucleotides which is at least 60% identical to SEQ ID NO:107, and encodes a diacylglycerol acyltransferase.

In one particular embodiment, the isolated and/or exogenous polynucleotide is at least 80%, or at least 90%, or at least 95%, or at least 99% identical to one of the sequences set forth in SEQ ID NOs: 3, 5, 7, 9, 11, 12, 14, 16, 18, 19, 27, 29, 93, 95, 107 or 125 to 129.

The present invention further provides a DNA construct for integration, and/or integrated, into the genome of a plant cell, the construct comprising a cluster of at least three open reading frames encoding proteins which modulate fatty acid synthesis in the plant cell, preferably each protein being a fatty acid desaturase or a fatty acid elongase, wherein each open reading frame having the same transcription orientation is separated by at least 750 bp, at least 1,000 bp or at least 1,250 bp, and at least two of the open reading frames have different transcription orientations, wherein each open reading frame is operably linked to a promoter which is active in the plant cell and each promoter may independently be the same or different.

Preferably, at least two of the promoters are in the DNA construct are different.

One or more or each open reading frame is preferably operably linked to a heterologous 5' leader sequence, each of which may independently be the same or different, wherein each heterologous 5' leader sequence enhances translation efficiency relative to the naturally occurring 5' leader sequence for the particular open reading frame.

In the DNA construct of the invention, the heterologous 5' leader sequence is preferably a tobacco mosaic virus (TMV) 5' leader sequence.

In the DNA construct according to the invention, the proteins preferably are elongases and/or desaturases, more preferably a combination as described herein.

In yet another embodiment, the DNA construct according to the invention has only three or four open reading frames that are translated into proteins.

The present invention further provides a vector comprising the polynucleotide according to the invention and/or the DNA construct according to the invention.

Preferably, the polynucleotide is operably linked to a promoter.

The present invention further provides a method of producing the desaturase or elongase according to the invention, the method comprising expressing in a cell or cell free expression system the polynucleotide of the invention, the DNA construct of the invention and/or the vector of the invention.

The present inventors have also surprisingly found that at least three independent extrachromosomal transfer nucleic acids comprising different exogenous polynucleotides can be transiently transfected into a eukaryotic cell and the activity of each exogenous polynucleotide detected in the cell, in combination. Thus, in another aspect the present invention further provides a method of transiently transfecting a eukaryotic cell with at least three different exogenous polynucleotides, the method comprising i) obtaining at least
- a) a first bacterium comprising an extrachromosomal transfer nucleic acid comprising a first exogenous polynucleotide,
- b) a second bacterium comprising an extrachromosomal transfer nucleic acid comprising a second exogenous polynucleotide, and
- c) a third bacterium comprising an extrachromosomal transfer nucleic acid comprising a third exogenous polynucleotide, and ii) contacting the cell with the bacteria of step i), wherein each of the extrachromosomal transfer nucleic acids are transferred from the bacteria to the cell to produce the transiently transfected cell, wherein each of the exogenous polynucleotides comprises a promoter which is active in the cell, wherein each promoter may independently be the same or different, and wherein at least one of the exogenous polynucleotides encodes a silencing suppressor.

Step ii) may be conducted sequentially or simultaneously with one or more of the bacteria. For example, the cell can be contacted with the first bacteria, then the second bacteria and so on. In another example, the cell is contacted with each bacterium at the same time, preferably as a mixture of the bacteria. The concentrations of the different bacteria may be varied relative to each other or may be the same or similar. The bacteria may be pooled isolates, for example comprising a number of isolates from a library of strains.

In an embodiment, the method further comprises obtaining, and then contacting the cell with, one or more additional bacteria each comprising an extrachromosomal transfer nucleic acid comprising different exogenous polynucleotides. For instance, in one embodiment, the method comprises obtaining, and then contacting the cell with, a fourth bacterium comprising an extrachromosomal transfer nucleic acid comprising a fourth exogenous polynucleotide. In an additional embodiment, the method comprises obtaining, and then contacting the cell with, a fifth bacterium comprising an extrachromosomal transfer nucleic acid comprising a fifth exogenous polynucleotide. In an additional embodiment, the method comprises obtaining, and then contacting the cell with, a sixth bacterium comprising an extrachromosomal transfer nucleic acid comprising a sixth exogenous polynucleotide. In an additional embodiment, the method comprises obtaining, and then contacting the cell with, a seventh bacterium comprising an extrachromosomal transfer nucleic acid comprising a seventh exogenous polynucleotide. In yet another additional embodiment, the method comprises obtaining, and then contacting the cell with, an eighth bacterium comprising an extrachromosomal transfer nucleic acid comprising an eighth exogenous polynucleotide.

Preferably, the different exogenous polynucleotides encode different RNA molecules and/or polypeptides.

In an embodiment, each exogenous polynucleotide encodes an enzyme which forms part of an enzymatic pathway or is a candidate for such an enzyme.

The above aspect is particularly useful for studying polynucleotides and/or polypeptides which form large and/or complex biological pathways. Accordingly, in a preferred embodiment, each exogenous polynucleotide encodes an enzyme, or is a candidate for such an enzyme, involved in fatty acid synthesis, fatty acid modification, diacylglycerol assembly, triacylglycerol assembly, or a combination of two or more thereof.

In an embodiment, one or more of the bacteria is in the form of a protoplast. Examples of bacterium useful for the invention include, but are not limited to, *Agrobacterium* sp., *Rhizobium* sp., *Sinorhizobium meliloti*, *Mezorhizobium loti*, *Shigella flexneri*, *Salmonella typhimurium*, *Salmonella choleraesuis*, *Listeria monocytogenes*, *Escherichia coli*, *Yersinia pseudotuberculosis* and *Yersinia enterocolitica*.

Examples of extrachromosomal transfer nucleic acids useful for the invention include, but are not limited to, are P-DNA, *Agrobacterium* sp. T-DNA, or a combination thereof.

Preferably, the cell of the above aspect is a plant cell or a mammalian cell. In an embodiment, the cell is part of a tissue or organ. In another embodiment, the cell is a plant cell, and the tissue or organ is a leaf, stem, root, meristem, callus, or ovule.

The present inventors have also determined that when the promoters are seed-specific promoters the expression of the exogenous polynucleotides in leaf cells can be enhanced by co-expression of a seed specific transcription factor such as leafy cotyledon 2, fusca3 or abscisic acid-senstive3. Examples of leafy cotyledon 2 proteins include, but are not limited to, those described in WO 01/70777. Thus, in a preferred embodiment, the plant cell is a plant leaf cell, at least one of the promoters is a seed-specific promoter and at least one of the exogenous polynucleotides encodes a seed-specific transcription such as leafy cotyledon 2.

In an embodiment, none of the exogenous polynucleotides are a viral gene. In an embodiment, one or more of the exogenous polynucleotides are only present in the extrachromosomal transfer nucleic acid as a single copy, not as a multimer or partial multimer of a defined nucleic acid sequence. In a further embodiment, at least one of the extrachromosomal transfer nucleic acids does not comprise an origin of replication which is functional in the cell, preferably not a viral origin of replication and more preferably not the FBNYV origin of replication. In a further embodiment, none of the exogenous polynucleotides encodes a viral replicase or a viral movement protein such as those described in WO 2007/137788 and by Marillonnet et al. (2005).

Also provided is a method of screening a transiently transfected cell for a desired activity, the method comprising performing the method of transiently transfecting a eukaryotic cell with at least three exogenous polynucleotides of the invention, and testing the cell for the desired activity.

The present inventors also identified that the transformation of cells, particularly plant cells, with more that six different genescan be enhanced providing the genes through different extrachromosomal transfer nucleic acids. Thus, in another aspect the present invention provides a method of transforming a eukaryotic cell with at least six different exogenous polynucleotides, the method comprising i) obtaining at least
- a) a first bacterium comprising a first extrachromosomal transfer nucleic acid which comprises three, four, five or six different exogenous polynucleotides, and
- b) a second bacterium comprising a second extrachromosomal transfer nucleic acid different to the first which comprises three, four, five or six different exogenous polynucleotides, ii) contacting the cell with the bacteria of step i), and iii) optionally selecting a cell stably transformed with the exogenous polynucleotides of the first and second extrachromosomal transfer nucleic acids, wherein each of the exogenous polynucleotides of the first and second extrachromosomal transfer nucleic acids are transferred from the bacteria to the cell to produce the transformed cell, wherein each of the exogenous polynucleotides comprises a promoter which is active in the cell or a cell derivable therefrom, and wherein each promoter may independently be the same or different.

Steps i)a) and i)b) may be conducted sequentially or simultaneously with the two bacteria. For example, the cell can be contacted with the first bacteria and then the second bacteria. The cell contacted with the second bacterium may be a progeny cell or derived from the cell contacted with the first bacterium. In another example, the cell is contacted with both of the bacteria at the same time.

In an embodiment, the i) first extrachromosomal transfer nucleic acid, has only three to six, only three to five, only three to four, only four to six, only four to five, or only five to six different exogenous polynucleotides, and ii) the second extrachromosomal transfer nucleic acid, has only three to six, only three to five, only three to four, only four to six, only four to five, or only five to six different exogenous polynucleotides.

Preferably, each of the exogenous polynucleotides encode polypeptides, and wherein each of the polypeptides are different.

In a further embodiment, i) the first extrachromosomal transfer nucleic acid comprises two exogenous polynucleotides independently encoding polypeptides selected from the group consisting of a Δ6 desaturase, a Δ12 desaturase and a Δ15 desaturase, and ii) the second extrachromosomal transfer nucleic acid comprises an exogenous polynucleotide which encodes a polypeptide which is the third enzyme from the group.

Preferably, the cell is a plant cell and the method further comprises the step of generating a transformed plant from the stably transformed cell.

Also provided is a cell produced by the method method of transiently transfecting a eukaryotic cell with at least three exogenous polynucleotides of the invention, or the method of transforming a eukaryotic cell with at least six different exogenous polynucleotides of the invention.

In yet a further aspect, the present invention provides a method of producing a stably transformed plant with at least six different exogenous polynucleotides, the method comprising i) obtaining a first stably transformed plant comprising a first exogenous genomic region comprising three, four, five or six different exogenous polynucleotides, ii) obtaining a second stably transformed plant of a sexually compatible species with the first and comprising a second exogenous genomic region different to the first comprising three, four, five or six different exogenous polynucleotides, iii) crossing the first stably transformed plant with the second stably transformed plant, and iv) selecting a plant produced from step iii) or a progeny thereof which comprises the first and second genomic regions thereby producing the stably transformed plant, wherein each of the exogenous polynucleotides comprises a promoter which is active in the plant, and wherein each promoter may independently be the same or different.

In a preferred embodiment, the exogenous polynucleotides of the first and/or second exogenous genomic regions are orientated and spaced as outlined above for the DNA construct of the invention.

Any one promoter sequence may be present multiple times, or may be used only once within the first and second exogenous genomic regions, or one or more promoters may be used multiple times and one or more other promoters be used only once in the first and second exogenous genomic regions. Each plant promoter may be, independently, preferentially active in a tissue or organ of the plant, such as in the leaf or seed, relative to other tissues or organs. This may allow for simultaneous expression, or overlapping expression, of all of the introduced protein coding regions, in the plant organ or tissue. In an alternative embodiment, one or more promoters are constitutively expressed in the plant and one or more other promoters are preferentially expressed in the plant organ or tissue.

In an embodiment, step i) comprises producing the first stably transformed plant by a) contacting a plant cell with a first bacterium comprising a first extrachromosomal transfer nucleic acid which comprises three, four, five or six different exogenous polynucleotides, b) generating a stably transformed plant from the plant cell of step a), and optionally c) producing a progeny plant from the stably transformed plant of step b); and/or step ii) comprises producing the second stably transformed plant by d) contacting a plant cell with a second bacterium comprising a second extrachromosomal transfer nucleic acid which comprises three, four, five or six different exogenous polynucleotides, e) generating a stably transformed plant from the plant cell of step d), and optionally f) producing a progeny plant from the stably transformed plant of step e).

In another aspect, the present invention provides a method of producing a stably transformed plant with at least six different exogenous polynucleotides, the method comprising i) obtaining a first stably transformed plant or plant part comprising a first exogenous genomic region comprising three, four, five or six different exogenous polynucleotides, ii) contacting a cell of the first stably transformed plant or plant part with a bacterium comprising an extrachromosomal transfer nucleic acid which comprises three, four, five or six different exogenous polynucleotides, iii) producing a plant from the cell, and iv) optionally, selecting a plant produced from step iii) which comprises the at least six different exogenous polynucleotides.

With regard to the step of "contacting the cell with the bacteria of step i)" of the above aspects, as the skilled addressee would be aware this is preformed for a suitable time and under suitable conditions for the extrachromosomal transfer nucleic acids to be transferred from the bacteria to the cell.

In a further aspect, the present invention provides a eukaryotic cell comprising at least a) a first extrachromosomal transfer nucleic acid comprising a first exogenous polynucleotide, b) a second extrachromosomal transfer nucleic acid comprising a second exogenous polynucleotide, and c) a third extrachromosomal transfer nucleic acid comprising a third exogenous polynucleotide.

In an embodiment, the cell further one or more additional bacteria each comprising an extrachromosomal transfer nucleic acid comprising different exogenous polynucleotides.

Also provided is a plant, or progeny thereof, or seed comprising a first exogenous genomic region comprising three, four, five or six different exogenous polynucleotides, and a second exogenous genomic region comprising three, four, five or six different exogenous polynucleotides. The exogenous polynucleotides of the exogenous genomic region(s) are preferably oriented and spaced as described above for the DNA construct.

The present invention further provides a transgenic non-human organism comprising a cell according to the invention. In an embodiment, each cell of the organism is a cell according to the invention.

Preferably, the transgenic non-human organism is a transgenic plant, more preferably a transgenic oilseed plant to produce the oil as listed below. In a further embodiment, the transgenic plant comprises at least one additional exogenous polynucleotide encoding a silencing suppressor operably linked to a plant storage organ specific promoter, wherein the plant is phenotypically normal.

The present invention further provides a seed comprising the cell according to the invention or obtained from the transgenic plant of the invention.

The present invention further provides oil produced by, or obtained from, the cell according to the invention, the transgenic non-human organism of the invention, or the seed of the invention.

In one embodiment, the oil is obtained by extraction of oil from an oilseed.

In one embodiment, the oil is canola oil (*Brassica napus, Brassica rapa* ssp.), mustard oil, other *Brassica* oil, sunflower oil (*Helianthus annus*), linseed oil (*Linum usitatissimum*), soybean oil (*Glycine max*), safflower oil (*Carthamus tinctorius*), corn oil (*Zea mays*), tobacco oil (*Nicotiana tabacum*), peanut oil (*Arachis hypogaea*), palm oil, cottonseed oil (*Gossypium hirsutum*), coconut oil (*Cocos nucifera*), avocado oil (*Persea americana*), olive oil (*Olea europaea*), cashew oil (*Anacardium occidentale*), macadamia oil (*Macadamia intergrifolia*), almond oil (*Prunus amygdalus*) or *Arabidopsis* seed oil (*Arabidopsis thaliana*).

The present invention further provides a fatty acid produced by, or obtained from, the cell according to the invention, the transgenic non-human organism of the invention, or the seed of the invention.

The present invention further provides a method of producing oil containing unsaturated fatty acids, the method comprising extracting oil from the cell according to the invention, the transgenic non-human organism of the invention, or the seed of the invention.

The present invention further provides a composition comprising a cell according to the invention, the desaturase or elongase according to the invention, a polynucleotide according to the invention, a DNA construct according to the invention, a vector of the invention, an oil according to the invention or a fatty acid of the invention.

The present invention further provides feedstuffs, cosmetics or chemicals comprising the cell according to the invention, the transgenic non-human organism according to the invention, the seed according to the invention, the oil according to the invention and/or the fatty acid of the invention.

The present invention further provides a method of performing a desaturase reaction, the method comprising contacting a polyunsaturated fatty acid esterified to CoA with the desaturase of the invention.

The present invention further provides a substantially purified antibody, or fragment thereof, that specifically binds a desaturase or elongase of the invention.

The present invention further provides a method of treating or preventing a condition which would benefit from a PUFA, the method comprising administering to a subject a cell according to the invention, the desaturase or elongase according to the invention, a polynucleotide according to the invention, a DNA construct according to the invention, a vector of the invention, a transgenic non-human organism according to the invention, a seed according to the invention, an oil according to the invention or a fatty acid of the invention and/or a feedstuff of the invention.

In one embodiment, the condition is cardiac arrhythmia's, angioplasty, inflammation, asthma, psoriasis, osteoporosis, kidney stones, AIDS, multiple sclerosis, rheumatoid arthritis, Crohn's disease, schizophrenia, cancer, foetal alcohol syndrome, attention deficient hyperactivity disorder, cystic fibrosis, phenylketonuria, unipolar depression, aggressive hostility, adrenoleukodystophy, coronary heart disease, hypertension, diabetes, obesity, Alzheimer's disease, chronic obstructive pulmonary disease, ulcerative colitis, restenosis after angioplasty, eczema, high blood pressure, platelet aggregation, gastrointestinal bleeding, endometriosis, premenstrual syndrome, myalgic encephalomyelitis, chronic fatigue after viral infections or an ocular disease.

The present invention further provides use of a cell according to the invention, the desaturase or elongase according to the invention, a polynucleotide according to the invention, a DNA construct according to the invention, a vector of the invention, a transgenic non-human organism according to the invention, a seed according to the invention, an oil according to the invention or a fatty acid of the invention and/or a feedstuff of the invention for the manufacture of a medicament for treating or preventing a condition which would benefit from a PUFA.

The present inventors have surprisingly found that silencing suppressors can preferentially be expressed in plant storage organs to enhance the levels of transgene expression in plant cells without significantly effecting plant development.

Accordingly, the present invention provides a plant cell comprising
  i) a first exogenous polynucleotide encoding a silencing suppressor, operably linked to a plant storage organ specific promoter, and
  ii) a second exogenous polynucleotide encoding an RNA molecule, operably linked to a promoter which directs gene transcription in the plant storage organ.

Preferably, the plant storage organ specific promoter is a seed specific promoter such as a cotyledon specific promoter or an endosperm specific promoter.

In an embodiment, the silencing suppressor is a viral suppressor protein such as, but not limited to, P1, P19, V2, P38, P15, Pe-Po and RPV-P0.

Typically, when the viral suppressor protein is constitutively expressed in a plant the plant is phenotypically abnormal, but when the silencing suppressor is expressed specifically in the storage organ, the plant is phenotypically normal.

Examples of such viral suppressor proteins include, but are not limited to, P1, P19 and P15.

In a further embodiment, the viral suppressor protein reduces microRNA accumulation and/or microRNA guided cleavage.

The RNA molecule may be functional per se such as, but not limited to, an antisense polynucleotide, catalytic polynucleotide, dsRNA and/or microRNA. Alternatively, the RNA molecule may encode a polypeptide with a desired function such as, but not limited to, an enzyme involved in fatty acid synthesis or modification, a seed storage protein such as for example, a cereal glutenin or gliadin, an enzyme involved in carbohydrate synthesis or modification, secondary metabolism or a pharmaceutical. Examples of pharmaceutical proteins include, but are not limited to, antibodies as well as antibody-related molecules and fragments thereof, antigenic polypeptides which can, for example, provide immune protection against cancer, an infectious agent, a cytokine such as, for example, granulocyte-macrophage colony stimulating factor, interferon-α, human serum albumin, and erythropoietin.

In a further embodiment, the cell comprises at least one, at least two, at least three, at least four or at least five or more additional different exogenous polynucleotides, each encoding an RNA molecule and being operably linked to a promoter which directs gene transcription in the storage organ. Each exogenous polynucleotide may be operably linked to the same promoter, different promoters or a combination thereof.

In an embodiment the exogenous polynucleotides are DNA.

In a further embodiment, the cell is in a plant storage organ such as a seed.

In a preferred embodiment, the RNA molecule is present at an increased level relative to an isogenic cell lacking the first exogenous polynucleotide. Preferably the level is increased at least 10%, at least 20%, and more preferably at least 30%.

In another embodiment, at least one RNA molecule encoded by at least of the additional exogenous polynucleotides is present at an increased level relative to an isogenic cell lacking the first exogenous polynucleotide.

Also provided is a transgenic plant comprising a cell of the above aspect. In an embodiment, each cell of the plant is as defined in the above aspect. In a particularly preferred embodiment, the plant is phenotypically normal when compared to a plant lacking said cell.

In yet another aspect provided is a plant storage organ comprising a cell of the above aspect and/or obtained from the transgenic plant defined above.

In an embodiment, the plant storage organ is a seed.

In a further aspect, provided is a method of obtaining a phenotypically normal plant having increased levels of an RNA molecule in its storage organ, comprising
a) introducing into a plant cell
  i) a first exogenous polynucleotide encoding a silencing suppressor operably linked to a plant storage organ specific promoter, and
  ii) a second exogenous polynucleotide encoding an RNA molecule operably linked to a promoter which directs gene transcription in the plant storage organ,
b) regenerating a transformed plant from the cell of step a),
c) growing the transformed plant until it produces storage organs,
d) determining the level of the RNA molecule in the storage organ, and
e) selecting a plant which is phenotypically normal, and wherein the RNA molecule is present at an increased level in the storage organ relative to a corresponding storage organ lacking the first exogenous polynucleotide.

In yet a further aspect, provided is a method of obtaining a phenotypically normal plant having stabilized expression of an RNA molecule in its storage organ, comprising
a) introducing into a plant cell
  i) a first exogenous polynucleotide encoding a silencing suppressor operably linked to a plant storage organ specific promoter, and
  ii) a second exogenous polynucleotide encoding an RNA molecule operably linked to a promoter which directs gene transcription in the plant storage organ,
b) regenerating a transformed plant from the cell of step a),
c) producing a third generation progeny plant which comprises the storage organ from the plant of step b), and
d) selecting a third generation progeny plant wherein the RNA molecule is present in the storage organ at a level which is at least 90% of the level in a storage organ of a previous generation of the plant.

Preferably, the exogenous polynucleotides of the above aspects are stably integrated into the genome of the cell.

In yet another aspect, the present invention provides a method of stabilising expression of an RNA molecule in a storage organ of a transgenic plant, comprising
  i) expressing a first exogenous polynucleotide encoding a silencing suppressor operably linked to a plant storage organ specific promoter, and
  ii) expressing a second exogenous polynucleotide encoding an RNA molecule operably linked to a promoter which directs gene transcription in the plant storage organ,
wherein the transgenic plant is at least a third generation progeny plant obtained from a parental plant transformed with the exogenous polynucleotides, and wherein the RNA molecule is present in the storage organ of the plant at a level which is at least 90% of the level in a storage organ of a previous generation of the plant.

In an embodiment, the plant is grown in the field.

As will be apparent, preferred features and characteristics of one aspect of the invention are applicable to many other aspects of the invention.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The invention is hereinafter described by way of the following non-limiting Examples and with reference to the accompanying figures.

BRIEF DESCRIPTION OF THE ACCOMPANYING DRAWINGS

FIG. 1. Aerobic DHA biosynthesis pathways.

Figure 2:
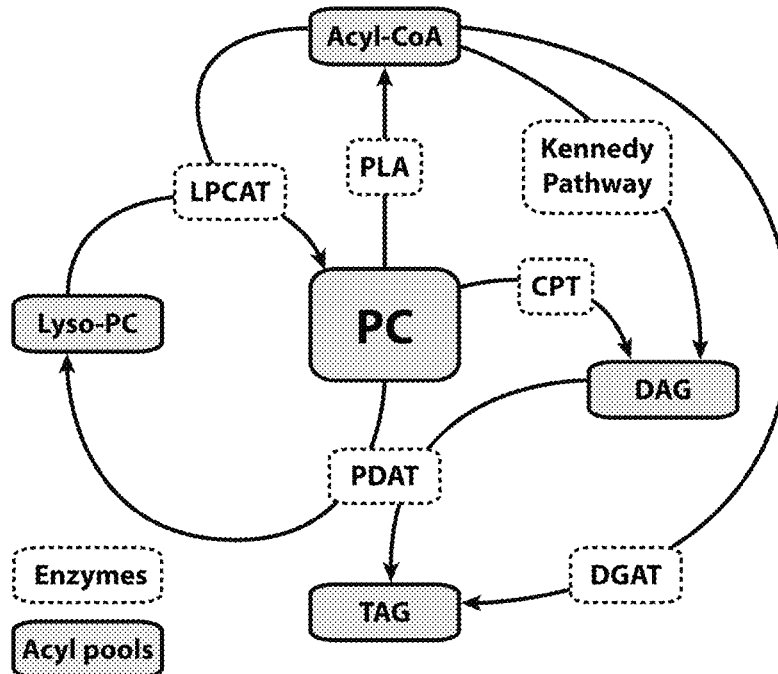

FIG. 2. The various acyl exchange enzymes which transfer fatty acids between PC, CoA pools, and TAG pools. Adapted from Singh et al. (2005).

Figure 3:
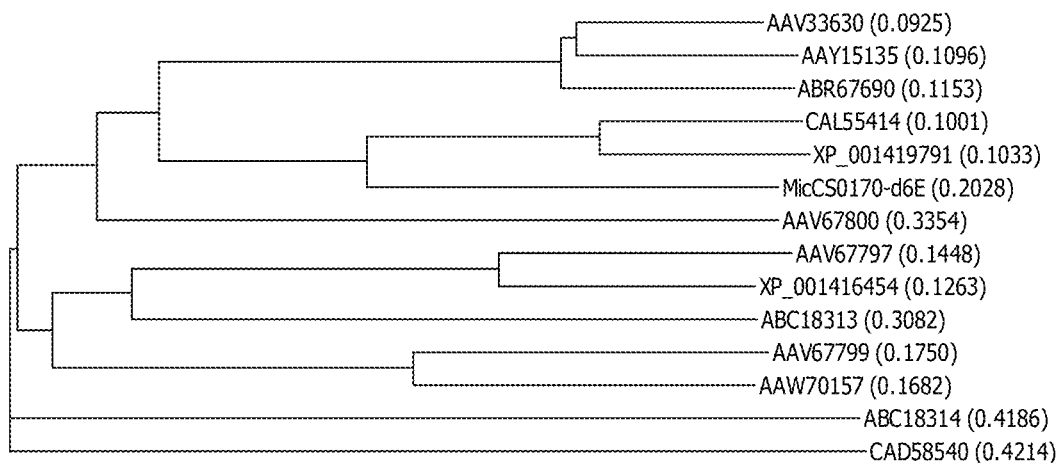

FIG. 3. Multiple alignment between the *Micromonas* CS-0170 Δ6-elongase and related genes. AAV33630, C20-polyunsaturated fatty acid elongating enzyme [*Pavlova* sp. CCMP459]; AAY15135, elongase 1 [*Pavlova salina*]; ABR67690, C20 elongase [*Pavlova viridis*]; AAV67797, polyunsaturated fatty acid elongase 1 [*Ostreococcus tauri*];

CAL55414, polyunsaturated fatty acid elongase 2 (ISS) [*Ostreococcus tauri*]; XP_001419791, predicted protein [*Ostreococcus lucimarinus* CCE9901]; MicCS0170-d6E, *Micromonas* CS-0170 Δ6-elongase (this work); AAV67800, polyunsaturated fatty acid elongase 2 [*Thalassiosira pseudonana*]; XP_001416454, predicted protein [*Ostreococcus lucimarinus* CCE9901]; ABC18313, polyunsaturated fatty acid elongase 1 [*Thraustochytrium* sp. FJN-10]; AAV67799, polyunsaturated fatty acid elongase 1 [*Thalassiosira pseudonana*]; AAW70157, delta-6-elongase [*Phaeodactylum tricornutum*]; ABC18314, polyunsaturated fatty acid elongase 2 [*Thraustochytrium* sp. FJN-10]; CAD58540, unnamed protein product [*Isochrysis galbana*].

Figure 4:
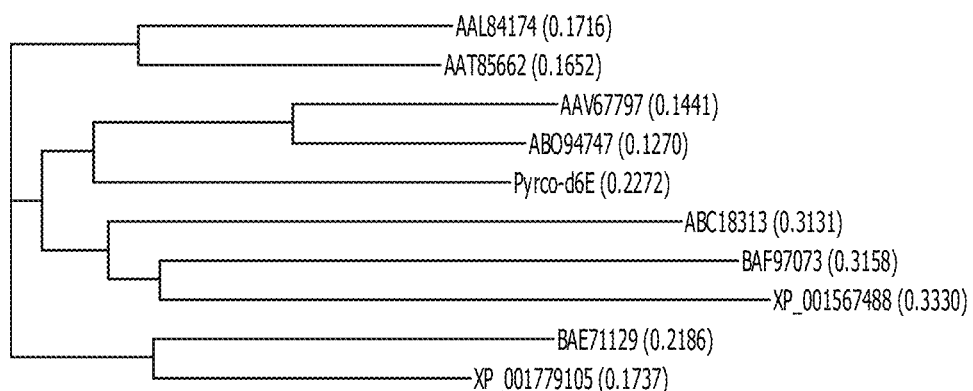

FIG. 4. Multiple alignment between the *Pyramimonas* CS-0140 Δ6-elongase and related genes. AAL84174, polyunsaturated fatty acid specific elongation enzyme 1 [*Physcomitrella patens*]; AAT85662, polyunsaturated fatty acid elongase [*Marchantia polymorpha*]; AAV67797, polyunsaturated fatty acid elongase 1 [*Ostreococcus tauri*]; ABO94747, predicted protein [*Ostreococcus lucimarinus* CCE9901]; Pyrco-d6E, *Pyramimonas* CS-0140 Δ6-elongase (this work); ABC18313, polyunsaturated fatty acid elongase 1 [*Thraustochytrium* sp. FJN-10]; BAF97073, polyunsaturated fatty acid elongation enzyme [*Mortierella alpina*]; XP_001567488, long chain polyunsaturated fatty acid elongation enzyme-like protein [*Leishmania braziliensis* MHOM/BR/75/M2904]; BAE71129, delta5-elongase [*Marchantia polymorpha*]; XP_001779105; predicted protein [*Physcomitrella patens*].

Figure 5:
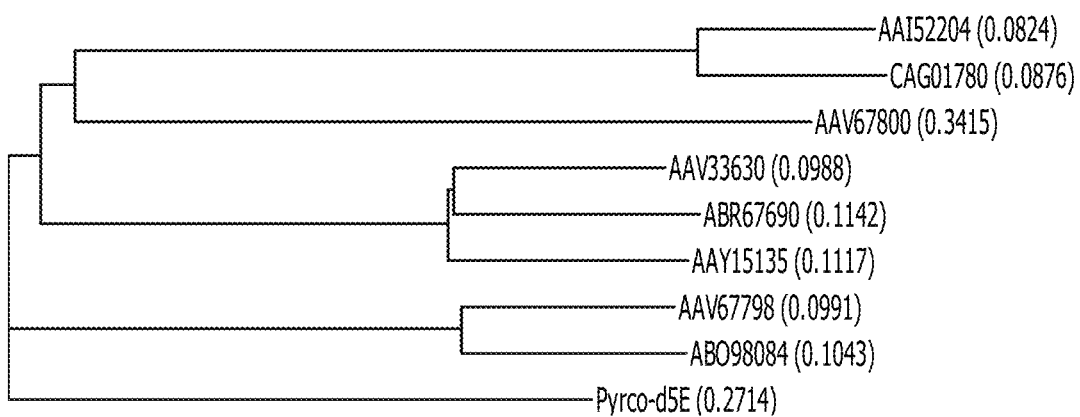

FIG. 5. Multiple alignment between the *Pyramimonas* CS-0140 Δ5-elongase and related genes. AAI52204, Elovl4 protein [*Danio rerio*]; CAG01780, unnamed protein product [*Tetraodon nigroviridis*]; AAV67800, polyunsaturated fatty acid elongase 2 [*Thalassiosira pseudonana*]; AAV33630, C20-polyunsaturated fatty acid elongating enzyme [*Pavlova* sp. CCMP459]; ABR67690, C20 elongase [*Pavlova viridis*]; AAY15135, elongase 1 [*Pavlova salina*]; AAV67798, polyunsaturated fatty acid elongase 2 [*Ostreococcus tauri*]; ABO98084, predicted protein [*Ostreococcus lucimarinus* CCE9901]; Pyrco-d5E, *Pyramimonas* CS-0140 Δ5-elongase (this work).

Figure 6:

FIG. 6. Multiple alignment between the *Micromonas* CCMP1545 Δ6-desaturase and related genes. AAM09687, Δ5-fatty acid desaturase [*Thraustochytrium* sp. ATCC21685]; AAV33631, Δ4-desaturase [*Isochrysis galbana*]; AAW70159, Δ6-desaturase [*Ostreococcus tauri*]; AB099366, predicted protein [*Ostreococcus lucimarinus* CCE9901]; Mic-d6D, *Micromonas* CCMP1545 Δ6-desaturase (this work); ABF58685, Δ5-desaturase [*Perkinsus marinus*]; ABL96295, Δ5-desaturase [*Pavlova salina*].

Figure 7:
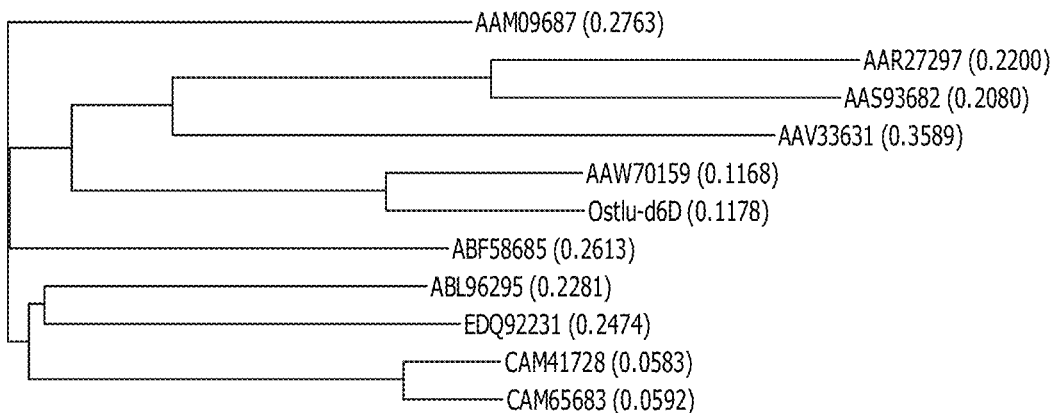

FIG. 7. Multiple alignment between the *Ostreococcus lucimarinus* Δ6-desaturase and related genes. AAM09687, Δ5-fatty acid desaturase [*Thraustochytrium* sp. ATCC21685]; AAR27297, Δ6-desaturase [*Amylomyces rouxii*]; AAS93682, Δ6-fatty acid desaturase [*Rhizopus oryzae*]; AAV33631, Δ4-desaturase [*Isochrysis galbana*]; AAW70159, Δ6-desaturase [*Ostreococcus tauri*]; Ostlu-d6D, *Ostreococcus lucimarinus* Δ6-desaturase (this work); ABF58685, Δ5-desaturase [*Perkinsus marinus*]; ABL96295, Δ5-desaturase [*Pavlova salina*]; EDQ92231, predicted protein [*Monosiga brevicollis* MX1]; CAM41728, fatty acid desaturase, putative [*Leishmania braziliensis*]; CAM65683, fatty acid desaturase, putative [*Leishmania infantum*].

Figure 8:
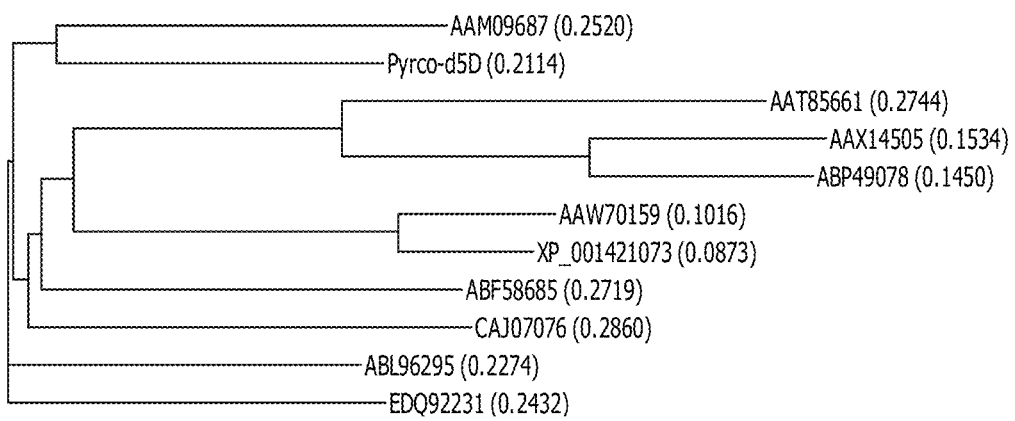

FIG. 8 Multiple alignment between the *Pyramimonas* CS-0140 Δ5-desaturase and related genes. AAM09687, Δ5-fatty acid desaturase [*Thraustochytrium* sp. ATCC21685]; Pyrco-d5D, *Pyramimonas* CS-0140 Δ5-desaturase (this work); AAT85661, Δ6-fatty acid desaturase [*Marchantia polymorpha*]; AAX14505, Δ6-fatty acid desaturase [*Thalassiosira pseudonana*]; ABP49078, Δ6-fatty acid desaturase [*Phaeodactylum tricornutum*]; AAW70159, Δ6-desaturase [*Ostreococcus tauri*]; XP_001421073, predicted protein [*Ostreococcus lucimarinus* CCE9901]; ABF58685, Δ5-desaturase [*Perkinsus marinus*]; CAJ07076, fatty acid desaturase, putative [*Leishmania major*]; ABL96295, Δ5-desaturase [*Pavlova salina*]; EDQ92231, predicted protein [*Monosiga brevicollis* MX1].

Figure 9:
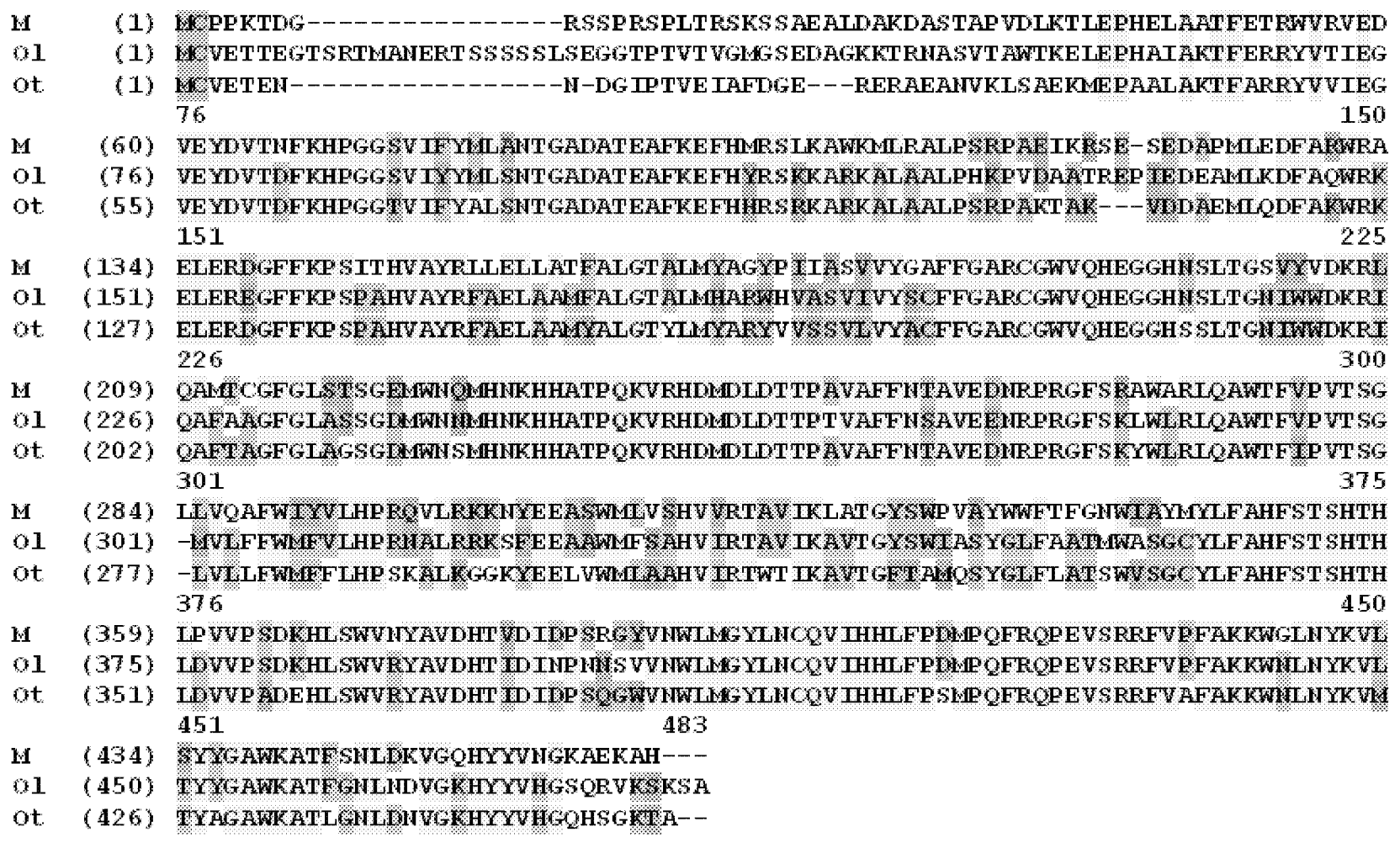

FIG. 9. Multiple alignment of the *Ostreococcus tauri* (Ot) (SEQ ID NO:30), *Ostreococcus lucimarinus* (01) (SEQ ID NO:10) and *Micromonas* (M) CCMP1545 Δ6-desaturase protein sequences (SEQ ID NO:8).

Figure 10:
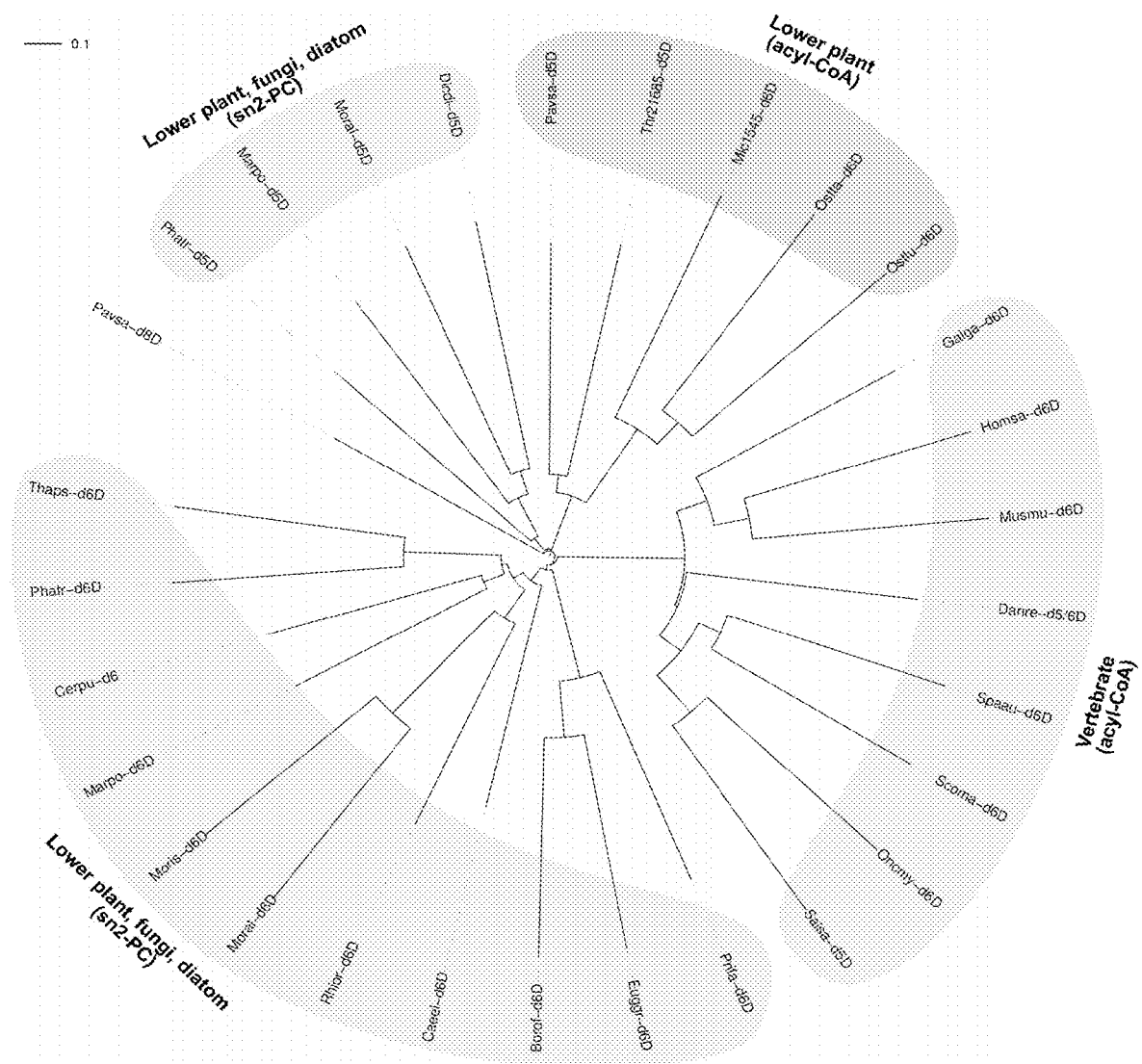

FIG. 10. Phylogenetic tree showing the relationship between various desaturases. Pavsa-d5D=*Pavlova salina* Δ5-desaturase (ABL96295); Thr21685-d5D=*Thraustochytrium* sp. ATCC21685 Δ5-desaturase (AAM09687); Mic1545-d6D=*Micromonas* CCMP1545 Δ6-desaturase (this work); Ostta-d6D=*Ostreococcus tauri* Δ6-desaturase (AAW70159); Ostlu-d6D=*Ostreococcus lucimarinus* Δ6-desaturase (this work); Galga-d6D=*Gallus gallus* Δ6-desaturase (XP_421053); Homsa-d6D=*Homo sapiens* Δ6-desaturase (AAG23121); Musmu-d6D=*Mus musculus* Δ6-desaturase (NP_062673); Danre-d5/6D=*Danio rerio* Δ5-/Δ6-desaturase (AAG25710); Spaau-d6D=*Sparus aurata* putative Δ6-desaturase (AAL17639); Scoma-d6D=*Scophthalmus maximus* Δ6-desaturase (AAS49163); Oncmy-d6D=*Oncorhynchus mykiss* Δ6-desaturase (AAK26745); Salsa-d5D=*Salmo salar* Δ5-desaturase (AAL82631); Prifa-d6D=*Primula farinosa* Δ6-desaturase (AAP23034); Euggr-d6D=*Euglena gracilis* Δ6-desaturase; Borof-d6D=*Borago officianalis* Δ6-desaturase (AAC49700); Caeel-d6D=*Caenorhabditis elegans* Δ6-desaturase (AAC15586); Rhior-d6D=*Rhizopus oryzae* Δ6-desaturase (AAS93682); Moral-d6D=*Mortierella alpina* Δ6-desaturase (AAF08685); Moris-d6D=*Mortierella isabellina* Δ6-desaturase (AAL73948); Marpo-d6D=*Marchantia polymorpha* Δ6-desaturase (AAT85661); Cerpu-d6D=*Ceratodon purpureus* Δ6-desaturase (CAB94993); Phatr-d6D=*Phaeodactylum tricornutum* Δ6-desaturase (AAL92563); Thaps-d6D=*Thalassiosira pseudonana* Δ6-desaturase (AAX14505); Pavsa-d8D=*Pavlova salina* Δ8-desaturase (ABL96296); Phatr-d5D=*Phaeodactylum tricornutum* Δ5-desaturase (AAL92562); Marpo-d5D=*Marchantia polymorpha* Δ5-desaturase (AAT85663); Moral-d5D=*Mortierella alpina* Δ5-desaturase (AAR28035); Dicdi-d5D=*Dictyostelium discoideum* Δ5-desaturase (BAA37090).

Figure 11:
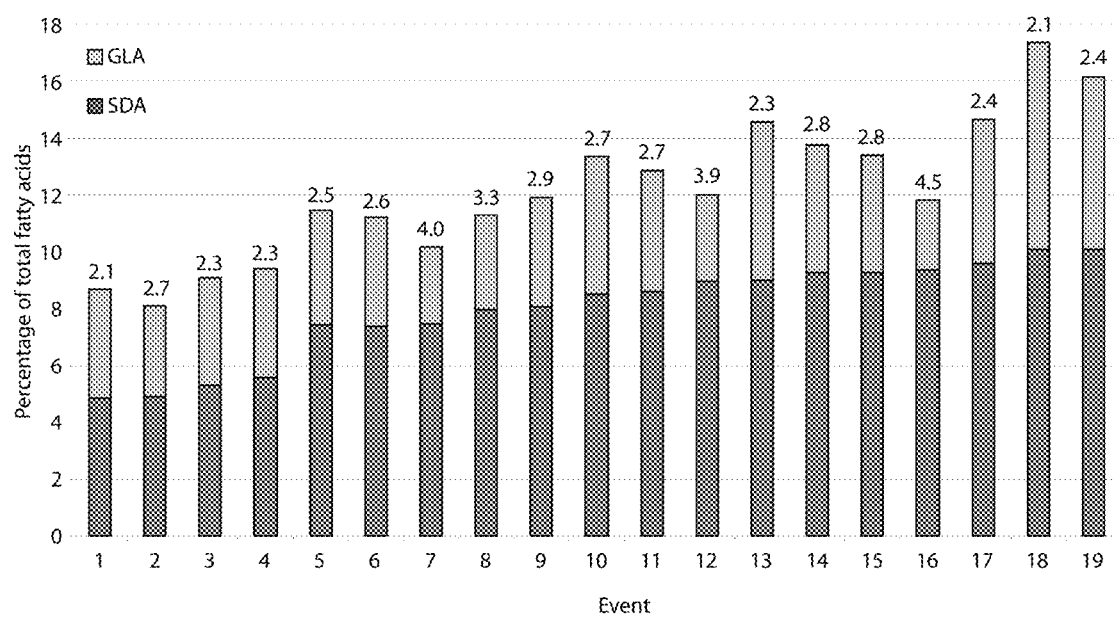

FIG. 11. GC results from T2 *Arabidopsis* seed transformed with the linP-mic1545-d6D-linT construct. SDA and GLA levels are shown for individual events 1-19, with the ratio of ω3 to ω6 conversion efficiencies displayed above each column. The *M. pusilla* Δ6-desaturase shows clear preference for the ω3 substrate.

Figure 12:
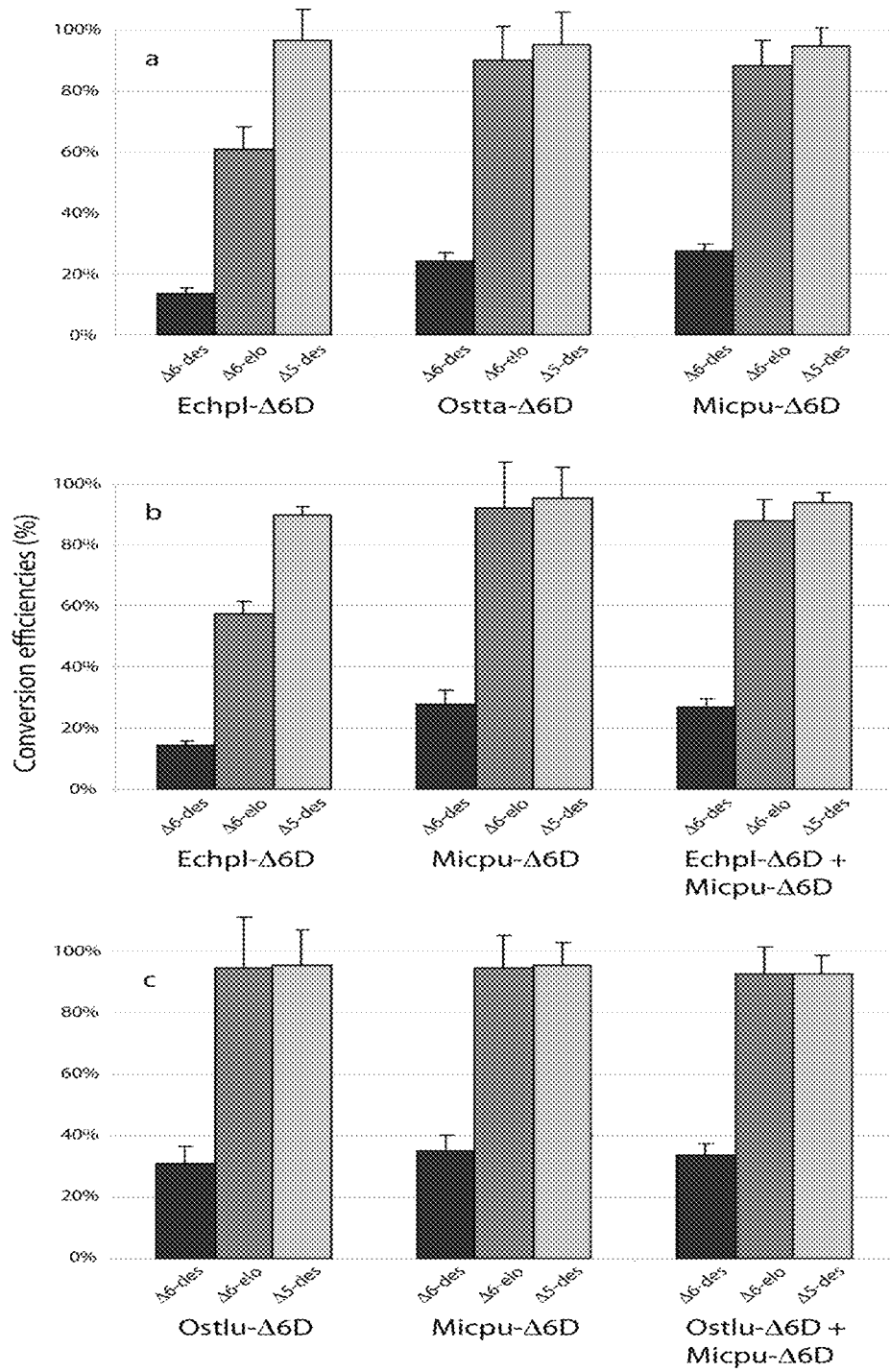

FIG. 12. Conversion efficiencies of enzymes constituting the EPA pathways infiltrated into *N. benthamiana*. The EPA pathways contain a Δ6-desaturase (*Echium plantagineum* Δ6-desaturase, *Ostreococcus tauri* Δ6-desaturase or *Micromonas pusilla* Δ6-desaturase), the *Pyramimonas cordata* Δ6-elongase and the *Pavlova salina* Δ5-desaturase. Panel a. shows the ω3 pool conversion efficiencies for each pathway; b. contains direct comparisons between the *E. plantagineum* pathway, the *M. pusilla* pathway and a pathway containing both these desaturases; c. contains direct comparisons between the *O. tauri* pathway, the *M. pusilla* pathway and a pathway containing both acyl-CoA desaturases.

Figure 13:
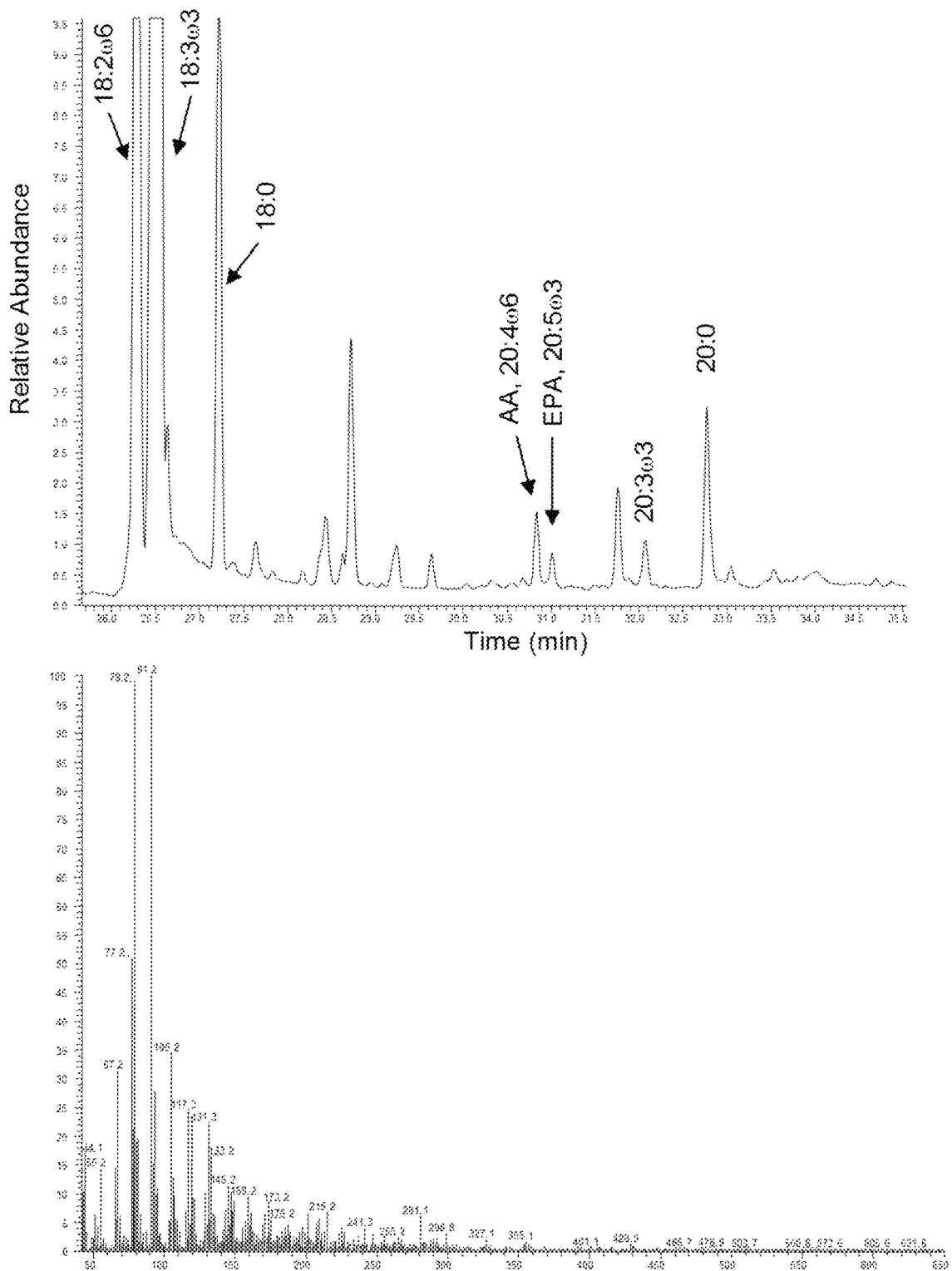

FIG. 13. GC and GC-MS confirmation of the production of EPA in *Nicotiana benthamiana* by a transiently-expressed *Micromonas* RCC299 ω3 desaturase.

Figure 14:
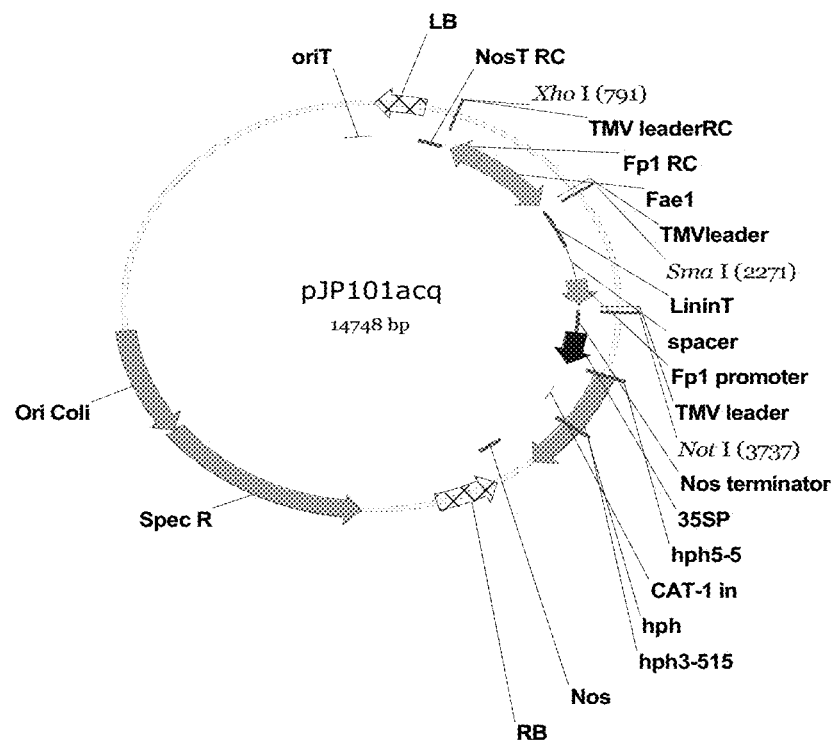

FIG. 14. Map of the binary vector pJP101acq showing the key features of the binary vector including the promoter orientations, TMV leader sequence locations, spacer region locations and unique cloning sites for gene insertions. NosT=NOS terminator, FP1=truncated napin terminator, LininT=Linin terminator.

Figure 15:
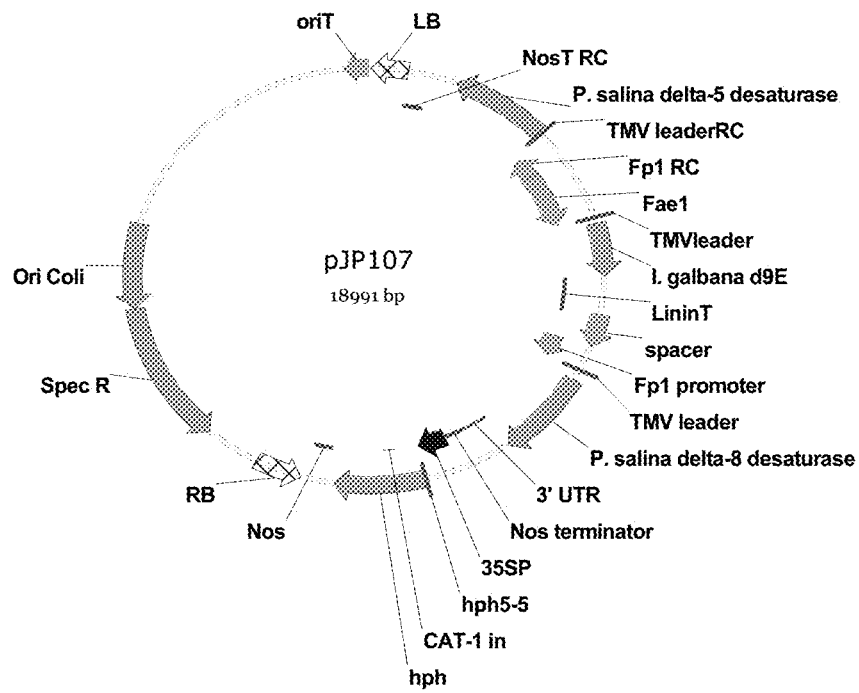

FIG. 15. Map of the binary vector pJP107.

Figure 16:
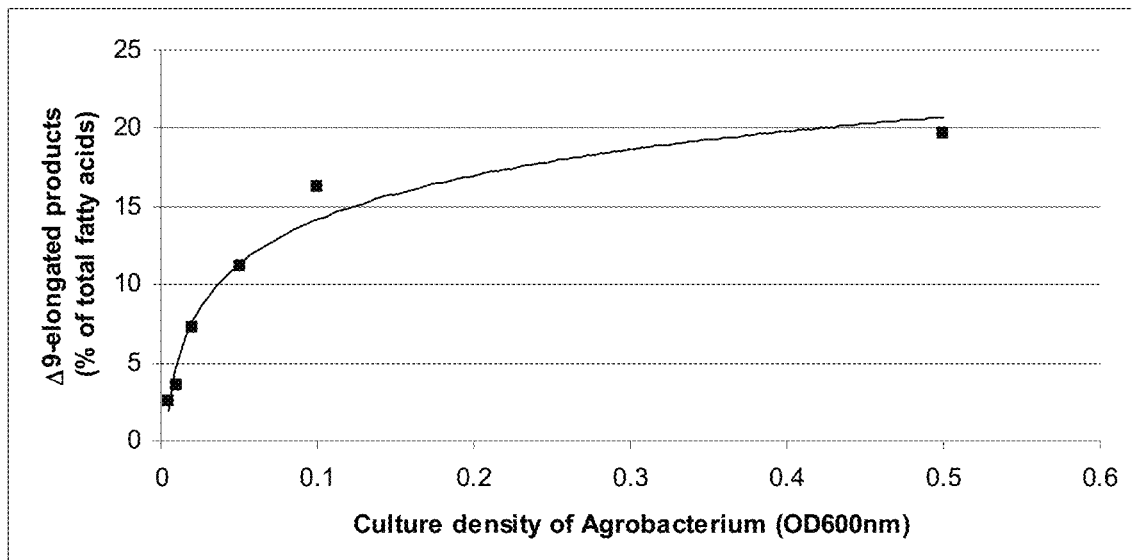

FIG. 16. Determination of the *Agrobacterium* concentration required to achieve near-maximal gene activity in the leaf-based assay. *Isochrysis galbana* Δ9-elongase (IgΔ9elo) activity in *N. benthamiana* after infiltration with varying culture densities of *Agrobacterium* AGL1 containing the binary expression construct IgΔ9elo. Co-infiltrated P19 was set at a concentration of $OD_{600\ nm}$ 0.4. The y-axis displays the sum of both IgΔ9elo activities to produce EDA and ETrA.

Figure 17:
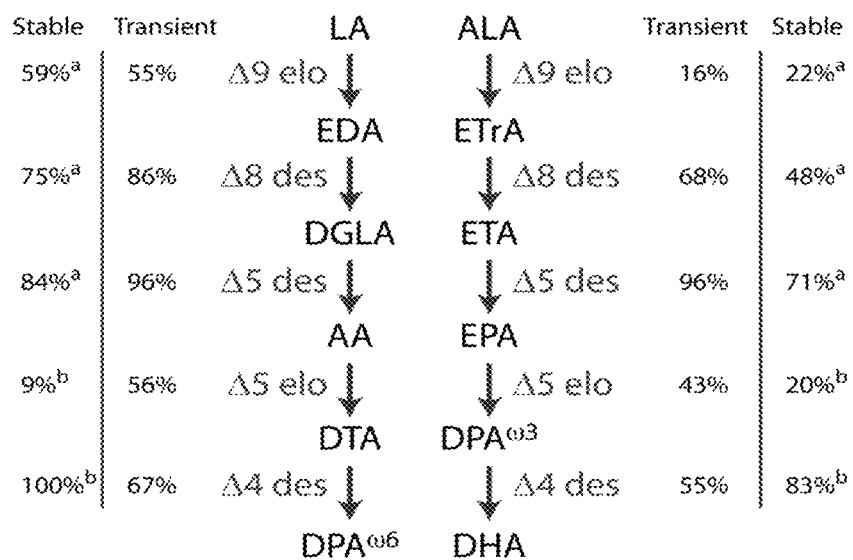

FIG. 17. Comparison of transgenic expression of LC-PUFA pathways using either transient or stable expression in leaves. Conversion efficiencies are based on total fatty acid profiles. $^a$results extracted from (Qi et al., 2004); $^b$results extracted from (Robert et al., 2005).

Figure 18:
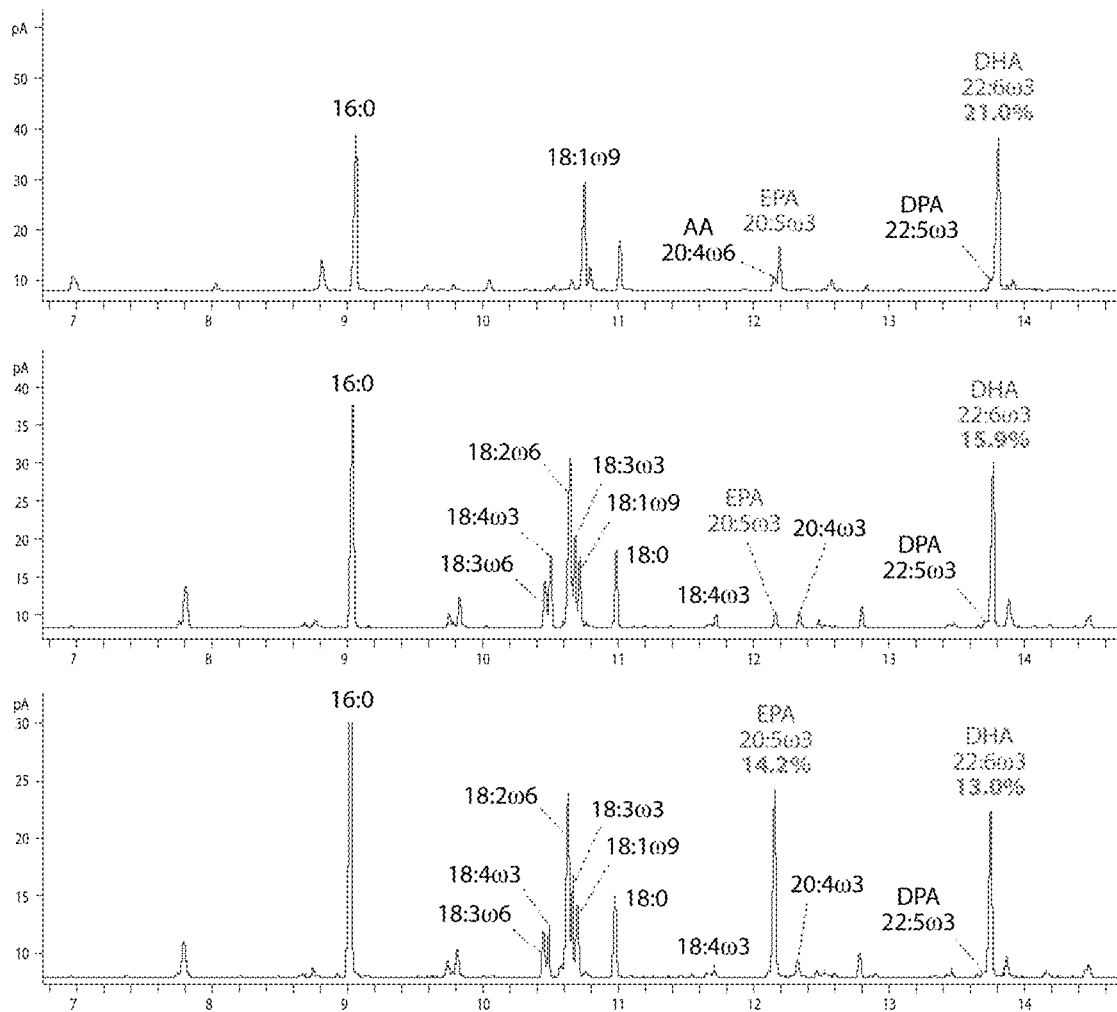

FIG. 18. Metabolic tailoring in *Nicotiana benthamiana*. Panel a. is a gas chromatography (GC) trace of fatty acid methyl esters (FAME) produced from tuna oil which contains only a small amount of EPA but a large amount of DHA. Panels b. and c. are GC traces of FAME derived from the TAG fraction of *N. benthamiana* leaf tissue transiently transformed with single-gene CaMV 35S binary constructs containing the *Micromonas pusilla* Δ6-desaturase, *Pyramimonas cordata* Δ6-elongase, *Pavlova salina* Δ5-desaturase, *P. cordata* Δ5-elongase (b.) or *P. salina* Δ5-elongase (c.) and the *P. salina* Δ4-desaturase. The accumulation of EPA in the sample using the *P. salina* Δ5-elongase demonstrates the manner in which metabolic pathways can be tailored by careful selection of a single gene in the pathway.

Figure 19:
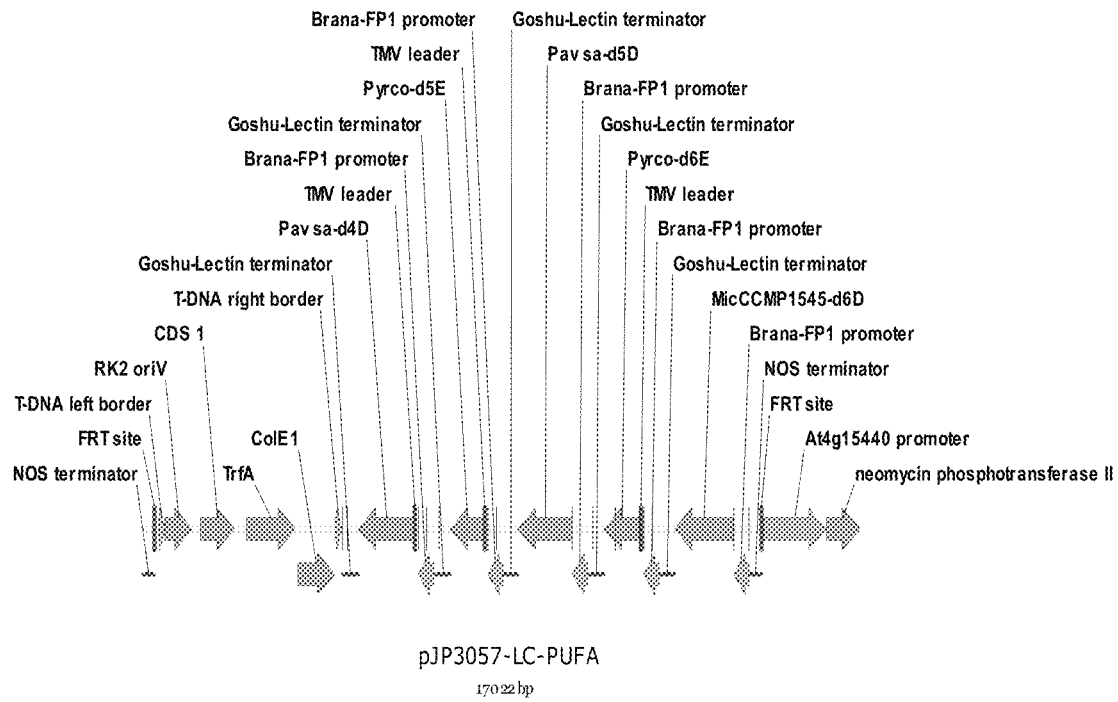

FIG. 19. Map of the region of vector pJP3075 comprising transgenes.

Figure 20:
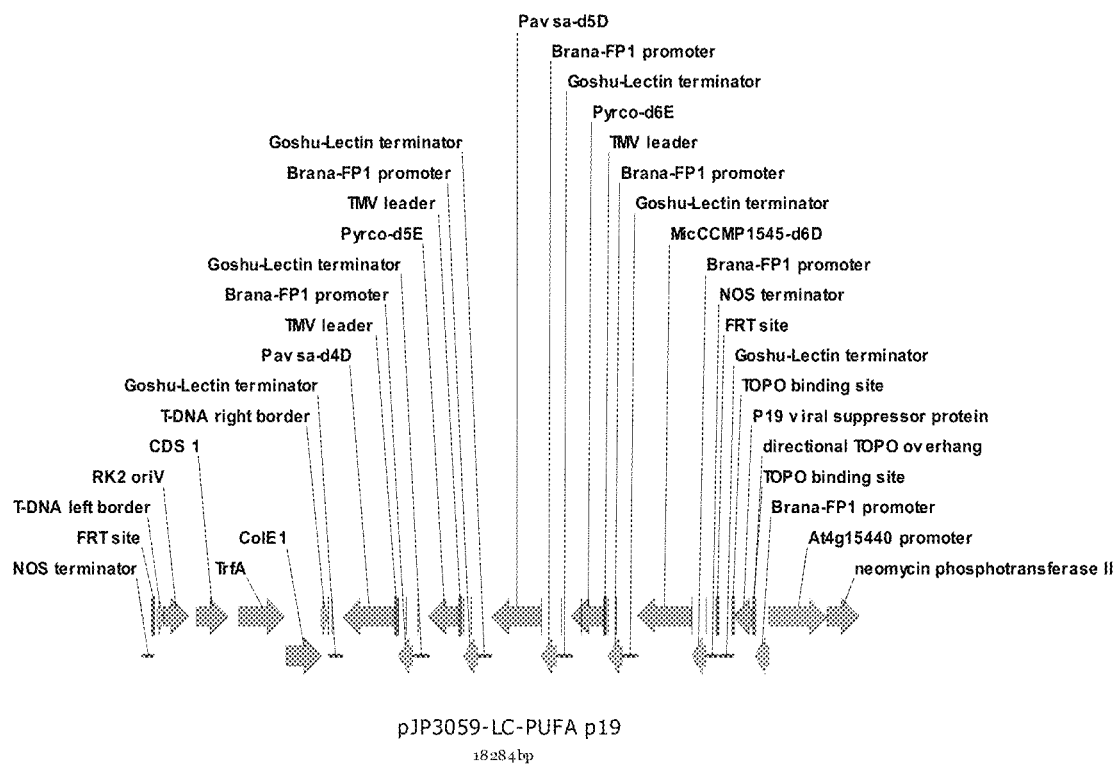

FIG. 20. Map of the region of vector pJP3059 comprising transgenes.

Figure 21:
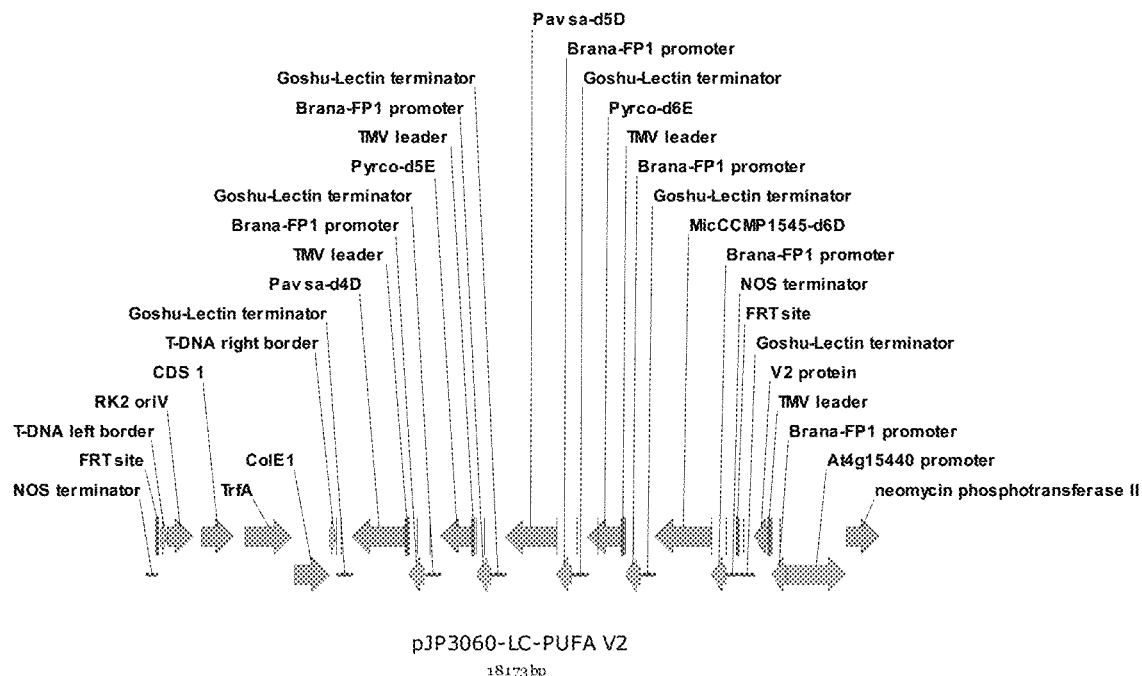

FIG. 21. Map of the region of vector pJP3060 comprising transgenes.

Figure 22:
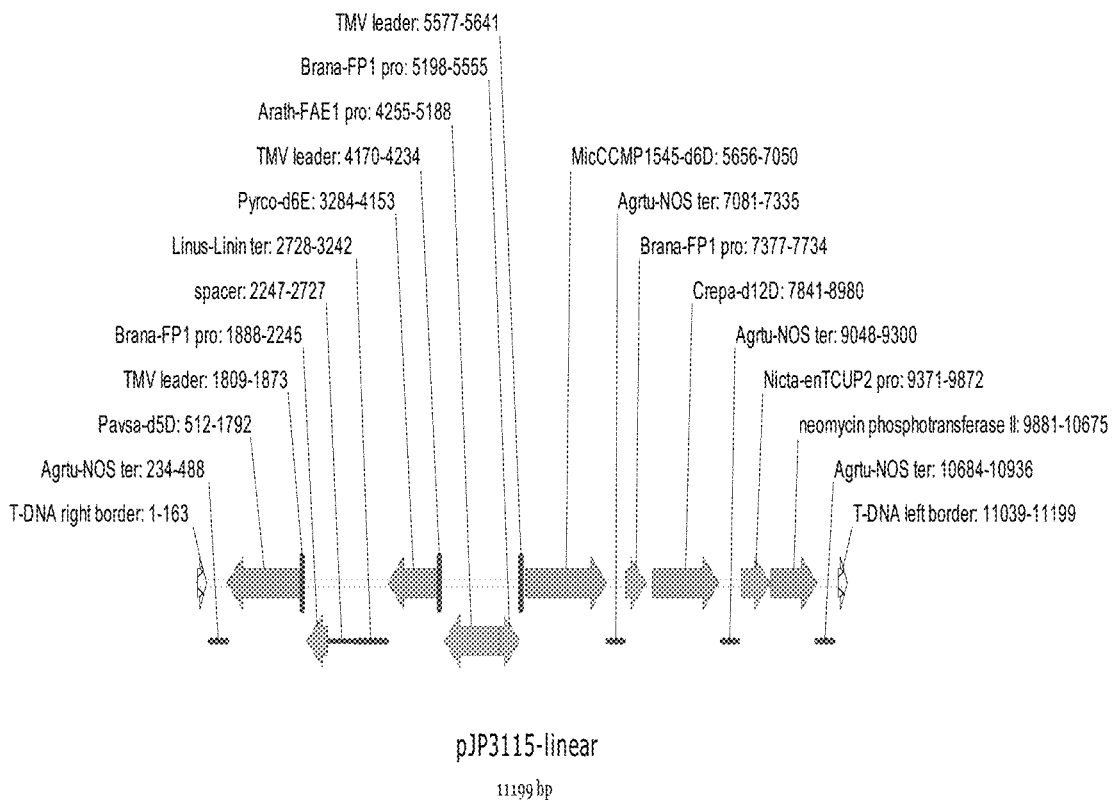

FIG. 22. Map of the region of vector pJP3115 comprising transgenes.

Figure 23:
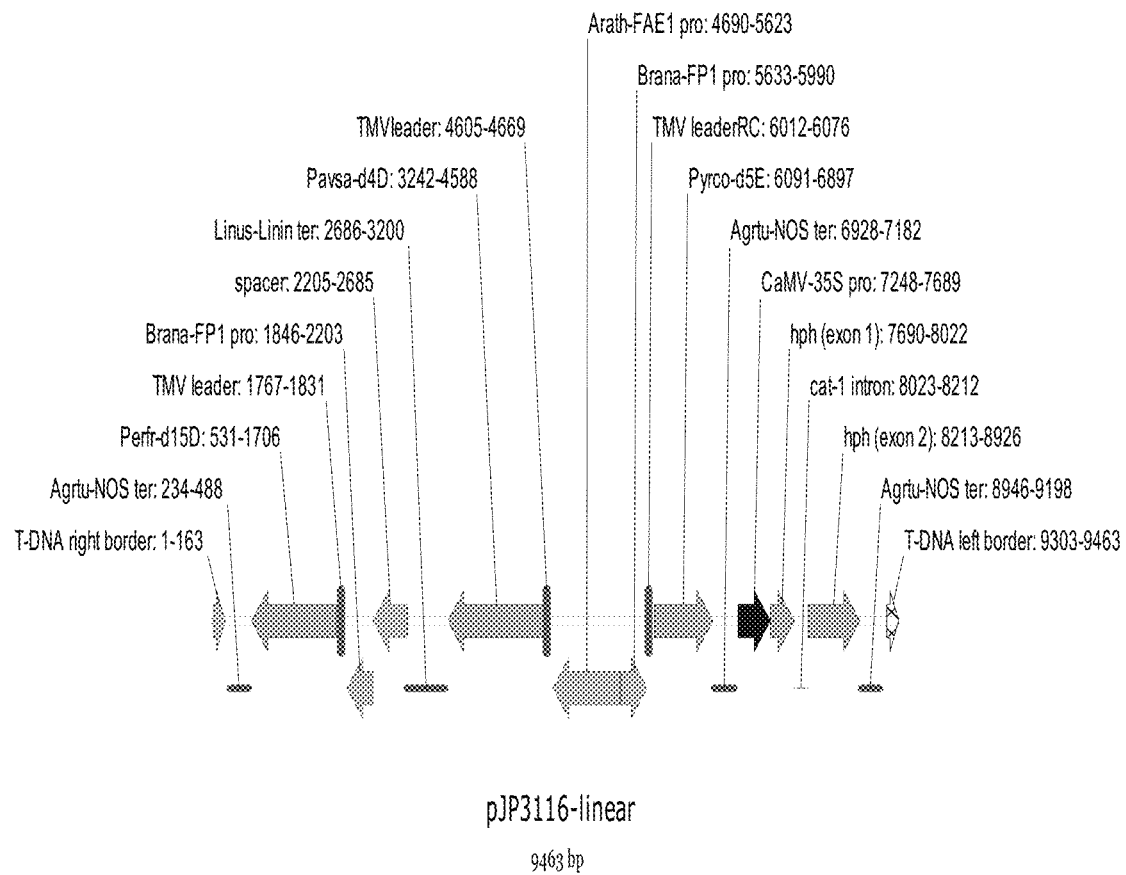

FIG. 23. Map of the region of vector pJP3116 comprising transgenes.

KEY TO THE SEQUENCE LISTING

SEQ ID NO:1—Open reading frame encoding *Micromonas* CS-0170 Δ6-elongase.

SEQ ID NO:2—*Micromonas* CS-0170 Δ6-elongase.

SEQ ID NO:3—Open reading frame encoding *Pyramimonas* CS-0140 Δ6-elongase/Δ9-elongase.

SEQ ID NO:4—*Pyramimonas* CS-0140 Δ6-elongase/Δ9-elongase.

SEQ ID NO:5—Open reading frame encoding *Pyramimonas* CS-0140 Δ5-elongase.

SEQ ID NO:6—*Pyramimonas* CS-0140 Δ5-elongase.

SEQ ID NO:7—Open reading frame encoding *Micromonas* CCMP1545 Δ6-desaturase/Δ8-desaturase.

SEQ ID NO:8—*Micromonas* CCMP1545 Δ6-desaturase/Δ8-desaturase.

SEQ ID NO:9—Open reading frame encoding *Ostreococcus lucimarinus* Δ6-desaturase.

SEQ ID NO:10—*Ostreococcus lucimarinus* Δ6-desaturase.

SEQ ID NO:11—Codon-optimized open reading frame for expression of *Ostreococcus lucimarinus* Δ6-desaturase in plants.

SEQ ID NO:12—Open reading frame encoding *Pyramimonas* CS-0140 Δ5-desaturase.

SEQ ID NO:13—*Pyramimonas* CS-0140 Δ5-desaturase.

SEQ ID NO:14—Partial open reading frame encoding *Micromonas* CS-0170 ω3-desaturase.

SEQ ID NO:15—Partial *Micromonas* CS-0170 ω3-desaturase.

SEQ ID NO:16—Open reading frame encoding *Micromonas* RCC299 ω3-desaturase

SEQ ID NO: 17—*Micromonas* RCC299 ω3-desaturase.

SEQ ID NO:18—Codon-optimized open reading frame for expression of *Micromonas* RCC299 ω3-desaturase in plants.

SEQ ID NO:19—Open reading frame encoding *Micromonas* CCMP1545 ω3-desaturase

SEQ ID NO:20—*Micromonas* CCMP1545 ω3-desaturase.

SEQ ID NO:21—Open reading frame encoding *Isochrysis galbana* Δ9-elongase.

SEQ ID NO:22—*Isochrysis galbana* Δ9-elongase.

SEQ ID NO:23—Open reading frame encoding *Pavlova salina* Δ8-desaturase.

SEQ ID NO:24—*Pavlova salina* Δ8-desaturase.

SEQ ID NO:25—Open reading frame encoding *Pavlova salina* Δ5-desaturase.

SEQ ID NO:26—*Pavlova salina* Δ5-desaturase.

SEQ ID NO:27—Open reading frame encoding *Emiliania huxleyi* CCMP1516 Δ9 elongase.

SEQ ID NO:28—*Emiliania huxleyi* CCMP1516 Δ9 elongase.

SEQ ID NO:29—Codon-optimized open reading frame for expression of *Emiliania huxleyi* Δ9 elongase in plants.

SEQ ID NO:30—*Ostreococcus tauri* Δ6-desaturase.

SEQ ID NO:31—Elongase consensus domain 1.

SEQ ID NO:32—Elongase consensus domain 2.

SEQ ID NO:33—Elongase consensus domain 3.

SEQ ID NO:34—Elongase consensus domain 4.

SEQ ID NO:35—Elongase consensus domain 5.

SEQ ID NO:36—Elongase consensus domain 6.

SEQ ID NO:37—Desaturase consensus domain 1.

SEQ ID NO:38—Desaturase consensus domain 2.

SEQ ID NO:39—Desaturase consensus domain 3.

SEQ ID NO:40—Desaturase consensus domain 4.

SEQ ID NOs:41-71 and 78-92—Oligonucleotide primers.

SEQ ID NO:72—Open reading frame encoding *Pavlova salina* Δ4-desaturase.

SEQ ID NO:73—*Pavlova salina* Δ4-desaturase.

SEQ ID NO:74—Open reading frame encoding *Arabidopsis thaliana* diacylglycerol acyltransferase 1.

SEQ ID NO:75—*Arabidopsis thaliana* diacylglycerol acyltransferase 1.

SEQ ID NO:76—Elongase consensus domain 7.

SEQ ID NO:77—Elongase consensus domain 8.

SEQ ID NO:93—Open reading frame encoding *Pavlova pinguis* Δ9-elongase.

SEQ ID NO:94—*Pavlova pinguis* Δ9-elongase.

SEQ ID NO:95—Open reading frame encoding *Pavlova salina* Δ9-elongase.

SEQ ID NO:96—*Pavlova salina* Δ9-elongase.
SEQ ID NO:97—P19 viral suppressor.
SEQ ID NO:98—V2 viral suppressor.
SEQ ID NO:99—P38 viral suppressor.
SEQ ID NO:100—Pe-P0 viral suppressor.
SEQ ID NO:101—RPV-P0 viral suppressor.
SEQ ID NO:102—Open reading frame encoding P19 viral suppressor.
SEQ ID NO:103—Open reading frame encoding V2 viral suppressor.
SEQ ID NO:104—Open reading frame encoding P38 viral suppressor.
SEQ ID NO:105—Open reading frame encoding Pe-P0 viral suppressor.
SEQ ID NO:106—Open reading frame encoding RPV-P0 viral suppressor.
SEQ ID NO:107—Codon optimized open reading frame encoding *Micromonas* CCMP1545 diacylglycerol acyltransferase 2.
SEQ ID NO:108—*Micromonas* CCMP1545 diacylglycerol acyltransferase 2.
SEQ ID NO's 109-124—Transfer nucleic acid border sequences.
SEQ ID NO:125—Codon-optimized open reading frame for expression of *Micromonas* CCMP1545 Δ6 desaturase/Δ8desaturase in plants.
SEQ ID NO:126—Codon-optimized open reading frame for expression of *Pyramimonas* CS-0140 Δ6 elongase/Δ9 elongase in plants (truncated at 3' end and encoding functional elongase).
SEQ ID NO:127—Codon-optimized open reading frame for expression of *Pavlova salina* Δ5 desaturase in plants.
SEQ ID NO:128—Codon-optimized open reading frame for expression of *Pyramimonas* CS-0140 Δ5 elongase in plants.
SEQ ID NO:129—Codon-optimized open reading frame for expression of *Pavlova salina* Δ4 desaturase in plants.

DETAILED DESCRIPTION OF THE INVENTION

General Techniques and Definitions

Unless specifically defined otherwise, all technical and scientific terms used herein shall be taken to have the same meaning as commonly understood by one of ordinary skill in the art (e.g., in cell culture, molecular genetics, fatty acid synthesis, transgenic plants, protein chemistry, and biochemistry).

Unless otherwise indicated, the recombinant protein, cell culture, and immunological techniques utilized in the present invention are standard procedures, well known to those skilled in the art. Such techniques are described and explained throughout the literature in sources such as, J. Perbal, A Practical Guide to Molecular Cloning, John Wiley and Sons (1984), J. Sambrook et al., Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, TRL Press (1995 and 1996), F. M. Ausubel et al. (editors), Current Protocols in Molecular Biology, Greene Pub. Associates and Wiley-Interscience (1988, including all updates until present), Ed Harlow and David Lane (editors), Antibodies: A Laboratory Manual, Cold Spring Harbour Laboratory, (1988), and J. E. Coligan et al. (editors), Current Protocols in Immunology, John Wiley & Sons (including all updates until present).

Selected Definitions

As used herein, the term "fatty acid" refers to a carboxylic acid (or organic acid), often with a long aliphatic tail, either saturated or unsaturated. Typically fatty acids have a carbon-carbon bonded chain of at least 8 carbon atoms in length, more preferably at least 12 carbons in length. Most naturally occurring fatty acids have an even number of carbon atoms because their biosynthesis involves acetate which has two carbon atoms. The fatty acids may be in a free state (non-esterified) or in an esterified form such as part of a triglyceride, diacylglyceride, monoacylglyceride, acyl-CoA (thio-ester) bound or other bound form. The fatty acid may be esterified as a phospholipid such as a phosphatidylcholine, phosphatidylethanolamine, phosphatidylserine, phosphatidylglycerol, phosphatidylinositol or diphosphatidylglycerol forms.

"Saturated fatty acids" do not contain any double bonds or other functional groups along the chain. The term "saturated" refers to hydrogen, in that all carbons (apart from the carboxylic acid [—COOH] group) contain as many hydrogens as possible. In other words, the omega (ω) end contains 3 hydrogens (CH3-) and each carbon within the chain contains 2 hydrogens (—CH2-).

"Unsaturated fatty acids" are of similar form to saturated fatty acids, except that one or more alkene functional groups exist along the chain, with each alkene substituting a singly-bonded "—CH2-CH2-" part of the chain with a doubly-bonded "—CH═CH—" portion (that is, a carbon double bonded to another carbon). The two next carbon atoms in the chain that are bound to either side of the double bond can occur in a cis or trans configuration.

As used herein, the term "monounsaturated fatty acid" refers to a fatty acid which comprises at least 12 carbon atoms in its carbon chain and only one alkene group (carbon-carbon double bond) in the chain. As used herein, the terms "polyunsaturated fatty acid" or "PUFA" refer to a fatty acid which comprises at least 12 carbon atoms in its carbon chain and at least two alkene groups (carbon-carbon double bonds).

As used herein, the terms "long-chain polyunsaturated fatty acid" and "LC-PUFA" refer to a fatty acid which comprises at least 20 carbon atoms in its carbon chain and at least two carbon-carbon double bonds, and hence include VLC-PUFAs. As used herein, the terms "very long-chain polyunsaturated fatty acid" and "VLC-PUFA" refer to a fatty acid which comprises at least 22 carbon atoms in its carbon chain and at least three carbon-carbon double bonds. Ordinarily, the number of carbon atoms in the carbon chain of the fatty acids refers to an unbranched carbon chain. If the carbon chain is branched, the number of carbon atoms excludes those in sidegroups. In one embodiment, the long-chain polyunsaturated fatty acid is an ω3 fatty acid, that is, having a desaturation (carbon-carbon double bond) in the third carbon-carbon bond from the methyl end of the fatty acid. In another embodiment, the long-chain polyunsaturated fatty acid is an ω6 fatty acid, that is, having a desaturation (carbon-carbon double bond) in the sixth carbon-carbon bond from the methyl end of the fatty acid. In a further embodiment, the long-chain polyunsaturated fatty acid is selected from the group consisting of, arachidonic acid (ARA, 20:4Δ5,8,11,14; ω6), eicosatetraenoic acid (ETA, 20:4Δ8,11,14,17, ω3) eicosapentaenoic acid (EPA, 20:5Δ5,8,11,14,17; ω3), docosapentaenoic acid (DPA, 22:5Δ7,10,13,16,19, ω3), or docosahexaenoic acid (DHA, 22:6Δ4,7,10,13,16,19, ω3). The LC-PUFA may also be dihomo-γ-linoleic acid (DGLA) or eicosatrienoic acid (ETrA, 20:3Δ11,14,17, ω3). It would readily be apparent that the LC-PUFA that is produced according to the invention may be a mixture of any or all of the above and may include other LC-PUFA or derivatives of any of these LC-PUFA. In a preferred embodiment, the ω3 fatty acid is EPA, DPA, and/or DHA, preferably, EPA and/or DPA, or preferably DPA and/or DHA.

Furthermore, as used herein the terms "long-chain polyunsaturated fatty acid" and "very long-chain polyunsaturated fatty acid" refer to the fatty acid being in a free state (non-esterified) or in an esterified form such as part of a triglyceride, diacylglyceride, monoacylglyceride, acyl-CoA bound or other bound form. The fatty acid may be esterified as a phospholipid such as a phosphatidylcholine (PC), phosphatidylethanolamine, phosphatidylserine, phosphatidylglycerol, phosphatidylinositol or diphosphatidylglycerol forms. Thus, the LC-PUFA may be present as a mixture of forms in the lipid of a cell or a purified oil or lipid extracted from cells, tissues or organisms. In preferred embodiments, the invention provides oil comprising at least 75% or 85% triacylglycerols, with the remainder present as other forms of lipid such as those mentioned, with at least said triacylglycerols comprising the LC-PUFA. The oil may be further purified or treated, for example by hydrolysis with a strong base to release the free fatty acid, or by fractionation, distillation or the like.

The desaturase, elongase and acyl transferase proteins and genes encoding them that may be used in the invention are any of those known in the art or homologues or derivatives thereof. Examples of such genes and encoded protein sizes are listed in Table 1. The desaturase enzymes that have been shown to participate in LC-PUFA biosynthesis all belong to the group of so-called "front-end" desaturases.

TABLE 1

Cloned genes involved in LC-PUFA biosynthesis

| Enzyme | Type of organism | Species | Accession Nos. | Protein size (aa's) | References |
|---|---|---|---|---|---|
| Δ4-desaturase | Protist | Euglena gracilis | AY278558 | 541 | Meyer et al., 2003 |
| | Algae | Pavlova lutherii | AY332747 | 445 | Tonon et al., 2003 |
| | | Isochrysis galbana | AAV33631 | 433 | Pereira et al., 2004b |
| | | Pavlova salina | AAY15136 | 447 | Zhou et al., 2007 |
| | Thraustochytrid | Thraustochytrium aureum | AAN75707 AAN75708 AAN75709 AAN75710 | 515 | N/A |
| | | Thraustochytrium sp. ATCC21685 | AAM09688 | 519 | Qiu et al. 2001 |
| Δ5-desaturase | Mammals | Homo sapiens | AF199596 | 444 | Cho et al., 1999b; Leonard et al., 2000b |
| | Nematode | Caenorhabditis elegans | AF11440, NM_069350 | 447 | Michaelson et al., 1998b; Watts and Browse, 1999b |
| | Fungi | Mortierella alpina | AF067654 | 446 | Michaelson et al., 1998a; Knutzon et al., 1998 |
| | | Pythium irregulare | AF419297 | 456 | Hong et al., 2002a |
| | | Dictyostelium discoideum | AB022097 | 467 | Saito et al., 2000 |
| | | Saprolegnia diclina | | 470 | WO02081668 |
| | Diatom | Phaeodactylum tricornutum | AY082392 | 469 | Domergue et al., 2002 |
| | Algae | Thraustochytrium sp | AF489588 | 439 | Qiu et al., 2001 |
| | | Thraustochytrium aureum | | 439 | WO02081668 |
| | | Isochrysis galbana | | 442 | WO02081668 |
| | Moss | Marchantia polymorpha | AY583465 | 484 | Kajikawa et al., 2004 |
| Δ6-desaturase | Mammals | Homo sapiens | NM_013402 | 444 | Cho et al., 1999a; Leonard et al., 2000 |
| | | Mus musculus | NM_019699 | 444 | Cho et al., 1999a |
| | Nematode | Caenorhabditis elegans | Z70271 | 443 | Napier et al., 1998 |
| | Plants | Borago officinales | U79010 | 448 | Sayanova et al., 1997 |
| | | Echium | AY055117 AY055118 | | Garcia-Maroto et al., 2002 |
| | | Primula vialii | AY234127 | 453 | Sayanova et al., 2003 |
| | | Anemone leveillei | AF536525 | 446 | Whitney et al., 2003 |
| | Mosses | Ceratodon purpureus | AJ250735 | 520 | Sperling et al., 2000 |
| | | Marchantia polymorpha | AY583463 | 481 | Kajikawa et al., 2004 |
| | | Physcomitrella patens | CAA11033 | 525 | Girke et al., 1998 |
| | Fungi | Mortierella alpina | AF110510 AB020032 | 457 | Huang et al., 1999; Sakuradani et al., 1999 |
| | | Pythium irregulare | AF419296 | 459 | Hong et al., 2002a |
| | | Mucor circinelloides | AB052086 | 467 | NCBI* |
| | | Rhizopus sp. | AY320288 | 458 | Zhang et al., 2004 |
| | | Saprolegnia diclina | | 453 | WO02081668 |
| | Diatom | Phaeodactylum tricornutum | AY082393 | 477 | Domergue et al., 2002 |
| | Bacteria | Synechocystis | L11421 | 359 | Reddy et al., 1993 |
| | Algae | Thraustochytrium aureum | | 456 | WO02081668 |

TABLE 1-continued

Cloned genes involved in LC-PUFA biosynthesis

| Enzyme | Type of organism | Species | Accession Nos. | Protein size (aa's) | References |
|---|---|---|---|---|---|
| Bifunctional Δ5/Δ6 desaturase | Fish | Danio rerio | AF309556 | 444 | Hastings et al., 2001 |
| C20 Δ8-desaturase | Algae | Euglena gracilis | AF139720 | 419 | Wallis and Browse, 1999 |
| Δ6-elongase | Plants | Borago officinales | AAG43277 | 446 | Sperling et al., 2001 |
| | Nematode | Caenorhabditis elegans | NM_069288 | 288 | Beaudoin at al., 2000 |
| | Mosses | Physcomitrella patens | AF428243 | 290 | Zank et al., 2002 |
| | | Marchantia polymorpha | AY583464 | 290 | Kajikawa et al., 2004 |
| | Fungi | Mortierella alpina | AF206662 | 318 | Parker-Barnes et al., 2000 |
| | Algae | Pavlova lutheri** | | 501 | WO 03078639 |
| | | Thraustochytrium | AX951565 | 271 | WO 03093482 |
| | | Thraustochytrium sp** | AX214454 | 271 | WO 0159128 |
| PUFA-elongase | Mammals | Homo sapiens | AF231981 | 299 | Leonard et al., 2000b; Leonard et al., 2002 |
| | | Rattus norvegicus | AB071985 | 299 | Inagaki et al., 2002 |
| | | Rattus norvegicus** | AB071986 | 267 | Inagaki et al., 2002 |
| | | Mus musculus | AF170907 | 279 | Tvrdik et al., 2000 |
| | | Mus musculus | AF170908 | 292 | Tvrdik et al., 2000 |
| | Fish | Danio rerio | AF532782 | 291 (282) | Agaba et al., 2004 |
| | | Danio rerio** | NM_199532 | 266 | Lo et al., 2003 |
| | Worm | Caenorhabditis elegans | Z68749 | 309 | Abbott et al 1998 Beaudoin et al 2000 |
| | Algae | Thraustochytrium aureum** | AX464802 | 272 | WO 0208401-A2 |
| | | Pavlova lutheri** | | 320 | WO 03078639 |
| Δ9-elongase | Algae | Isochrysis galbana | AF390174 | 263 | Qi etal., 2002 |
| | | Euglena gracilis | | 258 | WO 08/128241 |
| Δ5-elongase | Algae | Ostreococcus tauri | AAV67798 | 300 | Meyer et al., 2004 |
| | | Pyramimonas cordata | | 268 | this work |
| | | Pavlova sp. CCMP459 | AAV33630 | 277 | Pereira et al., 2004b |
| | | Pavlova salina | AAY15135 | 302 | Robert et al., 2009 |
| | Diatom | Thalassiosira pseudonana | AAV67800 | 358 | Meyer et al., 2004 |
| | Fish | Oncorhynchus mykiss | CAM55862 | 295 | WO 06/008099 |
| | Moss | Marchantia polymorpha | BAE71129 | 348 | Kajikawa et al., 2006 |

*http://www.ncbi.nlm.nih.gov/
**Function not proven/not demonstrated

As used herein, the term "front-end desaturase" refers to a member of a class of enzymes that introduce a double bond between the carboxyl group and a pre-existing unsaturated part of the acyl chain of lipids, which are characterized structurally by the presence of an N-terminal cytochrome b5 domain, along with a typical fatty acid desaturase domain that includes three highly conserved histidine boxes (Napier et al., 1997).

Activity of any of the elongases or desaturases for use in the invention may be tested by expressing a gene encoding the enzyme in a cell such as, for example, a yeast cell or a plant cell, and determining whether the cell has an increased capacity to produce LC-PUFA compared to a comparable cell in which the enzyme is not expressed.

In one embodiment the desaturase and/or elongase for use in the invention can purified from a microalga.

Whilst certain enzymes are specifically described herein as "bifunctional", the absence of such a term does not necessarily imply that a particular enzyme does not possess an activity other than that specifically defined.

Desaturases

As used herein, the term "desaturase" refers to an enzyme which is capable of introducing a carbon-carbon double bond into the acyl group of a fatty acid substrate which is typically in an esterified form such as, for example, fatty acid CoA esters. The acyl group may be esterified to a phospholipid such as phosphatidylcholine (PC), or to acyl carrier protein (ACP), or in a preferred embodiment to CoA. Desaturases generally may be categorized into three groups accordingly. In one embodiment, the desaturase is a front-end desaturase.

As used herein, a "Δ4 desaturase" refers to a protein which performs a desaturase reaction that introduces a carbon-carbon double bond at the $4^{th}$ position from the carboxyl end of a fatty acid substrate. The "Δ4 desaturase" is at least capable of converting DPA to DHA. The desaturation step to produce DHA from DPA is catalysed by a Δ4 desaturase in organisms other than mammals, and a gene encoding this enzyme has been isolated from the freshwater protist species *Euglena gracilis* and the marine species *Thraustochytrium* sp. (Qiu et al., 2001; Meyer et al., 2003). In one embodiment, the Δ4 desaturase comprises amino acids having a sequence as provided in SEQ ID NO:73, a biologically active fragment thereof, or an amino acid sequence which is at least 80% identical to SEQ ID NO:73.

As used herein, a "Δ5 desaturase" refers to a protein which performs a desaturase reaction that introduces a carbon-carbon double bond at the $5^{th}$ position from the carboxyl end of a fatty acid substrate. Examples of Δ5 desaturases are listed in Table 1. In one embodiment, the Δ5 desaturase comprises amino acids having a sequence as provided in SEQ ID NO:26, a biologically active fragment thereof, or an amino acid sequence which is at least 80% identical to SEQ ID NO:26. In another embodiment, the Δ5 desaturase comprises amino acids having a sequence as provided in SEQ ID NO:13, a biologically active fragment thereof, or an amino acid sequence which is at least 53% identical to SEQ ID NO:13.

As used herein, a "Δ6 desaturase" refers to a protein which performs a desaturase reaction that introduces a carbon-carbon double bond at the $6^{th}$ position from the carboxyl end of a fatty acid substrate. Examples of Δ6 desaturases are listed in Table 1.

In one embodiment, the Δ6 desaturase is further characterised by having at least two, preferably all three and preferably in a plant cell, of the following: i) greater Δ6 desaturase activity on α-linolenic acid (ALA, 18:3Δ9,12,15, ω3) than linoleic acid (LA, 18:2Δ9,12, ω6) as fatty acid substrate; ii) greater Δ6 desaturase activity on ALA-CoA as fatty acid substrate than on ALA joined to the sn-2 position of PC as fatty acid substrate; and iii) Δ8 desaturase activity on ETrA.

In another embodiment the Δ6 desaturase has greater activity on an ω3 substrate than the corresponding ω6 substrate and has activity on ALA to produce octadecatetraenoic acid (stearidonic acid, SDA, 18:4Δ6,9,12, 15, ω3) with an efficiency of at least 5%, more preferably at least 7.5%, or most preferably at least 10% when expressed from an exogenous polynucleotide in a recombinant cell, or at least 35% when expressed in a yeast cell. In one embodiment, the Δ6 desaturase has greater activity, for example, at least about a 2-fold greater Δ6 desaturase activity, on ALA than LA as fatty acid substrate. In another embodiment, the Δ6 desaturase has greater activity, for example, at least about 5 fold greater Δ6 desaturase activity or at least 10-fold greater activity, on ALA-CoA as fatty acid substrate than on ALA joined to the sn-2 position of PC as fatty acid substrate.

In one embodiment, the Δ6 desaturase has no detectable Δ5 desaturase activity on ETA. In another embodiment, the Δ6 desaturase comprises amino acids having a sequence as provided in SEQ ID NO:10, a biologically active fragment thereof, or an amino acid sequence which is at least 77% identical to SEQ ID NO:10. In another embodiment, the Δ6 desaturase comprises amino acids having a sequence as provided in SEQ ID NO:8, a biologically active fragment thereof, or an amino acid sequence which is at least 67% identical to SEQ ID NO:8. The Δ6 desaturase may also have Δ8 desaturase activity.

As used herein, a "Δ8 desaturase" refers to a protein which performs a desaturase reaction that introduces a carbon-carbon double bond at the $8^{th}$ position from the carboxyl end of a fatty acid substrate. The Δ8 desaturase is at least capable of converting ETrA to ETA. Examples of Δ8 desaturases are listed in Table 1. In one embodiment, the Δ8 desaturase comprises amino acids having a sequence as provided in SEQ ID NO:24, a biologically active fragment thereof, or an amino acid sequence which is at least 80% identical to SEQ ID NO:24.

As used herein, an "ω3 desaturase" refers to a protein which performs a desaturase reaction that introduces a carbon-carbon double bond at the 3rd position from the methyl end of a fatty acid substrate. Examples of ω3 desaturases include those described by Pereira et al. (2004a), Horiguchi et al. (1998), Berberich et al. (1998) and Spychalla et al. (1997).

In one embodiment, the ω3 desaturase is at least capable of converting one of ARA to EPA, dGLA to ETA, γ-linolenic acid (GLA, 18:3Δ6,9,12, ω6) to SDA, both ARA to EPA and dGLA to ETA, both ARA to EPA and GLA to SDA, or all three of these.

In one embodiment, the ω3 desaturase has Δ17 desaturase activity on a C20 fatty acid which has at least three carbon-carbon double bonds, preferably ARA. In another embodiment, the ω3 desaturase has Δ15 desaturase activity on a C18 fatty acid which has three carbon-carbon double bonds, preferably GLA.

As used herein, a "Δ15 desaturase" refers to a protein which performs a desaturase reaction that introduces a carbon-carbon double bond at the $15^{th}$ position from the carboxyl end of a fatty acid substrate.

As used herein, a "Δ17 desaturase" refers to a protein which performs a desaturase reaction that introduces a carbon-carbon double bond at the $17^{th}$ position from the carboxyl end of a fatty acid substrate.

In another embodiment, the ω3 desaturase has greater activity on an acyl-CoA substrate, for example, ARA-CoA, than a corresponding acyl-PC substrate. As used herein, a "corresponding acyl-PC substrate" refers to the fatty acid esterified at the sn-2 position of phosphatidylcholine (PC) where the fatty acid is the same fatty acid as in the acyl-CoA substrate. In an embodiment, the activity is at least two-fold greater.

In a further embodiment, the ω3 desaturase comprises amino acids having a sequence as provided in SEQ ID NO:15, 17 or 20, a biologically active fragment thereof, or an amino acid sequence which is at least 35% identical to SEQ ID NO:15, at least 60% identical to SEQ ID NO:17 and/or at least 60% identical to SEQ ID NO:20.

In yet a further embodiment, a desaturase for use in the present invention has greater activity on an acyl-CoA substrate than a corresponding acyl-PC substrate. As outlined above, a "corresponding acyl-PC substrate" refers to the fatty acid esterified at the sn-2 position of phosphatidylcholine (PC) where the fatty acid is the same fatty acid as in the acyl-CoA substrate. In an embodiment, the activity is at least two-fold greater. In an embodiment, the desaturase is a Δ5 or Δ6 desaturase, examples of which are provided, but not limited to, those listed in Table 2.

TABLE 2

Desaturases with greater activity on an acyl-CoA substrate than a corresponding acyl-PC substrate

| Enzyme | Type of organism | Species | Accession Nos. | Protein size (aa's) | References |
| --- | --- | --- | --- | --- | --- |
| Δ6-desaturase | Algae | Mantoniella squamata | CAQ30479 | 449 | Hoffmann et al. 2008 |
|  |  | Ostreococcus tauri | AAW70159 | 456 | Domergue et al. 2005 |
| Δ5-desaturase | Algae | Mantoniella squamata | CAQ30478 | 482 | Hoffmann et al. 2008 |
|  | Plant | Anemone leveillei | N/A |  | Sayanova et al. 2007 |

Elongases

Biochemical evidence suggests that the fatty acid elongation consists of 4 steps: condensation, reduction, dehydration and a second reduction. In the context of this invention, an "elongase" refers to the polypeptide that catalyses the condensing step in the presence of the other members of the elongation complex, under suitable physiological conditions. It has been shown that heterologous or homologous expression in a cell of only the condensing component ("elongase") of the elongation protein complex is required for the elongation of the respective acyl chain. Thus, the introduced elongase is able to successfully recruit the reduction and dehydration activities from the transgenic host to carry out successful acyl elongations. The specificity of the elongation reaction with respect to chain length and the degree of desaturation of fatty acid substrates is thought to reside in the condensing component. This component is also thought to be rate limiting in the elongation reaction.

As used herein, a "Δ5 elongase" is at least capable of converting EPA to DPA. Examples of Δ5 elongases include those disclosed in WO2005/103253. In one embodiment, the Δ5 elongase has activity on EPA to produce DPA with an efficiency of at least 60%, more preferably at least 65%, more preferably at least 70% or most preferably at least 75%. In a further embodiment, the Δ5 elongase comprises an amino acid sequence as provided in SEQ ID NO:6, a biologically active fragment thereof, or an amino acid sequence which is at least 47% identical to SEQ ID NO:6

As used herein, a "Δ6 elongase" is at least capable of converting SDA to ETA. Examples of Δ6 elongases include those listed in Table 1. In one embodiment, the elongase comprises amino acids having a sequence as provided in SEQ ID NO:4, a biologically active fragment thereof, or an amino acid sequence which is at least 55% identical to SEQ ID NO:4.

As used herein, a "Δ9 elongase" is at least capable of converting ALA to ETrA. Examples of Δ9 elongases include those listed in Table 1. In one embodiment, the Δ9 elongase comprises amino acids having a sequence as provided in SEQ ID NO:22, a biologically active fragment thereof, or an amino acid sequence which is at least 80% identical to SEQ ID NO:22. In another embodiment, the Δ9 elongase comprises amino acids having a sequence as provided in SEQ ID NO:28, a biologically active fragment thereof, or an amino acid sequence which is at least 81% identical to SEQ ID NO:28. In another embodiment, the Δ9 elongase comprises amino acids having a sequence as provided in SEQ ID NO:94, a biologically active fragment thereof, or an amino acid sequence which is at least 50% identical to SEQ ID NO:94. In another embodiment, the Δ9 elongase comprises amino acids having a sequence as provided in SEQ ID NO:96, a biologically active fragment thereof, or an amino acid sequence which is at least 50% identical to SEQ ID NO:96. In a further embodiment, the Δ9 elongase comprises amino acids having a sequence as provided in SEQ ID NO:94 or SEQ ID NO:96, a biologically active fragment thereof, or an amino acid sequence which is at least 50% identical to SEQ ID NO:94 and/or SEQ ID NO:96, and wherein the elongase has greater activity on an ω6 substrate than the corresponding ω3 substrate.

As used herein, the term "has greater activity on an ω6 substrate than the corresponding ω3 substrate" refers to the relative activity on the enzyme on substrates that differ by the action of an ω3 desaturase. Preferably, the ω6 substrate is LA and the ω3 substrate is ALA.

As used herein, an "elongase with Δ6 elongase and Δ9 elongase activity" is at least capable of (i) converting SDA to ETA and (ii) converting ALA to ETrA and has greater Δ6 elongase activity than Δ9 elongase activity. In one embodiment, the elongase has an efficiency of conversion on SDA to produce ETA which is at least 50%, more preferably at least 60%, and/or an efficiency of conversion on ALA to produce ETrA which is at least 6% or more preferably at least 9%. In another embodiment, the elongase has at least about 6.5 fold greater Δ6 elongase activity than Δ9 elongase activity. In a further embodiment, the elongase has no detectable Δ5 elongase activity. In yet a further embodiment, the elongase comprises amino acids having a sequence as provided in SEQ ID NO.4, a biologically active fragment thereof, or an amino acid sequence which is at least 55% identical to SEQ ID NO.4.

Other Enzymes

As used herein, the term "diacylglycerol acyltransferase" (EC 2.3.1.20; DGAT) refers to a protein which transfers a fatty acyl group from acyl-CoA to a diacylglycerol substrate to produce a triacylglycerol. Thus, the term "diacylglycerol acyltransferase activity" refers to the transfer of acyl-CoA to diacylglycerol to produce triacylglycerol. There are three known types of DGAT referred to as DGAT1, DGAT2 and DGAT3 respectively. DGAT1 polypeptides typically have 10 transmembrane domains, DGAT2 typically have 2 transmembrane domains, whilst DGAT is typically soluble. Examples of DGAT1 polypeptides include polypeptides encoded by DGAT1 genes from *Aspergillus fumigatus* (Accession No. XP_755172), *Arabidopsis thaliana* (CAB44774), *Ricinus communis* (AAR11479), *Vernicia fordii* (ABC94472), *Vernonia galamensis* (ABV21945, ABV21946), *Euonymus alatus* (AAV31083), *Caenorhabditis elegans* (AAF82410), *Rattus norvegicus* (NP 445889), *Homo sapiens* (NP_036211), as well as variants and/or mutants thereof. Examples of DGAT2 polypeptides include polypeptides encoded by DGAT2 genes from *Arabidopsis thaliana* (Accession No. NP_566952), *Ricinus communis* (AAY16324), *Vernicia fordii* (ABC94474), *Mortierella ramanniana* (AAK84179), *Homo sapiens* (Q96PD7, Q58HT5), *Bos taurus* (Q70VD8), *Mus musculus* (AAK84175), *Micromonas* CCMP1545, as well as variants and/or mutants thereof. Examples of DGAT3 polypeptides include polypeptides encoded by DGAT3 genes from peanut (*Arachis hypogaea*, Saha, et al., 2006), as well as variants and/or mutants thereof.

Polypeptides/Peptides

The invention also provides for polypeptides which may be purified or recombinant. By "substantially purified polypeptide" or "purified polypeptide" we mean a polypeptide that has generally been separated from the lipids, nucleic acids, other peptides, and other contaminating molecules with which it is associated in a cell in which it is produced or in its native state. Preferably, the substantially purified polypeptide is at least 60% free, more preferably at least 75% free, and more preferably at least 90% free from other components in the cell in which it is produced or with which it is naturally associated.

The term "recombinant" in the context of a polypeptide refers to the polypeptide when produced by a cell, or in a cell-free expression system, in an altered amount or at an altered rate, compared to its native state if it is produced naturally. In one embodiment the cell is a cell that does not naturally produce the polypeptide. However, the cell may be a cell which comprises a non-endogenous gene that causes an altered amount of the polypeptide to be produced. A recombinant polypeptide of the invention includes polypeptides in the cell, tissue, organ or organism, or cell-free expression system, in which it is produced i.e. a polypeptide which has not been purified or separated from other components of the transgenic (recombinant) cell in which it was produced, and polypeptides produced in such cells or cell-free systems which are subsequently purified away from at least some other components.

The terms "polypeptide" and "protein" are generally used interchangeably.

A polypeptide or class of polypeptides may be defined by the extent of identity (% identity) of its amino acid sequence to a reference amino acid sequence, or by having a greater % identity to one reference amino acid sequence than to another. The % identity of a polypeptide to a reference amino acid sequence is typically determined by GAP analysis (Needleman and Wunsch, 1970; GCG program) with parameters of a gap creation penalty=5, and a gap extension penalty=0.3. The query sequence is at least 15 amino acids in length, and the GAP analysis aligns the two sequences over a region of at least 15 amino acids. More preferably, the query sequence is at least 50 amino acids in length, and the GAP analysis aligns the two sequences over a region of at least 50 amino acids. More preferably, the query sequence is at least 100 amino acids in length and the GAP analysis aligns the two sequences over a region of at least 100 amino acids. Even more preferably, the query sequence is at least 250 amino acids in length and the GAP analysis aligns the two sequences over a region of at least 250 amino acids. Even more preferably, the GAP analysis aligns two sequences over their entire length. The polypeptide or class of polypeptides may have the same enzymatic activity as, or a different activity than, or lack the activity of, the reference polypeptide. Preferably, the polypeptide has an enzymatic activity of at least 10% of the activity of the reference polypeptide.

As used herein a "biologically active" fragment is a portion of a polypeptide of the invention which maintains a defined activity of a full-length reference polypeptide, for example possessing desaturase and/or elongase activity or other enzyme activity. Biologically active fragments as used herein exclude the full-length polypeptide. Biologically active fragments can be any size portion as long as they maintain the defined activity. Preferably, the biologically active fragment maintains at least 10% of the activity of the full length protein.

With regard to a defined polypeptide or enzyme, it will be appreciated that % identity figures higher than those provided herein will encompass preferred embodiments. Thus, where applicable, in light of the minimum % identity figures, it is preferred that the polypeptide/enzyme comprises an amino acid sequence which is at least 60%, more preferably at least 65%, more preferably at least 70%, more preferably at least 75%, more preferably at least 76%, more preferably at least 80%, more preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to the relevant nominated SEQ ID NO.

In an embodiment, the substantially purified and/or recombinant Δ6 desaturase of the invention does not comprise a sequence provided in accession no. EEH58637.1 or XP_001421073.1. In another embodiment, the substantially purified and/or recombinant ω3 desaturase of the invention does not comprise a sequence provided in accession no. XP_002505536.1. In another embodiment, the substantially purified and/or recombinant DGAT of the invention does not comprise a sequence provided in accession no. EEH54819.1.

Amino acid sequence mutants of the polypeptides of the defined herein can be prepared by introducing appropriate nucleotide changes into a nucleic acid defined herein, or by in vitro synthesis of the desired polypeptide. Such mutants include, for example, deletions, insertions or substitutions of residues within the amino acid sequence. A combination of deletion, insertion and substitution can be made to arrive at the final construct, provided that the final peptide product possesses the desired characteristics.

Mutant (altered) peptides can be prepared using any technique known in the art. For example, a polynucleotide of the invention can be subjected to in vitro mutagenesis. Such in vitro mutagenesis techniques include sub-cloning the polynucleotide into a suitable vector, transforming the vector into a "mutator" strain such as the *E. coli* XL-1 red (Stratagene) and propagating the transformed bacteria for a suitable number of generations. In another example, the polynucleotides of the invention are subjected to DNA shuffling techniques as broadly described by Harayama (1998). Products derived from mutated/altered DNA can readily be screened using techniques described herein to determine if they possess desaturase and/or elongase activity.

In designing amino acid sequence mutants, the location of the mutation site and the nature of the mutation will depend on characteristic(s) to be modified. The sites for mutation can be modified individually or in series, e.g., by (1) substituting first with conservative amino acid choices and then with more radical selections depending upon the results achieved, (2) deleting the target residue, or (3) inserting other residues adjacent to the located site.

Amino acid sequence deletions generally range from about 1 to 15 residues, more preferably about 1 to 10 residues and typically about 1 to 5 contiguous residues.

Substitution mutants have at least one amino acid residue in the polypeptide molecule removed and a different residue inserted in its place. The sites of greatest interest for substitutional mutagenesis include sites identified as the active site(s). Other sites of interest are those in which particular residues obtained from various strains or species are identical. These positions may be important for biological activity. These sites, especially those falling within a sequence of at least three other identically conserved sites, are preferably substituted in a relatively conservative manner. Such conservative substitutions are shown in Table 3 under the heading of "exemplary substitutions".

In a preferred embodiment a mutant/variant polypeptide has only, or not more than, one or two or three or four conservative amino acid changes when compared to a naturally occurring polypeptide. Details of conservative amino acid changes are provided in Table 3. As the skilled person would be aware, such minor changes can reasonably be predicted not to alter the activity of the polypeptide when expressed in a recombinant cell.

TABLE 3

Exemplary substitutions.

| Original Residue | Exemplary Substitutions |
| --- | --- |
| Ala (A) | val; leu; ile; gly |
| Arg (R) | lys |
| Asn (N) | gln; his |
| Asp (D) | glu |
| Cys (C) | ser |
| Gln (Q) | asn; his |
| Glu (E) | asp |
| Gly (G) | pro, ala |
| His (H) | asn; gln |
| Ile (I) | leu; val; ala |
| Leu (L) | ile; val; met; ala; phe |
| Lys (K) | arg |
| Met (M) | leu; phe |
| Phe (F) | leu; val; ala |
| Pro (P) | gly |
| Ser (S) | thr |
| Thr (T) | ser |
| Trp (W) | tyr |
| Tyr (Y) | trp; phe |
| Val (V) | ile; leu; met; phe, ala |

Also included within the scope of the invention are polypeptides defined herein which are differentially modified during or after synthesis, for example, by biotinylation, benzylation, glycosylation, acetylation, phosphorylation, amidation, derivatization by known protecting/blocking groups, proteolytic cleavage, linkage to an antibody molecule or other cellular ligand, etc. These modifications may serve to increase the stability and/or bioactivity of the polypeptide of the invention.

Polypeptides can be produced in a variety of ways, including production and recovery of natural polypeptides, production and recovery of recombinant polypeptides, and chemical synthesis of the polypeptides. In one embodiment, a recombinant polypeptide is produced by culturing a cell capable of expressing the polypeptide under conditions effective to produce the polypeptide. The recombinant polypeptide may subsequently be secreted from the cell and recovered, or extracted from the cell and recovered, and is preferably purified away from contaminating molecules. It may or may not be further modified chemically or enzymatically. A preferred cell to culture is a recombinant cell defined herein. Effective culture conditions include, but are not limited to, effective media, bioreactor, temperature, pH and oxygen conditions that permit polypeptide production. An effective medium refers to any medium in which a cell is cultured to produce a polypeptide defined herein. Such medium typically comprises an aqueous medium having assimilable carbon, nitrogen and phosphate sources, and appropriate salts, minerals, metals and other nutrients, such as vitamins. Cells defined herein can be cultured in conventional fermentation bioreactors, shake flasks, test tubes, microtiter dishes, and petri plates. Culturing can be carried out at a temperature, pH and oxygen content appropriate for a recombinant cell. Such culturing conditions are within the expertise of one of ordinary skill in the art. A more preferred cell to produce the polypeptide is a cell in a plant, especially in a seed in a plant.

For the purposes of this invention, the term "antibody", unless specified to the contrary, includes fragments of whole antibodies which retain their binding activity for a target analyte, as well as compounds comprising said fragments. Such fragments include Fv, F(ab') and F(ab')$_2$ fragments, as well as single chain antibodies (scFv). Antibodies of the invention may be monoclonal or polyclonal and can be produced using standard procedures in the art.

Polynucleotides

The invention also provides for polynucleotides which may be, for example, a gene, an isolated polynucleotide, or a chimeric DNA. It may be DNA or RNA of genomic or synthetic origin, double-stranded or single-stranded, and combined with carbohydrate, lipids, protein or other materials to perform a particular activity defined herein. The term "polynucleotide" is used interchangeably herein with the term "nucleic acid molecule". By "isolated polynucleotide" we mean a polynucleotide which, if obtained from a natural source, has been separated from the polynucleotide sequences with which it is associated or linked in its native state, or a non-naturally occurring polynucleotide. Preferably, the isolated polynucleotide is at least 60% free, more preferably at least 75% free, and more preferably at least 90% free from other components with which it is naturally associated.

As used herein, the term "gene" is to be taken in its broadest context and includes the deoxyribonucleotide sequences comprising the transcribed region and, if translated, the protein coding region, of a structural gene and including sequences located adjacent to the coding region on both the 5' and 3' ends for a distance of at least about 2 kb on either end and which are involved in expression of the gene. In this regard, the gene includes control signals such as promoters, enhancers, termination and/or polyadenylation signals that are naturally associated with a given gene, or heterologous control signals in which case the gene is referred to as a "chimeric gene". The sequences which are located 5' of the protein coding region and which are present on the mRNA are referred to as 5' non-translated sequences. The sequences which are located 3' or downstream of the protein coding region and which are present on the mRNA are referred to as 3' non-translated sequences. The term "gene" encompasses both cDNA and genomic forms of a gene. A genomic form or clone of a gene contains the coding region which may be interrupted with non-coding sequences termed "introns" or "intervening regions" or "intervening sequences." Introns are segments of a gene which are transcribed into nuclear RNA (hnRNA). Introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide. The term "gene" includes a synthetic or fusion molecule encoding all or part of the proteins of the invention described herein and a complementary nucleotide sequence to any one of the above.

As used herein, a "chimeric DNA" refers to any DNA molecule that is not a native DNA molecule in its native location, also referred to herein as a "DNA construct". Typically, a chimeric DNA or chimeric gene comprises regulatory and transcribed or protein coding sequences that are not found together in nature. Accordingly, a chimeric DNA or chimeric gene may comprise regulatory sequences and coding sequences that are derived from different sources, or regulatory sequences and coding sequences derived from the same source, but arranged in a manner different than that found in nature.

The term "endogenous" is used herein to refer to a substance that is normally present or produced in an unmodified plant at the same developmental stage as the plant under investigation. An "endogenous gene" refers to a native gene in its natural location in the genome of an organism. As used herein, "recombinant nucleic acid molecule", "recombinant polynucleotide" or variations thereof refer to a nucleic acid molecule which has been constructed or modified by recombinant DNA technology. The terms "foreign polynucleotide" or "exogenous polynucleotide" or "heterologous polynucleotide" and the like refer to any nucleic acid which is introduced into the genome of a cell by experimental manipulations. Foreign or exogenous genes may be genes that are inserted into a non-native organism, native genes introduced into a new location within the native host, or chimeric genes. A "transgene" is a gene that has been introduced into the genome by a transformation procedure. The terms "genetically modified", "transgenic" and variations thereof include introducing genes into cells by transformation or transduction, mutating genes in cells and altering or modulating the regulation of a gene in a cell or organisms to which these acts have been done or their progeny. A "genomic region" as used herein refers to a position within the genome where a transgene, or group of transgenes (also referred to herein as a cluster), have been inserted into a cell, or an ancestor thereof. Such regions only comprise nucleotides that have been incorporated by the intervention of man such as by methods described herein.

The term "exogenous" in the context of a polynucleotide refers to the polynucleotide when present in a cell in an altered amount compared to its native state. In one embodiment, the cell is a cell that does not naturally comprise the polynucleotide. However, the cell may be a cell which comprises a non-endogenous polynucleotide resulting in an altered amount of production of the encoded polypeptide. An exogenous polynucleotide of the invention includes polynucleotides which have not been separated from other components of the transgenic (recombinant) cell, or cell-free expression system, in which it is present, and polynucleotides produced in such cells or cell-free systems which are subsequently purified away from at least some other components. The exogenous polynucleotide (nucleic acid) can be a contiguous stretch of nucleotides existing in nature, or comprise two or more contiguous stretches of nucleotides from different sources (naturally occurring and/or synthetic) joined to form a single polynucleotide. Typically such chimeric polynucleotides comprise at least an open reading frame encoding a polypeptide of the invention operably linked to a promoter suitable of driving transcription of the open reading frame in a cell of interest.

As used herein, the term "different exogenous polynucleotides" or variations thereof means that the nucleotide sequence of each polynucleotide are different by at least one, preferably more, nucleotides. The polynucleotides encode RNAs which may or may not be translated to a protein within the cell. In an example, it is preferred that each polynucleotide encodes a protein with a different activity. In another example, each exogenous polynucleotide is less than 95%, less than 90%, or less than 80% identical to the other exogenous polynucleotides. Preferably, the exogenous polynucleotides encode functional proteins/enzymes. Furthermore, it is preferred that the different exogenous polynucleotides are non-overlapping in that each polynucleotide is a distinct region of the, for example, extrachromosomal transfer nucleic acid which does not overlap with another exogenous polynucleotide. At a minimum, each exogenous polynucleotide has a transcription start and stop site, as well as the designated promoter. An individual exogenous polynucleotide may or may not comprise introns.

With regard to the defined polynucleotides, it will be appreciated that % identity figures higher than those provided above will encompass preferred embodiments. Thus, where applicable, in light of the minimum % identity figures, it is preferred that the polynucleotide comprises a polynucleotide sequence which is at least 60%, more preferably at least 65%, more preferably at least 70%, more preferably at least 75%, more preferably at least 80%, more preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to the relevant nominated SEQ ID NO.

In an embodiment, the isolated and/or exogenous polynucleotide encoding a Δ6 desaturase of the invention does not comprise the sequence from the *Micromonas* or *Ostreococcus* genome predicted to encode the amino acid sequence provided in accession no. EEH58637.1 or XP_001421073.1 respectively. In another embodiment, the isolated and/or exogenous polynucleotide encoding a ω3 desaturase of the invention does not comprise the sequence from the *Micromonas* genome predicted to encode the amino acid sequence provided in accession no. XP_002505536.1. In another embodiment, the isolated and/or exogenous polynucleotide encoding a DGAT of the invention does not comprise the sequence from the *Micromonas* genome predicted to encode the amino acid sequence provided in accession no. EEH54819.1.

A polynucleotide of the present invention may selectively hybridise, under stringent conditions, to a polynucleotide that encodes a polypeptide of the present invention. As used herein, stringent conditions are those that (1) employ during hybridisation a denaturing agent such as formamide, for example, 50% (v/v) formamide with 0.1% (w/v) bovine serum albumin, 0.1% Ficoll, 0.1% polyvinylpyrrolidone, 50 mM sodium phosphate buffer at pH 6.5 with 750 mM NaCl, 75 mM sodium citrate at 42° C.; or (2) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 g/ml), 0.1% SDS and 10% dextran sulfate at 42° C. in 0.2×SSC and 0.1% SDS and/or (3) employ low ionic strength and high temperature for washing, for example, 0.015 M NaCl/0.0015 M sodium citrate/0.1% SDS at 50° C.

Polynucleotides of the invention may possess, when compared to naturally occurring molecules, one or more mutations which are deletions, insertions, or substitutions of nucleotide residues. Polynucleotides which have mutations relative to a reference sequence can be either naturally occurring (that is to say, isolated from a natural source) or synthetic (for example, by performing site-directed mutagenesis or DNA shuffling on the nucleic acid as described above). It is thus apparent that polynucleotides of the invention can be either from a naturally occurring source or recombinant.

Recombinant Vectors

One embodiment of the present invention includes a recombinant vector, which comprises at least one polynucleotide molecule defined herein, inserted into any vector capable of delivering the polynucleotide molecule into a host cell. Recombinant vectors include expression vectors. Recombinant vectors contain heterologous polynucleotide sequences, that is polynucleotide sequences that are not naturally found adjacent to polynucleotide molecules defined herein that preferably are derived from a species other than the species from which the polynucleotide molecule(s) are derived. The vector can be either RNA or DNA, either prokaryotic or eukaryotic, and typically is a viral vector, derived from a virus, or a plasmid. Plasmid vectors typically include additional nucleic acid sequences that provide for easy selection, amplification, and transformation of the expression cassette in prokaryotic cells, e.g., pUC-derived vectors, pSK-derived vectors, pGEM-derived vectors, pSP-derived vectors, pBS-derived vectors, or binary vectors containing one or more T-DNA regions. Additional nucleic acid sequences include origins of replication to provide for autonomous replication of the vector, selectable marker genes, preferably encoding antibiotic or herbicide resistance, unique multiple cloning sites providing for multiple sites to insert nucleic acid sequences or genes encoded in the nucleic acid construct, and sequences that enhance transformation of prokaryotic and eukaryotic (especially plant) cells. The recombinant vector may comprise more than one polynucleotide defined herein, for example three, four, five or six polynucleotides of the invention in combination, each operably linked to expression control sequences that are operable in the cell of interest. Such more than one polynucleotide of the invention, for example 3, 4, 5 or 6 polynucleotides, are preferably covalently joined together in a single recombinant vector, which may then be introduced as a single molecule into a cell to form a recombinant cell according to the invention, and preferably integrated into the genome of the recombinant cell, for example in a transgenic plant. Thereby, the polynucleotides which are so joined will be inherited together as a single genetic locus in progeny of the recombinant cell or plant. The recombinant vector or plant may comprise two or more such recombinant vectors, each containing multiple polynucleotides, for example wherein each recombinant vector comprises 3, 4, 5 or 6 polynucleotides.

"Operably linked" as used herein refers to a functional relationship between two or more nucleic acid (e.g., DNA) segments. Typically, it refers to the functional relationship of transcriptional regulatory element (promoter) to a transcribed sequence. For example, a promoter is operably linked to a coding sequence, such as a polynucleotide defined herein, if it stimulates or modulates the transcription of the coding sequence in an appropriate cell. Generally, promoter transcriptional regulatory elements that are operably linked to a transcribed sequence are physically contiguous to the transcribed sequence, i.e., they are cis-acting. However, some transcriptional regulatory elements, such as enhancers, need not be physically contiguous or located in close proximity to the coding sequences whose transcription they enhance.

When there are multiple promoters present, each promoter may independently be the same or different.

Recombinant molecules such as the chimeric DNAs may also contain (a) one or more secretory signals which encode signal peptide sequences, to enable an expressed polypeptide defined herein to be secreted from the cell that produces the polypeptide or which provide for localisation of the expressed polypeptide, for example for retention of the polypeptide in the endoplasmic reticulum (ER) in the cell or transfer into a plastid, and/or (b) contain fusion sequences which lead to the expression of nucleic acid molecules as fusion proteins. Examples of suitable signal segments include any signal segment capable of directing the secretion or localisation of a polypeptide defined herein. Preferred signal segments include, but are not limited to, *Nicotiana nectarin* signal peptide (U.S. Pat. No. 5,939,288), tobacco extensin signal or the soy oleosin oil body binding protein signal. Recombinant molecules may also include intervening and/or untranslated sequences surrounding and/or within the nucleic acid sequences of nucleic acid molecules defined herein.

To facilitate identification of transformants, the nucleic acid construct desirably comprises a selectable or screenable marker gene as, or in addition to, the foreign or exogenous polynucleotide. By "marker gene" is meant a gene that imparts a distinct phenotype to cells expressing the marker gene and thus allows such transformed cells to be distinguished from cells that do not have the marker. A selectable marker gene confers a trait for which one can "select" based on resistance to a selective agent (e.g., a herbicide, antibiotic, radiation, heat, or other treatment damaging to untransformed cells). A screenable marker gene (or reporter gene) confers a trait that one can identify through observation or testing, i.e., by "screening" (e.g., β-glucuronidase, luciferase, GFP or other enzyme activity not present in untransformed cells). The marker gene and the nucleotide sequence of interest do not have to be linked. The actual choice of a marker is not crucial as long as it is functional (i.e., selective) in combination with the cells of choice such as a plant cell. The marker gene and the foreign or exogenous polynucleotide of interest do not have to be linked, since co-transformation of unlinked genes as, for example, described in U.S. Pat. No. 4,399,216 is also an efficient process in plant transformation.

Examples of bacterial selectable markers are markers that confer antibiotic resistance such as ampicillin, erythromycin, chloramphenicol or tetracycline resistance, preferably kanamycin resistance. Exemplary selectable markers for selection of plant transformants include, but are not limited to, a hyg gene which encodes hygromycin B resistance; a neomycin phosphotransferase (nptII) gene conferring resistance to kanamycin, paromomycin, G418; a glutathione-S-transferase gene from rat liver conferring resistance to glutathione derived herbicides as, for example, described in EP 256223; a glutamine synthetase gene conferring, upon overexpression, resistance to glutamine synthetase inhibitors such as phosphinothricin as, for example, described in WO 87/05327, an acetyltransferase gene from *Streptomyces viridochromogenes* conferring resistance to the selective agent phosphinothricin as, for example, described in EP 275957, a gene encoding a 5-enolshikimate-3-phosphate synthase (EPSPS) conferring tolerance to N-phosphonomethylglycine as, for example, described by Hinchee et al. (1988), a bar gene conferring resistance against bialaphos as, for example, described in WO91/02071; a nitrilase gene such as bxn from *Klebsiella ozaenae* which confers resistance to bromoxynil (Stalker et al., 1988); a dihydrofolate reductase (DHFR) gene conferring resistance to methotrexate (Thillet et al., 1988); a mutant acetolactate synthase gene (ALS), which confers resistance to imidazolinone, sulfonylurea or other ALS-inhibiting chemicals (EP 154,204); a mutated anthranilate synthase gene that confers resistance to 5-methyl tryptophan; or a dalapon dehalogenase gene that confers resistance to the herbicide.

Preferred screenable markers include, but are not limited to, a uidA gene encoding a β-glucuronidase (GUS) enzyme for which various chromogenic substrates are known, a β-galactosidase gene encoding an enzyme for which chromogenic substrates are known, an aequorin gene (Prasher et al., 1985), which may be employed in calcium-sensitive bioluminescence detection; a green fluorescent protein gene (Niedz et al., 1995) or derivatives thereof; a luciferase (luc) gene (Ow et al., 1986), which allows for bioluminescence detection, and others known in the art. By "reporter molecule" as used in the present specification is meant a molecule that, by its chemical nature, provides an analytically identifiable signal that facilitates determination of promoter activity by reference to protein product.

Preferably, the nucleic acid construct is stably incorporated into the genome of the cell, such as the plant cell. Accordingly, the nucleic acid may comprise appropriate elements which allow the molecule to be incorporated into the genome, or the construct is placed in an appropriate vector which can be incorporated into a chromosome of the cell.

Expression

As used herein, an expression vector is a DNA or RNA vector that is capable of transforming a host cell and of effecting expression of one or more specified polynucleotide molecule(s). Preferably, the expression vector is also capable of replicating within the host cell. Expression vectors can be either prokaryotic or eukaryotic, and are typically viruses or plasmids. Expression vectors of the present invention include any vectors that function (i.e., direct gene expression) in recombinant cells of the present invention, including in bacterial, fungal, endoparasite, arthropod, animal, and plant cells. Particularly preferred expression vectors of the present invention can direct gene expression in yeast and/or plant cells.

Expression vectors of the present invention contain regulatory sequences such as transcription control sequences, translation control sequences, origins of replication, and other regulatory sequences that are compatible with the recombinant cell and that control the expression of polynucleotide molecules of the present invention. In particular, polynucleotides or vectors of the present invention include transcription control sequences. Transcription control sequences are sequences which control the initiation, elongation, and termination of transcription. Particularly important transcription control sequences are those which control transcription initiation, such as promoter, enhancer, operator and repressor sequences. Suitable transcription control sequences include any transcription control sequence that can function in at least one of the recombinant cells of the present invention. The choice of the regulatory sequences used depends on the target organism such as a plant and/or target organ or tissue of interest. Such regulatory sequences may be obtained from any eukaryotic organism such as plants or plant viruses, or may be chemically synthesized. A variety of such transcription control sequences are known to those skilled in the art. Particularly preferred transcription control sequences are promoters active in directing transcription in plants, either constitutively or stage and/or tissue specific, depending on the use of the plant or parts thereof.

A number of vectors suitable for stable transfection of plant cells or for the establishment of transgenic plants have been described in, e.g., Pouwels et al., Cloning Vectors: A Laboratory Manual, 1985, supp. 1987; Weissbach and Weissbach, Methods for Plant Molecular Biology, Academic Press, 1989; and Gelvin et al., Plant Molecular Biology Manual, Kluwer Academic Publishers, 1990. Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

A number of constitutive promoters that are active in plant cells have been described. Suitable promoters for constitutive expression in plants include, but are not limited to, the cauliflower mosaic virus (CaMV) 35S promoter, the Figwort mosaic virus (FMV) 35S, the sugarcane bacilliform virus promoter, the commelina yellow mottle virus promoter, the light-inducible promoter from the small subunit of the ribulose-1,5-bis-phosphate carboxylase, the rice cytosolic triosephosphate isomerase promoter, the adenine phosphoribosyltransferase promoter of *Arabidopsis*, the rice actin 1 gene promoter, the mannopine synthase and octopine synthase promoters, the Adh promoter, the sucrose synthase promoter, the R gene complex promoter, and the chlorophyll α/β binding protein gene promoter. These promoters have been used to create DNA vectors that have been expressed in plants; see, e.g., WO 84/02913. All of these promoters have been used to create various types of plant-expressible recombinant DNA vectors.

For the purpose of expression in source tissues of the plant, such as the leaf, seed, root or stem, it is preferred that the promoters utilized in the present invention have relatively high expression in these specific tissues. For this purpose, one may choose from a number of promoters for genes with tissue- or cell-specific or -enhanced expression. Examples of such promoters reported in the literature include the chloroplast glutamine synthetase GS2 promoter from pea, the chloroplast fructose-1,6-biphosphatase promoter from wheat, the nuclear photosynthetic ST-LS1 promoter from potato, the serine/threonine kinase promoter and the glucoamylase (CHS) promoter from *Arabidopsis thaliana*. Also reported to be active in photosynthetically active tissues are the ribulose-1,5-bisphosphate carboxylase promoter from eastern larch (*Larix laricina*), the promoter for the Cab gene, Cab6, from pine, the promoter for the Cab-1 gene from wheat, the promoter for the Cab-1 gene from spinach, the promoter for the Cab 1R gene from rice, the pyruvate, orthophosphate dikinase (PPDK) promoter from *Zea mays*, the promoter for the tobacco Lhcb1*2 gene, the *Arabidopsis thaliana* Suc2 sucrose-$H^{30}$ symporter promoter, and the promoter for the thylakoid membrane protein genes from spinach (PsaD, PsaF, PsaE, PC, FNR, AtpC, AtpD, Cab, RbcS).

Other promoters for the chlorophyll α/β-binding proteins may also be utilized in the present invention, such as the promoters for LhcB gene and PsbP gene from white mustard (*Sinapis alba*). A variety of plant gene promoters that are regulated in response to environmental, hormonal, chemical, and/or developmental signals, also can be used for expression of RNA-binding protein genes in plant cells, including promoters regulated by (1) heat, (2) light (e.g., pea RbcS-3A promoter, maize RbcS promoter); (3) hormones, such as abscisic acid, (4) wounding (e.g., WunI); or (5) chemicals, such as methyl jasmonate, salicylic acid, steroid hormones, alcohol, Safeners (WO 97/06269), or it may also be advantageous to employ (6) organ-specific promoters.

As used herein, the term "plant storage organ specific promoter" refers to a promoter that preferentially, when compared to other plant tissues, directs gene transcription in a storage organ of a plant. Preferably, the promoter only directs expression of a gene of interest in the storage organ, and/or expression of the gene of interest in other parts of the plant such as leaves is not detectable by Northern blot analysis and/or RT-PCR. Typically, the promoter drives expression of genes during growth and development of the storage organ, in particular during the phase of synthesis and accumulation of storage compounds in the storage organ. Such promoters may drive gene expression in the entire plant storage organ or only part thereof such as the seedcoat, embryo or cotyledon(s) in seeds of dicotyledonous plants or the endosperm or aleurone layer of a seeds of monocotyledonous plants.

For the purpose of expression in sink tissues of the plant, such as the tuber of the potato plant, the fruit of tomato, or the seed of soybean, canola, cotton, *Zea mays*, wheat, rice, and barley, it is preferred that the promoters utilized in the present invention have relatively high expression in these specific tissues. A number of promoters for genes with tuber-specific or -enhanced expression are known, including the class I patatin promoter, the promoter for the potato tuber ADPGPP genes, both the large and small subunits, the sucrose synthase promoter, the promoter for the major tuber proteins including the 22 kD protein complexes and proteinase inhibitors, the promoter for the granule bound starch synthase gene (GBSS), and other class I and II patatins promoters. Other promoters can also be used to express a protein in specific tissues, such as seeds or fruits. The promoter for β-conglycinin or other seed-specific promoters such as the napin, zein, linin and phaseolin promoters, can be used. Root specific promoters may also be used. An example of such a promoter is the promoter for the acid chitinase gene. Expression in root tissue could also be accomplished by utilizing the root specific subdomains of the CaMV 35S promoter that have been identified.

In a particularly preferred embodiment, the promoter directs expression in tissues and organs in which fatty acid and oil biosynthesis take place. Such promoters act in seed development at a suitable time for modifying oil composition in seeds.

In a further particularly preferred embodiment, and in some aspects of the invention, the promoter is a plant storage organ specific promoter. In one embodiment, the plant storage organ specific promoter is a seed specific promoter. In a more preferred embodiment, the promoter preferentially directs expression in the cotyledons of a dicotyledonous plant or in the endosperm of a monocotyledonous plant, relative to expression in the embryo of the seed or relative to other organs in the plant such as leaves. Preferred promoters for seed-specific expression include i) promoters from genes encoding enzymes involved in fatty acid biosynthesis and accumulation in seeds, such as desaturases and elongases, ii) promoters from genes encoding seed storage proteins, and iii) promoters from genes encoding enzymes involved in carbohydrate biosynthesis and accumulation in seeds. Seed specific promoters which are suitable are the oilseed rape napin gene promoter (U.S. Pat. No. 5,608,152), the *Vicia faba* USP promoter (Baumlein et al., 1991), the *Arabidopsis* oleosin promoter (WO 98/45461), the *Phaseolus vulgaris* phaseolin promoter (U.S. Pat. No. 5,504,200), the *Brassica* Bce4 promoter (WO 91/13980) or the legumin B4 promoter (Baumlein et al., 1992), and promoters which lead to the seed-specific expression in monocots such as maize, barley, wheat, rye, rice and the like. Notable promoters which are suitable are the barley lpt2 or lpt1 gene promoter (WO 95/15389 and WO 95/23230) or the promoters described in WO 99/16890 (promoters from the barley hordein gene, the rice glutelin gene, the rice oryzin gene, the rice prolamin gene, the wheat gliadin gene, the wheat glutelin gene, the maize zein gene, the oat glutelin gene, the sorghum kasirin gene, the rye secalin gene). Other promoters include those described by Broun et al. (1998), Potenza et al. (2004), US 20070192902 and US 20030159173. In an embodiment, the seed specific promoter is preferentially expressed in defined parts of the seed such as the cotyledon(s) or the endosperm. Examples of cotyledon specific promoters include, but are not limited to, the FP1 promoter (Ellerstrom et al., 1996), the pea legumin promoter (Perrin et al., 2000), and the bean phytohemagglutnin promoter (Perrin et al., 2000). Examples of endosperm specific promoters include, but are not limited to, the maize zein-1 promoter (Chikwamba et al., 2003), the rice glutelin-1 promoter (Yang et al., 2003), the barley D-hordein promoter (Horvath et al., 2000) and wheat HMW glutenin promoters (Alvarez et al., 2000). In a further embodiment, the seed specific promoter is not expressed, or is only expressed at a low level, in the embryo and/or after the seed germinates.

In another embodiment, the plant storage organ specific promoter is a tuber specific promoter. Examples include, but are not limited to, the potato patatin B33, PAT21 and GBSS promoters, as well as the sweet potato sporamin promoter (for review see Potenza et al., 2004). In a preferred embodiment, the promoter directs expression preferentially in the pith of the tuber, relative to the outer layers (skin, bark) or the embryo of the tuber.

In another embodiment, the plant storage organ specific promoter is a fruit specific promoter. Examples include, but are not limited to, the tomato polygalacturonase, E8 and Pds promoters, as well as the apple ACC oxidase promoter (for review see Potenza et al., 2004). In a preferred embodiment, the promoter preferentially directs expression in the edible parts of the fruit, for example the pith of the fruit, relative to the skin of the fruit or the seeds within the fruit.

The 5' non-translated leader sequence can be derived from the promoter selected to express the heterologous gene sequence of the polynucleotide of the present invention, or may be heterologous with respect to the coding region of the enzyme to be produced, and can be specifically modified if desired so as to increase translation of mRNA. For a review of optimizing expression of transgenes, see Koziel et al. (1996). The 5' non-translated regions can also be obtained from plant viral RNAs (Tobacco mosaic virus, Tobacco etch virus, Maize dwarf mosaic virus, Alfalfa mosaic virus, among others) from suitable eukaryotic genes, plant genes (wheat and maize chlorophyll α/β binding protein gene leader), or from a synthetic gene sequence. The present invention is not limited to constructs wherein the non-translated region is derived from the 5' non-translated sequence that accompanies the promoter sequence. The leader sequence could also be derived from an unrelated promoter or coding sequence. Leader sequences useful in context of the present invention comprise the maize Hsp70 leader (U.S. Pat. Nos. 5,362,865 and 5,859,347), and the TMV omega element as exemplified in Example 8.

The termination of transcription is accomplished by a 3' non-translated DNA sequence operably linked in the chimeric vector to the polynucleotide of interest. The 3' non-translated region of a recombinant DNA molecule contains a polyadenylation signal that functions in plants to cause the addition of adenylate nucleotides to the 3' end of the RNA. The 3' non-translated region can be obtained from various genes that are expressed in plant cells. The nopaline synthase 3' untranslated region, the 3' untranslated region from pea small subunit Rubisco gene, the 3' untranslated region from soybean 7S seed storage protein gene are commonly used in this capacity. The 3' transcribed, non-translated regions containing the polyadenylate signal of *Agrobacterium* tumor-inducing (Ti) plasmid genes are also suitable.

Recombinant DNA technologies can be used to improve expression of a transformed polynucleotide molecule by manipulating, for example, the number of copies of the polynucleotide molecule within a host cell, the efficiency with which those polynucleotide molecules are transcribed, the efficiency with which the resultant transcripts are translated, and the efficiency of post-translational modifications. Recombinant techniques useful for increasing the expression of polynucleotide molecules defined herein include, but are not limited to, operatively linking polynucleotide molecules to high-copy number plasmids, integration of the polynucleotide molecule into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of polynucleotide molecules to correspond to the codon usage of the host cell, and the deletion of sequences that destabilize transcripts.

Transfer Nucleic Acids

Transfer nucleic acids of the invention at least comprise one, preferably two, border sequences and an exogenous polynucleotide. The transfer nucleic acid may or may not encode a selectable marker. Preferably, the transfer nucleic acid forms part of a binary vector in the bacterium, where the binary vector further comprises elements which allows replication of the vector in the bacterium or allows selection or maintenance of bacterial cells containing the vector. Upon transfer to a eukaryotic cell the transfer nucleic acid component of the binary vector is capable of integration into the genome of the eukaryotic cell.

As used herein, the term "extrachromosomal transfer nucleic acid" refers to a nucleic acid molecule that is capable of being transferred from a bacterium, such as *Agrobacterium* sp., to a eukaryotic cell, such as a plant leaf cell. An extrachromosomal transfer nucleic acid is a genetic element that is well-known as an element capable of being transferred with the subsequent integration of a nucleotide sequence contained within its borders into the genome of the recipient cell. In this respect, a transfer nucleic acid is flanked, typically, by two "border" sequences, although in some instances a single border at one end can be used and the second end of the transferred nucleic acid is generated randomly in the transfer process. A desired exogenous polynucleotide is typically positioned between the left border-like sequence and the right border-like sequence of a transfer nucleic acid. The desired polynucleotide contained within the transfer nucleic acid may be operably linked to a variety of different promoter and terminator regulatory elements that facilitate its expression, i.e., transcription and/or translation of the polynucleotide. T-DNAs from *Agrobacterium* sp. such as *Agrobacterium tumefaciens* or *Agrobacterium rhizogenes*, and man made variants/mutants thereof are probably the best characterized examples of transfer nucleic acids. Another example is P-DNA ("plant-DNA") which comprises T-DNA border-like sequences from plants.

As used herein, "T-DNA" refers to, for example, T-DNA of an *Agrobacterium tumefaciens* Ti plasmid or from an *Agrobacterium rhizogenes* Ri plasmid, or a man made variants thereof which function as T-DNA (transferred-DNA). The T-DNA may comprise an entire T-DNA including both right and left border sequences, but need only comprise the minimal sequences required in cis for transfer i.e., the right and T-DNA border sequence. The T-DNAs of the invention have inserted into them, anywhere between the right and left border sequences (if present), the exogenous polynucleotide flanked by target sites for a site-specific recombinase. The sequences encoding factors required in trans for transfer of the T-DNA into a plant cell, such as vir genes, may be inserted into the T-DNA, or may be present on the same replicon as the T-DNA, or preferably are in trans on a compatible replicon in the *Agrobacterium* host. Such "binary vector systems" are well known in the art.

As used herein, "P-DNA" refers to a transfer nucleic acid isolated from a plant genome, or a man made variants/mutants thereof, and comprises at each end, or at only one end, a T-DNA border-like sequence. The border-like sequence preferably shares at least 50%, at least 60%, at least 70%, at least 75%, at least 80%, at least 90% or at least 95%, but less than 100% sequence identity, with a T-DNA border sequence from an *Agrobacterium* sp., such as *Agrobacterium tumefaciens* or *Agrobacterium rhizogenes*. Thus, P-DNAs can be used instead of T-DNAs to transfer a nucleotide sequence contained within the P-DNA from, for example *Agrobacterium*, to another cell. The P-DNA, before insertion of the exogenous polynucleotide which is to be transferred, may be modified to facilitate cloning and should preferably not encode any proteins. The P-DNA is characterized in that it contains, at least a right border sequence and preferably also a left border sequence.

As used herein, a "border" sequence(s) of a transfer nucleic acid can be isolated from selected organism such as a plant or bacteria, or be a man made variant/mutant thereof. The border sequence promotes and facilitates the transfer of the exogenous polynucleotide to which it is linked and may facilitate its integration in the recipient cell genome.

In an embodiment, a border-sequence is between 5-100 bp in length, 10-80 bp in length, 15-75 bp in length, 15-60 bp in length, 15-50 bp in length, 15-40 bp in length, 15-30 bp in length, 16-30 bp in length, 20-30 bp in length, 21-30 bp in length, 22-30 bp in length, 23-30 bp in length, 24-30 bp in length, 25-30 bp in length, or 26-30 bp in length.

Border sequences from T-DNA from *Agrobacterium* sp. are well known in the art and include those described in Lacroix et al. (2008), Tzfira and Citovsky (2006) and Glevin (2003). The border sequences of P-DNA can be isolated from any plant, such as from potato and wheat. In an embodiment, the P-DNA has the nucleic acid sequence ANGATNTATN6GT (SEQ ID NO:109), where "N" is any nucleotide, such as those represented by "A," "G," "C," or "T". Examples of other border sequences useful for the invention include, but are not limited to,

```
                                         (SEQ ID NO: 110)
          TGACAGGATATATTGGCGGGTAAAC;

(SEQ ID NO: 111)
          TGGCAGGATATATTGTGGTGTAAAC;

(SEQ ID NO: 112)
          TGGCAGGATATATACCGTTGTAATT;

(SEQ ID NO: 113)
          CGGCAGGATATATTCAATTGTAATT;

(SEQ ID NO: 114)
          TGGTAGGATATATACCGTTGTAATT;

(SEQ ID NO: 115)
          TGGCAGGATATATGGTACTGTAATT;

(SEQ ID NO: 116)
          YGRYAGGATATATWSNVBKGTAAWY;

(SEQ ID NO: 117)
          CGGCAGGATATATCCTGATGTAAAT;

(SEQ ID NO: 118)
          TGGCAGGAGTTATTCGAGGGTAAAC;

(SEQ ID NO: 119)
          TGACAGGATATATCGTGATGTCAAC;

(SEQ ID NO: 120)
          GGGAAGTACATATTGGCGGGTAAAC;

(SEQ ID NO: 121)
          TTACAGGATATATTAATATGTATGA;

(SEQ ID NO: 122)
          TAACATGATATATTCCCTTGTAAAT;

(SEQ ID NO: 123)
          TGACAGGATATATGGTAATGTAAAC;
          and (SEQ ID NO: 124)
          TGGCAGGATATATACCGATGTAAAC,
``` where * Y=C or T; R=A or G; K=G or T; W=A or T; S=C or G; V=A, C, or G; B=C, G, or T.

Whilst traditionally only *Agrobacterium* sp. have been used transfer genes to plants cells, there are now a large number of systems which have been identified/developed which act in a similar manner to *Agrobacterium* sp. Several non-*Agrobacterium* species have recently been genetically modified to be competent for gene transfer (Chung et al., 2006; Broothaerts et al., 2005). These include *Rhizobium* sp.

NGR234, *Sinorhizobium meliloti* and *Mezorhizobium loti*. The bacteria are made competent for gene transfer by providing the bacteria with the machinery needed for the transformation process: i.e. a set of virulence genes encoded by an *Agrobacterium* Ti-plasmid and the T-DNA segment residing on a separate, small binary plasmid. Bacteria engineered in this way are capable of transforming different plant tissues (leaf disks, calli and oval tissue), monocots or dicots, and various different plant species (e.g. tobacco, rice).

Direct transfer of eukaryotic expression plasmids from bacteria to eukaryotic hosts was first achieved several decades ago by the fusion of mammalian cells and protoplasts of plasmid-carrying *Escherichia coli* (Schaffner, 1980). Since then, the number of bacteria capable of delivering genes into mammalian cells has steadily increased (Weiss, 2003), being discovered by four groups independently (Sizemore et al. 1995; Courvalin et al., 1995; Powell et al., 1996; Darji et al., 1997).

Attenuated *Shigella flexneri, Salmonella typhimurium* or *E. coli* that had been rendered invasive by the virulence plasmid (pWR100) of *S. flexneri* have been shown to be able to transfer expression plasmids after invasion of host cells and intracellular death due to metabolic attenuation. Mucosal application, either nasally or orally, of such recombinant *Shigella* or *Salmonella* induced immune responses against the antigen that was encoded by the expression plasmids. In the meantime, the list of bacteria that was shown to be able to transfer expression plasmids to mammalian host cells in vitro and in vivo has been more then doubled and has been documented for *S. typhi, S. choleraesuis, Listeria monocytogenes, Yersinia pseudotuberculosis,* and *Y. enterocolitica* (Fennelly et al., 1999; Shiau et al., 2001; Dietrich et al., 1998, 2001; Hense et al., 2001; Al-Mariri et al., 2002).

In general, it could be assumed that all bacteria that are able to enter the cytosol of the host cell (like *S. flexneri* or *L. monocytogenes*) and lyse within this cellular compartment, should be able to transfer DNA. This is known as 'abortive' or 'suicidal' invasion as the bacteria have to lyse for the DNA transfer to occur (Grillot-Courvalin et al., 1999). In addition, even many of the bacteria that remain in the phagocytic vacuole (like *S. typhimurium*) may also be able to do so. Thus, recombinant laboratory strains of *E. coli* that have been engineered to be invasive but are unable of phagosomal escape, could deliver their plasmid load to the nucleus of the infected mammalian cell nevertheless (Grillot-Courvalin et al., 1998). Furthermore, *Agrobacterium tumefaciens* has recently also been shown to introduce transgenes into mammalian cells (Kunik et al., 2001).

The transfer process using extrachromosomal transfer elements typically transfers multiple copies of the element into the recipient cell. As used herein, the term "transiently transfected" means that although some of the exogenous polynucleotides may become stably integrated into the genome of the cell, the cells are not selected for stable integration. As a result, much of the transfer nucleic acid remains extrachromosomal in the cell, for example greater than 90% of the copies of the exogenous polynucleotide that are transferred into the recipient cell are not integrated into the genome.

As used herein, the terms "transfection", "transformation" and variations thereof are generally used interchangeably. "Transfected" or "transformed" cells may have been manipulated to introduce the exogenous polynucleotide(s), or may be progeny cells derived therefrom.

Recombinant Cells

The invention also provides a recombinant cell, preferably a recombinant plant cell, which is a host cell transformed with one or more recombinant molecules, such as the polynucleotides, chimeric DNAs or recombinant vectors defined herein. The recombinant cell may comprise any combination thereof, such as two or three recombinant vectors, or a recombinant vector and one or more additional polynucleotides or chimeric DNAs. Suitable cells of the invention include any cell that can be transformed with a polynucleotide, chimeric DNA or recombinant vector of the invention, such as for example, a molecule encoding a polypeptide or enzyme described herein. The cell is preferably a cell which is thereby capable of being used for producing LC-PUFA. The recombinant cell may be a cell in culture, a cell in vitro, or in an organism such as for example a plant, or in an organ such as for example a seed or a leaf. Preferably, the cell is in a plant, more preferably in the seed of a plant.

Host cells into which the polynucleotide(s) are introduced can be either untransformed cells or cells that are already transformed with at least one nucleic acid molecule. Such nucleic acid molecules may be related to LC-PUFA synthesis, or unrelated. Host cells of the present invention either can be endogenously (i.e., naturally) capable of producing proteins defined herein, in which case the recombinant cell derived therefrom has an enhanced capability of producing the polypeptides, or can be capable of producing such proteins only after being transformed with at least one polynucleotide of the invention. In an embodiment, a recombinant cell of the invention has a enhanced capacity to synthesize a long chain polyunsaturated fatty acid. As used herein, the term "cell with an enhanced capacity to synthesize a long chain polyunsaturated fatty acid" is a relative term where the recombinant cell of the invention is compared to the host cell lacking the polynucleotide(s) of the invention, with the recombinant cell producing more long chain polyunsaturated fatty acids, or a greater concentration of LC-PUFA such as EPA, DPA or DHA (relative to other fatty acids), than the native cell. The cell with an enhanced capacity to synthesize another product, such as for example another fatty acid, a lipid, a carbohydrate such as starch, an RNA molecule, a polypeptide, a pharmaceutical or other product has a corresponding meaning.

Host cells of the present invention can be any cell capable of producing at least one protein described herein, and include bacterial, fungal (including yeast), parasite, arthropod, animal and plant cells. The cells may be prokaryotic or eukaryotic. Preferred host cells are yeast and plant cells. In a preferred embodiment, the plant cell is a seed cell, in particular a cell in a cotyledon or endosperm of a seed. In one embodiment, the cell is an animal cell or an algal cell. The animal cell may be of any type of animal such as, for example, a non-human animal cell, a non-human vertebrate cell, a non-human mammalian cell, or cells of aquatic animals such as, fish or crustacea, invertebrates, insects, etc. Non limiting examples of arthropod cells include insect cells such as *Spodoptera frugiperda* (Sf) cells, e.g. Sf9, Sf21, *Trichoplusia ni* cells, and *Drosophila* S2 cells. An example of a bacterial cell useful as a host cell of the present invention is Synechococcus spp. (also known as *Synechocystis* spp.), for example Synechococcus *elongatus*.

The cells may be of an organism suitable for a fermentation process. As used herein, the term the "fermentation process" refers to any fermentation process or any process comprising a fermentation step. A fermentation process includes, without limitation, fermentation processes used to produce alcohols (e.g., ethanol, methanol, butanol); organic acids (e.g., citric acid, acetic acid, itaconic acid, lactic acid, gluconic acid); ketones (e.g., acetone); amino acids (e.g., glutamic acid); gases (e.g., $H_2$ and $CO_2$); antibiotics (e.g., penicillin and tetracycline); enzymes; vitamins (e.g., riboflavin, beta-carotene); and hormones. Fermentation processes also include fermentation processes used in the consumable alcohol industry (e.g., beer and wine), dairy industry (e.g., fermented dairy products), leather industry and tobacco industry. Preferred fermentation processes include alcohol fermentation processes, as are well known in the art. Preferred fermentation processes are anaerobic fermentation processes, as are well known in the art. Suitable fermenting cells, typically microorganisms are able to ferment, i.e., convert, sugars, such as glucose or maltose, directly or indirectly into the desired fermentation product. Examples of fermenting microorganisms include fungal organisms, such as yeast. As used herein, "yeast" includes *Saccharomyces* spp., *Saccharomyces cerevisiae*, *Saccharomyces carlbergensis*, *Candida* spp., *Kluveromyces* spp., *Pichia* spp., *Hansenula* spp., *Trichoderma* spp., *Lipomyces starkey*, and *Yarrowia lipolytica*. Preferred yeast include strains of the *Saccharomyces* spp., and in particular, *Saccharomyces cerevisiae*.

Transgenic Plants

The invention also provides a plant comprising a cell of the invention, such as a transgenic plant comprising one or more polynucleotides of the invention. The term "plant" as used herein as a noun refers to whole plants, but as used as an adjective refers to any substance which is present in, obtained from, derived from, or related to a plant, such as for example, plant organs (e.g. leaves, stems, roots, flowers), single cells (e.g. pollen), seeds, plant cells and the like. The term "plant part" refers to all plant parts that comprise the plant DNA, including vegetative structures such as, for example, leaves or stems, roots, floral organs or structures, pollen, seed, seed parts such as an embryo, endosperm, scutellum or seed coat, plant tissue such as, for example, vascular tissue, cells and progeny of the same.

A "transgenic plant", "genetically modified plant" or variations thereof refers to a plant that contains a gene construct ("transgene") not found in a wild-type plant of the same species, variety or cultivar. Transgenic plants as defined in the context of the present invention include plants and their progeny which have been genetically modified using recombinant techniques to cause production of at least one polypeptide defined herein in the desired plant or plant organ. Transgenic plant cells and transgenic plant parts have corresponding meanings. A "transgene" as referred to herein has the normal meaning in the art of biotechnology and includes a genetic sequence which has been produced or altered by recombinant DNA or RNA technology and which has been introduced into a cell of the invention, preferably a plant cell. The transgene may include genetic sequences derived from a plant cell which may be of the same species, variety or cultivar as the plant cell into which the transgene is introduced or of a different species, variety or cultivar, or from a cell other than a plant cell. Typically, the transgene has been introduced into the cell, such as a plant, by human manipulation such as, for example, by transformation but any method can be used as one of skill in the art recognizes.

The terms "seed" and "grain" are used interchangeably herein. "Grain" refers to mature grain such as harvested grain or grain which is still on a plant but ready for harvesting, but can also refer to grain after imbibition or germination, according to the context. Mature grain commonly has a moisture content of less than about 18-20%. "Developing seed" as used herein refers to a seed prior to maturity, typically found in the reproductive structures of the plant after fertilisation or anthesis, but can also refer to such seeds prior to maturity which are isolated from a plant.

As used herein, the term "plant storage organ" refers to a part of a plant specialized to storage energy in the form of, for example, proteins, carbohydrates, fatty acids and/or oils. Examples of plant storage organs are seed, fruit, tuberous roots, and tubers. A preferred plant storage organ of the invention is seed.

As used herein, the term "phenotypically normal" refers to a genetically modified plant or plant organ, particularly a storage organ such as a seed, tuber or fruit of the invention not having a significantly reduced ability to grow and reproduce when compared to an unmodified plant or plant organ. In an embodiment, the genetically modified plant or plant organ which is phenotypically normal comprises an exogenous polynucleotide encoding a silencing suppressor operably linked to a plant storage organ specific promoter and has an ability to grow or reproduce which is essentially the same as an isogenic plant or organ not comprising said polynucleotide. Preferably, the biomass, growth rate, germination rate, storage organ size, seed size and/or the number of viable seeds produced is not less than 90% of that of a plant lacking said exogenous polynucleotide when grown under identical conditions. This term does not encompass features of the plant which may be different to the wild-type plant but which do not effect the usefulness of the plant for commercial purposes such as, for example, a ballerina phenotype of seedling leaves.

Plants provided by or contemplated for use in the practice of the present invention include both monocotyledons and dicotyledons. In preferred embodiments, the plants of the present invention are crop plants (for example, cereals and pulses, maize, wheat, potatoes, tapioca, rice, sorghum, millet, cassava, barley, or pea), or other legumes. The plants may be grown for production of edible roots, tubers, leaves, stems, flowers or fruit. The plants may be vegetables or ornamental plants. The plants of the invention may be: corn (*Zea mays*), canola (*Brassica napus, Brassica rapa* ssp.), flax (*Linum usitatissimum*), alfalfa (*Medicago sativa*), rice (*Oryza sativa*), rye (*Secale cerale*), sorghum (*Sorghum bicolour, Sorghum vulgare*), sunflower (*Helianthus annus*), wheat (*Tritium aestivum*), soybean (*Glycine max*), tobacco (*Nicotiana tabacum*), potato (*Solanum tuberosum*), peanuts (*Arachis hypogaea*), cotton (*Gossypium hirsutum*), sweet potato (*Lopmoea batatus*), cassava (*Manihot esculenta*), coffee (*Cofea* spp.), coconut (*Cocos nucifera*), pineapple (*Anana comosus*), citris tree (*Citrus* spp.), cocoa (*Theobroma cacao*), tea (*Camellia senensis*), banana (*Musa* spp.), avocado (*Persea americana*), fig (*Ficus casica*), guava (*Psidium guajava*), mango (*Mangifer indica*), olive (*Olea europaea*), papaya (*Carica papaya*), cashew (*Anacardium occidentale*), macadamia (*Macadamia intergrifolia*), almond (*Prunus amygdalus*), sugar beets (*Beta vulgaris*), oats, or barley.

In a preferred embodiment, the plant is an angiosperm.

In an embodiment, the plant is an oilseed plant, preferably an oilseed crop plant. As used herein, an "oilseed plant" is a plant species used for the commercial production of oils from the seeds of the plant. The oilseed plant may be oil-seed rape (such as canola), maize, sunflower, soybean, sorghum, flax (linseed) or sugar beet. Furthermore, the oilseed plant may be other Brassicas, cotton, peanut, poppy, mustard (i.e. Brassicaceae), castor bean, sesame, safflower, or nut producing plants. Oilseed plants in the Brassicaceae family include: the genera *Brassica, Camelina, Melanosinapis, Sinapis, Arabadopsis* eg the genera and species

*Brassica napus, Brassica rapa* ssp., *Sinapis arvensis, Brassica juncea, Brassica juncea* var. *Juncea, Brassica juncea* var. *crispifolia, Brassica juncea* var. *Foliosa, Brassica nigra, Brassica sinapioides, Camelina sativa, Melanosinapis communis, Brassica oleracea* or *Arabidopsis thaliana*. The plant may produce high levels of oil in its fruit, such as olive, oil palm or coconut. Horticultural plants to which the present invention may be applied are lettuce, endive, or vegetable brassicas including cabbage, broccoli, or cauliflower. The present invention may be applied in tobacco, cucurbits, carrot, strawberry, tomato, or pepper.

In a further preferred embodiment, the non-transgenic plant used to produce a transgenic plant of the invention produces oil, especially in the seed, which has i) less than 20%, less than 10% or less than 5% 18:2 fatty acids and/or ii) less than 10% or less than 5% 18:3 fatty acids.

In a preferred embodiment, the transgenic plant is homozygous for each and every gene that has been introduced (transgene) so that its progeny do not segregate for the desired phenotype. The transgenic plant may also be heterozygous for the introduced transgene(s), preferably uniformly heterozygous for the transgene, such as for example in F1 progeny which have been grown from hybrid seed. Such plants may provide advantages such as hybrid vigour, well known in the art.

Where relevant, the transgenic plants may also comprise additional transgenes encoding enzymes involved in the production of LC-PUFAs such as, but not limited to, a Δ6 desaturase, a Δ9 elongase, a Δ8 desaturase, a Δ6 elongase, a Δ5 desaturase, an ω3 desaturase, a Δ4 desaturase, a Δ5 elongase, diacylglycerol acyltransferase, a Δ17 desaturase, a Δ15 desaturase and/or a Δ12 desaturase. Examples of such enzymes with one of more of these activities are known in the art and include those described herein and in WO 05/103253 (see, for example, Table 1 of WO 05/103253). In specific examples, the transgenic plant at least comprises exogenous polynucleotides encoding;

a) a Δ4 desaturase, a Δ5 desaturase, a Δ6 desaturase, a Δ5 elongase and a Δ6 elongase, b) a Δ4 desaturase, a Δ5 desaturase, a Δ8 desaturase, a Δ5 elongase and a Δ9 elongase, c) a Δ4 desaturase, a Δ5 desaturase, a Δ6 desaturase, a Δ5 elongase, a Δ6 elongase, and a Δ15 desaturase, d) a Δ4 desaturase, a Δ5 desaturase, a Δ8 desaturase, a Δ5 elongase, a Δ9 elongase, and a Δ15 desaturase, e) a Δ4 desaturase, a Δ5 desaturase, a Δ6 desaturase, a Δ5 elongase, a Δ6 elongase, and a Δ17 desaturase, or f) a Δ4 desaturase, a Δ5 desaturase, a Δ8 desaturase, a Δ5 elongase, a Δ9 elongase, and a Δ17 desaturase.

Transformation of Plants

Transgenic plants can be produced using techniques known in the art, such as those generally described in A. Slater et al., Plant Biotechnology—The Genetic Manipulation of Plants, Oxford University Press (2003), and P. Christou and H. Klee, Handbook of Plant Biotechnology, John Wiley and Sons (2004).

As used herein, the terms "stably transforming", "stably transformed" and variations thereof refer to the integration of the exogenous nucleic acid molecules into the genome of the cell such that they are transferred to progeny cells during cell division without the need for positively selecting for their presence. Stable transformants, or progeny thereof, can be selected by any means known in the art such as Southern blots on chromosomal DNA or in situ hybridization of genomic DNA.

*Agrobacterium*-mediated transfer is a widely applicable system for introducing genes into plant cells because DNA can be introduced into cells in whole plant tissues or plant organs or explants in tissue culture, for either transient expression or for stable integration of the DNA in the plant cell genome. The use of *Agrobacterium*-mediated plant integrating vectors to introduce DNA into plant cells is well known in the art (see, for example, U.S. Pat. Nos. 5,177,010, 5,104,310, 5,004,863 or U.S. Pat. No. 5,159,135). The region of DNA to be transferred is defined by the border sequences, and the intervening DNA (T-DNA) is usually inserted into the plant genome. Further, the integration of the T-DNA is a relatively precise process resulting in few rearrangements. In those plant varieties where *Agrobacterium*-mediated transformation is efficient, it is the method of choice because of the facile and defined nature of the gene transfer. Preferred *Agrobacterium* transformation vectors are capable of replication in *E. coli* as well as *Agrobacterium*, allowing for convenient manipulations as described (Klee et al., In: Plant DNA Infectious Agents, Hohn and Schell, eds., Springer-Verlag, New York, pp. 179-203 (1985).

Acceleration methods that may be used include, for example, microprojectile bombardment and the like. One example of a method for delivering transforming nucleic acid molecules to plant cells is microprojectile bombardment. This method has been reviewed by Yang et al., Particle Bombardment Technology for Gene Transfer, Oxford Press, Oxford, England (1994). Non-biological particles (microprojectiles) that may be coated with nucleic acids and delivered into cells by a propelling force. Exemplary particles include those comprised of tungsten, gold, platinum, and the like. A particular advantage of microprojectile bombardment, in addition to it being an effective means of reproducibly transforming monocots, is that neither the isolation of protoplasts, nor the susceptibility of *Agrobacterium* infection are required. An illustrative embodiment of a method for delivering DNA into *Zea mays* cells by acceleration is a biolistics α-particle delivery system, that can be used to propel particles coated with DNA through a screen, such as a stainless steel or Nytex screen, onto a filter surface covered with corn cells cultured in suspension. A particle delivery system suitable for use with the present invention is the helium acceleration PDS-1000/He gun available from Bio-Rad Laboratories.

For the bombardment, cells in suspension may be concentrated on filters. Filters containing the cells to be bombarded are positioned at an appropriate distance below the microprojectile stopping plate. If desired, one or more screens are also positioned between the gun and the cells to be bombarded.

Alternatively, immature embryos or other target cells may be arranged on solid culture medium. The cells to be bombarded are positioned at an appropriate distance below the microprojectile stopping plate. If desired, one or more screens are also positioned between the acceleration device and the cells to be bombarded. Through the use of techniques set forth herein one may obtain up to 1000 or more foci of cells transiently expressing a marker gene. The number of cells in a focus that express the exogenous gene product 48 hours post-bombardment often range from one to ten and average one to three.

In bombardment transformation, one may optimize the pre-bombardment culturing conditions and the bombardment parameters to yield the maximum numbers of stable transformants. Both the physical and biological parameters for bombardment are important in this technology. Physical factors are those that involve manipulating the DNA/microprojectile precipitate or those that affect the flight and velocity of either the macro- or microprojectiles. Biological factors include all steps involved in manipulation of cells before and immediately after bombardment, the osmotic adjustment of target cells to help alleviate the trauma associated with bombardment, and also the nature of the transforming DNA, such as linearized DNA or intact supercoiled plasmids. It is believed that pre-bombardment manipulations are especially important for successful transformation of immature embryos.

In another alternative embodiment, plastids can be stably transformed. Methods disclosed for plastid transformation in higher plants include particle gun delivery of DNA containing a selectable marker and targeting of the DNA to the plastid genome through homologous recombination (U.S. Pat. Nos. 5,451,513, 5,545,818, 5,877,402, 5,932,479, and WO 99/05265).

Accordingly, it is contemplated that one may wish to adjust various aspects of the bombardment parameters in small scale studies to fully optimize the conditions. One may particularly wish to adjust physical parameters such as gap distance, flight distance, tissue distance, and helium pressure. One may also minimize the trauma reduction factors by modifying conditions that influence the physiological state of the recipient cells and that may therefore influence transformation and integration efficiencies. For example, the osmotic state, tissue hydration and the subculture stage or cell cycle of the recipient cells may be adjusted for optimum transformation. The execution of other routine adjustments will be known to those of skill in the art in light of the present disclosure.

Transformation of plant protoplasts can be achieved using methods based on calcium phosphate precipitation, polyethylene glycol treatment, electroporation, and combinations of these treatments. Application of these systems to different plant varieties depends upon the ability to regenerate that particular plant strain from protoplasts. Illustrative methods for the regeneration of cereals from protoplasts are described (Fujimura et al., 1985; Toriyama et al., 1986; Abdullah et al., 1986).

Other methods of cell transformation can also be used and include but are not limited to introduction of DNA into plants by direct DNA transfer into pollen, by direct injection of DNA into reproductive organs of a plant, or by direct injection of DNA into the cells of immature embryos followed by the rehydration of desiccated embryos.

The regeneration, development, and cultivation of plants from single plant protoplast transformants or from various transformed explants is well known in the art (Weissbach et al., In: Methods for Plant Molecular Biology, Academic Press, San Diego, Calif., (1988). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

The development or regeneration of plants containing the foreign, exogenous gene is well known in the art. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present invention containing a desired exogenous nucleic acid is cultivated using methods well known to one skilled in the art.

Methods for transforming dicots, primarily by use of *Agrobacterium tumefaciens*, and obtaining transgenic plants have been published for cotton (U.S. Pat. Nos. 5,004,863, 5,159,135, 5,518,908); soybean (U.S. Pat. Nos. 5,569,834, 5,416,011); *Brassica* (U.S. Pat. No. 5,463,174); peanut (Cheng et al., 1996); and pea (Grant et al., 1995).

Methods for transformation of cereal plants such as wheat and barley for introducing genetic variation into the plant by introduction of an exogenous nucleic acid and for regeneration of plants from protoplasts or immature plant embryos are well known in the art, see for example, CA 2,092,588, AU 61781/94, AU 667939, U.S. Pat. No. 6,100,447, PCT/US97/10621, U.S. Pat. Nos. 5,589,617, 6,541,257, and other methods are set out in Patent specification WO99/14314. Preferably, transgenic wheat or barley plants are produced by *Agrobacterium tumefaciens* mediated transformation procedures. Vectors carrying the desired nucleic acid construct may be introduced into regenerable wheat cells of tissue cultured plants or explants, or suitable plant systems such as protoplasts.

The regenerable wheat cells are preferably from the scutellum of immature embryos, mature embryos, callus derived from these, or the meristematic tissue.

To confirm the presence of the transgenes in transgenic cells and plants, a polymerase chain reaction (PCR) amplification or Southern blot analysis can be performed using methods known to those skilled in the art. Expression products of the transgenes can be detected in any of a variety of ways, depending upon the nature of the product, and include Western blot and enzyme assay. One particularly useful way to quantitate protein expression and to detect replication in different plant tissues is to use a reporter gene, such as GUS. Once transgenic plants have been obtained, they may be grown to produce plant tissues or parts having the desired phenotype. The plant tissue or plant parts, may be harvested, and/or the seed collected. The seed may serve as a source for growing additional plants with tissues or parts having the desired characteristics.

A transgenic plant formed using *Agrobacterium* or other transformation methods typically contains a single genetic locus on one chromosome. Such transgenic plants can be referred to as being hemizygous for the added gene(s). More preferred is a transgenic plant that is homozygous for the added gene(s); i.e., a transgenic plant that contains two added genes, one gene at the same locus on each chromosome of a chromosome pair. A homozygous transgenic plant can be obtained by self-fertilising a hemizygous transgenic plant, germinating some of the seed produced and analyzing the resulting plants for the gene of interest.

It is also to be understood that two different transgenic plants that contain two independently segregating exogenous genes or loci can also be crossed (mated) to produce offspring that contain both sets of genes or loci. Selfing of appropriate F1 progeny can produce plants that are homozygous for both exogenous genes or loci.

Back-crossing to a parental plant and out-crossing with a non-transgenic plant are also contemplated, as is vegetative propagation. Descriptions of other breeding methods that are commonly used for different traits and crops can be found in Fehr, In: Breeding Methods for Cultivar Development, Wilcox J. ed., American Society of Agronomy, Madison Wis. (1987).

Transgenic Non-Human Animals

A "transgenic non-human animal" refers to an animal, other than a human, that contains a gene construct ("transgene") not found in a wild-type animal of the same species or breed. A "transgene" as referred to in this context has the normal meaning in the art of biotechnology and includes a genetic sequence which has been produced or altered by recombinant DNA or RNA technology and which has been introduced into an animal cell. The transgene may include genetic sequences derived from an animal cell, which may be of the same or different species or breed as the cell into which the transgene is introduced. Typically, the transgene has been introduced into the animal by human manipulation such as, for example, by transformation but any method can be used as one of skill in the art recognizes.

Techniques for producing transgenic animals are well known in the art. A useful general textbook on this subject is Houdebine, Transgenic animals—Generation and Use (Harwood Academic, 1997). Transformation of a polynucleotide molecule into a cell can be accomplished by any method by which a polynucleotide molecule can be inserted into the cell. Transformation techniques include, but are not limited to, transfection, electroporation, microinjection, lipofection, adsorption, and cell fusion. A recombinant cell may remain unicellular or may grow into a tissue, organ or a multicellular organism. Transformed polynucleotide molecules can remain extrachromosomal or can integrate into one or more sites within a chromosome of the transformed (i.e., recombinant) cell in such a manner that their ability to be expressed is retained. Heterologous DNA can be introduced, for example, into fertilized mammalian ova. For instance, totipotent or pluripotent stem cells can be transformed by microinjection, calcium phosphate mediated precipitation, liposome fusion, retroviral infection or other means, the transformed cells are then introduced into the embryo, and the embryo then develops into a transgenic animal. In a highly preferred method, developing embryos are infected with a retrovirus containing the desired DNA, and transgenic animals produced from the infected embryo. In a most preferred method, however, the appropriate DNAs are coinjected into the pronucleus or cytoplasm of embryos, preferably at the single cell stage, and the embryos allowed to develop into mature transgenic animals.

Another method used to produce a transgenic animal involves microinjecting a nucleic acid into pro-nuclear stage eggs by standard methods. Injected eggs are then cultured before transfer into the oviducts of pseudopregnant recipients.

Transgenic animals may also be produced by nuclear transfer technology. Using this method, fibroblasts from donor animals are stably transfected with a plasmid incorporating the coding sequences for a binding domain or binding partner of interest under the control of regulatory sequences. Stable transfectants are then fused to enucleated oocytes, cultured and transferred into female recipients.

Enhancing Exogenous RNA Levels and Stabilized Expression

Silencing Suppressors

Post-transcriptional gene silencing (PTGS) is a nucleotide sequence-specific defense mechanism that can target both cellular and viral mRNAs for degradation PTGS occurs in plants or fungi stably or transiently transformed with foreign (heterologous) or endogenous DNA and results in the reduced accumulation of RNA molecules with sequence similarity to the introduced nucleic acid.

It has widely been considered that co-expression of a silencing suppressor with a transgene of interest will increase the levels of RNA present in the cell transcribed from the transgene. Whilst this has proven true for cells in vitro, significant side-effects have been observed in many whole plant co-expression studies. More specifically, as described in Mallory et al. (2002), Chapman et al. (2004), Chen et al. (2004), Dunoyer et al. (2004), Zhang et al. (2006), Lewsey et al. (2007) and Meng et al. (2008) plants expressing silencing suppressors, generally under constitutive promoters, are often phenotypically abnormal to the extent that they are not useful for commercial production.

As outlined above, the present inventors have found that RNA molecule levels can be increased, and/or RNA molecule levels stabilized over numerous generations, by limiting the expression of the silencing suppressor to a storage organ of a plant or part thereof. As used herein, a "silencing suppressor" is any polynucleotide or polypeptide that can be expressed in a plant cell that enhances the level of expression product from a different transgene in the plant cell, particularly over repeated generations from the initially transformed plant. In an embodiment, the silencing suppressor is a viral silencing suppressor or mutant thereof. A large number of viral silencing suppressors are known in the art and include, but are not limited to P19, V2, P38, Pe-Po and RPV-P0. In an embodiment, the viral silencing suppressor comprises amino acids having a sequence as provided in any one of SEQ ID NOs 97 to 101, a biologically active fragment thereof, or an amino acid sequence which is at least 50% identical to any one or more of SEQ ID NOs 97 to 101 and which has activity as a silencing suppressor.

As used herein, the terms "stabilising expression", "stably expressed", "stabilised expression" and variations thereof refer to level of the RNA molecule being essentially the same or higher in progeny plants over repeated generations, for example at least three, at least five or at least 10 generations, when compared to isogenic plants lacking the exogenous polynucleotide encoding the silencing suppressor. However, this term(s) does not exclude the possibility that over repeated generations there is some loss of levels of the RNA molecule when compared to a previous generation, for example not less than a 10% loss per generation.

The suppressor can be selected from any source e.g. plant, viral, mammal etc. The suppressor may be, for example:
flock house virus B2;
pothos latent virus P14;
pothos latent virus AC2;
African cassava mosaic virus AC4;
bhendi yellow vein mosaic disease C2;
bhendi yellow vein mosaic disease C4;
bhendi yellow vein mosaic disease βC1;
tomato chlorosis virus p22;
tomato chlorosis virus CP;
tomato chlorosis virus CPm;
tomato golden mosaic virus AL2;
tomato leaf curl Java virus βC1
tomato yellow leaf curl virus V2;
tomato yellow leaf curl virus-China C2
tomato yellow leaf curl China virus Y10 isolate βC1;
tomato yellow leaf curl Israeli isolate V2;
mungbean yellow mosaic virus-Vigna AC2;
hibiscus chlorotic ringspot virus CP;
turnip crinkle virus P38;
turnip crinkle virus CP;
cauliflower mosaic virus P6;
beet yellows virus p21;
citrus tristeza virus p20;
citrus tristeza virus p23;
citrus tristeza virus CP;
cowpea mosaic virus SCP;
sweet potato chlorotic stunt virus p22
cucumber mosaic virus 2b;
tomato aspermy virus HC-Pro
beet curly top virus L2;

soil borne wheat mosaic virus 19K;
barley stripe mosaic virus Gammab;
poa semilatent virus Gammab;
peanut clump pecluvirus P15;
rice dwarf virus Pns10;
curubit aphid borne yellows virus P0;
beet western yellows virus P0;
potato virus X P25;
cucumber vein yellowing virus P1b;
plum pox virus HC-Pro;
sugarcane mosaic virus HC-Pro
potato virus Y strain HC-Pro;
tobacco etch virus P1/HC-Pro;
turnip mosaic virus P1/HC-Pro;
cocksfoot mottle virus P1;
cocksfoot mottle virus-Norwegian isolate P1
rice yellow mottle virus P1;
rice yellow mottle virus-Nigerian isolate P1;
rice hoja blanca virus NS3
rice stripe virus NS3
crucifer infecting tobacco mosaic virus 126K;
crucifer infecting tobacco mosaic virus p122;
tobacco mosaic virus p122;
tobacco mosaic virus 126
tobacco mosaic virus 130K;
tobacco rattle virus 16K;
tomato bushy stunt virus P19;
tomato spotted wilt virus NSs;
apple chlorotic leaf spot virus P50;
grapevine virus A p10;
grapevine leafroll associated virus-2 homolog of BYV p21, as well as variants/mutants thereof. The list above provides the virus from which the suppressor can be obtained and the protein (eg B2, P14 etc) or coding region designation for the suppressor from each particular virus.

Multiple copies of a suppressor may be used. Different suppressors may be used together (e. g., in tandem).

RNA Molecules

Essentially any RNA molecule which is desirable to be expressed in a plant storage organ can be co-expressed with the silencing suppressor. The RNA molecule may influence an agronomic trait, insect resistance, disease resistance, herbicide resistance, sterility, grain characteristics, and the like. The encoded polypeptides may be involved in metabolism of oil, starch, carbohydrates, nutrients, etc., or may be responsible for the synthesis of proteins, peptides, fatty acids, lipids, waxes, oils, starches, sugars, carbohydrates, flavors, odors, toxins, carotenoids. hormones, polymers, flavonoids, storage proteins, phenolic acids, alkaloids, lignins, tannins, celluloses, glycoproteins, glycolipids, etc.

In a particular example, the plants produced increased levels of enzymes for oil production in plants such as Brassicas, for example oilseed rape or sunflower, safflower, flax, cotton, soya bean or maize; enzymes involved in starch synthesis in plants such as potato, maize, and cereals such as wheat barley or rice; enzymes which synthesize, or proteins which are themselves, natural medicaments, such as pharmaceuticals or veterinary products.

Types of polypeptides that are contemplated for production in a method of the present invention include pharmaceutical proteins for use in mammals, including man, such as insulin, preproinsulin, proinsulin, glucagon, interferons such as α-interferon and γ-interferon, blood-clotting factors such as Factor VII, VIII, IX, X, XI, and XII, fertility hormones such as luteinising hormone, follicle stimulating hormone growth factors such as epidermal growth factor, platelet-derived growth factor, granulocyte colony stimulating factor, prolactin, oxytocin, thyroid stimulating hormone, adrenocorticotropic hormone, calcitonin, parathyroid hormone, somatostatin, erythropoietin (EPO), enzymes such as β-glucocerebrosidase, haemoglobin, serum albumin, collagen, growth hormone, human serum albumin, human-secreted alkaline phosphatase, aprotinin, α1-antitrypsin, IgG1 (phosphonate ester), IgM (neuropeptide hapten), SIgA/G (*Streptococcus mutans* adhesin), scFv-bryodin 1 immunotoxin (CD 40), IgG (HSV), LSC (HSV) and the like.

Furthermore, the method of the invention can be used for the production of specific antibodies, including antibody-related molecules or active fragments thereof which bind, for example, bone morphogenetic protein receptor-type IB; E16; STEAP1; MPF; Napi3b; Sema 5b; PSCA; Endothelin type B receptor; MSG783; STEAP2; TrpM4; CRIPTO; CD21; CD79b; FcRH2; HER2; NCA; MDP; IL20Rα; Brevican; EphB2R; ASLG659; PSCA; GEDA; B cell-activating factor receptor; CD22; CD79a; CXCR5; HLA-DOB; P2X5; CD72; LY64; FcRH1; IRTA2; TENB2; CD20; VEGF including VEGF_A, B, C or D; p53; EGFR; progesterone receptor; cathepsin D; Bcl-2; E cadherin; CEA; Lewis X; Ki67; PCNA; CD3; CD4; CD5; CD7; CD11c; CD11d; c-Myc; tau; PrPSC; or A3.

In addition, the method of the invention can be used for the production of an antigen, which may or may not be delivered by consumption of the storage organ, examples of which include Hepatitis B virus envelope protein, rabies virus glycoprotein, *Escherichia coli* heat-labile entertoxin, Norwalk virus capsid protein, diabetes autoantigen, cholera toxin B subunit, cholera toxin B and A2 subunits, rotavirus entertoxin and enterotoxigenic *E. coli* fimbrial antigen fusions, porcine transmissible gastroenteritis virus glycoprotein S, human rhinovirus 15 (HRV-14) and human immunodeficiency virus type (HIV-1) epitopes, Mink Enteritis Virus epitopes, foot and mouth disease virus VP1 structural protein, human cytomegalovirus glycoprotein B, dental caries (*S. mutans*) antigens, and respiratory syncytial virus antigens.

Levels of LC-PUFA Produced

The levels of the LC-PUFA or combination of LC-PUFAs that are produced in the recombinant cell are of importance. The levels may be expressed as a composition (in percent) of the total fatty acid that is a particular LC-PUFA or group of related LC-PUFA, for example the ω3 LC-PUFA or the ω6 LC-PUFA, or the VLC-PUFA, or other which may be determined by methods known in the art. The level may also be expressed as a LC-PUFA content, such as for example the percentage of LC-PUFA in the dry weight of material comprising the recombinant cells, for example the percentage of the dry weight of seed that is LC-PUFA. It will be appreciated that the LC-PUFA that is produced in an oilseed may be considerably higher in terms of LC-PUFA content than in a vegetable or a grain that is not grown for oil production, yet both may have similar LC-PUFA compositions, and both may be used as sources of LC-PUFA for human or animal consumption.

The levels of LC-PUFA may be determined by any of the methods known in the art. In a preferred method, total lipid is extracted from the cells, tissues or organisms and the fatty acid converted to methyl esters before analysis by gas chromatography (GC). Such techniques are described in Example 1. The peak position in the chromatogram may be used to identify each particular fatty acid, and the area under each peak integrated to determine the amount. As used herein, unless stated to the contrary, the percentage of particular fatty acid in a sample is determined as the area under the peak for that fatty acid as a percentage of the total area for fatty acids in the chromatogram. This corresponds essentially to a weight percentage (w/w). The identity of fatty acids may be confirmed by GC-MS. Total lipid may be separated by techniques known in the art to purify fractions such as the TAG fraction. For example, thin-layer chromatography (TLC) may be performed at an analytical scale to separate TAG from other lipid fractions such as DAG, acyl-CoAs or phospholipid in order to determine the fatty acid composition specifically of TAG.

In one embodiment, the sum total of ARA, EPA, DPA and DHA in the fatty acids in the cell comprises at least 15%, more preferably at least 20% or at least 25% of the total fatty acids in the cell. In a more preferred embodiment, the sum total of those fatty acids is at least 29%, at least 30% or at least 31% of the total fatty acids in the cell. In a further embodiment, the total fatty acid in the cell has less than 1% C20:1. In another embodiment, the amount of DHA in the fatty acids in the cell is at least 3%, more preferably at least 4%, more preferably at least 5% or at least 7%, or most preferably at least 10%, of the total fatty acids in the cell. In preferred embodiments, the extractable TAG in the cell comprises the fatty acids at the levels referred to in this paragraph. Each possible combination of these features is also encompassed. For example, the sum total of ARA, EPA, DPA and DHA in the fatty acids in the cell may comprises at least 15%, at least 20%, at least 25%, at least 29%, at least 30% or at least 31% of the total fatty acids in the cell, of which at least 3%, at least 4%, at least 5%, at least 7% or at least 10% of the total fatty acids in the cell is DHA, while the level of C20:1 may be less than 1%.

In each of these embodiments, the recombinant cell may be a cell of an organism that is suitable for fermentation such as, for example, a unicellular microorganism which may be a prokaryote or a eukaryote such as yeast, or a plant cell. In a preferred embodiment, the cell is a cell of an angiosperm (higher plant). In a further preferred embodiment, the cell is a cell in a seed such as, for example, an oilseed or a grain or cereal.

The level of production of LC-PUFA in the recombinant cell may also be expressed as a conversion ratio, i.e., the amount of the LC-PUFA formed as a percentage of one or more substrate PUFA or LC-PUFA. With regard to EPA, for example, this may be expressed as the ratio of the level of EPA (as a percentage in the total fatty acid) to the level of a substrate fatty acid (ALA, SDA, ETA or ETrA).

In one embodiment, the efficiency of conversion of ALA to EPA is at least 80%, or more preferably at 90%. In another embodiment, the efficiency of conversion of ALA to EPA, DPA or DHA (calculated as the sum of the percentages for EPA, DPA and DHA/the sum of the percentages for ALA and all Δ6-desaturated fatty acid products from ALA) is at least 17.3%, or at least 23%. In another embodiment, the efficiency of conversion of ALA to DPA or DHA (calculated as the sum of the percentages for DPA and DHA/the sum of the percentages for ALA and all Δ6-desaturated fatty acid products from ALA) is at least 15.4%, or at least 21%. In another embodiment, the efficiency of conversion of ALA to DHA (calculated as the percentage for DHA/the sum of the percentages for ALA and all Δ6-desaturated fatty acid products from ALA) is at least 9.5%, or at least 10.8%. In another embodiment, the efficiency of conversion of EPA to DHA (calculated as the percentage for DHA/the sum of the percentages for EPA and all Δ5-elongated fatty acid products from EPA) is at least 45%, or at least 50%. In another embodiment, the efficiency of conversion of SDA to produce ETA (calculated as the sum of the percentages for ETA and Δ5-desaturated fatty acid products from ETA/the sum of the percentages for SDA and all Δ6-elongated fatty acid products from SDA) is at least 50%, more preferably at least 60%. In another embodiment, the efficiency of conversion of ALA to ETrA is at least 6%, more preferably at least 9%. In another embodiment, the conversion efficiency of EPA to DPA (calculated as the sum of the percentages for DPA and DHA/the sum of the percentages for EPA, DPA and DHA) through a Δ5 elongase step is at least 60%, more preferably at least 65%, more preferably at least 70% or most preferably at least 75%.

The content of the LC-PUFA in the recombinant cell may be maximized if the parental cell used for introduction of the genes is chosen such that the level of fatty acid substrate that is produced or provided exogenously is optimal. The level of LC-PUFA may also be maximized by growing or incubating the cells under optimal conditions, for example at a slightly lower temperature than the standard temperature for that cell, which is thought to favour accumulation of polyunsaturated fatty acid. In particular however, evidence to date suggests that some desaturases expressed heterologously in yeast or plants have relatively low activity in combination with some elongases. This may be alleviated by providing a desaturase with the capacity of to use an acyl-CoA form of the fatty acid as a substrate in LC-PUFA synthesis, and this is thought to be advantageous in recombinant cells other than yeast such as plant cells.

Production of Oils

Techniques that are routinely practiced in the art can be used to extract, process, and analyze the oils produced by cells, plants, seeds, etc of the instant invention. Typically, plant seeds are cooked, pressed, and extracted to produce crude oil, which is then degummed, refined, bleached, and deodorized. Generally, techniques for crushing seed are known in the art. For example, oilseeds can be tempered by spraying them with water to raise the moisture content to, e.g., 8.5%, and flaked using a smooth roller with a gap setting of 0.23 to 0.27 mm. Depending on the type of seed, water may not be added prior to crushing. Application of heat deactivates enzymes, facilitates further cell rupturing, coalesces the oil droplets, and agglomerates protein particles, all of which facilitate the extraction process.

The majority of the seed oil is released by passage through a screw press. Cakes expelled from the screw press are then solvent extracted, e.g., with hexane, using a heat traced column. Alternatively, crude oil produced by the pressing operation can be passed through a settling tank with a slotted wire drainage top to remove the solids that are expressed with the oil during the pressing operation. The clarified oil can be passed through a plate and frame filter to remove any remaining fine solid particles. If desired, the oil recovered from the extraction process can be combined with the clarified oil to produce a blended crude oil.

Once the solvent is stripped from the crude oil, the pressed and extracted portions are combined and subjected to normal oil processing procedures (i.e., degumming, caustic refining, bleaching, and deodorization). Degumming can be performed by addition of concentrated phosphoric acid to the crude oil to convert non-hydratable phosphatides to a hydratable form, and to chelate minor metals that are present. Gum is separated from the oil by centrifugation. The oil can be refined by addition of a sufficient amount of a sodium hydroxide solution to titrate all of the fatty acids and removing the soaps thus formed.

Deodorization can be performed by heating the oil to 260° C. under vacuum, and slowly introducing steam into the oil at a rate of about 0.1 ml/minute/100 ml of oil. After about 30 minutes of sparging, the oil is allowed to cool under vacuum. The oil is typically transferred to a glass container and flushed with argon before being stored under refrigeration. If the amount of oil is limited, the oil can be placed under vacuum, e.g., in a Parr reactor and heated to 260° C. for the same length of time that it would have been deodorized. This treatment improves the color of the oil and removes a majority of the volatile substances.

Feedstuffs

The present invention includes compositions which can be used as feedstuffs. For purposes of the present invention, "feedstuffs" include any food or preparation for human or animal consumption (including for enteral and/or parenteral consumption) which when taken into the body (a) serve to nourish or build up tissues or supply energy; and/or (b) maintain, restore or support adequate nutritional status or metabolic function. Feedstuffs of the invention include nutritional compositions for babies and/or young children.

Feedstuffs of the invention comprise, for example, a cell of the invention, a plant of the invention, the plant part of the invention, the seed of the invention, an extract of the invention, the product of the method of the invention, the product of the fermentation process of the invention, or a composition along with a suitable carrier(s). The term "carrier" is used in its broadest sense to encompass any component which may or may not have nutritional value. As the skilled addressee will appreciate, the carrier must be suitable for use (or used in a sufficiently low concentration) in a feedstuff such that it does not have deleterious effect on an organism which consumes the feedstuff.

The feedstuff of the present invention comprises an oil, fatty acid ester, or fatty acid produced directly or indirectly by use of the methods, cells or plants disclosed herein. The composition may either be in a solid or liquid form. Additionally, the composition may include edible macronutrients, vitamins, and/or minerals in amounts desired for a particular use. The amounts of these ingredients will vary depending on whether the composition is intended for use with normal individuals or for use with individuals having specialized needs, such as individuals suffering from metabolic disorders and the like.

Examples of suitable carriers with nutritional value include, but are not limited to, macronutrients such as edible fats, carbohydrates and proteins. Examples of such edible fats include, but are not limited to, coconut oil, borage oil, fungal oil, black current oil, soy oil, and mono- and diglycerides. Examples of such carbohydrates include (but are not limited to): glucose, edible lactose, and hydrolyzed search. Additionally, examples of proteins which may be utilized in the nutritional composition of the invention include (but are not limited to) soy proteins, electrodialysed whey, electrodialysed skim milk, milk whey, or the hydrolysates of these proteins.

With respect to vitamins and minerals, the following may be added to the feedstuff compositions of the present invention: calcium, phosphorus, potassium, sodium, chloride, magnesium, manganese, iron, copper, zinc, selenium, iodine, and Vitamins A, E, D, C, and the B complex. Other such vitamins and minerals may also be added.

The components utilized in the feedstuff compositions of the present invention can be of semi-purified or purified origin. By semi-purified or purified is meant a material which has been prepared by purification of a natural material or by de novo synthesis.

A feedstuff composition of the present invention may also be added to food even when supplementation of the diet is not required. For example, the composition may be added to food of any type, including (but not limited to): margarine, modified butter, cheeses, milk, yogurt, chocolate, candy, snacks, salad oils, cooking oils, cooking fats, meats, fish and beverages.

The genus *Saccharomyces* spp is used in both brewing of beer and wine making and also as an agent in baking, particularly bread. Yeast is a major constituent of vegetable extracts. Yeast is also used as an additive in animal feed. It will be apparent that genetically engineered yeast strains can be provided which are adapted to synthesise LC-PUFA as described herein. These yeast strains can then be used in food stuffs and in wine and beer making to provide products which have enhanced fatty acid content.

Additionally, fatty acids produced in accordance with the present invention or host cells transformed to contain and express the subject genes may also be used as animal food supplements to alter an animal's tissue or milk fatty acid composition to one more desirable for human or animal consumption. Examples of such animals include sheep, cattle, horses and the like.

Furthermore, feedstuffs of the invention can be used in aquaculture to increase the levels of fatty acids in fish for human or animal consumption.

Preferred feedstuffs of the invention are the plants, seed and other plant parts such as leaves and stems which may be used directly as food or feed for humans or other animals. For example, animals may graze directly on such plants grown in the field or be fed more measured amounts in controlled feeding. The invention includes the use of such plants and plant parts as feed for increasing the LC-PUFA levels in humans and other animals.

Compositions

The present invention also encompasses compositions, particularly pharmaceutical compositions, comprising one or more of the fatty acids and/or resulting oils produced using the methods of the invention.

A pharmaceutical composition may comprise one or more of the fatty acids and/or oils, in combination with a standard, well-known, non-toxic pharmaceutically-acceptable carrier, adjuvant or vehicle such as phosphate-buffered saline, water, ethanol, polyols, vegetable oils, a wetting agent or an emulsion such as a water/oil emulsion. The composition may be in either a liquid or solid form. For example, the composition may be in the form of a tablet, capsule, ingestible liquid or powder, injectable, or topical ointment or cream. Proper fluidity can be maintained, for example, by the maintenance of the required particle size in the case of dispersions and by the use of surfactants. It may also be desirable to include isotonic agents, for example, sugars, sodium chloride, and the like. Besides such inert diluents, the composition can also include adjuvants, such as wetting agents, emulsifying and suspending agents, sweetening agents, flavoring agents and perfuming agents.

Suspensions, in addition to the active compounds, may comprise suspending agents such as ethoxylated isostearyl alcohols, polyoxyethylene sorbitol and sorbitan esters, microcrystalline cellulose, aluminum metahydroxide, bentonite, agar-agar, and tragacanth or mixtures of these substances.

Solid dosage forms such as tablets and capsules can be prepared using techniques well known in the art. For example, fatty acids produced in accordance with the present invention can be tableted with conventional tablet bases such as lactose, sucrose, and cornstarch in combination with binders such as acacia, cornstarch or gelatin, disintegrating agents such as potato starch or alginic acid, and a lubricant such as stearic acid or magnesium stearate. Capsules can be prepared by incorporating these excipients into a gelatin capsule along with antioxidants and the relevant fatty acid (s).

For intravenous administration, the fatty acids produced in accordance with the present invention or derivatives thereof may be incorporated into commercial formulations.

A typical dosage of a particular fatty acid is from 0.1 mg to 20 g, taken from one to five times per day (up to 100 g daily) and is preferably in the range of from about 10 mg to about 1, 2, 5, or 10 g daily (taken in one or multiple doses). As known in the art, a minimum of about 300 mg/day of fatty acid, especially LC-PUFA, is desirable. However, it will be appreciated that any amount of fatty acid will be beneficial to the subject.

Possible routes of administration of the pharmaceutical compositions of the present invention include, for example, enteral (e.g., oral and rectal) and parenteral. For example, a liquid preparation may be administered orally or rectally. Additionally, a homogenous mixture can be completely dispersed in water, admixed under sterile conditions with physiologically acceptable diluents, preservatives, buffers or propellants to form a spray or inhalant.

The dosage of the composition to be administered to the patient may be determined by one of ordinary skill in the art and depends upon various factors such as weight of the patient, age of the patient, overall health of the patient, past history of the patient, immune status of the patient, etc.

Additionally, the compositions of the present invention may be utilized for cosmetic purposes. It may be added to pre-existing cosmetic compositions such that a mixture is formed or a fatty acid produced according to the subject invention may be used as the sole "active" ingredient in a cosmetic composition.

EXAMPLES

Example 1. Materials and Methods

Culturing Microalgae

*Micromonas* CS-0170 and *Pyramimonas* CS-0140 isolates from the CSIRO Collection of Living Microalgae (www.marine.csiro.au/microalgae) were cultivated under standard culture conditions. A stock culture from the Collection was sub-cultured and scaled-up in a dilution of 1 in 10 over consecutive transfers in 1 L Erlenmeyer flasks and then into 10 L polycarbonate carboys. The culture medium was f/2, a modification of Guillard and Ryther's (1962) f medium containing half-strength nutrients, with a growth temperature of 20±1° C. Other culturing conditions included a light intensity of 100 µmol. photons PAR·m−2·s−1, 12:12 hour light:dark photoperiod, and bubbling with 1% $CO_2$ in air at a rate of 200 $mL·L^{-1}·min^{-1}$.

Isolation of Microalgal Genomic DNA

Genomic DNA from *Micromonas* CS-0170 and *Pyramimonas* CS-0140 was isolated using the DNeasy Plant Mini Kit system as described in the accompanying instruction manual (QIAGEN, catalogue #69106).

Isolation of Microalgal Total RNA

Total RNA was isolated from *Micromonas* CS-0170 and *Pyramimonas* CS-0140 cells using the following method. 2 g (wet weight) of cells were powdered using a mortar and pestle in liquid nitrogen and sprinkled slowly into a beaker containing 22 mL of extraction buffer that was being stirred constantly. To this, 5% insoluble polyvinylpyrrolidone, 90 mM 2-mercaptoethanol, and 10 mM dithiothreitol were added and the mixture stirred for a further 10 minutes prior to being transferred to a Corex™ tube. 18.4 mL of 3 M ammonium acetate was added and mixed well. The sample was then centrifuged at 6000×g for 20 minutes at 4° C. The supernatant was transferred to a new tube and nucleic acid precipitated by the addition of 0.1 volume of 3 M NaAc (pH 5.2) and 0.5 volume of cold isopropanol. After a 1 hour incubation at −20° C., the sample was centrifuged at 6000×g for 30 minutes in a swing rotor. The pellet was resuspended in 1 mL of water extracted with phenol/chloroform. The aqueous layer was transferred to a new tube and nucleic acids were precipitated once again by the addition of 0.1 volume 3 M NaAc (pH 5.2) and 2.5 volumes of ice cold ethanol. The pellet was resuspended in water and the concentration of nucleic acid determined by spectrophotometer.

Vectors and Strains

Plasmid pYES2 and yeast strain INVSC1 were obtained from Invitrogen, plasmid vector pGEMT-Easy from Promega, plasmid vector pBluescript II KS—from Stratagene. *Agrobacterium tumefaciens* strain AGL1 was referred to by Lazo et al. (1991) and the pORE binary vector series by Coutu et al. (2007).

PCR Conditions

To amplify DNA fragments by polymerase chain reaction (PCR), standard conditions were used unless specified otherwise. Optimisation of conditions was carried out by varying the number of amplification cycles, the temperature for annealing of the primers, $Mg^{2+}$ concentration and other parameters as is typically done in the art. Buffers were as specified by the suppliers of the polymerases. Typically, reaction conditions were as follows. After an initial denaturation at 94° C. for 2-3 min, reaction mixtures were treated for 20-40 cycles of denaturation/annealing/extension with denaturation at 94° C. for 30-60 sec, primer annealing at 40-60° C. for 30 sec, and polymerase extension for 30-60 sec at 70-72° C., followed by a further extension step of 3 min at 70-72° C.

Reverse transcription-PCR (RT-PCR) amplification was typically carried out using the Superscript III One-Step RT-PCR system (Invitrogen) in a volume of 25 µL using 10 pmol of the forward primer and 30 pmol of the reverse primer, $MgSO_4$ to a final concentration of 2.5 mM, 400 ng of total RNA with buffer and nucleotide components according to the manufacturer's instructions. Typical temperature regimes were: 1 cycle of 45° C. for 30 minutes for the reverse transcription to occur; then 1 cycle of 94° C. for 2 minutes followed by 40 cycles of 94° C. for 30 seconds, 52° C. for 30 seconds, 70° C. for 1 minute; then 1 cycle of 72° C. for 2 minutes before cooling the reaction mixtures to 5° C.

5' and 3'-RACE

To obtain full length cDNAs corresponding to partial length gene fragments, the 5' and/or 3' ends of cDNAs were obtained by 5'- and 3'-RACE (Rapid Amplification of cDNA Ends) methods. The 3' end of a cDNA was isolated using a gene specific forward primer as specified in the Examples and an oligo-dT reverse primer 5'-ATTTAGGTGACAC-TATAGTTTTTTTTTTTTTTTTTTV-3' (SEQ ID NO:41), where V represents either A, G or C, which was in common to all of the 3'-RACE reactions. An RT-PCR amplification was carried out using the Superscript III One-Step RT-PCR system (Invitrogen) in a volume of 25 µL using 10 pmol of the forward primer and 30 pmol of the reverse primer, $MgSO_4$ to a final concentration of 2.5 mM, 400 ng of total RNA as template for cDNA synthesis, and buffer and nucleotide components as specified by the supplier. The cycling conditions were typically: 1 cycle of 45° C. for 30 minutes for reverse transcription; then 1 cycle of 94° C. for 2 minutes; followed by 40 cycles of 94° C. for 30 seconds, 52° C. for 30 seconds, 70° C. for 1 minute and 1 cycle of 72° C. for 2 minutes before cooling to 5° C. The amplicons generated in the reaction were ligated into pGEM-T Easy, cloned into E. coli and sequenced by standard methods.

Unless specified otherwise, the 5' end of cDNAs were isolated using a modified terminal-transferase method with 2 μg of total RNA as template for cDNA synthesis. pmol of a gene specific reverse primer was added to the total RNA and 10.8 μL water before the mixture was heated at 65° C. for 5 minutes and chilled on ice for 2 minutes. The following components were then added: 4 μL of Superscript III first-strand cDNA buffer (Invitrogen), 1 μL of 0.1 M dithiothreitol, 1 μL RNAseOUT (Invitrogen) and 1 μL of Superscript III reverse transcriptase. The mixture was then incubated at 55° C. for 60 minutes and the reaction terminated by a further incubation at 70° C. for 15 minutes. After being cooled briefly on ice the reaction was then treated with 2 units of RNAseH at 37° C. for 20 minutes. The cDNA was then purified using the QIAQUICK PCR Purification Kit (QIAGEN, catalogue #28106). 25 μL of the eluate was then A-tailed using 10 units of TdT (NEB), 5 μL of NEB Buffer #4, 5 μL of 2.5 mM $CoCl_2$, 0.5 μL of 10 mM dATP in a total of 50 μL. The reaction was performed at 37° C. for 30 minutes followed by inactivation of the enzyme at 70° C. for 10 minutes. A PCR reaction was then performed using 2.5 units of Taq DNA polymerase (NEB) in the reaction mixture including 5 μL of the A-tailed cDNA, 10 pmol of the gene specific reverse primer, 30 pmol of a modified oligo-dT primer 5'-ATTTAGGTGACAC-TATAGTTTTTTTTTTTTTTTTTTV-3' (SEQ ID NO:41), where V represents either A, G or C, and buffer and nucleotide components as specified in the accompanying manual. The cycling conditions were typically: 1 cycle of 94° C. for 2 minutes; 5 cycles of 94° C. for 20 seconds, 54° C. for 1 minute, 72° C. for 1 minute; 30 cycles of 94° C. for 20 seconds, 60° C. for 30 seconds, 72° C. for 1 minute; 1 cycle of 72° C. for 5 minutes; 4° C. hold. If no clear product band was visible in the expected size range after gel electrophoresis, the region of the gel was excised and DNA products purified from the gel. A sample of 1 μL of a 1:20 dilution of the eluate was used as template in a second round of PCR. The amplicons generated in the reaction were ligated into pGEM-T Easy and sequenced.

Yeast Culturing and Feeding with Precursor Fatty Acids

Plasmids were introduced into yeast by heat shock and transformants were selected on yeast minimal medium (YMM) plates containing 2% raffinose as the sole carbon source. Clonal inoculum cultures were established in liquid YMM with 2% raffinose as the sole carbon source. Experimental cultures in were inoculated from these, in YMM+1% NP-40, to an initial OD600 of ~0.3. Cultures were grown at 30° C. with shaking (~60 rpm) until OD600 was approximately 1.0. At this point galactose was added to a final concentration of 2% and precursor fatty acids were added to a final concentration of 0.5 mM. Cultures were incubated at 20° C. with shaking for a further 48 hours prior to harvesting by centrifugation. Cell pellets were washed with 1% NP-40, 0.5% NP-40 and water to remove any unincorporated fatty acids from the surface of the cells.

Expression of Genes in Plant Cells in a Transient Expression System

Genes were expressed in plant cells in a transient expression system essentially as described by Voinnet et al. (2003). Plasmids containing the coding region to be expressed from a strong constitutive promoter such as the 35S promoter were introduced into Agrobacterium tumefaciens strain AGL1. A chimeric gene 35S:p19 for expression of the p19 viral silencing suppressor was separately introduced into AGL1. The recombinant cells were grown at 28° C. in LB broth supplemented with 50 mg/mL kanamycin and 50 mg/mL rifampicin to stationary phase. The bacteria were then pelleted by centrifugation at 5000 g for 15 min at room temperature before being resuspended to OD600=1.0 in an infiltration buffer containing 10 mM MES pH 5.7, 10 mM $MgCl_2$ and 100 uM acetosyringone. The cells were then incubated at 28° C. with shaking for 3 hours before equal volumes of Agrobacterium cultures containing 35S:p19 and the test chimeric gene(s) of interest were mixed prior to infiltration into leaf tissue. The plants were typically grown for a further five days after infiltration before leaf discs were taken for GC analysis of the fatty acids.

Where leaf tissue was supplied with exogenous fatty acids, the fatty acids were prepared by heating the appropriate fatty acid in 2M ammonium hydroxide solution for 20 minutes at 60° C. after which the solution was evaporated, also at 60° C. The resulting salt was then resuspended in 0.1M phosphate buffer (pH 7.2) to a final concentration of 0.5 μg/mL. The fatty acid salt was injected into the leaf four days after Agrobacterium infiltration and leaf discs taken at various time points after feeding, for example from 2-48 hours after addition of the exogenous fatty acid, for analysis of the fatty acid composition. Controls were included where the exogenous fatty acid was omitted, or where the Agrobacterium strain used for the infiltration did not contain the gene of interest.

Gas Chromatography (GC) Analysis of Fatty Acids

Fatty Acid Preparation

Where a sample contained a large amount of water, including all Nicotiana benthamiana leaf samples and other non-seed tissues, the total lipids were extracted using the method described by Bligh and Dyer (1959) prior to methylation. Fatty acid methyl esters (FAME) were formed by transesterification of the centrifuged yeast pellet, Arabidopsis seeds, total lipids from Nicotiana benthamiana or other total lipid samples by heating with MeOH—$CHCl_3$—HCl (10:1:1, v/v/v) at 90-100° C. for 2 hours in a glass test tube fitted with a Teflon-lined screw-cap. FAME were extracted into hexane-dichloromethane (4:1, v/v) and analysed by GC and GC-MS.

Capillary Gas-Liquid Chromatography (GC)

FAME were analysed by gas chromatography (GC) using an Agilent Technologies 6890N GC (Palo Alto, California, USA) equipped with an Equity™-1 fused silica capillary column (15 m×0.1 mm i.d., 0.1 μm film thickness), an FID, a split/splitless injector and an Agilent Technologies 7683 Series auto sampler and injector. Helium was used as the carrier gas. Samples were injected in splitless mode at an oven temperature of 120° C. After injection, the oven temperature was raised to 270° C. at 10° C.·$min^{-1}$ and finally to 310° C. at 5° C.·$min^{-1}$. Peaks were quantified with Agilent Technologies ChemStation software (Rev B.03.01 (317), \ Palo Alto, California, USA).

Gas Chromatography-Mass Spectrometry (GC-MS)

GC-MS was carried out on a Finnigan GCQ Plus GC-MS ion-trap fitted with on-column injection set at 4° C. Samples were injected using an AS2000 auto sampler onto a retention gap attached to an HP-5 Ultra 2 bonded-phase column (50 m×0.32 mm i.d.×0.17 μm film thickness). The initial temperature of 45° C. was held for 1 minute, followed by temperature programming at 30° C.·$min^{-1}$ to 140° C. then at 3° C.·$min^{-1}$ to 310° C. where it was held for 12 minutes. Helium was used as the carrier gas. Mass spectrometer operating conditions were: electron impact energy 70 eV; emission current 250 μamp, transfer line 310° C.; source temperature 240° C.; scan rate 0.8 scans·s$^{-1}$ and mass range 40-650 Dalton. Mass spectra were acquired and processed with Xcalibur™ software.

Yeast Culturing and Feeding with Precursor Fatty Acids

Plasmids were introduced into yeast by heat shock and transformants were selected on yeast minimal medium (YMM) plates containing 2% raffinose as the sole carbon source. Clonal inoculum cultures were established in liquid YMM with 2% raffinose as the sole carbon source. Experimental cultures in were inoculated from these, in YMM+1% NP-40, to an initial OD$_{600}$ of ~0.3. Cultures were grown at 30° C. with shaking (~60 rpm) until OD$_{600}$ was approximately 1.0. At this point galactose was added to a final concentration of 2% and precursor fatty acids were added to a final concentration of 0.5 mM. Cultures were incubated at 20° C. with shaking for a further 48 hours prior to harvesting by centrifugation. Cell pellets were washed with 1% NP-40, 0.5% NP-40 and water to remove any unincorporated fatty acids from the surface of the cells.

Example 2. Isolation and Characterisation of cDNAs Encoding Δ6-Elongase from Microalgae Isolation of a *Micromonas* CS-0170 Δ6-Elongase Gene Fragment The *Micromonas* CS-0170 strain in the CSIRO Living Collection of Microalgae (WO2005/103253) was identified as a microalgal strain that had a high native level of Δ5- and Δ6-elongation (Table 4).

TABLE 4

Conversion of fatty acids in the CSIRO Collection of Living Microalgae strains *Micromonas* CS-0170 and *Pyramimonas* CS-0140.

| Type | PRASINOPHYCEAE | PRASINOPHYCEAE |
|---|---|---|
| Species | *Micromonas pusilla* | *Pyramimonas cordata* |
| Strain | CS0170 | CS0140 |
| Phase | logarithmic | logarithmic |
| 16:1 (n-7) | 0.7 | 0.8 |
| 18:1 (n-9) | 0.3 | 0.2 |
| 18:1 (n-7) | 5.5 | 14.8 |
| 16:2 (n-7) | 0.2 | 0.0 |
| 18:2 (n-6) | 0.1 | 0.7 |
| 18:3 (n-6) | 0.0 | 0.0 |
| 20:4 n-6) | 0.0 | 0.0 |
| 16:3 (n-3) | 0.0 | 0.0 |
| 16:4 (n-3) | 20.4 | 14.3 |
| 18:3 (n-3) | 1.4 | 4.6 |
| 18:4 (n-3) | 20.7 | 25.6 |
| 18:5 (n-3) | 16.7 | 3.4 |
| 20:3 (n-3) | 0.1 | 1.2 |
| 20:4 (n-3) | 0.0 | 0.0 |
| 20:5 (n-3) | 0.3 | 0.4 |
| 22:5 (n-3) | 0.3 | 4.1 |
| 22:6 (n-3) | 8.5 | 4.5 |

In an attempt to identify conserved sequences, elongase amino acid sequences from GenBank accession numbers AAV67800, ABC18314, CAD58540, CAL55414, AAV67797, XP_001416454, AAW70157, AAV67799, ABC18313, AAY15135 were aligned using the ClustalW algorithm. Amongst numerous regions of homology of various degrees of identity, the consensus amino acid sequence blocks KXXXXXDT (SEQ ID NO:31) and MYXYY (SEQ ID NO:32) were chosen (where each X is, independently, any amino acid), corresponding to amino acid positions 144-151 and 204-208, respectively, of AAY15135. The degenerate primers 5'-AAGWWCIKSGARYI-SYTCGACAC-3' (SEQ ID NO:42) and 5'-AIIMIRTAR-TASGTGTACAT-3' (SEQ ID NO:43) where I=inosine, W=A or T, R=A or G, Y=C or T, K=G or T, M=A or C, S=C or G, were synthesised based on the sequences of these two blocks. An RT-PCR amplification was carried out using the Superscript III One-Step RT-PCR system (Invitrogen) in a volume of 50 µL using 20 pmol of each primer, MgSO$_4$ to a final concentration of 2.5 mM, 200 ng of *Micromonas* CS-0170 total RNA with buffer and nucleotide components as specified. The cycling conditions were: initial 48° C. for 30 minutes for reverse transcription, then 1 cycle of 94° C. for 2 minutes, followed by 5 cycles of 94° C. for 30 seconds, 40° C. for seconds, 70° C. for 30 seconds; then 40 cycles of 94° C. for 30 seconds, 45° C. for 30 seconds, 70° C. for 30 seconds and then 72° C. for 2 minutes. A 209 bp amplicon was generated, ligated into pGEM-T Easy and sequenced.

Isolation of a Full Length cDNA Encoding *Micromonas* CS-0170 Δ6-Elongase

Primers were designed to extend the 209 bp fragment by 5'- and 3'-RACE. The 3' end of the gene was isolated as described in Example 1 using the gene specific forward primer 5'-GAACAACGACTGCATCGACGC-3' (SEQ ID NO:44) and 200 ng of *Micromonas* CS-0170 total RNA. A 454 bp amplicon was generated, ligated into pGEM-T Easy and sequenced. The 5' end of the gene was isolated using the GeneRacer Kit (Invitrogen, catalogue #L1500-01) with a reverse-transcription incubation of 55° C. for 1 hour to generate 5'-adapted cDNA as described in the accompanying manual. The GeneRacer 5' Primer 5'-CGACTG-GAGCACGAGGACACTGA-3' (SEQ ID NO:45) and the gene specific reverse primer 5'-TTGCGCAGCACCAT-AAAGACGGT-3' (SEQ ID NO:46) were used in a PCR amplification using PFU Ultra II Fusion DNA polymerase in a volume of 50 µL using 10 pmol of each primer, 1 µl of the GeneRacer cDNA template with buffer and nucleotide components as specified by the manufacturer (Stratagene, catalogue #600670). The cycling conditions were: 1 cycle of 94° C. for 2 minutes; 35 cycles of 94° C. for 20 seconds, 55° C. for 30 seconds, 72° C. for 30 seconds; then 72° C. for 2 minutes before cooling to 4° C. This product was then diluted 1:10 and 1 µl used as template in a second round of PCR using the GeneRacer 5' Nested Primer 5'-GGACACTGACATGGACTGAAGGAGTA-3' (SEQ ID NO:47) and the gene specific reverse primer 5'-TTGCGCAGCACCATAAAGACGGT-3' (SEQ ID NO:46) using the same PCR conditions as used in the first round of amplification. A 522 bp amplicon was generated, ligated into pGEM-T Easy and sequenced.

The nucleotide sequences of the three amplicons were assembled into one sequence which was predicted to be the full-length sequence. The full length coding region with a short region of 5' UTR was then amplified from genomic DNA from *Micromonas* strain CS-0170 using forward primer 5'-CAGGCGACG CGCGCCAGAGTCC-3' (SEQ ID NO:48), reverse primer 5'-TTATTAGT-TACTTGGCCTTTACCTTC-3' (SEQ ID NO:49) and PFU Ultra II Fusion DNA polymerase (Stratagene). An 860 bp amplicon was generated, ligated into pGEM-T Easy and sequenced. The sequence of the open reading frame of the gene is presented in having the sequence of SEQ ID NO: 1.

The full-length amino acid sequence encoded by the gene is presented as SEQ ID NO:2. BLAST analysis of the protein sequence revealed that the isolated cDNA encoded either a Δ5- or Δ6-elongase. These two types of elongases are similar at the amino acid level and it was uncertain from amino acid sequence alone which activity was encoded. When used as a query sequence to the Genbank protein sequence database using BLASTP, the maximum degree of identity between the *Micromonas* CS-0170 elongase and other elongases was 65% with Accession No. CAL55414 which is the sequence for *Ostreococcus tauri* polyunsaturated fatty acid elongase 2. The conserved GNS1/SUR4 family domain (NCBI conserved domain pfam01151) is represented in this sequence at amino acids 49 to 274, which typically indicates that the protein is involved in long chain fatty acid elongation systems.

A sequence relationship tree based on multiple alignment of sequences similar to the *Micromonas* CS-0170 elongase, including those used to design the original degenerate primers, is provided in FIG. 3.

Functional Characterisation of the *Micromonas* CS-0170 Δ6-Elongase in Yeast

The entire protein coding region of this clone, contained within a SalI/SphI fragment in pGEM-T Easy was inserted into pYES2 at the XhoI/SphI sites, generating vector pYES2+MicElo1 for introduction and functional characterisation in yeast. Cells of yeast strain INVSC1 were transformed with pYES2+MicElo1 and transformants were selected on medium without uracil. The yeast cells containing pYES2+MicElo1 were grown in culture and the GAL promoter induced by galactose for expression of the MicElo1 gene. After the addition of ALA, SDA or EPA (0.5 mM) to the culture medium and 48 hours of further culturing at 30C the fatty acids in total cellular lipids were analysed. When ALA was added to the medium the presence of ETrA in the cellular lipid of the yeast transformants was detected at 0.2 of total fatty acids, representing a low but measurable 0.4% conversion efficiency. Similarly, when SDA was added to the medium, the presence of ETA in the cellular lipid of the yeast transformants was detected at 0.2%, representing 0.4% conversion efficiency, indicating a low level of Δ6-elongase activity. However, when EPA was added to the medium, the presence of DPA in the cellular lipid of the yeast transformants was not detected, indicating a lack of Δ5-elongase activity in the yeast cells (Table 5).

TABLE 5

Conversion of fatty acids in yeast cells transformed with genetic constructs expressing elongases isolated from *Micromonas* CS-0170 and *Pyramimonas* CS-0140.

| Clone | Fatty acid precursor/ % of total FA | Fatty acid formed/ % of total FA | Conversion ratio |
|---|---|---|---|
| pYES2 + Mic-Elo1 | ALA, 18:3ω3/52.2% | ETrA, 20:3ω3/0.2% | 0.4% |
| pYES2 + Mic-Elo1 | SDA, 18:4ω3/54.3% | ETA, 20:4ω3/0.2% | 0.4% |
| pYES2 + Mic-Elo1 | EPA, 20:5ω3/2.0% | DPA, 22:5ω3/0% | 0% |
| pYES2 + Pyrco-Elo1 | ALA, 18:3ω3/51.4% | ETrA, 20:3ω3/5.3% | 9.3% |
| pYES2 + Pyrco-Elo1 | SDA, 18:4ω3/17.9% | ETA, 20:4ω3/34.1% | 65.6% |
| pYES2 + Pyrco-Elo1 | EPA, 20:5ω3/2.1% | DPA, 22:5ω3/trace | — |
| pYES2 + Pyrco-Elo2 | ALA, 18:3ω3/56.4% | ETrA, 20:3ω3/0.3% | 0.5% |
| pYES2 + Pyrco-Elo2 | SDA, 18:4ω3/51.7% | ETA, 20:4ω3/0.7% | 1.3% |
| pYES2 + Pyrco-Elo2 | EPA, 20:5ω3/0.6% | DPA, 22:5ω3/1.8% | 75.0% |

Isolation and Characterisation of a *Pyramimonas* CS-0140 Δ6-Elongase
Isolation of a *Pyramimonas* CS-0140 Δ6-Elongase Gene Fragment From an alignment of elongase amino acid sequences from GenBank accession numbers ABO9747, CAI58897, CAJ30869, CAL23339 and AAV67797, we identified the consensus amino acid sequence blocks KIYEFVDT (SEQ TD NO:33) and VHVCMYT (SEQ ID NO:34) corresponding to amino acid positions 143-150 and 199-205, respectively, of AAV67797. The degenerate primers 5'-AARATMTAYGAGTTYGTIGATAC-3' (SEQ ID NO:50) and 5'-TAIGTGTACATGCACACRTGWACCC-3' (SEQ ID NO:51) (abbreviations as above) were synthesised based on the sequences of these two blocks. An RT-PCR amplification was carried out using the Superscript III One-Step RT-PCR system with 100 ng of *Pyramimonas* CS-0140 total RNA. A 191 bp amplicon was generated, ligated into pGEM-T Easy and sequenced.

Isolation of a Full Length *Pyramimonas* CS-0140 Δ6-Elongase Gene

Primers were designed to extend the 191 bp fragment by 5'- and 3'-RACE. The 3' end of the gene was isolated using the gene specific forward primer 5'-TTCGTGGATACGTT-CATCATGC-3' (SEQ ID NO:52) as described in Example 1. A 945 bp amplicon was generated, ligated into pGEM-T Easy and sequenced. The 5' end of the gene was isolated from 1 µg of *Pyramimonas* CS-0140 total RNA using the GeneRacer Kit with a reverse-transcription incubation of 55° C. for 1 hour to generate 5'-adapted cDNA as described in the accompanying manual. The GeneRacer 5' Primer and the gene specific reverse primer 5'-AGTT-GAGCGCCGCCGAGAAGTAC-3' (SEQ ID NO:53) were used in a PCR amplification using PFU Ultra II Fusion DNA polymerase. This product was then diluted 1:10 and 1 µl used as template in a second round of PCR using the GeneRacer 5' Nested Primer 5'-GGACACTGA-CATGGACTGAAGGAGTA-3' (SEQ ID NO:47) and the gene specific reverse primer 5'-ACCTGGTTGACGTTGCCCTTCA-3' (SEQ ID NO:54) using the same PCR conditions as used in the first round of amplification. A 743 bp amplicon was generated, ligated into pGEM-T Easy and sequenced. The three partial sequences were then assembled into one predicted full length sequence.

The full length coding region with a short region of 5' UTR was then amplified from total RNA by RT-PCR. The forward primer 5'-GCTATGGAGTTCGCTCAGCCT-3' (SEQ ID NO:55) and the reverse primer 5'-TTAC-TACTGCTTCTTGCTGGCCAGCT-3' (SEQ ID NO:56) were used with 100 ng of *Pyramimonas* CS-0140 total RNA. A 900 bp amplicon generated, ligated into pGEM-T Easy and sequenced. The nucleotide sequence of the open reading frame of the amplicon is given as SEQ ID NO:3 and the amino acid sequence of the encoded protein is given as SEQ ID NO:4.

BLAST analysis indicated that the full-length amino acid sequence provided as SEQ ID NO:4) has similarity to other Δ5- and Δ6-elongases. The maximum degree of identity between the *Pyramimonas* CS-0140 elongase and other proteins (BLASTX) was 54% with AAV67797, the *Ostreococcus tauri* polyunsaturated fatty acid elongase 1. A sequence relationship tree based on multiple alignment of sequences similar to the *Pyramimonas* CS-0140 elongase, including those used to design the original degenerate primers, is provided in FIG. 4. The conserved GNS1/SUR4 family domain (NCBI conserved domain pfam01151) is represented in this sequence at amino acids 52 to 297, which typically indicates that the protein is involved in long chain fatty acid elongation systems.

Function Characterisation of the *Pyramimonas* CS-0140 Δ6-Elongase in Yeast

The entire protein coding region of this clone, contained within an EcoRI fragment in pGEM-T Easy was inserted into pYES2 at the EcoRI site, generating the vector pYES2+Pyrco-Elo1 for introduction and functional characterisation in yeast. Cells of yeast strain INVSC1 were transformed with pYES2+Pyrco-Elo1 and transformants were selected on medium without uracil. The yeast cells containing pYES2+Pyrco-Elo1 were grown in culture and then induced by galactose to express the Pyrco-Elo1 cDNA. Fatty acids were added to the culture medium to a final concentration of 0.5 mM and further cultured at 30° C. for 48 hrs, after which the fatty acids in total cellular lipids were analysed. When ALA was added to the medium, the presence of ETrA in the cellular lipid of the yeast transformants was detected at 5.3% of total fatty acids, representing a conversion efficiency (Δ9-elongase activity) of 9.3%. When SDA was added to the medium, the presence of ETA in the cellular lipid of the yeast transformants was detected at 34.1%, representing 65.6% conversion efficiency, a high level of Δ6-elongase activity. However, when EPA was added to the medium, the presence of DPA in the cellular lipid of the yeast transformants was not detected (Table 5), indicating the cDNA encoded Δ6-elongase activity with some Δ9-elongase activity, but no Δ5-elongase activity in the yeast cells.

The data described above for the two Δ6-elongase genes showed that the gene from *Pyramimonas* encoded an enzyme that was much more active than the gene from *Micromonas*. This was unexpected. The possibilities that the coding region amplified from the *Micromonas* genomic DNA contained a mutation or that the coding region was incomplete were not excluded.

Example 3. Isolation and Characterisation of cDNAs Encoding Δ5-Elongase from Microalgae Isolation of a *Pyramimonas* CS-0140 Δ5-Elongase Gene Fragment The *Pyramimonas* CS-0140 strain in the CSIRO Living Collection of Microalgae was identified as a microalgal strain that had a high native level of Δ5- and Δ6-elongation (Table 4).

An alignment was carried out of elongase amino acid sequences from GenBank accession numbers AAV67798 and AB098084. From numerous matching sequences, we chose the consensus amino acid sequence blocks YLELLDT (SEQ ID NO:35) and MYSYY (SEQ ID NO:36) corresponding to amino acid positions 136-142 and 198-202, respectively, of AAV67798. The degenerate primers 5'-AR-TAYYTSGARYTRYTGGAYAC-3' (SEQ ID NO:57) and 5'-CATKARRTARTASGAGTACAT-3' (SEQ ID NO:58) (abbreviations as above) were synthesised based on the sequences of these two blocks. An RT-PCR amplification was carried out using the Superscript III One-Step RT-PCR system as described in Example 1. 0.5 μl of this reaction was then used as template in a second round of PCR using Taq DNA polymerase (NEB) with the same primers. A 200 bp amplicon was generated, ligated into pGEM-T Easy and sequenced.

Isolation of a Full Length *Pyramimonas* CS-0140 Δ5-Elongase Gene

Primers were designed to extend the 200 bp fragment by 5'- and 3'-RACE. The 3' end of the gene was isolated using the gene specific forward primer 5'-CATCATACCCTGTT-GATCTGGTC-3' (SEQ ID NO:59) and an oligo-dT reverse primer as in Example 1. A 408 bp amplicon was generated, ligated into pGEM-T Easy (Promega) and sequenced. The 5' end of the gene was isolated from 1 μg of *Pyramimonas* CS-0140 total RNA using the GeneRacer Kit with a reverse-transcription incubation of 55° C. for 1 hour to generate 5'-adapted cDNA as described in the accompanying manual. The gene specific reverse primer 5'-CCAGAT-CAACAGGGTATGATGGT-3' (SEQ ID NO:60) was used in the PCR amplification using PFU Ultra II Fusion DNA polymerase as specified by the manufacturer. This product was then diluted 1:10 and 1 μl used as template in a second round of PCR using the GeneRacer 5' Nested Primer 5'-GGACACTGACATGGACTGAAGGAGTA-3' (SEQ ID NO:47) and the gene specific reverse primer 5'-CGAAAGCTGGTCAAACTTCTTGCGCAT-3' (SEQ ID NO:61). A 514 bp amplicon was generated, ligated into pGEM-T Easy (Promega) and sequenced. The full length sequence was assembled from the three partial sequences.

The full length coding region with a short region of 5' UTR was then amplified from total RNA by RT-PCR. The forward primer 5'-AACATGGCGTCTATTGCGAT-TCCGGCT-3' (SEQ ID NO:62) and the reverse primer 5'-TTATTACTGCTTCTTGGCACCCTTGCT-3' (SEQ ID NO:63) were used in a RT-PCR amplification as described in Example 1. An 810 bp amplicon was generated, ligated into pGEM-T Easy and sequenced. The nucleotide sequence of the open reading frame of the insert as provided as SEQ ID NO:5, and the predicted amino acid sequence encoded by the cDNA is shown as SEQ ID NO:6.

BLAST analysis indicated that the full-length amino acid sequence had homology with other Δ5- and Δ6-elongases. BLASTP analysis showed that the maximum degree of identity between the *Pyramimonas* CS-0140 elongase and other proteins in the Genbank database was 46%, with Accession No. ABR67690 corresponding to a *Pavlova viridis* C20 elongase. A sequence relationship tree based on multiple alignment of sequences similar to the *Pyramimonas* CS-0140 elongase, including those used to design the original degenerate primers, is provided in FIG. 5.

Functional Characterisation of the *Pyramimonas* CS-0140 Δ5-Elongase in Yeast

The entire protein coding region of this clone, contained within an EcoRI fragment of the cDNA in pGEM-T Easy was inserted into pYES2 at the EcoRI site, generating pYES2+Pyrco-Elo2 for introduction and functional characterisation in yeast. Cells of yeast strain INVSC1 were transformed with pYES2+Pyrco-Elo2 and transformants were selected on medium without uracil. The yeast cells containing pYES2+Pyrco-Elo2 were grown in culture and then induced by galactose to express the cDNA. After the addition of fatty acids to the culture medium and 48 hours of further culturing at 30° C., the fatty acids in cellular lipids were analysed. When ALA was added to the medium the presence of ETrA in the cellular lipid of the yeast transformants was detected at 0.3% of total fatty acids, representing an 0.5% conversion efficiency (Δ9-elongase activity). When SDA was added to the medium the presence of ETA in the cellular lipid of the yeast transformants was detected at 0.7%, representing a 1.3% conversion efficiency (Δ6-elongase activity). When EPA was added to the medium, the presence of DPA in the cellular lipid of the yeast transformants was detected at 1.8%, representing a surprisingly high 75% conversion efficiency, indicating strong Δ5-elongase activity in the yeast cells (Table 6).

The present inventors believe such efficient conversion of EPA to DPA in a recombinant cell has not been reported previously. It is predicted that the conversion efficiency in planta for this enzyme will be similarly high. The conserved GNS1/SUR4 family domain (NCBI conserved domain pfam01151) is represented in this sequence at amino acids 50 to 267, which typically indicates that the protein is involved in long chain fatty acid elongation systems.

TABLE 6

Conversion of fatty acids in yeast cells transformed with genetic constructs expressing elongases isolated from *Micromonas* CS-0170 and *Pyramimonas* CS-0140.

| Clone | Fatty acid precursor/ % of total FA | Fatty acid formed/ % of total FA | Conversion ratio |
|---|---|---|---|
| pYES2 + Mic-Elo1 | ALA, 18:3ω3/52.2% | ETrA, 20:3ω3/0.2% | 0.4% |
| pYES2 + Mic-Elo1 | SDA, 18:4ω3/54.3% | ETA, 20:4ω3/0.2% | 0.4% |
| pYES2 + Mic-Elo1 | EPA, 20:5ω3/2.0% | DPA, 22:5ω3/0% | 0% |
| pYES2 + Pyrco-Elo1 | ALA, 18:3ω3/51.4% | ETrA, 20:3ω3/5.3% | 9.3% |
| pYES2 + Pyrco-Elo1 | SDA, 18:4ω3/17.9% | ETA, 20:4ω3/34.1% | 65.6% |
| pYES2 + Pyrco-Elo1 | EPA, 20:5ω3/2.1% | DPA, 22:5ω3/trace | — |
| pYES2 + Pyrco-Elo2 | ALA, 18:3ω3/56.4% | ETrA, 20:3ω3/0.3% | 0.5% |
| pYES2 + Pyrco-Elo2 | SDA, 18:4ω3/51.7% | ETA, 20:4ω3/0.7% | 1.3% |
| pYES2 + Pyrco-Elo2 | EPA, 20:5ω3/0.6% | DPA, 22:5ω3/1.8% | 75.0% |

Example 4. Isolation and Characterisation of Genes Encoding Δ6-Desaturase from Microalgae Synthesis of a Full Length *Micromonas* CCMP1545 Δ6-Desaturase Gene The *Micromonas* CCMP1545 filtered protein models genome sequence produced by the US Department of Energy Joint Genome Institute (www.jgi.doe.gov/) was analysed with the BLASTP program using the *Ostreococcus tauri* Δ6-desaturase amino acid sequence, Genbank Accession No. AAW70159, as the query sequence. This analysis revealed the presence of a predicted protein in *Micromonas* CCMP1545 that had homology with AAW70159. The *Micromonas* CCMP1545 predicted protein sequence was used to design and synthesize a codon-optimized nucleotide sequence that was most suitable for expression in dicotyledonous plants such as *Brassica napus*. The nucleotide sequence of the protein coding region is given in SEQ ID NO:7. The plasmid construct was designated pGA4. The amino acid sequence is shown as SEQ ID NO:8.

BLASTP analysis using the *Micromonas* CCMP1545 desaturase amino acid sequence SEQ ID NO:8 as query to other proteins in the Genbank database showed that the protein had homology with Δ6-desaturases. The highest degree of identity was 66% along the full-length with the amino acid sequence of Accession No. AAW70159, the sequence of an *Ostreococcus tauri* Δ6-desaturase. A sequence relationship tree based on multiple alignment of sequences similar to the *Micromonas* CCMP1545 desaturase is provided in FIG. 6. This front-end desaturase contains a cytochrome b5 domain (NCBI conserved domain pfam00173) at amino acids 54 to 104 and the Δ6-FADS-like conserved domain (NCBI conserved domain cd03506) at amino acids 172 to 428. The three histidine boxes indicative of a front-end desaturase are present in this sequence at 190-195, 227-232 and 401-405, respectively. Proteins containing both of these domains are typically front-end desaturases required for the synthesis of highly unsaturated fatty acids. Interestingly, this desaturase clusters closely with AAW70159, the only biochemically confirmed plant-like acyl-CoA desaturase published to date.

Function Characterisation of the *Micromonas* CCMP1545 Δ6-Desaturase in Yeast Cells The entire coding region of the *Micromonas* desaturase, contained within a KpnI-SacI fragment from plasmid pGA4 was inserted into yeast vector pYES2 at the KpnI-SacI site, generating pYES2+Micd6D for introduction and functional characterisation in yeast. Cells of yeast strain INVSC1 were transformed with pYES2+Micd6D and transformants were selected on medium without uracil. The yeast cells containing pYES2+Micd6D were grown in culture and then induced by galactose. After the addition of 0.5 mM LA, ALA, ETrA, DGLA or ETA to the culture medium and 48 hours of further culturing at 30° C., the fatty acids in total cellular lipids were analysed. When LA was added to the medium the presence of GLA in the cellular lipid of the yeast transformants was detected at 39% of total fatty acids, representing a Δ6-desaturation conversion efficiency of 11.40%. When ALA was added to the medium the presence of SDA in the cellular lipid of/the yeast transformants was detected at 13.9% of total fatty acids, representing a Δ6-desaturation conversion efficiency of 39.0%. That is, the conversion efficiency for ω3 fatty acid substrates was 3.5-fold greater than for the corresponding 6 fatty acid substrate. When ETrA was added to the medium the presence of ETA in the cellular lipid of the yeast transformants was detected at 0.21% of total fatty acids, representing a Δ8-desaturation conversion efficiency of 8.0%. However, when either DGLA or ETA were added to the medium, the presence of ARA or EPA, respectively, was not detected. This indicated the absence of any Δ5-desaturation activity (Table 7).

TABLE 7

Conversion of fatty acids in yeast cells transformed with genetic constructs expressing desaturases isolated from Micromonas CCMP1545, *Ostreococcus lucimarinus* and *Pyramimonas* CS-0140.

| Clone | Fatty acid precursor/ % of total FA | Fatty acid formed/ % of total FA | Conversion ratio |
|---|---|---|---|
| pYES2 + Mic-d6D | LA, 18:2ω6/30.3% | GLA, 18:3ω6/3.9% | 11.4% |
| pYES2 + Mic-d6D | ALA, 18:3ω3/21.7% | SDA, 18:4ω3/13.9% | 39.0% |
| pYES2 + Mic-d6D | ETrA, 20:3ω3/2.4% | ETA, 20:4ω3/0.21% | 8.0% |
| pYES2 + Mic-d6D | DGLA, 20:3ω6/2.6% | ARA, 20:4ω6/0% | — |
| pYES2 + Mic-d6D | ETA, 20:4ω3/6.2% | EPA, 20:5ω3/0% | — |
| pYES2 + Ostlu-d6D | LA, 18:2ω6/29.5% | GLA, 18:3ω6/2.1% | 6.6% |
| pYES2 + Ostlu-d6D | ALA, 18:3ω3/21.8% | SDA, 18:4ω3/13.8% | 38.8% |
| pYES2 + Ostlu-d6D | ETrA, 20:3ω3/2.2% | ETA, 20:4ω3/0% | — |
| pYES2 + Ostlu-d6D | GLA, 18:3ω6/29.2% | 18:4ω6/0% | — |
| pYES2 + Ostlu-d6D | SDA, 18:4ω3/41.7% | 18:5ω3/0% | — |
| pYES2 + Ostlu-d6D | DGLA, 20:3ω6/2.3% | ARA, 20:4ω6/0% | — |
| pYES2 + Ostlu-d6D | ETA, 20:4ω3/4.9% | EPA, 20:5ω3/0% | — |
| pYES2 + Pyrco-d5D | LA, 18:2ω6/35.1% | GLA, 18:3ω6/0% | — |
| pYES2 + Pyrco-d5D | ALA, 18:3ω3/40.9% | SDA, 18:4ω3/0% | — |
| pYES2 + Pyrco-d5D | DGLA, 20:3ω6/2.9% | ARA, 20:4ω6/0.12% | 4.0% |
| pYES2 + Pyrco-d5D | ETA, 20:4ω3/7.2% | EPA, 20:5ω3/0.26% | 3.5% |

Function Characterisation of the *Micromonas* CCMP1545 Δ6-Desaturase in Plant Cells The enzyme activities of the *Micromonas* CCMP1545 Δ6-desaturase (Mic1545-d6D) and an *Echium plantagineum* Δ6-desaturase (Echpl-d6D; Zhou et al., 2006), used here as a positive control sample, were demonstrated in planta using an enhanced *Nicotiana benthamiana* transient expression system as described in Example 1. A vector designated 35S-pORE04 was made by inserting a PstI fragment containing a 35S promoter into the SfoI site of vector pORE04 after T4 DNA polymerase treatment to blunt the ends (Coutu et al., 2007). A genetic construct 35S:Mic1545-d6D was made by inserting the entire coding region of pGA4, contained within a SwaI fragment, into 35S-pORE04 at the SmaI-EcoRV site, generating pJP2064.

These chimeric vectors were introduced into *Agrobacterium tumefaciens* strain AGL1 and cells from cultures of these infiltrated into leaf tissue of *Nicotiana benthamiana* plants in the greenhouse. The plants were grown for a further five days after infiltration before leaf discs were taken for GC analysis which revealed that both genes were functioning as Δ6-desaturases in *Nicotiana benthamiana*.

Leaf tissue transformed with the *Echium plantagineum* Δ6-desaturase contained GLA (0.4%) and SDA (1.2%), which represented conversion efficiencies of 3.8% and 4.4%, respectively. Leaf tissue transformed with the *Micromonas* CCMP1545 Δ6-desaturase contained SDA (2.2%) which represented a conversion efficiency of 6.9% but no detectable GLA. The absence of GLA in the leaf tissue could be due to an extreme preference in planta for the ω3 substrate ALA compared with the ω6 substrate LA, or in part to the presence of native *Nicotiana benthamiana* ω3 desaturase activity which would convert some of the GLA produced by Δ6-desaturation to SDA. Such effects have been noted as likely in previous experiments describing acyl-PC Δ6-desaturases with ω3 substrate preference (Sayanova et al., 2006), although the extent to which this occurs was not quantified in that study.

Omega-3 Substrate Preference of *Micromonas* Δ6-Desaturase

The Δ6-desaturase isolated from *Micromonas* had a surprisingly strong preference for ω3 substrates in planta as well as in yeast. The enzyme expressed in yeast cells was observed to have 3.5-fold greater activity on ω3-desaturated fatty acid substrates than the corresponding ω6-desaturated fatty acid substrates. The observed preference for ω3 substrates was entirely surprising and unexpected based on the reported lack of preference for the *O. tauri* enzyme (Domergue et al., 2005). Reports on expression of the *O. tauri* Δ6-desaturase in yeast or in plant seed indicate similar activity on LA and ALA.

The use of this gene or other genes with such high specificity for ω3-desaturated fatty acid substrates together with other fatty acid desaturases and elongases as part of a recombinant VLC-PUFA pathway in plants was therefore predicted to increase the levels of EPA, DPA and DHA relative to the use of desaturases without preference for ω3-desaturated substrates. Such an increase was predicted to occur as a result of reducing the conversion of LA to GLA and the subsequent ω6 PUFAs DGLA and ARA which are not efficiently converted in planta to their ω3 counterparts by fungal or yeast Δ17-desaturases. Whilst a Δ6 desaturase with a preference for ω3 fatty acid substrates has been isolated (Sayanova et al., 2003), it had activity on phospholipid-linked acyl chains. In contrast, the desaturase obtained from *Micromonas* are predicted to have activity on acyl-CoA substrates.

Dual Δ6 Δ8 Function of *Micromonas* CCMP1545 Δ6-Desaturase

It was interesting to note that the *Micromonas* CCMP1545 Δ6-desaturase displayed a significant level of Δ8-desaturase activity and so had significant dual activities, in contrast to the *Ostreococcus lucimarinus* enzyme which did not have detectable Δ8-desaturase activity (below). The dual desaturase activity is predicted to be useful in the construction of dual Δ6/Δ8-desaturase pathways in planta, or where the elongase that is used in construction of such pathways has both Δ9-elongase and Δ6-elongase activities. The use of such a gene would help to reduce the accumulation of ETrA by converting it to ETA, which would then be Δ5-desaturated to EPA.

Synthesis of a Full Length *Ostreococcus lucimarinus* Δ6-Desaturase Gene

The GenBank database of non-redundant protein sequences was analysed by BLASTX using the *Ostreococcus tauri* Δ6-desaturase nucleotide sequence (Accession No. AY746357) as the query sequence. From this analysis, an *Ostreococcus lucimarinus* gene was identified which encoded a partial-length protein with amino acid sequence of Accession No. XP_001421073. The genomic DNA sequences flanking the region coding for XP_001421073 were then examined to identify putative translation start and stop codons to define the full-length protein coding region, the nucleotide sequence of which is given as SEQ ID NO:9. The coding region was then translated into a protein sequence, given as SEQ ID NO:10. This amino acid sequence was used to design and synthesize a codon-optimized nucleotide sequence that was most suitable for expression in *Brassica napus* and other dicotyledonous plants, having the nucleotide sequence shown in SEQ ID NO:11.

BLASTP analysis using the *Ostreococcus lucimarinus* desaturase amino acid sequence as query to other proteins in the Genbank database showed that SEQ ID NO:10 had homology with Δ6-desaturases. The highest degree of identity along the full-length sequence was 76% with the amino acid sequence of Accession No. AAW70159, the sequence for the *Ostreococcus tauri* Δ6-desaturase. A sequence relationship tree based on multiple alignment of sequences similar to the *Ostreococcus lucimarinus* desaturase is provided in FIG. 7. This front-end desaturase contained a cytochrome b5 domain (NCBI conserved domain pfam00173) at amino acids 55 to 108 and the Δ6-FADS-like conserved domain (NCBI conserved domain cd03506) at amino acids 198 to 444. The three histidine boxes indicative of a front-end desaturase are present in this sequence at amino acids 207-212, 244-249 and 417-421. Proteins containing both of these domains are typically front-end desaturases required for the synthesis of highly unsaturated fatty acids. Interestingly, this desaturase clusters closely with AAW70159, the only biochemically confirmed plant-like acyl-CoA desaturase published to date.

Functional Characterisation of the *Ostreococcus lucimarinus* Δ6-Desaturase in Yeast Cells The entire coding region of the *Ostreococcus* gene (SEQ ID NO:11), contained within a NotI fragment in pGEM-T Easy was inserted into pYES2 at the NotI site, generating the chimeric vector pYES2+Ostlud6D, for introduction and functional characterisation in yeast. Cells of yeast strain INVSC1 were transformed with pYES2+Ostlud6D and transformants were selected on medium without uracil. The yeast cells containing pYES2+Ostlud6D were grown in culture and then induced by galactose. After the addition of LA, ALA, SDA or EPA each to a final concentration of 0.5 mM in the culture medium, and 48 hours of further culturing at 30° C., the fatty acids in cellular lipids were analysed. When substrate LA was added to the medium, the presence of product GLA in the cellular lipid of the yeast transformants was detected at 2.1% of total fatty acids, representing a Δ6-desaturation conversion efficiency of 6.6%. When substrate ALA was added to the medium, the presence of product SDA was detected at 13.8% of total fatty acids in the cellular lipid of the yeast transformants, representing a Δ6-desaturation conversion efficiency of 38.8%. However, when any of ETrA, DGLA or ETA were added to the medium, the presence of ETA, ARA or EPA, respectively, was not detected. This indicated the absence of any Δ5- or Δ8-desaturation activity (Table 7), and also a preference for the ω3 fatty acid substrate relative to the corresponding ω6 fatty acid of the same length and unsaturation pattern.

Acyl-CoA Substrate Specificity of Desaturases

The desaturases described in this Example were more closely related to the previously isolated Δ6-desaturase from *Ostreococcus tauri* than to other Δ6-desaturases (FIG. 9). This similarity was further highlighted when a phylogenetic tree of these genes alongside other members of the desaturase family was produced (FIG. 10). The *Ostreococcus tauri* Δ6-desaturase has been reported to be active on acyl-CoA substrates (Domergue et al., 2005). Based on these observations, it was predicted that the Δ6-desaturases encoded by the genes described above would also be active on acyl-CoA substrates rather than acyl-PC substrates. Interestingly, the *Pavlova salina* Δ5-desaturase also clustered with the *O. tauri* Δ6-desaturase and the Δ8-desaturase formed a separate branch.

To establish whether the *M. pusilla* (*Micromonas* CCMP1545) Δ6-desaturase is capable of using acyl-CoA fatty acids as substrates and thereby producing Δ6-desaturated acyl-CoA fatty acids, *S. cerevisiae* was transformed with a gene construct encoding the desaturase alone and triplicate cultures of the transformant cell lines grown in the presence of 250 μM exogenous $18:3^{\Delta9,12,15}$. Total lipids were then extracted from the cultures and fractionated into neutral lipids (NL), phosphatidylcholine (PC), phosphatidylinositol (PI), phosphatidylserine (PS) and phosphatidylethanolamine (PE) classes by thin layer chromatography (TLC), after which FAME were produced from each class and analysed by GC. The data is shown in Table 8.

ecotype Columbia and the fatty acid composition in T2 seeds of the transformed plants analysed by GC (FIG. 11).

Biochemical studies in both yeast and *N. benthamiana* provided evidence that the Δ6-desaturase from *M. pusilla* is an acyl-CoA desaturase. Analysis of the kinetics of an ensuing elongation step has been used in other studies as an indirect method to determine the ability of a desaturase to yield an acyl-CoA product: the availability of the Δ6-desaturated product (SDA) for the subsequent Δ6-elongation step, which occurs in the acyl-CoA metabolic pool, is affected by the substrate specificity of the Δ6-desaturase (Domergue et al., 2003, 2005; Hoffmann et al., 2008). Similar rates of Δ6-elongation were obtained when the Δ6-desaturases from *O. tauri* and *M. pusilla* were used, in contrast with the significantly lower level of elongation observed when the *E. plantagineum* acyl-PC Δ6-desaturase was used (FIG. 12a). Further evidence was observed when the distribution of the Δ6-desaturase product SDA in the yeast lipid classes was analysed (Table 8). No enrichment in the PC fraction was observed when compared with the total lipid fraction although such enrichment would be expected if and when the SDA was produced by an acyl-PC desaturase (Domergue et al., 2005). The relatively low levels of Δ6-desaturation observed in our study (FIG. 12) were expected since the bulk of the substrates LA and ALA in *N. benthamiana* leaf are located in the plastid and are unavailable for desaturation. However, since these fatty acids are also isolated during FAME preparation their presence effectively reduces the calculated overall conversion efficiency. Seed-

TABLE 8

Fatty acid composition (percent of total fatty acids) of total lipid and fractionated neutral lipids (NL), phosphatidylcholine (PC), phosphatidylinositol (PI), phosphatidylserine (PS) and phosphatidylethanolamine (PE) of *S. cerevisiae* transformed with the *M. pusilla* Δ6-desaturase cloned into pYES2.

| Fatty acid | Total | NL | PC | PI | PS | PE |
|---|---|---|---|---|---|---|
| 16:0 | 24.3 ± 1.5 | 24.5 ± 4.3 | 36.8 ± 3.4 | 45.6 ± 2.4 | 45.8 ± 3.9 | 37.0 ± 3.9 |
| $16:1^{\Delta3t}$ | 14.7 ± 0.4 | 12.1 ± 0.9 | 15.7 ± 0.5 | 8.1 ± 0.7 | 19.4 ± 1.0 | 21.5 ± 3.5 |
| 18:0 | 8.1 ± 0.7 | 11.5 ± 1.4 | 11.7 ± 0.7 | 17.4 ± 3.1 | 0.9 ± 1.3 | 3.6 ± 3.8 |
| $18:1^{\Delta9}$ | 11.0 ± 1.3 | 10.0 ± 2.0 | 7.0 ± 1.2 | 14.6 ± 0.9 | 26.3 ± 1.8 | 18.6 ± 2.5 |
| $18:3^{\Delta9,12,15}$ | 12.1 ± 0.7 | 12.2 ± 2.4 | 7.1 ± 0.8 | 5.6 ± 0.1 | 2.3 ± 2.0 | 6.9 ± 2.3 |
| $18:4^{\Delta6,9,12,15}$ | 29.4 ± 0.9 | 29.4 ± 1.9 | 21.0 ± 0.2 | 7.7 ± 0.7 | 4.1 ± 0.3 | 9.9 ± 1.9 |
| Other | 0.3 | 0.3 | 0.8 | 1.1 | 1.2 | 2.5 |
| Total | 100 | 100 | 100 | 100 | 100 | 100 |

In the total lipids, 71% of $18:3^{\Delta9,12,15}$ had been Δ6-desaturated to $18:4^{\Delta6,9,12,15}$. No enrichment of the product in the PC fraction was detected when compared with the total lipid extract. Indeed, there was a substantially lower percentage of $18:4^{\Delta6,9,12,15}$ in the PC fraction than in the total lipids (21.0% vs. 29.4%), indicating that the desaturase was producing $18:4^{\Delta6,9,12,15}$ as an acyl-CoA thioester (Domergue et al., 2003).

The gene encoding the *M. pusilla* Δ6-desaturase was also introduced into *Arabidopsis* plants by transformation. A genetic construct Linin:Micpu-d6D was generated by inserting the entire coding region of the *M. pusilla* Δ6-desaturase, contained within a SwaI fragment, into Linin-pWVEC8 at the SmaI site, generating linP-mic1545-d6D-linT. The promoter for this construct was the seed-specific linin promoter from flax. This construct was transformed into *A. thaliana* specific conversion efficiencies would therefore be expected to be much higher with the same genes.

Comparison Between Acyl-CoA and Acyl-PC Δ6-Desaturases

Additional comparisons were made between the *Micromonas* CCMP1545 Δ6-desaturase, *Echium plantagineum* Δ6-desaturase and *Ostreococcus tauri* Δ6-desaturase (Domergue et al., 2005) in plant cells. Genetic constructs 35S:Mic1545-d6D and 35S:Echpl-d6D as described in Example 4 were compared with a genetic construct 35S:Ostta-d6D which was made by inserting the entire coding region of the *Ostreococcus tauri* Δ6-desaturase, contained within a SwaI fragment, into 35S-pORE04 at the SmaI-EcoRV site, generating pJP3065.

Direct comparisons between the *E. plantagineum* and either the *O. tauri* and *M. pusilla* EPA pathways showed that the acyl-CoA desaturase pathways yielded far higher levels of EPA due to both more efficient Δ6-desaturation and more efficient, subsequent Δ6-elongation (FIG. 12a). The E. plantagineum Δ6-desaturase catalysed conversion of 14% of the ω3 substrate ($18:3^{\Delta 9,12,15}$ to $18:4^{\Delta 6,9,12,15}$) and 30% of the ω6 substrate ($18:2^{\Delta 9,12}$ to $18:3^{\Delta 6,9,12}$). Use of the O. tauri Δ6-desaturase resulted in 24% ω3 conversion and 40% ω6 conversion whilst use of the M. pusilla Δ6-desaturase resulted in 27% ω3 conversion and 15% ω6 conversion. These conversions resulted in the production of 1.3% $20:4^{\Delta 5,8,11,14}$ and 3.4% $20:5^{\Delta 5,8,11,14,17}$ for the E. plantagineum pathway, 1.2% $20:4^{\Delta 5,8,11,14}$ and 9.6% $20:5^{\Delta 5,8,11,14,17}$ for the O. tauri pathway and 0.6% $20:4^{\Delta 5,8,11,14}$ and 10.7% $20:5^{\Delta 5,8,11,14,17}$ for the M. pusilla pathway.

Δ6-elongation was far higher when either the O. tauri or M. pusilla Δ6-desaturases produced the substrate $18:4^{\Delta 6,9,12,15}$ compared to when the E. plantagineum desaturase was used (FIG. 12a). In addition to the ω3 substrate specificity shown by the M. pusilla Δ6-desaturase, the P. cordata Δ6-elongase (see Example 2) proved to be highly specific and converted the ω3 substrate $18:4^{\Delta 6,9,12,15}$ at a far higher rate than $18:3^{\Delta 6,9,12}$ (89% and 21%, respectively, for the M. pusilla EPA pathway).

Use of Dual Δ6-Desaturase Pathways

Comparisons were made in which the possibility of increasing Δ6-desaturation by using a pathway containing two Δ6-desaturases was explored. First, the combination of the E. plantagineum acyl-PC desaturase and the M. pusilla acyl-CoA desaturase did not significantly increase conversion efficiencies above those seen in a pathway containing only the M. pusilla desaturase (FIG. 12b). Similar results were obtained when the E. plantagineum and the O. tauri Δ6-desaturases were combined. A dual acyl-CoA Δ6-desaturase pathway in which both the O. tauri and M. pusilla desaturases were combined also did not result in increased ω3 conversion efficiencies when compared with either the O. tauri or M. pusilla pathways (FIG. 12c).

The effect of using dual Δ6-desaturases in an EPA-producing pathway was also tested. The first test was to combine the acyl-PC desaturase from E. plantagineum with both of the acyl-CoA desaturases in separate experiments. It was hypothesised that the addition of a lipid-linked desaturase might increase the conversion of any acyl-PC substrate LA or ALA to GLA or SDA, respectively. Similarly, we also tested whether the use of two acyl-CoA desaturases might increase the accumulation of EPA. Neither of these scenarios proved true in the transient assays in N. benthamiana.

Example 5. Isolation and Characterisation of Genes Encoding Δ5-Desaturase from Microalgae Isolation of a Pyramimonas CS-0140 Δ5-Desaturase Gene Fragment An alignment of desaturase amino acid sequences from GenBank accession numbers ABL96295, ABP49078, XP_001421073, AAM09687, AAT85661, AAW70159 and AAX14505 identified the consensus amino acid sequence blocks WKNNHNKHHA (SEQ ID NO:37) and HHLFPSMP (SEQ ID NO:38) corresponding to amino acid positions 197-206 and 368-375, respectively, of ABL96295. The degenerate primers 5'-GGTG-GAAGAACAAGCACAACrdncaycaygc-3' (SEQ ID NO:64) and 5'-GGGCATCGTGGGGwanarrtgrtg-3' (SEQ ID NO:65) were designed using the CODEHOP program (Rose et al., 1998) based on the sequences of these two blocks. A touchdown PCR amplification was carried out using Taq DNA polymerase (NEB) in a volume of 20 μL using 10 pmol of each primer, 50 ng of Pyramimonas CS-0140 genomic DNA with buffer and nucleotide components as specified in the accompanying manual. The cycling conditions were: 1 cycle of 94° C. for 3 minutes; 20 cycles of 94° C. for 1 minute, 70° C. for 2 minutes (−1° C. per cycle), 72° C. for 1 minute; cycles of 94° C. for 1 minute, 55° C. for 1 minute, 72° C. for 1 minute; 1 cycle of 72° C. for 5 minutes; 4° C. hold. A 551 bp amplicon was generated, ligated into pGEM-T Easy (Promega) and sequenced.

Isolation of a Full Length Pyramimonas CS-0140 Δ5-Desaturase Gene

Primers were designed to extend the 551 bp fragment by 5'- and 3'-RACE and used as described in Example 1. The 3' end of the cDNA for the gene encoding the Δ5-desaturase was isolated using the gene specific forward primer 5'-AGCGAGTACCTGCATTGGGT-3' (SEQ ID NO:66) and the modified oligo-dT reverse primer as in Example 1. A 477 bp amplicon was generated, ligated into pGEM-T Easy and sequenced. The 5' end of the gene was isolated by the modified terminal-transferase method as in Example 1. The gene specific reverse primer was 5'-ATAGTGCTTGGTGCGCAAGCTGTGCCT-3' (SEQ ID NO:67). After two rounds of PCR amplification, a 317 bp amplicon was generated, ligated into pGEM-T Easy (Promega) and sequenced. The three partial sequences were assembled into the predicted sequence of the full length gene.

The full length protein coding region with a short region of 5' UTR was then amplified from genomic DNA. The forward primer 5'-CACCATGGGAAAGG-GAGGCAATGCT-3' (SEQ ID NO:68) and the reverse primer 5'-TTACTAGTGCGCCTTGGAGTGAGAT-3' (SEQ ID NO:69) were used in a PCR amplification using PFU Ultra II Fusion DNA polymerase (Stratagene) in a volume of 20 μL using 4 pmol of each primer and 50 ng of Pyramimonas CS-0140 genomic DNA with buffer components as specified in the accompanying PFU Ultra II Fusion manual. An 1336 bp amplicon representing the full-length cDNA was generated, ligated into pGEM-T Easy and sequenced. The nucleotide sequence of the open reading frame of the cDNA is given in SEQ ID NO:12.

BLAST analysis showed that the full-length amino acid sequence encoded by the gene, given as SEQ ID NO:13, encoded a protein with similarity to known Δ5- or Δ6-desaturases. These two types of desaturases are similar at the amino acid level and it was uncertain from amino acid sequence alone which activity was encoded. Analysis of enzyme activity was carried out as described below, showing the encoded protein had Δ5-desaturase activity. The highest degree of identity between the Pyramimonas CS-0140 desaturase and other desaturases in the Genbank database as determined by BLASTP was 52%, to Accession No. EDQ92231, which was the amino acid sequence of a protein with undefined enzyme activity from Monosiga brevicollis MX1. A sequence relationship tree based on multiple alignment of sequences similar to the Pyramimonas CS-0140 desaturase, including those used to design the original degenerate primers, is provided in FIG. 8. This front-end desaturase contains a cytochrome b5 domain (NCBI conserved domain pfam00173) at amino acids 16 to 67 and the Δ6-FADS-like conserved domain (NCBI conserved domain cd03506) at amino acids 159 to 411. The three histidine boxes indicative of a front-end desaturase are present in this sequence at amino acids 175-180, 212-217 and 384-388. Proteins containing these domains are typically front-end desaturases required for the synthesis of multiply unsaturated fatty acids.

Function Characterisation of the *Pyramimonas* CS-0140 Δ5-Desaturase in Yeast

The entire coding region of this clone, contained within a NotI fragment in pGEM-T Easy was inserted into pYES2 (Invitrogen) at the NotI site, generating pYES2+Pyrco-des2 for introduction and functional characterisation in yeast. Cells of yeast strain INVSC1 (Invitrogen) were transformed with pYES2+Pyrco-des2 and transformants were selected on medium without uracil. The yeast cells containing pYES2+Pyrco-des2 were grown in culture and then induced by galactose. After the addition of 0.5 mM LA, ALA, DGLA or ETA to the culture medium and 48 hours of further culturing at 30° C., the fatty acids in cellular lipids were analysed. When DGLA was added to the medium, ARA was detected in the cellular lipid of the yeast transformants at 0.12% of total fatty acids, representing a Δ5-desaturation conversion efficiency of 4.0%. When ETA was added to the medium, EPA was detected in the cellular lipid of the yeast transformants at 0.26% of total fatty acids, representing a Δ6-desaturation conversion efficiency of 3.5%. However, when either LA or ALA were added to the medium, GAL or SDA, respectively, was not produced in the yeast transformants. This indicated that the protein did not have any Δ6-desaturation activity in the yeast cells (Table 7).

Expression of the *Pyramimonas cordata* Δ5-Desaturase in Plant Cells

The enzyme activities of the *Micromonas* CCMP1545 Δ6-desaturase (SEQ ID NO:8 encoded by SEQ ID NO:7), *Pyramimonas* CS-0140 Δ6-elongase (SEQ ID NO:4 encoded by SEQ ID NO:3) and *Pyramimonas* CS-0140 Δ5-desaturase (SEQ ID NO:13 encoded by SEQ ID NO:12) along with the *Arabidopsis thaliana* DGAT1 (SEQ ID NO:74 encoded by SEQ ID NO:75) were demonstrated in planta using an enhanced *Nicotiana benthamiana* transient expression system as described in Example 1.

A genetic construct 35S:Pyrco-d5D encoding the Δ5-desaturase under the control of the constitutive 35S promoter was made by inserting the entire coding region of the *Pyramimonas* CS-0140 Δ5-desaturase, contained within an EcoRI fragment, into 35S-pORE04 (Example 4, above) at the EcoRI site, generating 35S:Pyrco-d5D. The chimeric vectors 35S:Mic1545-d6D (Example 10), 35S:Pyrco-d6E (Example 10) and 35S:Pyrco-d5D were introduced individually into *Agrobacterium tumefaciens* strain AGL1 and transgenic cells from cultures of these were mixed and the mixture infiltrated into leaf tissue of *Nicotiana benthamiana* plants in the greenhouse. The plants were grown for a further five days after infiltration before leaf discs were taken for GC analysis which revealed that these genes were functioning to produce EPA in *Nicotiana benthamiana*. Leaf tissue transformed with these genes contained SDA (1.0%), ETA (0.1%), EPA (10.0%). The leaf tissue also contained trace levels of GLA, ETA and ARA. The Δ5-desaturase conversion efficiency was calculated to be 98.8%.

This experiment demonstrated that the microalgal Δ5-desaturases are capable of converting ETA to EPA with an efficiency of at least 90% or at least 95% in plant cells.

Example 6. Isolation and Characterisation of Genes Encoding ω3-Desaturase from Microalgae Isolation of a *Micromonas* CS-0170 ω3-Desaturase Gene Fragment In an attempt to determine whether microalgae such as *Micromonas* had genes encoding ω3 desaturases and perhaps identify such a gene, a search was made of the *Micromonas* strain RCC299 genomic sequence for genes showing homology to FAD3. However, this search failed to identify any candidate genes. The inventors therefore considered whether an ω3 desaturase could be represented in other types of desaturases in *Micromonas*. This hypothesis was supported by the finding (Example 4) that the Δ6 desaturase in the same strain was of the front-end, acyl-CoA dependent type. However, when examined, the *Micromonas* RCC299 genome appeared to contain genes for at least 30 putative fatty acid desaturases and there was no information as to which of these, if indeed any, might encode an ω3 desaturase.

In one experiment, an alignment of desaturase amino acid sequences from Genbank accession numbers BAD91495, ABL63813, BAD11952 and AAR20444 identified the consensus amino acid sequence blocks WCIGHDCG (SEQ ID NO:39) and TFLQHHDEDM (SEQ ID NO:40) corresponding to amino acid positions 106-113 and 296-305, respectively, of BAD91495. The degenerate primers 5'-TGTGGTGCATCGGCCAYGANKSNGG-3' (SEQ ID NO:70) and 5'-TGTCCTCGTCGTTGTGCTGNARR-WANGT-3' (SEQ ID NO:71) were designed using the CODEHOP program based on the sequences of these two blocks. A touchdown PCR amplification was carried out using Taq DNA polymerase (NEB) in a volume of 20 μL using 10 pmol of each primer, 50 ng of *Micromonas* CS-0170 genomic DNA with buffer and nucleotide components as specified in the accompanying manual. The cycling conditions were: 1 cycle of 94° C. for 3 minutes; 20 cycles of 94° C. for 1 minute, 70° C. for 2 minutes (−1° C. per cycle), 72° C. for 1 minute; cycles of 94° C. for 1 minute, 56° C. for 1 minute, 72° C. for 1 minute; 1 cycle of 72° C. for 5 minutes; 4° C. hold. A 528 bp amplicon was generated, ligated into pGEM-T Easy (Promega) and sequenced. The nucleotide sequence of this amplicon is provided as SEQ ID NO:14, and the encoded partial protein sequence is provided as SEQ ID NO:15.

Synthesis of a Full Length *Micromonas* RCC299 ω3-Desaturase Gene

The 528 bp fragment generated by degenerate PCR was compared with the completed *Micromonas* RCC299 filtered protein models genome sequence (produced by the US Department of Energy Joint Genome Institute www.jgi.doe.gov/). BLAST analysis revealed regions of high homology between a region of *Micromonas* RCC299 chromosome 13 and SEQ ID NO:14. Based on the near identity of the two sequences it was likely that the *Micromonas* strains CS-0170 and RCC299 were very closely related (nucleotide sequence of *Micromonas* RCC299 provided as SEQ ID NO:16). The *Micromonas* RCC299 predicted protein sequence (SEQ ID NO:17) was used to design and synthesize a codon-optimized nucleotide sequence that was most suitable for expression in *Brassica napus* or other dicotyledonous plants (SEQ ID NO:18). A shorter version of this gene starting at nucleotide of 164 of SEQ ID NO:18 was tested in yeast but no ω3 desaturase activity was detected.

BLAST analysis indicated that the full-length amino acid sequence (SEQ ID NO:17) has homology with FAT-1, FAT-2 and ω3 desaturases. It was not possible to predict on sequence alone which activity was encoded. The maximum degree of identity between the *Micromonas* CS-0170 desaturase and other proteins in the Genbank database by BLASTX was 35% with XP_001899085.1, which was a *Brugia malayi* protein in the fatty acid desaturase family. This front-end desaturase contained a Δ12-FADS-like conserved domain (NCBI conserved domain cd03507). Proteins containing both of these domains are typically front-end desaturases required for the synthesis of fatty acids, including the ω3 desaturase family.

Functional Characterisation of the *Micromonas* RCC299 ω3-Desaturase in Planta

The enzymatic function of the putative ω3-desaturase encoded by the full-length gene isolated from *Micromonas* RCC299 (Mic299-w3D, as described above) and the *Phytophthora infestans* Δ17-desaturase (Phyin-d17D, GenBank Accession No. CAM55882), used here as a positive control sample, were tested in planta using the enhanced *Nicotiana benthamiana* transient expression system as described above.

The 35S:Mic299-w3D construct was built by cloning the entire protein coding region of SEQ ID NO:18, contained within an EcoRI fragment, into vector 35S-pORE04 (Example 4) at the EcoRI site, generating the genetic construct designated pJP2073. The 35S:Phyin-d17D construct was made by cloning the entire coding region of the *Phytophthora infestans* Δ17 desaturase, contained within an EcoRI fragment, into 35S-pORE04 at the EcoRI site, generating pJP2074. Similarly, a 35S:Arath-DGAT1 construct was built by cloning the entire coding region of the *Arabidopsis thaliana* DGAT1 (AF051849), contained within an EcoRI fragment, into 35S-pORE04 at the EcoRI site, generating pJP2078.

*Agrobacterium tumefaciens* strain AGL1 was grown at 28° C. in LB broth supplemented with 50 mg/mL kanamycin and 50 mg/mL rifampicin to stationary phase. The bacteria were then pelleted by centrifugation at 5000 g for 15 min at room temperature before being resuspended to OD600=1.0 in an infiltration buffer containing 10 mM MES pH 5.7, 10 mM MgCl$_2$ and 100 μM acetosyringone. The cells were then incubated at 28° C. with shaking for 3 hours before equal volumes of *Agrobacterium* cells containing 35S:p19, 35S:Arath-DGAT1 and either 35S:Phyin-d17D or 35S:Mic299-w3D cultures were mixed prior to infiltration into leaf tissue. An arachidonic acid salt was prepared and fed to the transformed leaf tissue as described above with leaf discs being taken for analysis at both 5 hours and 24 hours after substrate feeding. Leaf spots infiltrated with the 35S:Phyin-d17D construct or, separately, the 35S:Mic299-w3D construct all demonstrated the conversion of ARA (20:4ω6) to EPA, (20:5ω3) at 37% and 50% efficiency, respectively (FIG. 13), indicating that the protein had Δ17-desaturase activity.

Discussion: Characterisation of the First Microalgal ω3-Desaturase with Δ17-Desaturase Activity The *Micromonas* RCC299 ω3 desaturase described in this study is the first microalgal, i.e. plant-like, Δ17 desaturase described, having activity on a C20 or longer fatty acid substrate. Land plants are not known to have ω3 desaturases of the front-end desaturase type, but rather of the FAD3 type. It was therefore surprising to find that a microalgal strain, which is more related to plants than fungi, possessed an ω3 desaturase of the front-end desaturase type.

It was considered likely, based on homology to other desaturases, that the fungal *Phytophthora infestans* desaturase used as a control gene in the experiments described above was active on acyl-PC substrates whilst the *Micromonas* RCC299 desaturase was active on acyl-CoA substrates. Other fungal desaturases are known to be active on acyl-PC substrates. This conclusion regarding the *Micromonas* gene was consistent with its observed similarity to the Δ6-desaturase gene from the same strain (Example 4). This substrate preference can be further examined by substrate feeding studies where substrates such as ARA fed to the transformed tissue will be immediately available to the acyl-CoA pool but available to the acyl-PC pool only after conversion by native plant (e.g. *Nicotiana benthamiana*) acyltransferases.

The *Micromonas* RCC299 ω3 desaturase gene will be very useful in the construction of recombinant pathways designed to yield EPA and downstream fatty acids DPA and DHA, and other ω3 VLC-PUFA in plants, in particular because of its ability to convert ω6 substrates such as ARA to ω3 products. Activity on acyl-CoA substrates enhances this usefulness when combined with elongases such as Δ5-elongases that also operate in the acyl-CoA pool. Furthermore, the fatty acid profile of *Micromonas* strains indicated that the *Micromonas* enzyme may also have the capability to convert ω6 C18 fatty acids such as GLA or LA to their ω3 counterparts such as SDA or ALA, respectively. Conversion of GLA to SDA can be demonstrated in either yeast cells or in planta by substrate feeding as described above for substrate ARA, while conversion of LA to ALA is better demonstrated in yeast cells because of the presence of endogenous Δ15 desaturases in plants.

Identification of Other ω3-Desaturases

The *Micromonas* CCMP1545 filtered protein models genome sequence produced by the US Department of Energy Joint Genome Institute (www.jgi.doe.gov/) was analysed with the BLASTP program using SEQ ID NO:17 as the query sequence. This analysis revealed the presence of a gene in *Micromonas* CCMP1545 (EuGene.0000150179) that had homology with SEQ ID NO:17. The open reading frame sequence is provided in SEQ ID NO:19 and the protein sequence is provided in SEQ ID NO:20.

BLAST analysis indicated that the full-length amino acid sequence SEQ ID NO:20 has homology with FAT-1, FAT-2 and ω3 desaturases. The maximum degree of identity between the *Micromonas* CCMP1545 desaturase and other proteins in the Genbank database (BLASTP) was 59% along the full length with SEQ ID NO:17. This front-end desaturase contained a Δ12-FADS-like conserved domain (NCBI conserved domain cd03507). Proteins containing both of these domains are typically front-end desaturases required for the synthesis of fatty acids, including the ω3 desaturase family. We predict that this protein will also function as an ω3 desaturase with Δ17-desaturase activity in planta.

Example 7. Isolation and Characterisation of Further Genes Encoding Δ9-Elongase from Microalgae Isolation and Characterisation of the *Emiliania huxleyi* CCMP1516 Δ9-Elongase The *Emiliania huxleyi* CCMP1516 filtered protein models genome sequence produced by the US Department of Energy Joint Genome Institute (www.jgi.doe.gov/) was analysed with the BLASTP program using the amino acid sequence of GenBank Accession No. AF390174 as the query sequence. This analysis revealed the presence of a predicted gene in *Emiliania huxleyi* CCMP1516 that had homology with AF390174. The protein sequence is provided in SEQ ID NO:28 and the encoding nucleotide sequence as SEQ ID NO:27. BLAST analysis indicated that the full-length amino acid sequence has homology with PUFA elongases. The maximum degree of identity between the *Emiliania huxleyi* CCMP1516 elongase and other proteins (BLASTP) was 80% with AF390174. The conserved GNS1/SUR4 family domain (NCBI conserved domain pfam01151) was represented in this sequence, which typically indicated that the protein was involved in long chain fatty acid elongation systems.

The *Emiliania huxleyi* CCMP1516 predicted protein sequence was used to design and synthesize a codon-optimized nucleotide sequence that was most suitable for expression in dicotyledonous plants such as *Brassica napus* (SEQ ID NO:29). The plasmid construct was designated 0835668_Emihu-d9E_pMA.

Isolation and Characterisation of the *P. pinguis* and *P. salina* Δ9-Elongases

To identify possible conserved regions within the *P. pinguis* and *P. salina* Δ9-elongases an alignment was carried out of deduced elongase amino acid sequences from the *E. huxleyi* Δ9-elongase, PLL00000665 (a *P. lutheri* EST sequence from TBestDB identified by BLAST analysis using the *E. huxleyi* elongase sequences as query) and Genbank accession AAL37626 (*I. galbana* Δ9-elongase). This revealed the consensus amino acid sequence blocks VDTRKGAYR (SEQ ID NO:76) and FIHTIMYTY (SEQ ID NO:77) corresponding to amino acid positions 40-48 and 170-178, respectively, of Emihu-d9E. The degenerate primers 5'-TGGTGGACACAAGGAAGGGNGCNTAYMG-3' (SEQ ID NO:78) and 5'-GTAGGTGTACATGATGGTRTG-DATRAA-3' (SEQ ID NO:79) were synthesised based on the sequences of these two blocks and RT-PCR and PCR amplifications using RNA from *P. pinguis* and a cDNA library from *P. salina* (Zhou et al., 2007) was carried out using the Superscript III™ Platinum® One-Step RT-PCR system or Taq DNA polymerase (NEB, Ipswich, MA, USA).

A 641 basepair amplicon was generated from *P. pinguis* by RT-PCR, ligated into pGEM-T Easy® and sequenced. Primers were designed to extend the 641 basepair fragment by 5'- and 3'-RACE, the 3' end of the gene being isolated by RT-PCR using the gene specific forward primer 5'-GTCCTTGCTCCAGGGCTTCCACCA-3' (SEQ ID NO:80) and the oligo-dT-SP6 reverse primer 5'-ATT-TAGGTGACACTATAGTTTTTTTTTTTTTTTTT-3' (SEQ ID NO:81). This product was diluted 1:10 and 1.0 μl used as template in a second round of PCR using Taq DNA polymerase (NEB) with the gene specific forward primer 5'-TTCCAGAACGAGGGCATCTACGT-3' (SEQ ID NO:82) and the same reverse primer. A 1079 basepair amplicon was generated, ligated into pGEM-T® Easy and sequenced. The 5' end of the gene was isolated from 1.0 μg of *P. pinguis* cDNA generated with the gene specific reverse primer 5'-TTGGGTGATCTGCATGAGCGTGATG-3' (SEQ ID NO:83) and A-tailed by terminal transferase. This cDNA was then used as template for a PCR reaction using the oligo-dT-SP6 primer and the gene specific primer 5'-CGAATACTTGAAGAGCTTGTTGGAGA-3' (SEQ ID NO:84). This product was diluted 1:10 and 1.0 μl used as template in a second round of PCR using the oligo-dT-SP6 primer and the gene specific primer 5'-GGGC-TACGAGCTGGCAGATGAAGCA-3' (SEQ ID NO:85). A 323 basepair amplicon was generated, ligated into pGEM-T® Easy and sequenced. The full length sequence was assembled from the three partial sequences. The full length coding region with a short region of 5' UTR was amplified from total RNA by RT-PCR using the forward primer 5'-GAAAAAATGGTTGCGCCACCCATCA-3' (SEQ ID NO:86) and the reverse primer 5'-TCAC-TACTTCTTCTTCTTGCCCGCGGC-3' (SEQ ID NO:87). An 828 basepair amplicon, Pavpi-Elo1, was generated and this was ligated into pGEM-T® Easy and sequenced (SEQ ID NO:93). The deduced amino acid sequence of the *P. pinguis* Δ9-elongase is provided as SEQ ID NO:94.

Similarly, a 425 basepair amplicon was generated from *P. salina* by PCR using the degenerate primers, ligated into pGEM-T Easy® and sequenced. Primers were designed to extend the 425 basepair fragment by 5'- and 3'-RACE, the 3' end of the gene being isolated by RT-PCR using the gene specific forward primer 5'-TTCCGGTACTCAGCGGTGGCG-3' (SEQ ID NO:88) and the oligo-dT-SP6 reverse primer. A 776 basepair amplicon was generated, ligated into pGEM-T® Easy and sequenced. The 5' end of the gene was isolated by PCR from the *P. salina* cDNA library using the M13R primer 5'-CAG-GAAACAGCTATGAC-3' (SEQ ID NO:89) and a gene specific reverse primer 5'-ACGTAGATGCCCTCGTTCTG-3' (SEQ ID NO:90) with PfuUltra II® Fusion DNA polymerase as specified by the manufacturer. A 710 basepair amplicon was generated, ligated into pGEM-T® Easy and sequenced. The full length sequence was assembled from the three partial sequences. The full length coding region with a short region of 5' UTR was amplified from total RNA by RT-PCR using the forward primer 5'-CACCGAATGGCGACTGAAGGGATGCC-3' (SEQ ID NO:91) and the reverse primer 5'-CTACTCGGTTTT-CATGCGGTTGCTGGA-3' (SEQ ID NO:92). An 846 basepair amplicon, Pavsa-Elo3, was generated and this was ligated into pGEM-T® Easy and sequenced (SEQ ID NO:95). The deduced amino acid sequence of the *P. salina* Δ9-elongase is provided as SEQ ID NO:96.

Function Characterisation of the Δ9-Elongases in Plant Cells

The entire coding regions of the *Emiliania* elongase (Emihu-d9E), *Pavlova pinguis* elongase (Pavpi-d9E) and *Pavlova salina* elongase (Pavsa-d9E), contained within EcoRI fragments, from plasmids 0835668_Emihu-d9E_pMA, pGEMT+Pavpi-d9E and pGEMT+Pavsa-d9E, respectively, were inserted into 35S-pORE04 at the EcoRI site to generate 35S:Emihu-d9E (designated pJP3027), 35S:Pavpi-d9E (designated pJP3103), 35S:Pavsa-d9E (designated pJP3081) and 35S:Isoga-d9E (designated pJP2062). The enzyme activities of Emihu-d9E, Pavpi-d9E and Pavsa-d9E along with Isoga-d9E (Qi et al., 2002), used here as a positive control sample, were demonstrated in planta using an enhanced *Nicotiana benthamiana* transient expression system as described in Example 1.

These chimeric vectors were introduced into *Agrobacterium tumefaciens* strain AGL1 and cells from cultures of these infiltrated into leaf tissue of *Nicotiana benthamiana* plants in the greenhouse. The plants were grown for a further five days after infiltration before leaf discs were taken for GC analysis which revealed, by presence of the product fatty acid, that both genes were functioning as Δ9-elongases in plant cells such as *Nicotiana benthamiana*.

Leaf tissue transformed with the *Emiliania huxleyi* CCMP1516 Δ9-elongase contained $20:2^{\Delta 11,14}$ (6.6%) and $20:3^{\Delta 11,14,17}$ (6.4%), which represented conversion efficiencies from LA and ALA of 39.9% and 12.4%, respectively. Leaf tissue transformed with the *Pavlova pinguis* Δ9-elongase contained $20:2^{\Delta 11,14}$ (10.1%) and $20:3^{\Delta 11,14,17}$ (6.6%), which represented conversion efficiencies of 56.0% and 13.3%, respectively. Leaf tissue transformed with the *Pavlova salina* Δ9-elongase contained $20:2^{\Delta 11,14}$ (7.7%) and $20:3^{\Delta 11,14,17}$ (4.6%), which represented conversion efficiencies of 45.0% and 9.2%, respectively. Leaf tissue transformed with the *Isochrysis galbana* Δ9-elongase contained $20:2^{\Delta 11,14}$ (9.2%) and $20:3^{\Delta 11,14,17}$ (7.5%), which represented conversion efficiencies of 48.9% and 15.4%, respectively (Table 9).

TABLE 9

Fatty acid composition (percent of total fatty acids) of *Nicotiana benthamiana* leaf tissue transiently transformed with Δ9-elongases. The standard deviations between separate infiltrations performed in triplicate are shown.

| Fatty acid | Control | Emihu-Δ9E | Pavsa-Δ9E | Pavpi-Δ9E | Isoga-Δ9E |
|---|---|---|---|---|---|
| Usual FA | | | | | |
| 16:0 | 15.7 ± 0.6 | 14.6 ± 0.1 | 15.2 ± 0.6 | 14.5 ± 0.8 | 14.2 ± 0 |
| 16:1$^{\Delta 3t}$ | 1.5 ± 0 | 1.4 ± 0 | 1.3 ± 0.1 | 1.3 ± 0 | 1.3 ± 0.1 |
| 16:3$^{\Delta 9, 12, 15}$ | 6.8 ± 0.7 | 6.5 ± 0.8 | 6.1 ± 0.8 | 6.1 ± 1.4 | 7.4 ± 0.5 |
| 18:0 | 3.0 ± 0.1 | 3.4 ± 0.2 | 4.2 ± 0.2 | 3.4 ± 0.5 | 3.1 ± 0.2 |
| 18:1$^{\Delta 9}$ | 2.2 ± 0 | 2.9 ± 0.2 | 3.2 ± 0.2 | 3.6 ± 0.7 | 3.2 ± 0.1 |
| 18:2$^{\Delta 9, 12}$ | 11.8 ± 0.4 | 9.9 ± 0.1 | 9.4 ± 0.2 | 7.9 ± 0.5 | 9.7 ± 0.4 |
| 18:3$^{\Delta 9, 12, 15}$ | 56.0 ± 1.4 | 45.3 ± 2.2 | 46.0 ± 1.4 | 43.4 ± 1.8 | 41.5 ± 1.3 |
| Other minor | 3.0 ± 0 | 3.0 ± 0 | 2.3 ± 0 | 3.1 ± 0 | 2.9 ± 0 |
| Total | 100 | 87.0 | 87.7 | 83.3 | 83.3 |
| New ω6 PUFA | | | | | |
| 20:2$^{\Delta 8, 11}$ | — | 6.6 ± 1.0 | 7.7 ± 0.7 | 10.1 ± 0.7 | 9.2 ± 0.8 |
| 20:3$^{\Delta 8, 11, 14}$ | — | — | — | — | — |
| 20:4$^{\Delta 5, 8, 11, 14}$ | — | — | — | — | — |
| 22:4$^{\Delta 7, 10, 13, 16}$ | — | — | — | — | — |
| 22:5$^{\Delta 4, 7, 10, 13, 16}$ | — | — | — | — | — |
| Total | 0 | 6.6 | 7.7 | 10.1 | 9.2 |
| New ω3 PUFA | | | | | |
| 20:3$^{\Delta 11, 14, 17}$ | — | 6.4 ± 1.5 | 4.6 ± 0.7 | 6.6 ± 0.4 | 7.5 ± 0.2 |
| 20:4$^{\Delta 8, 11, 14, 17}$ | — | — | — | — | — |
| 20:5$^{\Delta 5, 8, 11, 14, 17}$ | — | — | — | — | — |
| 22:5$^{\Delta 7, 10, 13, 16, 19}$ | — | — | — | — | — |
| 22:6$^{\Delta 4, 7, 10, 13, 16, 19}$ | — | — | — | — | — |
| Total | 0 | 6.4 | 4.6 | 6.6 | 7.5 |
| Total new FA | 0 | 13.0 | 12.3 | 16.7 | 16.7 |
| Total FA | 100 | 100 | 100 | 100 | 100 |

The apparently high preference for the ω3 substrate ALA in the leaf tissue was expected since the bulk of the substrate ALA in *N. benthamiana* leaf is located in the plastid and thus unavailable for extra-plastidial elongation and since both the plastidial and cytoplasmic ALA are isolated from the leaf during direct methylation the ω3 conversion ratio artificially reduced. The *E. huxleyi* and *I. galbana* Δ9-elongases displayed identical substrate preferences in *N. benthamiana* with ω3 to ω6 conversion ratios of 0.31. The most efficient conversion in the ω6 pool was seen with the *P. salina* Δ9-elongase with 56.0% of substrate being converted. In contrast, 13.3% of the ω3 substrate was converted, a ratio of 0.24. The *P. pinguis* enzyme displayed the highest preference for ω6 substrates with a conversion ratio of 0.20 resulting from 45.0% ω6 conversion but only 9.2% ω3 conversion.

Example 8. Construction of a Biosynthetic Pathway Including Δ9 Elongase to Yield ARA Construction of a Transgenic Delta-9 Elongase Pathway A binary vector containing the *Isochrysis galbana* Δ9-elongase (amino acid sequence GenBank Accession No. AF390174—open reading frame provided as SEQ ID NO:21, amino acid sequence as SEQ ID NO:22), *Pavlova salina* Δ8-desaturase (Accession No. ABL96296—open reading frame provided as SEQ ID NO:23, amino acid sequence as SEQ ID NO:24) and *Pavlova salina* Δ5-desaturase (Accession No. ABL96295—open reading frame provided as SEQ ID NO:25, amino acid sequence as SEQ ID NO:26) was constructed from the binary vector pJP101acq. The design of this vector without the gene inserts is shown schematically in FIG. 14.

First, the SmaI-EcoRV fragment of a pBluescript clone containing the *Isochrysis galbana* Δ9-elongase was ligated into the SmaI site of pJP101acq to yield pJP105. The XhoI fragment of a pBluescript clone containing the *Pavlova salina* Δ5-desaturase was ligated into the XhoI site of pJP105 to yield pJP106. The NotI fragment of a pBluescript clone containing the *Pavlova salina* Δ8-desaturase was ligated into the NotI site of pJP106 to yield pJP107, which is shown schematically in FIG. 15.

Several points are notable about the design. Firstly, two of the three genes were transcribed divergently on the T-DNA, i.e. away from each other. This was done to prevent transcription from either gene being directed toward, and potentially interfering with, expression of the other gene and thereby maximising expression of both. Secondly, the third gene in the genetic construct, in this case encoding the Δ8-desaturase, was spaced apart from the second gene oriented in the same direction, encoding the Δ9-elongase, by the insertion of a spacer. It was thought that a distance of at least 1.0 kb between the stop codon of the upstream gene and the start codon of the downstream gene would reduce the risk of transcription of the former interfering with the latter, or potentially causing gene silencing. Thirdly, the 5'-UTR of each of the three genes was modified to include a TMV leader sequence which was known to provide for efficient translation. Any other 5'UTR sequence which is known to confer high translation efficiency could have been used instead of the TMV sequence.

pJP107 was introduced into *Agrobacterium* strain AGLI by electroporation and the transformed strain used to introduce the genetic construct into *Arabidopsis thaliana*, ecotype MC49, which was a fad3/fae1 mutant with high levels of LA as potential beginning fatty acid substrate for the Δ8-desaturase. Plant transformation and analysis was carried out using the floral dipping method (Clough and Bent, 1998). Seeds (T1 seeds) from the treated plants (T0 plants) were plated out on hygromycin (20 mg/L) selective media and transformed plants were selected and transferred to soil to establish 24 confirmed T1 transgenic plants. Most of these T1 plants were expected to be heterozygous for the introduced genetic construct. T2 seed from the 24 transgenic plants were collected at maturity and analysed for fatty acid composition. These T2 lines included lines that were homozygous for the genetic construct as well as ones which were heterozygous. T2 plants were established from the T2 seed for the 6 lines containing the highest ARA levels, using selection on MS medium containing hygromycin (20 mg/mL) to determine the presence of the transgenes. For example, the T2 seeds were planted from the T1 plant designated FW-10, containing 5.8% ARA and showing a 3:1 segregation ratio of resistant to susceptible progeny on the hygromycin medium, indicating that FW-10 contained the genetic construct at a single genetic locus. The fatty acid profiles of T3 seed lots from FW-10 were analysed and the data are presented in Table 10.

TABLE 10

Fatty acid composition of *Arabidopsis* seed transformed with the genetic construct pJP107 containing the *Isochrysis galbana* Δ9-elongase, *Pavlova salina* Δ8-desaturase and *Pavlova salina* Δ5-desaturase genes.

| Sample | FW10-23 P1235 | Control MC49 P1254 |
|---|---|---|
| 14:0 | 0.0 | 0.1 |
| 16:1ω7 | 0.6 | 0.4 |
| 16:0 | 9.5 | 8.4 |
| 18:2 ω6 | 30.9 | 50.9 |
| 18:3 ω3 | 0.0 | 1.0 |
| 18:1 ω9 | 21.4 | 30.9 |
| 18:1 ω7 | 3.3 | 3.5 |
| 18:0 | 4.3 | 3.4 |
| 20:4 ω6 | 21.0 | 0.0 |
| 20:5 ω3 | 1.3 | 0.0 |
| 20:3 ω6 | 1.1 | 0.0 |
| 20:4 ω3* | 0.2 | 0.0 |
| 20:2 ω6 | 2.6 | 0.0 |
| 20:3 ω3 | 0.2 | 0.0 |
| 20:1 ω9/ω1 | 1.6 | 0.2 |
| 20:0 | 0.7 | 0.5 |
| 22:4 ω6 | 0.8 | 0.0 |
| 22:5 ω3 | 0.0 | 0.0 |
| 22:0 | 0.0 | 0.2 |
| 24:1 ω11/13 | 0.2 | 0.1 |
| 24:0 | 0.2 | 0.2 |
| Sum | 100 | 100 |
| Sum ω6 PUFA | 56 | 51 |
| % conversions Δ9E | | |
| LA → 20:2 ω6 | 45 | 0 |
| ALA → 20:3 ω3 | 100 | 0 |
| Δ8D | | |
| 20:2 ω6 → 20:3 ω6 | 90 | 0 |
| 20:3 ω3 → 20:4 ω3 | 88 | 0 |

TABLE 10-continued

Fatty acid composition of *Arabidopsis* seed transformed with the genetic construct pJP107 containing the *Isochrysis galbana* Δ9-elongase, *Pavlova salina* Δ8-desaturase and *Pavlova salina* Δ5-desaturase genes.

| Sample | FW10-23 P1235 | Control MC49 P1254 |
|---|---|---|
| Δ5D | | |
| 20:3 ω6 → 20:4 ω6 | 95 | 0 |
| 20:4 ω3 → 20:5 ω3 | 90 | 0 |

As summarised in Table 10, seed of untransformed *Arabidopsis* (ecotype MC49) contained significant amounts of the precursor ω6 substrate LA but did not contain any ARA or the intermediate fatty acids expected to occur along the Δ9 elongase pathway. In contrast, seed from transformed plant FW10-23 containing the pJP107 construct contained significant levels of 20:2n-6, 20:3n-6 and 20:4n-6 (ARA), including 21% ARA, the product of the three enzymatic steps starting with LA. Furthermore, the low level of ALA in the seedoil (1.0% in control MC49) was very efficiently converted to EPA, which was present at a level of 1.3% in transformed line FW10-23.

Discussion: Conversion Efficiencies and Biochemical Implications

The relative efficiencies of the individual enzymatic steps encoded by the pJP107 construct could be assessed by examining the percentage conversion of substrate fatty acid to product fatty acids (including subsequent derivatives) in FW-10-23. In the ω6 pool, the *Isochrysis galbana* Δ9 elongase showed 45% conversion of LA to EDA and subsequently desaturated fatty acids. In the same seed, the *Pavlova salina* Δ8-desaturase and Δ5-desaturase showed conversion efficiencies of 90% and 95%, respectively of the ω6 fatty acids to their relevant products. In comparison, in the ω3 pool, the *Isochrysis galbana* Δ9 elongase showed essentially 100% conversion of ALA to elongated products, whilst the *Pavlova salina* Δ8-desaturase and Δ5-desaturase showed conversion efficiencies of 88% and 90%, respectively. These enzymatic steps resulted in the synthesis of 1.3% EPA, even though the *Arabidopsis thaliana* MC49 background contains only low levels of ALA. In the most dramatic result, it was noted that ALA was not detected in the seedoil, indicating essentially 100% conversion of ALA to elongated products of ALA by the Δ9 elongase.

It is interesting to note that the levels of unusual intermediate fatty acids found in FW-10-23 were low (<0.4% in the ω3 pool) and comparable to those already found in the food-chain in various seafoods (Table 11). Even though untransformed MC49 seedoil contained only low levels of ALA and this might have contributed to the low observed levels of, for example, the intermediate fatty acid ETrA, it is predicted that when the same pathway is assembled in a genetic background having higher ALA levels, the resultant seedoil would still have relatively low levels (<3%) of ETrA. The presence of such low levels of these intermediates was likely due to the very efficient desaturation of the Δ9 elongated intermediates.

TABLE 11

Comparison of the fatty acids in *Arabidopsis* seed transformed with the genetic construct pJP107 containing the *Isochrysis galbana* Δ9-elongase, *Pavlova salina* Δ8-desaturase and *Pavlova salina* Δ5-desaturase genes and the intermediate fatty acids found in a range of seafood samples.

| Sample | P1235 | Seafood Mean | range-maximum |
|---|---|---|---|
| 14:0 | 0.0 | 1.7 | 31.1 |
| 16:1 ω7 | 0.6 | 2.9 | 8.2 |
| 16:0 | 9.5 | 18.7 | 53.6 |
| 18:2 ω6 | 30.9 | 1.9 | 14.6 |
| 18:3 ω3* | 0.0 | 0 | 0 |
| 18:1 ω9 | 21.4 | 13.9 | 59.5 |
| 18:1 ω7 | 3.3 | 3 | 7.9 |
| 18:0 | 4.3 | 8.5 | 14.7 |
| 20:4 ω6 | 21.0 | 6.7 | 19.1 |
| 20:5 ω3 | 1.3 | 7.1 | 22.2 |
| 20:3 ω6 | 1.1 | 0.3 | 1.5 |
| 20:4 ω3 | 0.2 | 0.5 | 2.8 |
| 20:2 ω6 | 2.6 | 0.4 | 1.8 |
| 20:3 ω3* | 0.2 | 0 | 0 |
| 20:1 ω9/ω11 | 1.6 | 2.2 | 21.1 |
| 20:0 | 0.7 | 0.4 | 4.2 |
| 22:4 ω6 | 0.8 | 1 | 4.4 |
| 22:5 ω3 | 0.0 | 2.4 | 14.9 |
| 22:0 | 0.0 | 0.2 | 0.7 |
| 24:1 ω911/13* | 0.2 | 0 | 0 |
| 24:0 | 0.2 | 0.2 | 1.6 |
| Sum ω6 PUFA | 56 | 10 | 41 |
| % conversions | | | |
| Δ9E | | | |
| LA→20:2 ω6 | 45 | 82 | |
| ALA→20:3 ω3 | 100 | 100 | |
| Δ8D | | | |
| 20:2w6→20:3 ω6 | 90 | 95 | |
| 20:3w3→20:4 ω3 | 88 | 100 | |
| Δ5D | | | |
| 20:3w6→20:4 ω6 | 95 | 96 | |
| 20:4w3→20:5 ω3 | 90 | 95 | |

It is worth noting that the *Pavlova salina* Δ8-desaturase was considerably more efficient in converting ETrA to ETA than other reported Δ8-desaturases, in particular when co-expressed with the Δ9 elongase and Δ5 desaturase. For example, it has been reported that when the *Euglena gracilis* Δ8-desaturase was co-expressed with either the *Euglena gracilis* or the *Isochrysis galbana* Δ9-elongase in soybean embryos, the conversion efficiencies of ω3 and ω6 substrates were 64% and 73%, respectively. The efficiency of each step observed in the experiment described above and the overall conversion efficiency of ALA to EPA was also much higher than that reported by Qi et al. (2004) in *Arabidopsis* leaves, where they observed only 3.0% EPA and substantial levels of the undesirable intermediates including ETrA (4.6%).

Elongases are known to only access substrates in the acyl-CoA pool. The fact that the subsequent Δ8-desaturase and Δ5-desaturase steps were observed to function at extremely high efficiency in the transformed seeds even though the Δ9-elongated product was undoubtedly produced in the acyl-CoA pool was a strong indication that both of the *Pavlova salina* desaturases were able to access acyl-CoA substrates with high efficiencies.

Biosynthesis of High ARA and EPA Levels Using the Δ9-Elongase Pathway

From these data and the observations on efficiency of the individual steps, it was predicted that it would be possible to generate high levels of ARA and EPA and subsequently DPA and DHA in a transgenic plants such as *Arabidopsis*, canola, soybean, linseed or cotton using a modified Δ9-elongase pathway. It was further predicted that even higher levels can be made with further addition of any one of three enzymatic functions, namely an acyl-CoA Δ12-desaturase function to increase the amount of available substrate LA in the acyl-CoA pool for Δ9-elongation, secondly the addition of a Δ15-desaturase to increase the level of ALA for direct conversion to EPA, and thirdly a Δ17-desaturase which can convert ARA to EPA such as the one described in Example 6. More preferably, the addition of both an acyl-CoA Δ12-desaturase and either the Δ15-desaturase or the Δ17-desaturase would provide maximal levels. Thus, use of enzymes capable of accessing substrates in the acyl-CoA pool is expected to result in more efficient conversion to EPA, DHA and DHA.

The observed synthesis of 1.3% EPA was remarkable and unexpected considering that the *Arabidopsis thaliana* MC49 background contained a fad3 mutation which resulted in low levels of ALA accumulation (1-3%). We predict that when this, or similar, Δ9-elongase pathways (Δ9-elongase, Δ8-desaturase and Δ5-desaturase) are transformed into a plant containing high levels of ALA, high levels of EPA will result. For example, we predict that transformation of this pathway into an *Arabidopsis* line overexpressing the *Perilla frutescens* Δ15-desaturase or other Δ15-desaturase genes will result in EPA levels of at least 25% of the total fatty acid in seedoil.

Example 9. Expression of PUFA Pathway Genes in Plant Cells

One alternative to the stable transformation of plants is the transient expression of transgenes in leaves, such as that first introduced by Kapila et al (1997). With this technique, nuclei of permissive leaf cells (Zipfel et al., 2006) are transformed via infiltration of abaxial air-spaces with *Agrobacterium* cultures harbouring expression constructs within $T_{DNA}$ borders. Expression of transgenes in leaves is significantly enhanced by the co-introduction of viral suppressor proteins, such as P19 (Voinnet et al., 2003) and HC-Pro (Johansen and Carrington, 2001; Kasschau et al., 2003), that inhibit the host cells' transgene silencing apparatus and extend transgene expression over a longer period of time.

Leaves have a complex lipid metabolism that is dominated by the large pools of plastidial galactolipids monogalactosyl diacylglycerols (MGDG) and digalactosyl diacylglycerols (DGDG). More minor pools of fatty acids exist outside the plastidial compartments including those esterified to phospatidylcholine (PC), coenzyme A (CoA) and mono- and di-acylglycerides (MAG, DAG; Ohlrogge and Browse, 1995). The enzymes of LC-PUFA synthesis used in this Example reside on the endoplasmic reticulum (ER; Napier, 2007) where they have access to the relatively minor leaf lipid pools esterified to PC and CoA. Metabolic products of PC-CoA-linked reactions, such as those active on the ER, can be accumulated in triacylglycerides (TAG) by the overexpression of a diacylglyceride-O-acyltrasferase (DGAT; Bouvier-Nave et al., 2000). Compared to MAG or DAG, fatty acids residing on TAG are more metabolically inert and are less likely to re-enter lipid biosynthesis pathways or traffic into plastids. Importantly, TAG can be readily separated from the more abundant lipid classes residing in leaf plastids using standard thin-layer chromatography (TLC) techniques. Therefore a combination of enhanced TAG accumulation and TAG/lipid class purification could be helpful to more fully understand the LC-PUFA enzyme reactions on the leaf ER.

This system was tested for production of LC-PUFA using genes encoding desaturases and elongases in this Example.

Plasmid Constructs for Transient Expression

Binary vectors were prepared by cloning the coding region of the gene into a modified version of the pORE04 binary vector described by Coutu et al (2007) in which the Cauliflower Mosaic Virus (CaMV) 35S promoter had been cloned into the SfoI site to yield 35S-pORE04. The *I. galbana* Δ9-elongase gene coding region (Genbank accession AAL37626) (SEQ ID NO:21) was amplified from genomic DNA cloned into 35S-pORE04 at the EcoRI site. Plant expression codon-optimised versions of the three *P. salina* desaturases (Genbank accessions ABL96296, ABL96295 and AAY15136—each described in WO 2005/103253) were cloned into the EcoRV-SmaI sites of 35S-pORE04 as SwaI inserts. The non-optimised *P. salina* Δ5-elongase (Genbank accession AAY15135) was cloned as an XhoI-XbaI fragment into 35S-pORE04 at the XhoI-NheI sites. A CaMV 35S-driven version of the P19 viral suppressor was kindly donated by Dr Peter Waterhouse. The *A. thaliana* DGAT1 gene coding region (Genbank accession AAF19262) (SEQ ID NO:74) was obtained by RT-PCR and was cloned as a BamHI-EcoRV fragment into the corresponding sites in 35S-pORE04. Total RNA was isolated from *Phytophthora infestans* using a RNeasy mini kit (QIAGEN) and Platinum Superscript III One-Step (QIAGEN) RT-PCR performed. The resulting amplicon which contained the *P. infestans* Δ17-desaturase protein coding region (WO 2005/012316) was cloned into pGEMT-Easy (Promega) and sequenced. The EcoRI fragment was then cloned into 35S-pORE04.

Agrobacteria Infiltrations and *N. benthamiana* Growth Conditions

*Agrobacterium tumefaciens* strain AGL1 harbouring each binary vector was grown at 28° C. in LB broth supplemented with the appropriate antibiotics. Cultures were centrifuged and gently resuspended in two volumes of infiltration buffer (5 mM MES, 5 mM $MgSO_4$, pH 5.7, 100 µM acetosyringone) and grown for a further 3 hours. Optical densities of each culture were measured and a final combination of cultures prepared so that each *Agrobacterium* construct equalled $OD_{600\ nm}$ 0.2 or as otherwise indicated for FIG. 16. The cells were infiltrated, as described by Voinnet et al. (2003), into the underside of leaves of one month-old *N. benthamiana* plants that had been housed in a 23° C. plant growth room with 10:14 light:dark cycle. Infiltrated areas were circled by a permanent marker. Following infiltration, the plants were left at 28° C. for an hour after which they were transferred to a 24° C. plant growth room until analysis. Unless otherwise indicated, all *N. benthamiana* agroinfiltrations were performed in the presence of a separate binary construct containing the P19 viral suppressor protein.

Lipid Analysis

The fatty acid profiles of leaf tissues, or lipid class samples were analysed in this Example by GC and GC-MS after transmethylating using a solution of methanol/HCl/dichloromethane (DCM; 10/1/1 by volume) at 80° C. for 2 hr to produce fatty acid methylesters (FAME). The FAME were extracted in hexane:DCM (4:1, v/v) and reconstituted in DCM prior to analysis by GC and GC-MS.

For lipid class analysis, total lipids were extracted two times from approximately 50 mg fresh weight of infiltrated leaf tissue using the method described by Bligh and Dyer (1959). Neutral lipids were purified by TLC on precoated silica gel plates (Silica gel 60, Merck) with hexane/diethyl ether/acetic acid (70/30/1 by vol.), while polar lipids were fractionated using two-dimensional TLC, chloroform/methanol/water (65/25/4 by vol.) for the first direction and chloroform/methanol/$NH_4OH$/ethylpropylamine (130/70/10/1 by vol.) for the second direction (Khozin et al., 1997). The lipid spots were visualized by iodine vapour, collected into vials and transmethylated to produce FAME for GC analysis as described above. TAG was quantified as the total amount of fatty acids present, which was estimated by GC analysis as mentioned above and according to known amount of external standards injected for each fatty acid.

GC was performed using an Agilent Technologies 6890N GC (Palo Alto, California, USA) equipped with a non-polar Equity™-1 fused silica capillary column (15 m×0.1 mm i.d., 0.1 µm film thickness), an FID, a split/splitless injector and an Agilent Technologies 7683 Series autosampler and injector using helium as the carrier gas. Samples were injected in splitless mode at an oven temperature of 120° C. and after injection the oven temperature was raised to 201° C. at 10° C.·$min^{-1}$ and finally to 270° C. and held for 20 min. Peaks were quantified with Agilent Technologies ChemStation software (Rev B.03.01 (317), Palo Alto, California, USA). Peak responses were similar for the fatty acids of authentic Nu-Check GLC standard-411 (Nu-Check Prep Inc, MN, USA) which contains equal proportions of 31 different fatty acid methyl esters, ranging from octanoate to DHA and several other LC-PUFAs. Slight variations of peak responses among peaks were balanced by multiplying the peak areas by normalization factors of each peak. The proportion of each fatty acid in total fatty acids was calculated on the basis of individual and total peaks areas of the fatty acids.

GC-MS was performed to confirm the identity of all new fatty acids formed and was carried out on a Finnigan GCQ Plus GC-MS ion-trap fitted with on-column injection set at 45° C. Samples were injected using an AS2000 autosampler onto a retention gap attached to a non-polar HP-5 Ultra 2 bonded-phase column (50 m×0.32 mm i.d.×0.17 µm film thickness). The initial temperature of 45° C. was held for 1 minute, followed by temperature programming an increase of 30° C.·$min^{-1}$ to 140° C. then at 3° C.·$min^{-1}$ to 310° C. where it was held for 12 minutes. Helium was used as the carrier gas. Mass spectrometer operating conditions were: electron impact energy 70 eV; emission current 250 µamp, transfer line 310° C.; source temperature 240° C.; scan rate 0.8 scans·$s^{-1}$ and mass range 40-650 Dalton. Mass spectra were acquired and processed with Xcalibur™ software.

Modifying the *N. benthamiana* Fatty Acid Profile with a Transiently-Expressed Fatty Acid Elongase To estimate the concentration of *Agrobacterium* required to generate maximal production of a functional transgenic enzyme, a gene was expressed which encodes the *Isochrysis galbana* Δ9-elongase (IgΔ9elo; Qi et al., 2002), which was known to act on the CoA-linked linoleic acid (LA) and ALA substrates known to be abundant in *N. benthamiana* leaves. Following transfer of this gene into a binary vector downstream of the Cauliflower Mosaic Virus (CaMV) 35S promoter, this construct was agroinfiltrated into *N. benthamiana* leaves in the presence of the P19 viral suppressor protein to suppress host-mediated transgene silencing and the level of Δ9-elongation assessed. The elongation products of LA and ALA, EDA and ETrA, respectively, were detected with near maximal gene activity obtained with *Agrobacterium* cultures having $OD_{600}$=0.2 (FIG. 16). It was interesting to note, however, that agroinfiltrations of quite dilute concentrations of the culture (as low as $OD_{600}$=0.05) also resulted in readily detectable levels of enzyme activity.

Effect of Transient DGAT Expression on Triacylglycerol Accumulation

It was next investigated whether the size of the TAG pool in N. benthamiana leaves could be increased to provide a larger sink in which to capture the products of the introduced fatty acid biosynthetic enzymes acting on the ER. A construct containing the *Arabidopsis thaliana* DGAT1 (AtDGAT1) gene which catalyses the last step in TAG biosynthesis by the Kennedy pathway was tested as a possible means to increase the TAG pool in leaves, since leaves naturally produce only low levels of TAGs. The construct was introduced into N. benthamiana leaves by agroinfiltration as above. To test for the presence of TAGs, segments of infiltrated leaves approximately 1 cm² in size were submerged in a small Petri dish containing 1% aqueous Nile Blue (BDH, Poole, UK), vacuum-infiltrated for 3 minutes, rinsed briefly in water, incubated in 1% acetic acid for 3 minutes, and mounted in water for observation. Fluorescence emission was collected at 570-670 nm using a 488 nm excitation on a Leica SP2 laser scanning confocal microscope (Leica Microsystems, Sydney, Australia). Untransformed sectors of the same leaves were used as controls. The relative amounts of TAG accumulation in each assay were estimated using ImageJ software.

Transient expression of the *Arabidopsis thaliana* DGAT1 (AtDGAT1) resulted in the production of significantly more lipid bodies that were stained with Nile Blue and observed using confocal microscopy. The increase in TAG was quantified by fractionating the total lipids into TAG, using neutral phase TLC separation from other leaf lipid classes, after which the amount of TAG was measured as the amount of total fatty acids in the TAG fraction. Transient expression of P19 or P19 and AtDGAT1 together resulted in an increase in TAG from 46 µg·g$^{-1}$ fresh weight to 206 µg·g$^{-1}$ fresh weight, respectively, showing that addition of the DGAT1 gene increased the levels of TAG that accumulated in leaf tissue. Therefore, this gene was included in subsequent experiments unless indicated otherwise.

Availability of Exogenous Fatty Acid Substrates to Transiently Expressed Genes

It was next examined whether an exogenous fatty acid substrate that was not native to N. benthamiana could be supplied to the leaf and become available for transgene-mediated conversion, thus allowing individual enzymatic steps to be tested in isolation. To test this, the gene encoding *Phytophthora infestans* Δ17-desaturase (PiΔ17des) which acts on ARA, a substrate not naturally present in N. benthamiana, was agroinfiltrated to produce EPA. Four days after infiltration with PiΔ17des, the leaf was fed an ARA-ammonium salt by injection in a manner similar to that performed to transform the leaf with *Agrobacterium* cultures. The leaf was then allowed to metabolise the substrate for four hours before the total lipids were extracted from the leaf tissue. GC and GC-MS analysis of these total lipids showed that 37% of the exogenously fed ARA was converted by Δ17-desaturation to EPA, an efficiency comparable to that reported in yeast-based assays (WO 2005/012316).

Rapid Assembly of Five-Step LC-PUFA Pathways from Separate Binary Vectors

Having established that the N. benthamiana system was a useful tool in determining the function of a single transgene and enhanced TAG accumulation, the extent to which the system could be used to assemble entire LC-PUFA pathways was investigated. In this study, genes encoding five LC-PUFA metabolic enzymes were tested, that produce two parallel linear LC-PUFA pathways, namely the ω6-pathway, converting LA to DPA$^{ω6}$, and the ω3-pathway, converting ALA to DHA (FIG. 1). The biosynthetic genes used were the *Isochrysis galbana* Δ9-elongase (IgΔ9elo), *Pavlova salina* Δ8-desaturase (PsΔ8des), P. salina Δ5-desaturase (PsΔ5des), P. salina Δ5-elongase (PsΔ5elo) and P. salina Δ4-desaturase (PsΔ4des; Qi et al., 2004; Robert et al., 2009; Zhou et al., 2007). Each gene was cloned separately into a plant binary expression vector downstream of the CaMV 35S promoter as described above and a mixture of these constructs, each present at a concentration of $OD_{600\,nm}$=0.2, was agroinfiltrated into the abaxial surfaces of N. benthamiana leaves alongside AtDGAT1 and P19, making a total of seven individual constructs with a total $OD_{600\,nm}$=1.4.

Five days after infiltration leaf discs were sampled and fatty acid methyl esters (FAME) were produced directly from the fresh tissue and analysed and identified by GC/MS (Table 12). It was clear that the all of the pathway enzymes were able to accept either the ω6 or ω3 PUFA as substrates and that their sequential action on LA or ALA, led to the synthesis of the LC-PUFA, ARA and DHA, respectively. A total percentage of newly-produced LC-PUFA of 16.9% was identified, including 9.8% ω6 LC-PUFA and 7.1% ω6 LC-PUFA. Of all of these newly-formed LC-PUFA, ARA, EPA and DHA are considered nutritionally important and constituted 3.6%, 2.6% and 1.1%, respectively, of the total fatty acids in the leaf tissues. Enzymatic conversion efficiencies were calculated for each step of the ω6 and ω3 pathways and compared to those from previous reports (FIG. 17). The first three steps of both the ω6 and ω3 five-step pathways were similar in efficiency compared to those described by Qi et al. (Qi et al., 2004), whilst the efficiencies of the last two steps of the pathways were the same as those used by Robert et al. (Robert et al., 2005). This comparison of transiently expressed genes and stably expressed genes indicated that both methods of introducing the pathways generate similar metabolic fluxes or efficiencies. These conversion efficiencies calculated on total fatty acid profiles are likely to be an underestimate, especially for the first step, a Δ9-elongation, due to the diluting effect of large LA and ALA pools in the plastid. This issue was addressed by fractionation of lipid classes as follows.

TABLE 12

Fatty acid profiles of N. benthamiana leaf spots producing both ω6- and ω3-LC-PUFA. Each infiltration contained a mixture of *Agrobacterium* cultures harbouring ectopic expression constructs of the P19 viral suppressor isolated from Tomato Bushy Stunt Virus and the *Arabidopsis thaliana* diacylglycerol O-acyltransferase (AtDGAT1). LC-PUFA pathway infiltrations include an extra five genes, namely, *Isochrysis galbana* Δ9 elongase (IgΔ9elo), *Pavlova salina* Δ8-desaturase (PsΔ8des), P. salina Δ5-desaturase (PsΔ5des), P. salina Δ5-elongase (PsΔ5elo) and P. salina Δ4-desaturase (PsΔ4des). For clarity, saturated and minor fatty acids were not included in the table, but were used for calculation of percentages. (—) indicates no detectable amounts of fatty acid. Data are generated from 3 replicates and standard errors are shown.

| | Total FAME (%) | |
| --- | --- | --- |
| Fatty acid | Control | 5 LC-PUFA genes |
| 16:0 | 15.9 ± 0.2 | 20.1 ± 0.9 |
| 16:1$^{Δ3t}$ | 1.7 ± 0.1 | 1.5 ± 0.2 |
| 16:3$^{Δ9, 12, 15}$ | 6.3 ± 0.3 | 5.2 ± 0.3 |
| 18:0 | 3.6 ± 0.3 | 3.7 ± 0.2 |
| 18:1$^{Δ9}$ | 2.8 ± 0.1 | 3.1 ± 0.7 |
| 18:2$^{Δ9, 12}$ (LA) | 18.6 ± 0.1 | 8.0 ± 0.7 |

TABLE 12-continued

Fatty acid profiles of *N. benthamiana* leaf spots producing both ω6- and ω3-LC-PUFA. Each infiltration contained a mixture of *Agrobacterium* cultures harbouring ectopic expression constructs of the P19 viral suppressor isolated from Tomato Bushy Stunt Virus and the *Arabidopsis thaliana* diacylglycerol O-acyltransferase (AtDGAT1). LC-PUFA pathway infiltrations include an extra five genes, namely, *Isochrysis galbana* Δ9 elongase (IgΔ9elo), *Pavlova salina* Δ8-desaturase (PsΔ8des), *P. salina* Δ5-desaturase (PsΔ5des), *P. salina* Δ5-elongase (PsΔ5elo) and *P. salina* Δ4-desaturase (PsΔ4des). For clarity, saturated and minor fatty acids were not included in the table, but were used for calculation of percentages. (—) indicates no detectable amounts of fatty acid. Data are generated from 3 replicates and standard errors are shown.

| | Total FAME (%) | |
|---|---|---|
| Fatty acid | Control | 5 LC-PUFA genes |
| 18:3$^{\Delta 9, 12, 15}$ (ALA) | 45.5 ± 1.4 | 38.0 ± 1.9 |
| 20:0 | 1.3 ± 0.4 | 0.8 ± 0 |
| Other minor | 4.1 | 2.6 |
| Total | 100 | 83.1 |
| New ω6 PUFA | | |
| 20:2$^{\Delta 11, 14}$ (EDA) | 0 | 1.4 ± 0.2 |
| 20:3$^{\Delta 8, 11, 14}$ (DGLA) | 0 | 0.3 ± 0 |
| 20:4$^{\Delta 5, 8, 11, 14}$ (AA) | 0 | 3.6 ± 0.4 |
| 22:4$^{\Delta 7, 10, 13, 16}$ (DTA) | 0 | 1.5 ± 0.1 |
| 22:5$^{\Delta 4, 7, 10, 13, 16}$ (DPA$^{\omega 6}$) | 0 | 3.0 ± 0.4 |
| Total New ω3 PUFA | 0 | 9.8 |
| 20:3$^{\Delta 11, 14, 17}$ (ETrA) | 0 | 2.3 ± 0.1 |
| 20:4$^{\Delta 8, 11, 14, 17}$ (ETA) | 0 | 0.2 ± 0 |
| 20:5$^{\Delta 5, 8, 11, 14, 17}$ (EPA) | 0 | 2.6 ± 0.3 |
| 22:5$^{\Delta 7, 10, 13, 16, 19}$ (DPA$^{\omega 3}$) | 0 | 0.9 ± 0.1 |
| 22:6$^{\Delta 4, 7, 10, 11, 16, 19}$ (DHA) | 0 | 1.1 ± 0.1 |
| Total | 0 | 7.1 |
| Total new fatty acids | 0 | 16.9 |
| Total fatty acids | 100 | 100 |

Lipid Class Partitioning of LC-PUFA

In order to assess the partitioning of the newly synthesised LC-PUFA between TAG phospholipids and plastidial galactolipids the total lipids of *N. benthamiana* leaves transiently expressing the LC-PUFA pathway genes were subjected to lipid class fractionation as described above and their fatty acid profiles determined (Table 13). *N. benthamiana* leaf lipids contain lipid classes and fatty acid profiles typical of leaves from higher plants (Fraser et al., 2004; Moreau et al., 1998). Both newly-synthesised ω6 and ω3 LC-PUFA were predominantly confined to lipid classes typically found outside the plastid while the plastidial lipids were essentially devoid of these fatty acids. For example, TAG and phospholipids (PC, PE and PA)—the dominant extraplastidial leaf lipids—contained up to 20.4% and 16.9% of newly-synthesised ω6 and ω3 LC-PUFA, respectively. Remarkably, leaves expressing the full LC-PUFA pathways, AtDGAT1 and P19 produced TAG enriched with 37% of LC-PUFA. Of particular interest was the accumulation of the nutritionally important fatty acids ARA, EPA and DHA, present at 7.2%, 5.9% and 3%, respectively, in leaf TAG. Fractionation revealed that the dominant plastidial lipid classes, MGDG, DGDG and PG, contained only 1.1% and 0.3% of the newly synthesised ω6 and ω3 LC-PUFA, respectively. Although these plastidial lipid classes represent the largest pools of fatty acids in the leaf, collectively, these classes contained only a small amount of ω6 and ω3 LC-PUFA compared to TAG. Interestingly, the SQDG lipid class was totally devoid of the newly-synthesised LC-PUFA.

Lipid class fractionations were also used to calculate enzymatic efficiencies at each step of the LC-PUFA pathways that are associated with the ER for the fatty acids in TAG, which have no access to the plastidial lipids (FIG. 17). The removal of the plastidial lipid classes from these calculations had the most dramatic effect on the Δ9-elongation step for ALA into ETrA, increasing the conversion efficiencies from 16% to 55%. This three-fold increase in the enzyme conversion efficiency at this step is due to the large pools of ALA in plastids that are unavailable to this ER-bound enzyme (Table 13).

TABLE 13

Fatty acid profiles of *N. benthamiana* lipid classes expressing P19, AtDGAT1 and the five LC-PUFA genes as described in Table 12. Data for TAG were generated from lipid class separations using 1-dimensional TLC and the other lipid classes were separated on 2-dimensional TLC. Experiments were conducted in triplicate and standard errors are shown.

| | Extra-Plastidial | | | | Plastidial | | | |
|---|---|---|---|---|---|---|---|---|
| Fatty acid | TAG | PC | PE | PA | MGDG | DGDG | SQDG | PG |
| 16:0 | 22.6 ± 0.6 | 24.3 ± 0.8 | 23.0 ± 0.4 | 22.5 ± 2.8 | 4.7 ± 0.5 | 20.9 ± 0.7 | 52.7 ± 2.1 | 31.9 ± 1.9 |
| 16:1$^{\Delta 3t}$ | 0.2 ± 0 | 0 | 0 | 0.8 ± 0.7 | 0 | 0 | 0.5 ± 0.5 | 21.6 ± 1.5 |
| 16:3$^{\Delta 9,12,15}$ | 0.4 ± 0 | 0.1 ± 0.1 | 0 | 0 | 17.1 ± 1.0 | 1.4 ± 0.2 | 1.2 ± 0.1 | 0 |
| 18:0 | 7.8 ± 0.7 | 8.9 ± 1.5 | 8.6 ± 1.6 | 8.7 ± 2.2 | 0.8 ± 0.1 | 3.8 ± 0.3 | 7.2 ± 1.1 | 5.2 ± 0.7 |
| 18:1$^{\Delta 9}$ | 3.2 ± 0.9 | 6.7 ± 2.3 | 1.8 ± 0.6 | 5.6 ± 2.2 | 0.9 ± 0.1 | 1.3 ± 0.1 | 2.3 ± 0.3 | 11.8 ± 0.2 |
| 18:2$^{\Delta 9,12}$ (LA) | 9.2 ± 0.2 | 16.6 ± 1.2 | 21.2 ± 1.5 | 18.1 ± 0.6 | 2.7 ± 0.1 | 3.9 ± 0.1 | 5.3 ± 0.1 | 12.9 ± 0.5 |
| 18:3$^{\Delta 9,12,15}$ (ALA) | 13.8 ± 1.6 | 12.7 ± 1.6 | 13.6 ± 1.7 | 14.4 ± 1.2 | 70.5 ± 1.9 | 66.8 ± 0.9 | 30.7 ± 2.2 | 15.1 ± 1.8 |
| 20:0 | 2.2 ± 0.1 | 0.6 ± 0 | 1.0 ± 0.1 | 0.4 ± 0.3 | 0 | 0 | 0 | 0 |
| Other minor | 3.3 | 2.8 | 4.2 | 1.1 | 1.3 | 1.0 | 0.1 | 0.9 |
| Total New ω6 PUFA | 62.7 | 72.7 | 73.4 | 71.6 | 98 | 99.1 | 100 | 99.4 |
| 20:2$^{\Delta 11,14}$ (EDA) | 4.2 ± 0.3 | 3.2 ± 0.2 | 1.9 ± 0.1 | 2.8 ± 0.1 | 0.2 ± 0 | 0.1 ± 0.1 | 0 | 0 |
| 20:3$^{\Delta 8,11,14}$ (DGLA) | 0.6 ± 0 | 0.8 ± 0.1 | 0.7 ± 0.1 | 0.5 ± 0.4 | 0 | 0 | 0 | 0 |
| 20:4$^{\Delta 5,8,11,14}$ (AA) | 7.2 ± 0.7 | 5.3 ± 0.3 | 8.4 ± 0.3 | 7.3 ± 0.2 | 0.5 ± 0.1 | 0 | 0 | 0.5 ± 0 |

TABLE 13-continued

Fatty acid profiles of N. benthamiana lipid classes expressing P19, AtDGAT1 and the five LC-PUFA genes as described in Table 12. Data for TAG were generated from lipid class separations using 1-dimensional TLC and the other lipid classes were separated on 2-dimensional TLC. Experiments were conducted in triplicate and standard errors are shown.

| Fatty acid | Extra-Plastidial | | | | Plastidial | | | |
|---|---|---|---|---|---|---|---|---|
| | TAG | PC | PE | PA | MGDG | DGDG | SQDG | PG |
| $22:4^{\Delta7,10,13,16}$ (DTA) | 1.7 ± 0.5 | 5.8 ± 0.1 | 3.7 ± 0.3 | 5.6 ± 0.2 | 0.2 ± 0 | 0 | 0 | 0.1 ± 0.2 |
| $22:5^{\Delta4,7,10,13,16}$ (DPA$^{\omega6}$) | 6.7 ± 0.4 | 1.9 ± 0.1 | 2.5 ± 0.3 | 1.8 ± 0.4 | 0.2 ± 0 | 0.2 ± 0 | 0 | 0 |
| Total new ω6 LC-PUFA | 20.4 | 17.0 | 17.2 | 18.0 | 1.1 | 0.3 | 0 | 0.6 |
| New ω3 PUFA | | | | | | | | |
| $20:3^{\Delta11,14,17}$ (ETrA) | 6.7 ± 0.6 | 3.3 ± 0.2 | 2.2 ± 0.1 | 3.0 ± 0.2 | 0.5 ± 0.1 | 0.6 ± 0 | 0 | 0 |
| $20:4^{\Delta8,11,14,17}$ (ETA) | 0.5 ± 0 | 0.1 ± 0.2 | 0.1 ± 0.2 | 0.1 ± 0.2 | 0 | 0 | 0 | 0 |
| $20:5^{\Delta5,8,11,14,17}$ (EPA) | 5.9 ± 0.4 | 2.3 ± 0.3 | 3.4 ± 0.2 | 3.1 ± 0.3 | 0.3 ± 0 | 0 | 0 | 0 |
| $22:5^{\Delta7,10,13,16,19}$ (DPA$^{\omega3}$) | 0.8 ± 0 | 3.2 ± 0.3 | 2.1 ± 0.1 | 3.2 ± 0.6 | 0.1 ± 0 | 0 | 0 | 0 |
| $22:6^{\Delta4,7,10,13,16,19}$ (DHA) | 3.0 ± 0.2 | 1.4 ± 0.1 | 1.6 ± 0.2 | 1.0 ± 0.8 | 0 | 0 | 0 | 0 |
| Total new ω3 LC-PUFA | 16.9 | 10.3 | 9.4 | 10.4 | 0.9 | 0.6 | 0 | 0 |
| Total new | 37.3 | 27.3 | 26.6 | 28.4 | 2.0 | 0.9 | 0 | 0.6 |
| Total fatty acids | 100 | 100 | 100 | 100 | 100 | 100 | 100 | 100 |

Discussion

These experiments showed that transient expression of a series of pathway genes in N. benthamiana or other plant leaves mimicked expression in stably-transformed plants and was therefore well-suited and predictive of expression of the pathways in seeds for production of LC-PUFA oils. The transient expression system provided an interchangeable expression platform that gave rapid and reliable results for the entire pathway, where single components could easily be exchanged in multi-step recombinant pathways. The transient assembly of LC-PUFA biosynthesis was robust and reproducible. Assays were conducted in triplicate and produced tight data points, typically with a standard error less than 5%.

The first step in the assembled LC-PUFA pathways, a Δ9 elongation, showed a higher rate of elongation of LA than ALA, as observed previously in stably-transformed plants (Fraser et al., 2004). This difference cannot be accounted for by fatty acid substrate preferences of the enzyme as expression in yeast showed the IgΔ9 elongase to have equal preference for LA and ALA (Qi et al., 2002). It is more likely that the higher rate of elongation observed for LA was a reflection of the existence of a higher amount of LA than ALA in the leaf extraplastidial acyl-CoA pool—the site of action of the elongase (Domergue et al., 2003; Fraser et al., 2004).

Lipid class analysis demonstrated that all of the newly-formed LC-PUFA were found in roughly equal ratios in both the PC pool and in TAG. There were slight variations in this ratio for the products of the second last step of the pathways, a Δ5-elongation producing DTA and DPA, which were less abundant on TAG compared to PC. Conversely, the products of the final Δ4 desaturation, DPA$^{\omega6}$ and DHA, were preferentially accumulated on TAG compared to PC. These variations may reflect subtle biases of the membrane editing enzymes or the AtDGAT1 for these products. It is worth noting that both Δ5-elongations and DGAT activities occur on CoA pools, and competition between these enzymes for substrate may alter the presence of fatty acids in these PC and TAG pools.

There are several implications that arise from this study. First, the transient leaf based assay was shown to be suitable for assaying fatty acid enzymes, either singly or in complex combinations. This is particularly apt for enzymes producing fatty acids that are easily distinguished from the endogenous fatty acid profile of N. benthamiana, such as the LC-PUFA in this study. The demonstration of fatty acid-feeding assays to isolated enzymes and the rapid assembly of LC-PUFA into oils indicated that the transient leaf assay was well suited for ER-associated desaturation, elongation and TAG assembly. Second, although LC-PUFA oils are a current target of plant transformation technologies, leaf cells provide a range of advantages to other heterologous expression platforms. Leaf cells provide a wide range of metabolites not available in other expression hosts, and these may now become targets for modification requiring recombinant pathways. Furthermore plants more faithfully process eukaryotic transgenes, including RNA editing, post-translation modifications and organelle localisation.

Finally, the N. benthamiana assay could be suitable for cDNA library screening assays. This suggestion is based on the detection of near-maximal activity for seven different genes in a single infiltration zone on the leaf, suggesting that in this configuration cDNA libraries cloned within a binary expression vector could be systematically infiltrated into leaves. Calculations suggest that at least 7 different clones, including P19 at $OD_{600\,nm}$ 0.2, could be expressed in a single spot. Alternatively, genes forming incomplete or partial pathways could be added to each infiltration and thereby pooled library clones could be routinely tested for novel steps or improved fluxes.

Example 10. Efficient DHA Biosynthesis in Plant Cells

The enzyme activities of the Micromonas CCMP1545 Δ6-desaturase (SEQ ID NO:8 encoded by SEQ ID NO:7), Pyramimonas CS-0140 Δ6-elongase (SEQ ID NO:4 encoded by SEQ ID NO:3), Pavlova salina Δ5-desaturase (SEQ ID NO:26 encoded by SEQ ID NO:25), Pyramimonas CS-0140 Δ5-elongase (SEQ ID NO:6 encoded by SEQ ID NO:5) and Pavlova salina Δ4-desaturase (SEQ ID NO:73 encoded by SEQ ID NO: 72) along with the Arabidopsis thaliana DGAT1 (SEQ ID NO:74 encoded by SEQ ID NO:75) were demonstrated in planta using an enhanced *Nicotiana benthamiana* transient expression system as described in Example 1.

A genetic construct 35S:Mic1545-d6D encoding the Δ6-desaturase under the control of the constitutive 35S promoter was made by inserting the entire coding region of pGA4, contained within a SwaI fragment, into 35S-pORE04 (Example 4, above) at the SmaI-EcoRV site, generating pJP2064. A genetic construct 35S:Pyrco-d6E encoding the Δ6-elongase was made by inserting the entire coding region of 0804673_Pyrco-elo1_pGA18, contained within a SwaI fragment, into 35S-pORE04 at the SmaI-EcoRV site, generating pJP2060. A genetic construct 35S:Pavsa-d5D encoding the Δ5-desaturase was made by inserting the entire coding region of 0804674_Pavsa-d5D_pGA15, contained within a SwaI fragment, into 35S-pORE04 at the SmaI-EcoRV site, generating pJP2067. A genetic construct 35S:Pyrco-d5E encoding the Δ5-elongase was made by inserting the entire coding region of 0804675_Pyrco-elo2_pGA4, contained within a SwaI fragment, into 35S-pORE04 at the SmaI-EcoRV site, generating pJP2061. A genetic construct 35S:Pavsa-d4D encoding the Δ4-desaturase was made by inserting the entire coding region of 0804676_Pavsa-d4D_pGA15, contained within a SwaI fragment, into 35S-pORE04 at the SmaI-EcoRV site, generating pJP2068. A genetic construct 35S:Arath-DGAT1 encoding the enzyme DGAT1 was made by inserting the entire coding region of pXZP513E, contained within a BamHI-EcoRV fragment, into 35S-pORE04 at the BamHI-EcoRV site, generating pJP2078.

These chimeric vectors were introduced individually into *Agrobacterium tumefaciens* strain AGL1 and transgenic cells from cultures of these were mixed and the mixture infiltrated into leaf tissue of *Nicotiana benthamiana* plants in the greenhouse. The plants were grown for a further five days after infiltration before leaf discs were taken for GC analysis which revealed that these genes were functioning to produce DHA in *Nicotiana benthamiana*. Leaf tissue transformed with these genes contained SDA (2.3%), ETA (0.7%), EPA (0.8%), DPA (2.8%) and DHA (4.4%) (Table 14). The leaf tissue also contained trace levels of GLA, ETrA and ARA. The conversion efficiencies were as follows: 17.4% of the ALA produced in the cell was converted to EPA (including EPA subsequently converted to DPA or DHA); 15.5% of ALA was converted to DPA or DHA; 9.6% of the ALA produced in the cell was converted to DHA; while 40% of the ALA produced in the cell that was Δ6-desaturated was subsequently converted to DHA. Due to the transient expression of the transgenes in this experiment, higher efficiencies than the above would be expected in stably transformed cells.

When the total lipid extracted from the leaf tissue was fractionated by TLC to separate the lipid classes, and the TAG and polar lipid fractions analysed for fatty acid composition by FAME, it was observed that the level of DHA in the TAG was 7% as a percentage of the total fatty acid, and in the polar-lipid the level of DHA was 2.8%. The lower level in the polar lipid class was thought to be due to the relative contribution of chloroplast lipids in the leaves, favouring polar-lipids, and the transient expression of the genes rather than stable insertion of the transgenes into the host cell genome.

TABLE 14

Fatty acid composition of lipid from leaves transformed with a combination of desaturases and elongases.

| Fatty acid | Fatty acid | Untransformed cells | Transformed cells |
| --- | --- | --- | --- |
| 16:0 | palmitic | 17.1 | 20.4 |
| 16:1d7 | | 0.1 | 0.4 |
| 16:1d9 | | 0.2 | 0.2 |
| C6:1d? | | 0.5 | 0.4 |
| 16:1d? | | 0.5 | 0.4 |
| 17:1d9 | | 0.9 | 0.7 |
| 16:2 | | 0.9 | 0.9 |
| 16:3 | | 6.6 | 5.4 |
| 18:0 | stearic | 2.1 | 3.6 |
| 18:1d7 | | 0.0 | 0.0 |
| 18:1d9 | oleic | 0.8 | 2.6 |
| 18:1d11 | | 0.0 | 0.0 |
| 18:1d12 | | 0.3 | 0.6 |
| 18:1d13 | | 0.2 | 0.2 |
| 18:2n6 | LA | 5.1 | 10.8 |
| 18:3n6 | GLA | 0.7 | 1.9 |
| 18:3n3 | ALA | 57.8 | 35.0 |
| 20:0 | | 0.4 | 0.7 |
| 20:1d5 | | 0.4 | 0.3 |
| 18:4n3 | SDA | 0.4 | 2.3 |
| 20:1d8 | | 0.0 | 0.0 |
| 20:1d11 | | 0.0 | 0.0 |
| 20:2n6 | EDA | 0.1 | 0.2 |
| 20:3n6 | DGLA | 0.3 | 0.4 |
| 20:4n6 | ARA | 0.4 | 0.5 |
| 20:3n3 | ETrA | 0.2 | 0.2 |
| 22:0 | | 0.2 | 0.2 |
| 20:4n3 | ETA | 0.0 | 0.7 |
| 22:1d9 | | 0.0 | 0.9 |
| 20:5n3 | EPA | 0.8 | 0.8 |
| 22:2n6 | | 0.1 | 0.2 |
| 22:4n6 | | 0.1 | 0.1 |
| 22:3n3 | | 1.1 | 1.2 |
| 24:0 | | 0.4 | 0.4 |
| 22:5n6 | | 0.4 | 0.2 |
| 24:1d9 | | 0.8 | 0.1 |
| 22:5n3 | DPA | 0.2 | 2.8 |
| 22:6n3 | DHA | 0.1 | 4.4 |

This experiment demonstrated that the isolated *Micromonas* CCMP1545 Δ6-desaturase had a substantial preference for the ω3 substrate ALA compared with the ω6 substrate LA. The experiment also demonstrated that the expression of suitable genes can result in the accumulation of substantial percentages of LC-PUFA in the leaf, most notably EPA, DPA and DHA.

This experiment also showed the use the *Nicotiana benthamiana* transient assay system for the rapid testing of various fatty acid biosynthesis pathways and for selecting optimal combinations of genes. This system could be used to rapidly compare the relative activities of genes with homologous function, as well as the comparison of entire biosynthetic pathways.

Discussion: Efficient DHA Synthesis in Leaf and Seed Tissue

On the basis of this data, it was predicted that the same levels of EPA, DPA and DHA, or even higher levels, would be produced in seed when seed-specific promoters are used to express this combination of genes, or a similar set. The observed efficient flux of fatty acids from ALA to EPA and through to DPA and DHA was thought to be due to the combination of efficient elongases with acyl-CoA desaturases, thereby operating on fatty acids predominantly in the acyl-CoA pool. Furthermore, it was predicted that production of EPA, DPA, DHA and other LC-PUFA in both leaf and seed of a transgenic plant, or in seed and another tissue other than leaves, could be achieved by the use of a promoters with the appropriate tissue specificity, or promoter combinations. Fused promoters would be able to drive the production of the enzymes in both tissue types. The resulting plant would likely be useful for both oil extraction, particularly from seed, and feedstock with minimal processing.

Example 11. More Efficient DHA Biosynthesis in Plant Cells

The enzyme activities of the *Micromonas* CCMP1545 Δ6-desaturase (SEQ ID NO:8 encoded by SEQ ID NO:7), *Pyramimonas* CS-0140 Δ6-elongase (SEQ ID NO:4 encoded by SEQ ID NO:3), *Pavlova salina* Δ5-desaturase (SEQ ID NO:26 encoded by SEQ ID NO:25), *Pyramimonas* CS-0140 Δ5-elongase (SEQ ID NO:6 encoded by SEQ ID NO:5) and *Pavlova salina* Δ4-desaturase (SEQ ID NO:73 encoded by SEQ ID NO:72) along with the *Arabidopsis thaliana* DGAT1 (SEQ ID NO:74 encoded by SEQ ID NO:75) were demonstrated in planta using an enhanced *Nicotiana benthamiana* transient expression system as described in Example 1 and Example 10. This experiment was optimised by using younger, healthier *N. benthamiana* plants.

These chimeric vectors described in Example 10 were introduced individually into *Agrobacterium tumefaciens* strain AGL1 and transgenic cells from cultures of these were mixed and the mixture infiltrated into leaf tissue of *Nicotiana benthamiana* plants in the greenhouse. The plants were grown for a further five days after infiltration before leaf discs were taken for GC analysis which revealed that these genes were functioning to produce DHA in *Nicotiana benthamiana* (Tables 15 and 16). Leaf tissue transformed with these genes contained SDA (2.0%), ETA (0.4%), EPA (0.7%), DPA (4.3%) and DHA (4.4%). The leaf tissue also contained trace levels of GLA, ETA and ARA. The conversion efficiencies were as follows: 23.4% of the ALA produced in the cell was converted to EPA (including EPA subsequently converted to DPA or DHA); 21.6% of ALA was converted to DPA or DHA; 10.9% of the ALA produced in the cell was converted to DHA; while 37.2% of the ALA produced in the cell that was D6-desaturated was subsequently converted to DHA. Due to the transient expression of the transgenes in this experiment, higher efficiencies than the above would be expected in stably transformed cells.

When the total lipid extracted from the leaf tissue was fractionated by TLC to separate the lipid classes, and the TAG and polar lipid fractions analysed for fatty acid composition by FAME, it was observed that the level of DHA in the TAG was 15.9% as a percentage of the total fatty acid, and in the polar-lipid the level of DHA was 4.4%. The lower level in the polar lipid class was thought to be due to the relative contribution of chloroplast lipids in the leaves, favouring polar-lipids, and the transient expression of the genes rather than stable insertion of the transgenes into the host cell genome.

TABLE 15

Fatty acid composition of lipid from leaves transformed with a combination of desaturases and elongases.

| Fatty acid | Control Total Lipid | Pavsa-D5E DHA Pathway Total Lipid | Pavsa-D5E DHA Pathway TAG | Pyrco-D5E DHA Pathway Total Lipid | Pyrco-D5E DHA Pathway TAG |
|---|---|---|---|---|---|
| Usual FA | | | | | |
| 16:0 | 15.9 ± 0.2 | 17.0 ± 0.1 | 20.2 | 16.6 ± 0.1 | 21.6 |
| 16:1$^{\Delta 3t}$ | 1.7 ± 0.1 | 1.5 ± 0.2 | 0.3 | 1.5 ± 0.1 | 0.3 |
| 16:3$^{\Delta 9, 12, 15}$ | 6.3 ± 0.3 | 5.2 ± 0.1 | 0.4 | 5.6 ± 0.1 | 0.6 |
| 18:0 | 3.6 ± 0.3 | 3.5 ± 0.1 | 5.9 | 3.3 ± 0.1 | 6.5 |
| 18:1$^{\Delta 9}$ | 2.8 ± 0.1 | 3.4 ± 0.1 | 5.1 | 2.8 ± 0.2 | 5.6 |
| 18:2$^{\Delta 9, 12}$ | 18.7 ± 0.1 | 14.1 ± 0.4 | 15.2 | 13.0 ± 0.1 | 17.3 |
| 18:3$^{\Delta 9, 12, 15}$ | 45.6 ± 1.4 | 39.1 ± 0.4 | 6.9 | 40.2 ± 0.5 | 6.7 |
| 20:0 | 1.3 ± 0.4 | 0.7 ± 0 | 1.8 | 0.6 ± 0 | 2.0 |
| Other minor | 4.1 | 2.5 | 6.3 | 2.3 | 6.2 |
| Total | 100 | 87.0 | 62.1 | 85.9 | 66.8 |
| New ω6 PUFA | | | | | |
| 18:3$^{\Delta 6, 9, 12}$ | — | 1.6 ± 0.1 | 3.3 | 2.1 ± 0.2 | 4.3 |
| 20:3$^{\Delta 8, 11, 14}$ | — | — | — | — | — |
| 20:4$^{\Delta 5, 8, 11, 14}$ | — | 0.3 ± 0.1 | 0.5 | 0.2 ± 0 | — |
| Total | 0 | 1.9 | 3.8 | 2.3 | 4.3 |
| New ω3 PUFA | | | | | |
| 18:4$^{\Delta 6, 9, 12, 15}$ | — | 1.5 ± 0.1 (22% D6D) | 3.8 | 2.0 ± 0 (23% D6D) | 6.4 |
| 20:4$^{\Delta 8, 11, 14, 17}$ | — | 0.5 ± 0 (86% D6E) | 1.5 | 0.4 ± 0 (83% D6E) | 1.6 |
| 20:5$^{\Delta 5, 8, 11, 14, 17}$ | — | 4.1 ± 0.2 (95% D5D) | 14.2 | 0.7 ± 0 (96% D5D) | 1.5 |
| 22:5$^{\Delta 7, 10, 13, 16, 19}$ | — | 2.4 ± 0.1 (55% D5E) | 1.6 | 4.3 ± 0 (93% D5E) | 3.5 |
| 22:6$^{\Delta 4, 7, 10, 13, 16, 19}$ | — | 2.6 ± 0.1 (52% D4D) | 13.0 | 4.4 ± 0.1 (51% D4D) | 15.9 |
| Total | 0 | 11.1 | 34.1 | 11.8 | 28.9 |
| Total new FA | 0 | 13.0 | 37.9 | 14.0 | 33.2 |
| Total FA | 100 | 100 | 100 | 100 | 100 |

TABLE 16

Conversion efficiencies from leaves transformed with a combination of desaturases and elongases.

| Fatty Acid | Total | | Enzyme | Converion Efficiency | |
|---|---|---|---|---|---|
| LA | 13 | | | | |
| GLA | 2.1 | 15.0% | d6D | | |
| DGLA | 0 | 8.7% | d6E | | |
| AA | 0.2 | 100.0% | d5D | | |
| ALA | 40.2 | | | | |
| SDA | 2 | 22.7% | d6D | 18.1% | d6D to EPA + DPA + DHA |
| ETA | 0.4 | 83.1% | d6E | 16.7% | d6D to DPA + DHA |
| EPA | 0.7 | 95.9% | d5D | 8.5% | ALA to DHA |
| DPA | 4.3 | 92.6% | d5E | 46.8% | EPA to DHA |
| DHA | 4.4 | 50.6% | d4D | | |
| TAG | | | | | |
| LA | 17.3 | | | | |
| GLA | 4.3 | 19.9% | d6D | | |
| DGLA | 0 | 0.0% | d6E | | |
| AA | 0 | 0.0% | d5D | | |
| ALA | 6.7 | | | | |
| SDA | 6.4 | 81.2% | d6D | 58.7% | d6D to EPA + DPA + DHA |
| ETA | 1.6 | 77.9% | d6E | 54.5% | d6D to DPA + DHA |

TABLE 16-continued

Conversion efficiencies from leaves transformed with a combination of desaturases and elongases.

| Fatty Acid | Total | Enzyme | | Converion Efficiency | |
|---|---|---|---|---|---|
| EPA | 1.5 | 92.9% | d5D | 44.7% | ALA to DHA |
| DPA | 3.5 | 92.8% | d5E | 76.1% | EPA to DHA |
| DHA | 15.9 | 82.0% | d4D | | |

Discussion: More Efficient DHA Synthesis in Leaf and Seed Tissue

This result is likely to pave the way for similar advances in yield in seed TAG due to the substantial conservation of extra-plastidial lipid synthesis mechanisms between leaf and seed tissues (Ohlrogge and Browse, 2004; Bates et al., 2007). We postulate that several elements are likely responsible for this large increase in production: 1. the use of an ω3-specific acyl-CoA Δ6-desaturase increases flux down the ω3 pathway and decreases competition with parallel ω6 substrates for subsequent metabolic steps; 2. a highly efficient Δ5-elongase clearly increases the amount of DPA available for Δ4-desaturation to DHA; 3. the reduction of gene silencing by the use of independent transcriptional units and the use of a viral suppressor protein (P19).

The strong ω3 preference displayed by the Δ6-desaturase is clearly desirable when attempting to engineer a land plant that accumulates the ω3 LC-PUFA EPA and DHA since the additional Δ17-desaturase activity required to convert AA ($20:4^{D5,8,11,14}$) to EPA is not required, thus simplifying both metabolic engineering and regulatory challenges.

In addition to the above optimised step, use of the highly efficient *P. cordata* Δ5-elongase resulted in a fatty acid profile of the TAG (oil) fraction that closely resembled tuna oil, a fish oil notable for high DHA and low intermediate content (FIG. 18). Also, the activity displayed by the *P. cordata* Δ5-elongase in *N. benthamiana* is by far the most efficient Δ5-elongation we have experienced and use of this gene effectively overcomes the large Δ5-elongation bottleneck that has been experienced in other attempts at transgenic DHA production.

Finally, whilst the use of optimal genes is clearly required we consider it probable that the method by which these transgenes were introduced (i.e. as independent expression cassettes and in the presence of a gene-silencing suppressor) played a key role in the high levels of DHA achieved in this study. Metabolic engineering for LC-PUFA production has thus far relied on relatively large multi-gene constructs being randomly inserted into the host genome and whilst many groups have had good results with this method there are indications that it is difficult to obtain events displaying equal expression of all the transgenes (WO 2004/017467). In addition, silencing effects may reduce efficiency over generations (Matzke et al., 2001). It is possible that alternative transformation approaches such as artificial chromosomes involving de novo centromere formation on an independently assembled unit and engineered mini-chromosomes might ultimately be required for successful stable LC-PUFA metabolic engineering (Yu et al., 2007).

Example 12. Transgenic Assembly of an Entire ALA to DHA Pathway Using Genes from a Single Organism The entire ALA to DHA pathway was reconstituted using genes encoding the enzymes from *P. salina*, consisting of the Δ9-elongase, Δ8-desaturase, Δ5-desaturase, Δ5-elongase and Δ4-desaturase, and assembled in *N. benthamiana*. GC analysis of the total leaf tissue five days after agroinfiltration demonstrated the production of 0.7% DHA (Table 17). This is the first time a transgenic pathway from ALA to DHA consisting of genes from a single organism has been reported.

TABLE 17

Fatty acid composition (percent of total fatty acids) of *Nicotiana benthamiana* leaf tissue transiently transformed with single-gene CaMV 35S binary constructs. The DHA pathway consists of the *P. salina* Δ9-elongase, Δ8-desaturase, Δ5-desaturase, Δ5-elongase and Δ4-desaturase. Standard deviations between separate infiltrations performed in triplicate are indicated.

| Fatty acid | Control | Pavpi-Δ9E DHA |
|---|---|---|
| Usual FA | | |
| 16:0 | 15.7 ± 0.6 | 15.9 ± 0.2 |
| $16:1^{\Delta 3t}$ | 1.5 ± 0 | 1.4 ± 0.1 |
| $163^{\Delta 9, 12, 15}$ | 6.8 ± 0.7 | 5.9 ± 0.3 |
| 18:0 | 3.0 ± 0.1 | 3.7 ± 0.2 |
| $18:1^{\Delta 9}$ | 2.2 ± 0 | 2.7 ± 0.3 |
| $18:2^{\Delta 9, 12}$ | 11.8 ± 0.4 | 8.6 ± 0.6 |
| $18:3^{\Delta 9, 12, 15}$ | 56.0 ± 1.4 | 49.0 ± 1.4 |
| Other minor | 3.0 ± 0 | 2.8 ± 0 |
| Total | 100 | 90.0 |
| New ω6 PUFA | | |
| $20:2^{\Delta 8, 11}$ | — | 1.7 ± 0.2 |
| $20:3^{\Delta 8, 11, 14}$ | — | 0.5 ± 0 |
| $20:4^{\Delta 5, 8, 11, 14}$ | — | 2.4 ± 0.1 |
| $22:4^{\Delta 7, 10, 13, 16}$ | 13 | 1.2 ± 0 |
| $22:5^{\Delta 4, 7, 10, 13, 16}$ | — | — |
| Total | 0 | 5.8 |
| New ω3 PUFA | | |
| $20:3^{\Delta 11, 14, 17}$ | — | 1.5 ± 0.2 |
| $20:4^{\Delta 8, 11, 14, 17}$ | — | 0.2 ± 0 |
| $20:5^{\Delta 5, 8, 11, 14, 17}$ | — | 1.2 ± 0.1 |
| $22:5^{\Delta 7, 10, 13, 16, 19}$ | — | 0.6 ± 0 |
| $22:6^{\Delta 4, 7, 10, 13, 16, 19}$ | — | 0.7 ± 0.1 |
| Total | 0 | 4.2 |
| Total new FA | 0 | 10.0 |
| Total FA | 100 | 100 |

Example 13. Specific Expression of VSPs in Developing Seeds of Plants

The protein coding regions of five viral suppressor proteins (VSP), namely P19, V2, P38, PePo and RPV-P0, were initially inserted into a binary vector pART27 (Gleave, 1992) under the control of the 35S promoter for strong constitutive expression in plant tissues. These proteins have been characterised as VSPs as follows. P19 is a suppressor protein from Tomato Bushy Stunt Virus (TBSV) which binds to 21 nucleotide long siRNAs before they guide Argonaute-guided cleavage of homologous RNA (Voinnet et al., 2003). V2, a suppressor protein from Tomato Yellow Leaf Roll Virus (TYLRV), binds to the plant protein SGS3 (Glick et al., 2008), a protein thought to be required for the production of double stranded RNA intermediates from ssRNA substrates (Beclin et al., 2002). P38 is a suppressor protein from Turnip Crinkle Virus (TCV) and inhibits the RNA dependent polymerase activity (RdRP) critical for the production of siRNA and binds to the Dicer protein DCL4 (Ding and Voinnet, 2007). P0 proteins such as PePo and RPV-P0, from poleroviruses, target Argonaut proteins for enhanced degradation (Baumberger et al., 2007; Bortolamiol et al., 2007). In order to establish the function of these proteins to increase transgene expression as suppressors of silencing, the five 35S driven VSP constructs in *Agrobacterium* were co-infiltrated with a 35S-driven GFP construct into *Nicotiana benthamiana* leaves. In all cases the presence of the VSP increased and extended expression of the GFP, conferring increased levels of GFP gene activity particularly after 4 days post-inoculation with the *Agrobacterium* strains, confirming the function of the proteins as silencing suppressors in this assay format.

The five VSP coding regions were each inserted into a second binary vector, pXRZ393, based on a pART27 backbone vector, so that expression of the VSPs was under the control of a seed-specific FP1 promoter (Ellerstrom et al., 1996) providing expression of the VSPs in cotyledons of developing seed in dicotyledonous plants. The constructs were used to generate transformed *Arabidopsis* plants according to the methods described in Example 1. At least 20 transformed plants were obtained for each chimeric gene encoding VSP. The plants were viable and phenotypically mostly normal as indicated by their growth on selection media and in soil, growing normally into fertile adult plants which set viable seed. The only morphological phenotype that appeared to be altered in the seedlings was in the cotyledons that emerged from some of the seeds after germination for P19, PePo and RPV-P0. Plantlets transformed with the construct seed-specifically encoding P19 had flat club-shaped cotyledons with no downward curl distinctive of wild-type plantlets. Plantlets transformed with the construct encoding PePo produced a 'ballerina' phenotype, where the cotyledons were up-ward pointing with an inward or concave curl. True leaves on these plants were normally developed. Plantlets expressing RPV-P0 were bushy, and tended to retain a bushy growth habit throughout vegetative growth. Plantlets of V2 and P38 displayed no apparent, significant phenotype.

Other than cotyledon development, plantlets transformed with the P19 and PoPe constructs grew normally and were indistinguishable from control plants in subsequent growth and development. The promoter expressing the VSPs in this experiment, FP1, is well characterised with a limited but strong expression in developing cotyledons of *Arabidopsis* during seed development (Ellerstrom et al., 1996). On the basis of the emergent cotyledon phenotypes, we suggest that FP1-driven expression of P19, PePo or RPV-P0 in developing seed may overlap with small RNA biogenesis required for normal cotyledon development. These VSP-related changes in cotyledon development do not impact on the overall development of the transgenic plants, and the normal subsequent growth and development of the plants indicated that any leaky expression of VSPs from the FP1 promoter in tissues other than the developing seed was minor and insignificant. This was in contrast to previous studies where constitutive expression of many VSPs in plant tissues was highly deleterious (Mallory et al., 2002; Chapman et al., 2004; Chen et al., 2004; Dunoyer et al., 2004; Zhang et al., 2006; Lewsey et al., 2007: Meng et al., 2008).

The lack of a phenotype for the VSPs V2 and P38 may reflect that these VSPs target small RNA metabolism in ways that do not affect developmental small RNA biogenesis or recognition. The functionality of each VSP was checked using a GFP assay in *Nicotiana benthamiana.*

Example 14. Development of a Seed-Specific Visual Marker to Find and Assess T1 Seed Transformed with VSP Constructs The data described in Example 13 indicated that seeds, and the subsequent progeny plants, could tolerate the expression of VSPs from seed-specific promoters without significant deleterious effects. The inventors also considered whether the transformed plants generated as described above were expressing only low levels of the VSPs, thereby allowing the seed to survive, effectively selecting against transformed seeds potentially expressing lethal amounts of VSP which would therefore not be recovered under the conditions used.

To more accurately assess the expression of transgenes in T1 seed, a visual marker of transformation and expression was developed for use in transgenic seed. *Arabidopsis* seeds as for other dicot seeds contain a paternal embryo and endosperm surrounded by a maternal seed coat. During *Agrobacterium*-mediated transformation of *Arabidopsis*, paternal tissue becomes transformed by the T-DNA whilst the maternal tissue remains untransformed. Transformed maternal tissue is not obtained until the production of T2 seed of the next generation. To provide a useful screening system, a gene encoding green fluorescent protein (GFP) was modified to promote strong secretion of the protein outside of the cell. Such a location of GFP had been show to allow visual recovery of transformed T1 seed (Nishizawa et al., 2003) by detection of the secreted GFP produced in the transformed T1 embryo and endosperm, through the thin but untransformed seed coat (Fuji et al., 2007).

A chimeric gene encoding a secreted GFP was constructed as follows. The gene contained two introns, one in the 5'untranslated region (5'UTR) and a second in the protein coding region of GFP. These introns were included to enhance expression of the chimeric gene (Chung et al., 2006) and to ensure that any GFP signal detected in the seeds could only result from expression of the gene in plant cells rather than leaky expression from the *Agrobacterium* cells. An intron-interrupted version of humanised GFP (Clontech) encoding a GFP protein that would be localised to the cytoplasm (Brosnan et al., 2007) was modified to promote secretion to the apoplast via the endoplasmic reticulum (ER) according to the report of Nishizawa et al. (2003). The modified GFP construct for apoplastic secretion included a conglycinin secretion peptide added as an in-frame translational fusion at the N-terminus of GFP and four glycine residues added at the C-terminus to facilitate secretion from the ER. These additions to the chimeric GFP gene were performed by gene synthesis for the 5' region and PCR-mediated sequence modifications for the C-terminal glycine additions. The coding region for this secreted GFP was inserted downstream of a FP1 promoter which had an intron from a catalase gene in the 5'UTR. The entire FP1-secreted GFP sequence was inserted upstream of a nos3' polyadenylation signal within a pORE series binary vector. The construct containing the chimeric gene encoding the secreted GFP was designated pCW141.

To confirm the expression and secretion of the GFP protein, the gene region encoding the secreted GFP sequence but without the FP1 promoter or the 5'UTR of pCW141 was subcloned into a pCaMV35S-OCS3' expression cassette, to produce pCW228, and introduced by *Agrobacterium*-mediated transformation into *N. benthamiana* leaves. Expression of the gene and secretion of GFP protein was confirmed using confocal microscopy (Leica).

On the basis that the construct was correct, pCW141 was introduced into plants of *Arabidopsis* Col-0 ecotype via Agrobacteria-mediated methods as described in Example 1. Seeds from *Arabidopsis* plants dipped with pCW141, the FP1-driven secreted GFP construct, were collected and screened for GFP-positive seeds using a dissecting microscope equipped for fluorescence detection (Leica MFZIII). Seeds that fluoresced green were easily identified even though the vast majority of T1 seeds in the populations were untransformed. These GFP-positive seeds were selected and grown on selective media to confirm the presence of the kanamycin-resistance selectable marker gene linked to the chimeric gene construct on the T-DNA. A further 20 positive seed were pooled and the expression of GFP protein was confirmed by Western Blotting using an antibody against GFP.

Selection of VSP Expression in T1 Seed Using a Secreted GFP Marker

Each of the four chimeric genes encoding the VSPs: P19, P38, V2 and P38, each under the control of the FP1 promoter for developing cotyledon-specific expression, were inserted into the GFP selection vector pCW141 described above to produce pCW161, pCW162, pCW163 and pCW164, respectively. These binary vectors each had linked chimeric genes for the expression of a VSP and the secreted GFP, and thereby allowed transgenic seed transformed with the constructs to be identified, selected and analysed by the GFP phenotype without growth on selective media. It was expected that in the majority of transformants, the gene encoding the VSP would be integrated and therefore linked with the gene encoding GFP.

Seeds obtained from *Arabidopsis* plants which had been inoculated with *Agrobacterium* containing the combination VSP-GFP constructs, according to the method in Example 1, were collected and screened for GFP fluorescence as described above. Seeds that fluoresced green were collected by hand and grown on selective media to determine whether they had also been transformed with the selectable marker gene. In all cases the GFP-positive seed grew on the selection media, and exhibited the same cotyledon phenotypes as plants that had been transformed with the VSP genes without the GFP gene as described above. In no cases were GFP positive seed observed that failed to grow on the selective media. Such seeds might have been expected if some transformation events gave rise to cells in the developing seeds in which the expression levels of VSP was too high and caused lethality. The absence of such seeds in the transformed populations indicated that the VSP expression was tolerated in seeds when expressed from the FP1 promoter. The absence of such deleterious effects was in contrast to reports of deleterious effects when many VSPs were expressed constitutively (Mallory et al., 2002; Chapman et al., 2004; Chen et al., 2004; Dunoyer et al., 2004; Zhang et al., 2006; Lewsey et al., 2007: Meng et al., 2008).

Thus, use of a visually-detectable marker such as GFP proved a powerful and efficient way to identify, select and analyse transgenic events incorporating linked genes such as those encoding VSPs, desaturase, elongases or other fatty acid-modifying enzymes.

Quantification of GFP Expression in Seeds Expressing VSP Post-Embryonically

GFP expression was quantified in T1 and T2 seed expressing VSP from FP1 promoter using fluorescent microscopy and digital image analysis. These analyses clearly showed that GFP expression was not affected by the co-introduction of a gene encoding VSP under the control of the developing cotyledon-specific promoter. Extended studies on the performance of GFP-VSP constructs over subsequent generations and in independent transformation events will be analysed. It is predicted that the presence of the VSP will result in more stable and higher average levels of expression in successive generations of seed.

Example 15. Co-Expression of VSPs with Genes for LC-PUFA Synthesis in Seeds

To establish that VSPs are capable of protecting or enhancing transgene performance in seeds, some expression vectors were designed that were considered to be more prone to host-mediated suppression (silencing) than a vector with only a single gene, to increase the relative effectiveness of the VSPs. A series of vectors each containing five desaturase or elongase genes for DHA synthesis in seeds were constructed, using the same configuration of the genes in each. One factor that was thought to make these constructs more prone to silencing (reduced expression) was the use of the same promoter (FP1) to drive each gene. The FP1 promoter was used as it was relatively small and reduced the overall vector size and the spacing between each coding region. Furthermore, each gene cassette had the same orientation, which we considered would enhance the likelihood of silencing. Three genes of the LC-PUFA pathway had coding regions which had been codon-optimised (A-B-C) for optimal plant expression while two (E-D) were native sequences as obtained from the microalgae. The same suite of five genes had previously been expressed in leaves to produce assemble a complete LC-PUFA biosynthetic pathway (Example 11). A further gene encoding the VSP P19 was included in the first vector of the series, a gene encoding V2 was included in the second vector, while the third vector in the series had no VSP.

These vectors pJP3057 (FIG. 19), pJP3059 (FIG. 20) and (FIG. 21) were constructed and transformed in parallel as follows. Desaturase or elongase genes or viral suppressor genes were first cloned between a FP1 promoter and nos terminator contained within a cloning vector. The promoter-gene-terminator cassettes were then cloned sequentially and in the same orientation into a binary vector backbone. pJP3057 contained the entire DHA pathway whilst pJP3059 and pJP3060 differed only in the addition of a FP1-P19-NOS or FP1-V2-NOS cassette, respectively. The construction steps were as follows. First, an AscI-PacI fragment containing the *Micromonas pusilla* Δ6-desaturase was cloned into the AscI-PacI site of pJP2015 before a SwaI fragment from this vector containing the entire promoter-gene-terminator cassette was cloned into the EcoRV site of pORE02 to generate pJP3050. Next, an AscI-PacI fragment containing the *Pyramimonas cordata* Δ6-elongase was cloned into the AscI-PacI site of pJP2015TMV (a slightly modified version of pJP2015 where the TMV leader was present downstream of the promoter and upstream of the gene) before a SwaI fragment from this vector containing the entire promoter-gene-terminator cassette was cloned into the T4 DNA polymerase-treated SacI site of pJP3050 to generate pJP3051. Next, an AscI-PacI fragment containing the *Pavlova salina* Δ5-desaturase was cloned into the AscI-PacI site of pJP2015TMV before a SwaI fragment from this vector containing the entire promoter-gene-terminator cassette was cloned into the SmaI site of pJP3051 to generate pJP3052. Next, an AscI-PacI fragment containing the *Pavlova salina* Δ5-desaturase was cloned into the AscI-PacI site of pJP2015TMV before a SwaI fragment from this vector containing the entire promoter-gene-terminator cassette was cloned into the SmaI site of pORE02 to generate pJP3054.

Next, an AscI-PacI fragment containing the *Pyramimonas cordata* Δ5-elongase was cloned into the AscI-PacI site of pJP2015TMV before a SwaI fragment from this vector containing the entire promoter-gene-terminator cassette was cloned into the StuI site of pJP3054 to generate pJP3055. Next, an AscI-PacI fragment containing the *Pavlova salina* Δ4-desaturase was cloned into the AscI-PacI site of pJP2015TMV before a SwaI fragment from this vector containing the entire promoter-gene-terminator cassette was cloned into the SfoI site of pJP3056 to generate pJP3056. The PmeI-NotI fragment of pJP3056 was then cloned into the PmeI-NotI site of pJP3051 to generate pJP3057, a binary vector containing the five genes for production of DHA from ALA.

Next, an AscI-PacI fragment containing the chimeric gene encoding the P19 viral suppressor was cloned into the AscI-PacI site of pJP2015TMV before a SwaI fragment from this vector containing the entire promoter-gene-terminator cassette was cloned into the ZraI site of pJP3057 to generate pJP3059. Similarly, an AscI-PacI fragment containing the chimeric gene encoding the V2 viral suppressor was cloned into the AscI-PacI site of pJP2015TMV before a SwaI fragment from this vector containing the entire promoter-gene-terminator cassette was cloned into the ZraI site of pJP3057 to generate pJP3060.

All three constructs were transformed in *Arabidopsis* (ecotype Columbia). *Arabidopsis* plants (Col-0 ecotype) were transformed with each of the constructs and pJP3057 was used to transform canola. T1 seeds will be collected, analysed on herbicide-containing media, and the resulting T2 seed analysed for general morphological changes and LC-PUFA synthesis.

The transformed plants (*Arabidopsis thaliana*, ecotype Columbia) generated with the three constructs pJP3057, pJP3059 and pJP3060 were self-fertilised and T1 seeds were collected. These were sown on kanamycin-containing media to determine heterozygosity/homozygosity of the T1 plants, and the resultant T2 seed from each of the T1 plants were analysed for general morphological changes and LC-PUFA synthesis (Table 18).

Representative T2 seed of plants transformed with pJP3057 contained, in the total fatty acid in the seedoil, SDA (0.4%), ETA (0.6%), EPA (0.2%), DPA (0.3%) and DHA (2.4%). The seedoil of the T2 plants also contained GLA (1.4%) and trace levels of ETrA and ARA. The conversion efficiencies in the seed were as follows: 18.4% of the ALA produced in the cell was Δ6-desaturated; 89.7% of the SDA produced in the cell was Δ6-elongated; 82.9% of the ETA in the cell was Δ5-desaturated; 93.1% of the EPA in the cell was Δ5-elongated; 88.9% of the DPA in the cell was Δ4-desaturated to produce DHA (Table 18).

Representative T2 seed of plants transformed with pJP3059 contained SDA (0.7%), ETA (0.3%), EPA (0.2%), DPA (0.9%) and DHA (1.3%). The seedoil also contained GLA (0.8%) and trace levels of ETrA and ARA. The conversion efficiencies were as follows: 15.7% of the ALA produced in the cell was Δ6-desaturated; 79.4% of the SDA produced in the cell was Δ6-elongated; 88.9% of the ETA in the cell was Δ5-desaturated; 91.7% of the EPA in the cell was Δ5-elongated; 59.1% of the DPA in the cell was Δ4-desaturated to produce DHA (Table 18).

TABLE 18

Representative fatty acid profiles of T2 *Arabidopsis* seeds transformed with pJP3057, pJP3059, pJP3060.

| Sample | Columbia | pJP3057 | pJP3059 | pJP3060 |
|---|---|---|---|---|
| 16:0 | 7.7 | 7.6 | 8.3 | 7.4 |
| 16:1d9 | 0.3 | 0.3 | 0.3 | 0.3 |
| 18:0 | 3.1 | 3.7 | 3.8 | 3.4 |
| 20:0 | 2.1 | 1.8 | 1.8 | 1.9 |
| 22:0 | 0.3 | 0.3 | 0.3 | 0.3 |
| 24:0 | 0.2 | 0.2 | 0.2 | 0.2 |
| 18:1d9 | 12.9 | 12.8 | 12.2 | 13.6 |
| 18:1d11 | 1.5 | 1.8 | 1.9 | 1.6 |
| 20:1d11 | 18.3 | 16.3 | 14.7 | 16.0 |
| 20:1 d13 | 1.7 | 1.5 | 2.0 | 1.9 |
| 22:1d13 | 1.6 | 1.2 | 1.2 | 1.3 |
| 24:1d15 | 0.2 | 0.2 | 0.2 | 0.2 |
| Other | 2.5 | 2.3 | 2.6 | 2.5 |
| 18:2n6 | 27.8 | 27.2 | 28.2 | 27.9 |
| 18:3n6 | 0.0 | 1.4 | 0.8 | 0.4 |
| 20:3n6 | 0.0 | 0.0 | 0.0 | 0.0 |
| 20:4n6 | 0.0 | 0.0 | 0.0 | 0.0 |
| 18:3n3 | 19.7 | 17.3 | 18.2 | 18.2 |
| 18:4n3 | 0.0 | 0.4 | 0.7 | 0.6 |
| 20:4n3 | 0.0 | 0.6 | 0.3 | 0.7 |
| 20:5n3 | 0.0 | 0.2 | 0.2 | 0.3 |
| 22:5n3 | 0.0 | 0.3 | 0.9 | 0.2 |
| 22:6n3 | 0.0 | 2.4 | 1.3 | 1.0 |
|  | 100.0 | 100.0 | 100.0 | 100.0 |

Representative T2 seed of plants transformed with pJP3060 contained SDA (0.6%), ETA (0.7%), EPA (0.3%), DPA (0.2%) and DHA (1.0%). The seedoil also contained trace levels of GLA, ETrA and ARA. The conversion efficiencies were as follows: 13.3% of the ALA produced in the cell was Δ6-desaturated; 78.6% of the SDA produced in the cell was Δ6-elongated; 68.2% of the ETA in the cell was Δ5-desaturated; 80.0% of the EPA in the cell was Δ5-elongated; 83.3% of the DPA in the cell was Δ4-desaturated to produce DHA (Table 18).

Results

All genes in the construct pJP3057 showed high activity/high efficiency of conversion with the exception of the Δ6-desaturase. This indicates that the Δ6-, Δ5- and Δ4-desaturases are likely acting on acyl-CoA substrates since the native substrate ALA is produced by an acyl-PC desaturase, resulting in the lower Δ6-desaturation, and the transgenic desaturase substrates ETA and DPA are produced by elongases which are known to act in the acyl-CoA pool. Furthermore, the high efficiency of the Δ6- and Δ5-elongase steps (>80% efficiency) indicated that the immediately preceding desaturases (Δ6- and Δ5-desaturases, respectively) were acting on acyl-CoA substrates. It is reasonably expected that the activities of these genes will increase in subsequent generations of transgenic plants when homozygosity is reached, and that levels of the LC-PUFA Products Will Increase as a Consequence.

The presence of the silencing suppressor in the constructs pJP3057 and pJP3059 increased both the total level of the new fatty acids in the seedoil, and the level of the final product of the pathway, DHA.

Discussion

With regard to Examples 13 to 15, introduced exogenous nucleic acids can be detected by plants as foreign DNA or RNA leading to reduced expression due to host-mediated transgene suppression mechanisms. These suppression mechanisms may target transgenes via the biogenesis of small RNA populations, and these small RNAs guide the suppression apparatus to limit expression of the transgene (Matzke et al., 2001). Transgene expression can be limited in various ways including direct modifications of the DNA at the site of insertion in the chromosome, such as by methylation, or by post-transcriptional silencing at the RNA (Hamilton and Baulcombe, 1999; Voinnet et al., 2003) or protein (Brodersen et al., 2008) level. The features of foreign DNA or RNA that trigger such suppression mechanism are not well understood (Lindbo et al., 1993; Lechtenberg et al., 2003). However, such host-mediated suppression of transgene expression is more likely for traits that require high expression, multiple transgenes and transgenes with regions of similarity with each other or to the host genome (Schubert et al., 2004). Furthermore transgene performance can progressively degrade with each subsequent generation, most likely due to DNA-methylation of promoter and coding regions of transgenes (Hagan et al., 2003).

Here we demonstrate that viral suppressor proteins (VSP) expressed from post-embryogenesis seed-specific promoters are developmentally tolerated in Arabidopsis. Co-expression of various VSP with a quantifiable trait, GFP, indicated that recombinant traits were also tolerated in VSP expressing seed (Example 14). As VSP are known to block small RNA metabolism that constitute the transgene suppression apparatus, we suggest that the co-expression of a VSP with recombinant traits in seeds will ensure that these traits perform at a high and undiminished level over many generations.

As the plants tolerated VSP expression such as P19 and PePo after embryogenesis, this suggested that endogenous developmental signals, at least those using small RNAs, are minor or less critical at this late stage of plant development. The four VSPs chosen for this study are likely to act upon different parts of the small RNA biogenesis and therefore function to different extents. By reducing the silencing effect in multi-gene transgenic cassettes via the use of a co-introduced VSP, a number of changes on transgenic expression strategies can be envisioned. Firstly, the same expression cassettes can be used repeatedly with less requirement to avoid sequence repetition between regulatory sequences or coding regions. This feature therefore can allow large multi-gene expression vectors to be built using the same promoter-polyadenylation signals. Alternatively, multiple copies of a single gene can be used to increase expression levels with reduced likelihood or extent of silencing effects occurring, or with increased stability of expression over plant generations.

Example 16. Transient Expression of Genes in Plant Leaf Cells Using Seed-Specific Promoters The enzyme activities of the proteins encoded by the Micromonas CCMP1545 Δ6-desaturase (SEQ ID NO:8 encoded by SEQ ID NO:7), Pyramimonas CS-0140 Δ6-elongase (SEQ ID NO:4 encoded by SEQ ID NO:3), Pavlova salina Δ5-desaturase (SEQ ID NO:26 encoded by SEQ ID NO:25), Pyramimonas CS-0140 Δ5-elongase (SEQ ID NO:6 encoded by SEQ ID NO:5) and Pavlova salina Δ4-desaturase (SEQ ID NO:73 encoded by SEQ ID NO:72) genes, each under the control of seed-specific promoters, were demonstrated in leaf tissue, in planta, using an enhanced Nicotiana benthamiana transient expression system, as follows.

The chimeric vector pJP3057 described in Example 15 and containing five DHA biosynthesis genes, each under the control of the seed-specific truncated napin promoter, FP1, was introduced into Agrobacterium tumefaciens strain AGL1. A chimeric vector, designated 35S:LEC2, was generated by cloning a codon-optimised Arabidopsis thaliana LEAFY COTYLEDON2 (Arath-LEC2) gene into the EcoRI site of 35S:pORE04. The 35S:LEC2 construct was introduced separately into Agrobacterium tumefaciens strain AGL1. Transgenic cells from separate cultures of AGL1 containing either pJP3057 or 35S:LEC2 were mixed and the mixture infiltrated into leaf tissue of Nicotiana benthamiana plants. The plants were grown for a further four days after infiltration before leaf discs were taken for GC analysis of the total fatty acids in the leaf lipid, and of separated lipid fractions. This revealed that these genes were functioning to produce DHA in Nicotiana benthamiana (Table 19). Leaf tissue transformed with these genes contained SDA (1.2%), ETA (2.0%), EPA (0.6%), DPA (1.7%) and DHA (2.5%). The leaf tissue also contained GLA (2.4%) and trace levels of other long-chain ω6 fatty acids.

The chimeric vectors pJP3115 and pJP3116 (Example 17) were introduced into Agrobacterium tumefaciens strain AGL1. Transgenic cells from four separate cultures of AGL1 containing one of pJP3115, pJP3116, 35S:P19 and 35S:LEC2 were mixed and the mixture infiltrated into leaf tissue of Nicotiana benthamiana plants. The plants were grown for a further four days after infiltration before leaf discs were taken for GC analysis which revealed that these genes were functioning to produce DHA in Nicotiana benthamiana (Table 19). Leaf tissue transformed with these genes contained SDA (5.6%), ETA (1.4%), EPA (0.2%), DPA (1.7%) and DHA (2.4%). The leaf tissue also contained trace levels of long-chain ω6 fatty acids.

This experiment confirmed that the dual constructs pJP3115 and pJP3116 were functioning in combination to produce DHA as efficiently as a single construct containing all eight genes.

TABLE 19

Fatty acid composition (percent of total fatty acids) of Nicotiana benthamiana leaf tissue transiently transformed with various constructs. Errors denote standard deviation between separate infiltrations performed in triplicate.

| Usual FA | P19 only | 35S: LEC2 | pJP3057 | pJP3057 + 35S: LEC2 |
|---|---|---|---|---|
| 16:0 | 13.2 ± 0.5 | 12.8 ± 1.0 | 13.3 ± 0.1 | 13.2 ± 0.6 |
| 16:1$^{\Delta 3t}$ | 1.5 ± 0.1 | 1.4 ± 0.2 | 1.3 ± 0.1 | 1.1 ± 0.0 |
| 16:3$^{\Delta 9, 12, 15}$ | 7.6 ± 0.3 | 8.2 ± 0.4 | 7.1 ± 0.3 | 7.5 ± 0.4 |
| 18:0 | 1.7 ± 0.2 | 2.0 ± 0.4 | 1.8 ± 0.1 | 2.4 ± 0.3 |
| 18:1$^{\Delta 9}$ | 0.9 ± 0.1 | 0.9 ± 0.1 | 1.1 ± 0.1 | 1.5 ± 0.2 |
| 18:2$^{\Delta 9, 12}$ | 12.6 ± 1.1 | 12.8 ± 0.6 | 13.8 ± 0.1 | 12.7 ± 0.4 |
| 18:3$^{\Delta 9, 12, 15}$ | 58.3 ± 1.9 | 56.3 ± 2.6 | 56.3 ± 0.7 | 44.8 ± 2.1 |
| 20:0 | 0.3 ± 0.0 | 0.4 ± 0.1 | 0.3 ± 0.0 | 0.5 ± 0.1 |
| Other minor | 3.8 | 4.6 | 3.9 | 4.8 |
| Total | 99.9 | 99.6 | 98.9 | 88.5 |
| New Δ6 PUFA | | | | |
| 18:3$^{\Delta 6, 9, 12}$ | — | 0.1 ± 0.0 | — | 2.4 ± 0.1 |
| 20:3$^{\Delta 8, 11, 14}$ | 0.1 ± 0.1 | 0.3 ± 0.1 | 0.2 ± 0.1 | 0.2 ± 0.1 |
| 20:4$^{\Delta 5, 8, 11, 14}$ | — | — | — | — |
| 22:4$^{\Delta 7, 10, 13, 16}$ | — | — | — | 0.6 ± 0.1 |
| 22:5$^{\Delta 4, 7, 10, 13, 16}$ | — | — | — | 0.3 ± 0.0 |
| Total New Δ 3 PUFA | 0.1 | 0.4 | 0.2 | 3.5 |
| 18:4$^{\Delta 6, 9, 12, 15}$ | — | — | 0.9 ± 0.1 | 1.2 ± 0.1 |
| 20:4$^{\Delta 8, 11, 14, 17}$ | — | — | — | 2.0 ± 0.1 |
| 20:5$^{\Delta 5, 8, 11, 14, 17}$ | — | — | — | 0.6 ± 0.0 |

TABLE 19-continued

Fatty acid composition (percent of total fatty acids) of Nicotiana benthamiana leaf tissue transiently transformed with various constructs. Errors denote standard deviation between separate infiltrations performed in triplicate.

| Usual FA | P19 only | 35S: LEC2 | pJP3057 | pJP3057 + 35S: LEC2 |
|---|---|---|---|---|
| 22:5$^{\Delta 7, 10, 13, 16, 19}$ | — | — | — | 1.7 ± 0.1 |
| 22:6$^{\Delta 4, 7, 10, 13, 16, 19}$ | — | — | — | 2.5 ± 0.2 |
| Total | — | — | 0.9 | 8.0 |
| Total new FA | 0.1 | 0.4 | 1.1 | 11.5 |
| Total FA | 100.0 | 100.0 | 100.0 | 100.0 |

Discussion: Rapid Failure and Validation of Seed-Specific Constructs

The experiments using a transcription factor, in this case LEC2, in combination with a suite of genes each under the control of a tissue-specific promoter such as a seed-specific promoter showed that such constructs can be tested in a heterologous system, such as leaves, where the tissue-specific promoter would not normally be expressed, and are predictive of expression in the seed. The ability to transiently express a seed-specific promoter in a leaf cell allows for rapid validation of construct design. Experiments to determine the effectiveness of seed-specific promoters, especially in a multi-gene construct context, previously relied on stable transformation into an oilseed model plant or crop, followed by the generation of progeny lines before phenotypic analysis could determine the effectiveness of the construct in the plant seed. The fact that the levels of fatty acids obtained in N. benthamiana were similar to those seen in stable Arabidopsis transformation with this same construct as described in Example 15 increases confidence in the applicability of this assay.

Example 17. Dual-Constructs for DHA Biosynthesis

The vector pJP3115 (FIG. 22) was constructed as follows. First, the SbfI-ApaI fragment of vector pJP101acq (FIG. 14) was cloned into the PstI-ApaI site of pORE03 to yield pJP3011. Next, a SwaI fragment containing the codon-optimised *Micromonas pusilla* Δ6-desaturase (SEQ ID NO:125) was cloned into a T4 DNA polymerase-treated XhoI site in pJP3011 to yield pJP3108. A SwaI fragment containing the codon-optimised *Pavlova salina* Δ5-desaturase (SEQ ID NO:127) was then cloned into a T4 DNA polymerase-treated NotI site in pJP3108 to yield pJP3109. A SwaI fragment containing the codon-optimised *Pyramimonas cordata* Δ6-elongase (SEQ ID NO:126) was cloned into the SmaI site in pJP3109 to yield pJP3110. The construct was then converted from a BASTA-resistant construct into a kanamycin-resistant construct by cloning the BsiWI-AsiSI fragment of pJP3110 into the BsiWI-AsiSI site of pORE04, yielding pJP3111. An NcoI (T4 DNA polymerase-treated)-SbfI fragment containing the truncated napin promoter FP1 and the *Crepis palestina* Δ12-desaturase was cloned into the EcoRV-PstI site in pJP3111 to yield pJP3115.

The vector pJP3116 (FIG. 23) was constructed as follows. First, a SwaI fragment containing the codon-optimised *Pyramimonas cordata* Δ5-elongase (SEQ ID NO:128) was cloned into a T4 DNA polymerase-treated XhoI site in pJP3011 to yield pJP3112. A SwaI fragment containing the codon-optimised *Pavlova salina* Δ4-desaturase (SEQ ID NO:129) was cloned into the SmaI site in pJP3112 to yield pJP3113. A NotI fragment containing the *Perilla frutescens* Δ15-desaturase was then cloned into the NotI site in pJP3113 to yield pJP3114. The construct was then converted from a BASTA-resistant construct into a hygromycin-resistant construct by cloning a XbaI-MluI fragment containing an hygromycin resistance cassette (consisting of the Cauliflower mosaic virus 35S promoter followed by the CAT-1 intron-interrupted hygromycin B phosphotransferase gene obtained from the binary vector pWVEC8 and the NOS terminator) into the AvrII-MluI site of pJP3114 to yield pJP3116.

The chimeric vectors pJP3115 and pJP3116 were introduced individually into *Agrobacterium tumefaciens* strain AGL1 and transgenic cells from cultures of these were mixed with AGL1 transformed with 35S:P19 and the mixture infiltrated into leaf tissue of *Nicotiana benthamiana* plants in the greenhouse. The plants were grown for a further five days after infiltration before leaf discs were taken for GC analysis which revealed that these genes were functioning to produce DHA in *Nicotiana benthamiana* (Table 20). Leaf tissue transformed with these genes contained SDA (5.6%), ETA (1.4%), EPA (0.2%), DPA (1.7%) and DHA (2.4%). The leaf tissue also contained trace levels of GLA, ETA and ARA. The conversion efficiencies were as follows: 98.9% of the oleic acid in the cell was Δ12-desaturated (not significantly different from the control sample); 95.4% of the LA in the cell was Δ15-desaturated; 18.1% of the ALA produced in the cell was Δ6-desaturated; 50.4% of the SDA produced in the cell was Δ6-elongated; 75.4% of the ETA in the cell was Δ5-desaturated; 95.4% of the EPA in the cell was Δ5-elongated; 58.5% of the DPA in the cell was Δ4-desaturated to produce DHA.

Both constructs were use to transform canola. T1 seeds will be collected and analysed for general morphological changes and levels of LC-PUFA synthesis.

TABLE 20

Fatty acid composition (percent of total fatty acids) of Nicotiana benthamiana leaf tissue transiently transformed with various constructs. Errors denote standard deviation between separate infiltrations performed in triplicate.

| Usual FA | P19 only | 35S: LEC2 | pJP3115 + pJP3116 + 35S:LEC2 |
|---|---|---|---|
| 16:0 | 13.2 ± 0.5 | 12.8 ± 1.0 | 16.1 ± 0.1 |
| 16:1$^{\Delta 3t}$ | 1.5 ± 0.1 | 1.4 ± 0.2 | 1.3 ± 0.1 |
| 16:3$^{\Delta 9, 12, 15}$ | 7.6 ± 0.3 | 8.2 ± 0.4 | 6.8 ± 0.1 |
| 18:0 | 1.7 ± 0.2 | 2.0 ± 0.4 | 3.4 ± 0.0 |
| 18:1$^{\Delta 9}$ | 0.9 ± 0.1 | 0.9 ± 0.1 | 0.7 ± 0.0 |
| 18:2$^{\Delta 9, 12}$ | 12.6 ± 1.1 | 12.8 ± 0.6 | 2.6 ± 0.1 |
| 18:3$^{\Delta 9, 12, 15}$ | 58.3 ± 1.9 | 56.3 ± 2.6 | 51.0 ± 0.1 |
| 20:0 | 0.3 ± 0.0 | 0.4 ± 0.1 | 0.6 ± 0.0 |
| Other minor | 3.8 | 4.6 | 5.7 |
| Total | 99.9 | 99.6 | 88.3 |
| New Δ6 PUFA | | | |
| 18:3$^{\Delta 6, 9, 12}$ | — | 0.1 ± 0.0 | 0.2 ± 0.0 |
| 20:3$^{\Delta 8, 11, 14}$ | 0.1 ± 0.1 | 0.3 ± 0.1 | 0.1 ± 0.1 |
| 20:4$^{\Delta 5, 8, 11, 14}$ | — | — | — |
| 22:4$^{\Delta 7, 10, 13, 16}$ | — | — | — |
| 22:5$^{\Delta 4, 7, 10, 13, 16}$ | — | — | 0.1 ± 0.0 |
| Total | 0.1 | 0.4 | 0.4 |
| New Δ3 PUFA | | | |
| 18:4$^{\Delta 6, 9, 12, 15}$ | — | — | 5.6 ± 0.1 |
| 20:4$^{\Delta 8, 11, 14, 17}$ | — | — | 1.4 ± 0.1 |

TABLE 20-continued

Fatty acid composition (percent of total fatty acids) of Nicotiana benthamiana leaf tissue transiently transformed with various constructs. Errors denote standard deviation between separate infiltrations performed in triplicate.

| Usual FA | P19 only | 35S:LEC2 | pJP3115 + pJP3116 + 35S:LEC2 |
|---|---|---|---|
| $20:5^{\Delta 5, 8, 11, 14, 17}$ | — | — | $0.2 \pm 0.0$ |
| $22:5^{\Delta 7, 10, 13, 16, 19}$ | — | — | $1.7 \pm 0.0$ |
| $22:6^{\Delta 4, 7, 10, 13, 16, 19}$ | — | — | $2.4 \pm 0.1$ |
| Total | — | — | 11.3 |
| Total new FA | 0.1 | 0.4 | 11.7 |
| Total FA | 100.0 | 100.0 | 100.0 |

Discussion pJP3115 and pJP3116 were designed to provide, in combination, all of the genes for production of DHA, namely the two recombinant vectors complement each other to constitute the pathway. The fatty acid produced by the Δ12-desaturase encoded by pJP3115 was used as substrate by the Δ15-desaturase encoded by pJP3116 which also contained genes for the subsequent Δ6-desaturase, Δ6-elongase and Δ5-desaturase. The product of the Δ5-desaturase, EPA, was then acted on by the Δ5-elongase encoded by pJP3115, the product of which was converted to DHA by the Δ4-desaturase also encoded by pJP3115. The principle of dividing the transgenes between two constructs, which were used to separately stably transform plants with subsequent crossing of elite plants to constitute the entire pathway, avoided some of the problems associated with containing numerous transgenes in a single construct, such as reduced transformation efficiency due to increased size and reduced gene expression. The combination of stable transformations of these constructs, either by super-transformation or by crossing two transgenic lines, will result in a transgenic plant containing the full complement of genes required for DHA synthesis.

It was also noted that construct pJP3115 contained four genes expressed in an inverted format i.e. two genes in one orientation and two genes in the other, so that the pairs of genes were transcribed in a divergent fashion (away from each other). When compared to the inverted design used to express three genes in construct pJP107 (Example 8), it was concluded that the addition of a fourth gene in this format did not hinder the expression of the genes.

It was interesting to note the relatively low Δ6-elongation efficiency (50.4%) compared to other experiments described above, which was likely due to the fact that the genes encoding the enzymes for the previous three desaturation steps were all expressed from the FP1 promoter whereas the gene encoding the Δ6-elongase was driven by the Arabidopsis thaliana FAE1 promoter. This was thought to cause a difference in promoter timing, with the FAE1 promoter being activated after the FP1 promoter. Compared to previous experiments where the Δ6-elongase was driven by the FP1 promoter, this resulted in a higher accumulation of SDA which was then removed from the metabolic pool accessed by the Δ6-elongase before it could be acted on by the Δ6-elongase.

Example 18. Isolation and Characterisation of a Gene Encoding a Microalgal DGAT2

Synthesis of a Full Length *Micromonas pusilla* DGAT2 Gene

The *Micromonas* CCMP1545 filtered protein models genome sequence produced by the US Department of Energy Joint Genome Institute (www.jgi.doe.gov/) was analysed with the BLASTP program using a putative amino acid sequence from *Ostreococcus lucimarinus*, Genbank Accession No. XP_00141576, as the query sequence. This analysis revealed the presence of a predicted protein in *Micromonas* CCMP1545 that had homology with XP_00141576. The *Micromonas* CCMP1545 predicted protein sequence was used to design and synthesize a codon-optimized nucleotide sequence that was most suitable for expression in dicotyledonous plants such as *Brassica napus*. The nucleotide sequence of the protein coding region is given in SEQ ID NO:107. The plasmid construct was designated 0928814_Mic1545-DGAT2_pMA. The amino acid sequence is shown as SEQ ID NO:108. BLASTP analysis using the *Micromonas* CCMP1545 desaturase amino acid sequence SEQ ID NO:108 as query to other proteins in the Genbank database showed that the protein had homology with DGATs. The highest degree of identity was 53% along the full-length with the amino acid sequence of Accession No. XP_002503155, the sequence of a *Micromonas* RCC299 putative protein. This gene contains a diacylglycerol acyltransferase motif (NCBI conserved domain pfam03982) at amino acids 74 to 334.

A genetic construct 35S:Mic1545-DGAT2 encoding the DGAT2 under the control of the constitutive 35S promoter was made by inserting the entire coding region of 0928814_Mic1545-DGAT2_pMA, contained within an EcoRI fragment, into 35S-pORE04 (Example 4, above) at the EcoRI site, generating pJP3128. This chimeric vector was introduced into *Agrobacterium tumefaciens* strain AGL1 and transgenic cells from cultures of these were mixed with 35S:P19 AGL1 and the mixture infiltrated into leaf tissue of *Nicotiana benthamiana* plants in the greenhouse. The plants were grown for a further five days after infiltration before leaf discs were taken for lipid analysis which revealed that the gene encoding DGAT2 was functioning to increase total TAG in transformed leaf cells, with preference for polyunsaturated fatty acids (Table 21). In particular, the level of polyunsaturated fatty acids in TAG in the transformed cells increased at least 3-fold.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The present application claims priority from U.S. 61/199,669 filed 18 Nov. 2008, and U.S. 61/270,710 filed 9 Jul. 2009, the contents of both of which are incorporated herein by reference.

All publications discussed and/or referenced herein are incorporated herein in their entirety.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

TABLE 21

Effect of expression of the *Micromonas pusilla* DGAT2 in *Nicotiana benthamiana* leaf. P19 is the control, DGAT2 also contains P19. The total amount of TAG in the leaf tissue increases two-fold when the DGAT2 is expression and polyunsaturated fatty acids are favoured.

|  | Amount in TAG, ug | | TAG profile | |  | Amount in PL, ug | | PL profile | |
|---|---|---|---|---|---|---|---|---|---|
|  | P19 | DGAT2 | P19 | DGAT2 |  | P19 | DGAT2 | P19 | DGAT2 |
| C16:0 | 0.73 | 0.86 | 55.8 | 32.7 | C16:0 | 26.33 | 20.37 | 14.2 | 14.5 |
| C16:1d7 | 0.00 | 0.00 | 0.0 | 0.0 | C16:1d7 | 0.00 | 0.00 | 0.0 | 0.0 |
| 16:1d13t | 0.00 | 0.00 | 0.0 | 0.0 | 16:1d13t | 3.40 | 2.96 | 1.8 | 2.1 |
| 16:2w6 | 0.00 | 0.00 | 0.0 | 0.0 | 16:2w6 | 1.60 | 1.19 | 0.9 | 0.8 |
| 16:2w4 | 0.00 | 0.05 | 0.0 | 1.7 | 16:2w4 | 1.15 | 1.00 | 0.6 | 0.7 |
| 16:3w3 | 0.00 | 0.00 | 0.0 | 0.0 | 16:3w3 | 12.65 | 9.05 | 6.8 | 6.4 |
| C18:0 | 0.27 | 0.32 | 20.7 | 12.0 | C18:0 | 4.50 | 3.56 | 2.4 | 2.5 |
| C18:1d9 | 0.00 | 0.21 | 0.0 | 8.0 | C18:1d9 | 1.89 | 1.82 | 1.0 | 1.3 |
| C18:1d11 | 0.00 | 0.00 | 0.0 | 0.0 | C18:1d11 | 0.85 | 0.78 | 0.5 | 0.6 |
| C18:2n6 | 0.14 | 0.68 | 11.0 | 25.9 | C18:2n6 | 24.36 | 16.52 | 13.2 | 11.7 |
| C18:3n6 | 0.00 | 0.00 | 0.0 | 0.0 | C18:3n6 | 0.00 | 0.00 | 0.0 | 0.0 |
| C18:3n3 | 0.16 | 0.52 | 12.5 | 19.6 | C18:3n3 | 106.38 | 82.16 | 57.6 | 58.4 |
| C20:0 | 0.00 | 0.00 | 0.0 | 0.0 | C20:0 | 0.59 | 0.51 | 0.3 | 0.4 |
| C18:4n3 | 0.00 | 0.00 | 0.0 | 0.0 | C18:4n3 | 0.00 | 0.00 | 0.0 | 0.0 |
| C20:3n3 | 0.00 | 0.00 | 0.0 | 0.0 | C20:3n3 | 0.34 | 0.00 | 0.2 | 0.0 |
| C22:0 | 0.00 | 0.00 | 0.0 | 0.0 | C22:0 | 0.37 | 0.37 | 0.2 | 0.3 |
| C20:4n3 | 0.00 | 0.00 | 0.0 | 0.0 | C20:4n3 | 0.00 | 0.00 | 0.0 | 0.0 |
| C20:5n3 | 0.00 | 0.00 | 0.0 | 0.0 | C20:5n3 | 0.00 | 0.00 | 0.0 | 0.0 |
| C22:3n3 | 0.00 | 0.00 | 0.0 | 0.0 | C22:3n3 | 0.00 | 0.00 | 0.0 | 0.0 |
| C24:0 | 0.00 | 0.00 | 0.0 | 0.0 | C24:0 | 0.43 | 0.41 | 0.2 | 0.3 |
| C22:5n6 | 0.00 | 0.00 | 0.0 | 0.0 | C22:5n6 | 0.00 | 0.00 | 0.0 | 0.0 |
| C22:5n3 | 0.00 | 0.00 | 0.0 | 0.0 | C22:5n3 | 0.00 | 0.00 | 0.0 | 0.0 |
| C22:6n3 | 0.00 | 0.00 | 0.0 | 0.0 | C22:6n3 | 0.00 | 0.00 | 0.0 | 0.0 |
| TFA (ug/g lf FW) | 26.2 | 52.7 | 100.0 | 100.0 | TFA (ug/g lf FW) | 3696.9 | 2814.0 | 100.0 | 100.0 |

REFERENCES

Abbadi et al. (2004) Plant Cell 16: 2734-2748.
Abbott et al. (1998) Science 282:2012-2018.
Abdullah et al. (1986) Biotech. 4:1087.
Agaba et al. (2004) Marine Biotechnol. (NY) 6:251-261.
Al-Mariri et al. (2002) Infect. Immun. 70:1915-1923.
Alvarez et al. (2000) Theor Appl Genet 100:319-327.
Bates et al. (2007) J. Biol. Chem. Vol. 282:31206-31216.
Baumberger et al. (2007) Curr. Biol. 17:1609-1614.
Baumlein et al. (1991) Mol. Gen. Genet. 225:459-467.
Baumlein et al. (1992) Plant J. 2:233-239.
Beaudoin et al. (2000) Proc. Natl. Acad. Sci. U.S.A. 97:6421-6426.
Beclin et al. (2002) Curr. Biol. 12:684-688.
Berberich. et al. (1998) Plant Mol. Biol. 36:297-306.
Bligh and Dyer (1959) Canadian J. Biochem. 37: 911-917.
Bortolamiol et al. (2007) Curr. Biol. 17:1615-1621.
Bouvier-Nave et al. (2000) Euro. J. Biochm. 267:85-96.
Brodersen et al. (2008) Science 320:1185-1190.
Broothaerts et al. (2005) Nature 433:629-633.
Brosnan et al. (2007) Proc. Natl. Acad. Sci U.S.A. 104: 14741-14746.
Broun et al. (1998) Plant J. 13:201-210.
Capecchi (1980) Cell 22:479-488.
Chapman et al. (2004) Gen. Dev. 18:1179-1186.
Chen et al. (2004) The Plant Cell 16:1302-1313.
Cheng et al. (1996) Plant Cell Rep. 15:653-657.
Chikwamba et al. (2003) Proc. Natl. Acad. Sci. U.S.A. 100:11127-11132.
Cho et al. (1999a) J. Biol. Chem. 274:471-477.
Cho et al. (1999b) J. Biol. Chem. 274:37335-37339.
Chung et al. (2006) BMC Genomics 7:120.
Clapp (1993) Clin. Perinatol. 20:155-168.
Clough and Bent (1998) Plant J. 16:735-43.
Courvalin et al (1995) Life Sci. 318:1209-1212.
Coutu et al. (2007) Transgenic Res. 16: 771-781.
Curiel et al. (1992) Hum. Gen. Ther. 3:147-154.
Darji et al. (1997) Cell 91:765-775.
Denic and Weissman (2007) Cell 130:663-677.
Dietrich et al. (1998) Nature Biotech. 18:181-185.
Dietrich et al. (2001) Vaccine 19:2506.
Ding and Voinnet (2007) Cell 130:413-426.
Domergue et al. (2002) Eur. J. Biochem. 269:4105-4113.
Domergue et al. (2003) J. Biol. Chem. 278: 35115-35126.
Domergue et al. (2005) Biochem. J. 1 389: 483-490.
Dunoyer et al. (2004) The Plant Cell 16:1235-1250.
Eglitis et al. (1988) Biotechniques 6:608-614.
Ellerstrom et al. (1996) Plant Mol. Biol. 32:1019-1027.
Fennelly et al. (1999) J. Immunol. 162:1603-1610.
Fraser et al. (2004) Plant Physiol. 135:859-866.
Fuji et al. (2007) Plant Cell 19:597-609.
Fujimura et al. (1985) Plant Tissue Culture Lett. 2:74.
Garcia-Maroto et al. (2002) Lipids 37:417-426.
Girke et al. (1998) Plant J. 15:39-48.
Gleave (1992) Plant Mol. Biol. 20:1203-1207.
Glevin et al (2003) Microbiol. Mol. Biol. Rev. 67:16-37.
Glick et al. (2008) Proc. Natl. Acad. Sci U.S.A. 105-157-161.
Graham et al. (1973) Virology 54:536-539.
Grant et al. (1995) Plant Cell Rep. 15:254-258.
Guillard and Rythers (1962) Can. J. Microbiol. 8:229-239.
Grillot-Courvalin et al. (1998) Nature Biotech. 16:862-866.
Grillot-Courvalin (1999) Curr. Opin. Biotech. 10-477-481.
Hagan et al. (2003) Plant. Biotech. J. 1:479-490.
Hamilton and Baulcombe (1999) Science 286:950-952.
Harayama (1998). Trends Biotechnol. 16: 76-82.
Hastings et al. (2001) Proc. Natl. Acad. Sci. U.S.A. 98:14304-14309.
Hense et al. (2001) Cell Microbiol. 3:599-609.
Hinchee et al. (1988) Biotechnology 6:915-922.
Hoffmann et al. (2008) J Biol. Chem. 283:22352-22362.

Hong et al. (2002a) Lipids 37:863-868.
Horiguchi et al. (1998) Plant Cell Physiol. 39:540-544.
Horvath et al. (2000) Proc. Natl. Acad. Sci. U.S.A. 97:1914-1919.
Huang et al. (1999) Lipids 34:649-659.
Huang et al. (2004) Biochimie 86(11): 793-8.
Inagaki et al. (2002) Biosci. Biotechnol. Biochem. 66:613-621.
Johansen and Carrington (2001) Plant Physiol. 126-930-938.
Kajikawa et al. (2004) Plant Mol. Biol. 54:335-52.
Kajikawa et al. (2006) FEBS Lett 580:149-154.
Kapila et al. (1997) Plant Sci. 122:101-108.
Kasschau et al. (2003) Devel. Cell 4:205-217.
Khozin et al. (1997) Plant Physiol. 114:223-230.
Knutzon et al. (1998) J. Biol Chem. 273:29360-6.
Koziel et al. (1996) Plant Mol. Biol. 32:393-405.
Kunik et al. (2001) Proc. Natl. Acad. Sci. U.S.A. 98:1871-1876.
Lacroix et al. Proc. Natl. Acad. Sci. U.S.A. 105: 15429-15434.
Lazo et al. (1991) Biotechnol. 9:693-697.
Lechtenberg et al. (2003) Plant J. 507-517.
Leonard et al. (2000) Biochem. J. 347:719-724.
Leonard et al. (2000b) Biochem. J. 350:765-770.
Leonard et al. (2002) Lipids 37:733-740.
Lewsey et al. (2007) Plant J. 50:240-252.
Lindbo et al. (1993) Plant Cell 5:1749-1759.
Lo et al. (2003) Genome Res. 13:455-466.
Lu et al. (1993) J. Exp. Med. 178:2089-2096.
Mallory et al (2002) Nat. Biotech. 20:622-625.
Marillonnet et al. (2005) Nature Biotechnology 23:718-723.
Matzke et al. (2001) Science 293:1080-1083.
Meng et al. (2008) J. Gen. Virol. 89:2349-2358.
Meyer et al. (2003) Biochem. 42:9779-9788.
Meyer et al. (2004) Lipid Res 45:1899-1909.
Michaelson et al. (1998a) J. Biol. Chem. 273:19055-19059.
Michaelson et al. (1998b) FEBS Lett. 439:215-218.
Moreau e al. (1998) Progress Lip. Res. 37:371-391.
Napier (2007) Ann. Rev. Plant. Biol. 58:295-319.
Napier et al. (1998) Biochem. J. 330:611-614.
Needleman and Wunsch (1970) J. Mol. Biol. 48:443-453.
Niedz et al (1995) Plant Cell Reports 14:403.
Nishizawa et al. (2003) Plant J. 34:647-659.
Ohlrogge and Browse (1995) Plant Cell 7:957-970.
Ow et al. (1986) Science 234:856-859.
Parker-Barnes et al. (2000) Proc. Natl. Acad. Sci. USA 97:8284-8289.
Pereira et al. (2004a) Biochem. J. 378:665-671.
Pereira et al. (2004b) Biochem. J. 384:357-366.
Perrin et al. (2000) Mol Breed 6:345-352.
Potenza et al. (2004) In Vitro Cell Dev Biol—Plant 40:1-22.
Prasher et al (1985) Biochem. Biophys. Res. Commun. 127:31-36.
Qi et al. (2002) FEBS Lett. 510:159-165.
Qi et al. (2004) Nat. Biotech. 22: 739-745.
Qiu et al. (2001) J. Biol. Chem. 276:31561-31566.
Reddy and Thomas (1996) Nat. Biotech. 14:639-642.
Reddy et al. (1993) Plant Mol. Biol. 22:293-300.
Robert et al. (2005) Func. Plant Biol. 32:473-479.
Robert et al. (2009) Marine Biotech 11:410-418.
Rose et al. (1998) Nucleic Acids Res. 26:1628-1635.
Saha et al. (2006) Plant Physiol. 141:1533-1543.
Saito et al. (2000) Eur. J. Biochem. 267:1813-1818.
Sakuradani et al. (1999) Gene 238:445-453.
Sato et al. (2004) Crop Sci. 44: 646-652.
Sayanova et al. (1997) Proc. Natl. Acad. Sci. U.S.A. 94:4211-4216.
Sayanova et al. (2003) FEBS Lett. 542:100-104.
Sayanova et al. (2006) Planta 224:1269-1277.
Sayanova et al. (2007) Plant Physiol 144:455-467.
Schaffner et al (1980) Proc. Natl. Acad. Sci. U.S.A. 77:2163-2167.
Schubert et al. (2004) Plant Cell 16:2561-2572.
Singh et al. (2005) Curr. Opin. in Plant Biol. 8:197-203.
Sizemore et al (1995) Science 270:299-302.
Shianu et al (2001) Vaccine 19:3947-3956.
Sperling et al. (2000) Eur. J. Biochem. 267:3801-3811.
Sperling et al. (2001) Arch. Biochm. Biophys. 388:293-8.
Sprecher et al. (1995) J. Lipid Res. 36:2471-2477.
Spychalla et al. (1997) Proc. Natl. Acad. Sci. U.S.A. 94:1142-1147.
Stalker et al (1998) J. Biol. Chem. 263:6310-6314.
Thillet et al (1988) J. Biol. Chem 263:12500-12508.
Tonon et al. (2003) FEBS Lett. 553:440-444.
Toriyama et al. (1986) Theor. Appl. Genet. 205:34.
Trautwein (2001) European J. Lipid Sci. and Tech. 103:45-55.
Tvrdik (2000) J. Cell Biol. 149:707-718.
Tzfira & Citovsky (2006) Curr. Opin. Biotech. 17:147-154.
Voinnet et al., (2003) Plant J. 33:949-956.
Wagner et al. (1992) Proc. Natl. Acad. Sci. USA 89:6099-6103.
Wallis and Browse (1999) Arch. Biochem. Biophys. 365: 307-316.
Watts and Browse (1999b) Arch. Biochem. Biophys. 362: 175-182.
Weiss et al (2003) Int. J. Med. Microbiol. 293:95:106.
Whitney et al. (2003) Planta 217:983-992.
Wu et al. (2005) Nat. Biotech. 23:1013-1017.
Yang et al. (2003) Planta 216:597-603.
Yu et al. (2007) Proc. Natl. Acad. Sci U.S.A. 104:8924-8929.
Zank et al. (2002) Plant J. 31:255-268.
Zank et al. (2005) WO 2005/012316
Zhang et al. (2004) FEBS Lett. 556:81-85.
Zhang et al. (2006) 20:3255-3268.
Zhang et al. (2007) Yeast 25: 21-27.
Zhou et al. (2006) Plant Sci. 170: 665-673.
Zhou et al. (2007) Phytochem. 68:785-796.
Zipfel et al. (2006) Cell 125:749-760.

The invention claimed is:

1. A process for producing seed comprising eicosapentaenoic acid (EPA) and docosapentaenoic acid (DPA), the process comprising the steps of
(i) growing a Brassicaceae plant comprising exogenous polynucleotides encoding a microalgal Δ6-desaturase which has greater Δ6-desaturase activity on α-linolenic acid (ALA) joined to CoA (ALA-CoA) as fatty acid substrate than on ALA joined to the sn-2 position of phosphatidylcholine (PC) as the fatty acid substrate, a Δ6-elongase, and a microalgal Δ5-desaturase, wherein each polynucleotide is operably linked to one or more promoters that direct expression of said polynucleotides during the development of the seed, to produce seed that comprises a total fatty acid content comprising ALA, stearidonic acid (SDA), eicosatetraenoic acid (ETA), EPA and DPA, wherein the ALA, SDA, ETA, EPA and DPA are each present at a level in the total fatty acid content of the seed, each level being expressed as a percentage of the total fatty acid content, such that the sum of the percentages for EPA and DPA divided by the sum of the percentages for ALA, SDA, ETA, EPA and DPA, expressed as a percentage, is at least 17.3%, and
(ii) harvesting seed from the plant, thereby producing the seed comprising EPA and DPA.

2. The process of claim 1, wherein arachidonic acid (ARA), EPA, DPA and docosahexaenoic acid (DHA), if present in the total fatty acid content, together comprise 15% of the total fatty acid content in the seed.

3. The process of claim 1, wherein the Δ6-desaturase is an *Ostreococcus tauri* Δ6-desaturase, *Mantoniella squamata* Δ6-desaturase or *Micromonas pusilla* Δ6-desaturase.

4. The process of claim 1, wherein the Δ6-elongase is a *Physcomitrella patens* Δ6-elongase or a Pyramimonas CS-0140 Δ6-elongase.

5. The process of claim 1, wherein the Δ5-desaturase is a *Thraustochytrium* sp Δ5-desaturase.

6. The process of claim 1, wherein the Δ6-desaturase is an *Ostreococcus tauri*, *Mantoniella* or *Micromonas squamata pusilla* Δ6-desaturase, the Δ6-elongase is a *Physcomitrella patens* Δ6-elongase, and the Δ5-desaturase is a *Thraustochytrium* sp Δ5-desaturase.

7. The process of claim 1, wherein the seed further comprises an exogenous polynucleotide encoding a Δ15-desaturase.

8. The process of claim 7, wherein the Δ15-desaturase is a *Perilla frutescens* Δ15-desaturase.

9. The process of claim 1, wherein the Brassicaceae plant is *Camelina sativa*.

10. The process of claim 1, further comprising a step of extracting oil from the harvested seed.

11. The process of claim 6, wherein the Brassicaceae plant is *Camelina sativa*.

12. The process of claim 7, wherein the Brassicaceae plant is *Camelina sativa*.

13. The process of claim 8, wherein the Brassicaceae plant is *Camelina sativa*.

14. The process of claim 6, wherein the seed further comprises an exogenous polynucleotide encoding a Δ15-desaturase.

15. The process of claim 14, wherein the Brassicaceae plant is *Camelina sativa*.

16. The process of claim 15, wherein the Δ15-desaturase is a *Perilla frutescens* Δ15-desaturase.

17. A process for producing seed comprising eicosapentaenoic acid (EPA) and docosapentaenoic acid (DPA), the process comprising the steps of:
(i) growing a *Camelina sativa* plant comprising exogenous polynucleotides encoding an *Ostreococcus tauri* Δ6-desaturase, a Δ6-elongase, and a microalgal Δ5-desaturase, wherein each polynucleotide is operably linked to one or more promoters that direct expression of said polynucleotides during the development of the seed, to produce seed that comprises a total fatty acid content comprising ALA, stearidonic acid (SDA), eicosatetraenoic acid (ETA), EPA and DPA, wherein the ALA, SDA, ETA, EPA and DPA are each present at a level in the total fatty acid content of the seed, each level being expressed as a percentage of the total fatty acid content, such that the sum of the percentages for EPA and DPA divided by the sum of the percentages for ALA, SDA, ETA, EPA and DPA, expressed as a percentage, is at least 17.3%, and
(ii) harvesting seed from the plant, thereby producing the seed comprising EPA and DPA.

* * * * *

SEQUENCE LISTING

```
Sequence total quantity: 129
SEQ ID NO: 1           moltype = DNA  length = 825
FEATURE                Location/Qualifiers
source                 1..825
                       mol_type = genomic DNA
                       organism = Micromonas sp.
                       strain = CS-0170
SEQUENCE: 1
```

-continued

```
atggctttcc ccgccgtcgc gaccgctgtc ttcggtatct atgcgtacgt gatgtactgg  60
tactccgtcc ccggcgcggg cttcctcgcc gagggcaagc aggacgtcgt ggcgtggatc 120
ggcgatctgt ccgtggcgct cccgccacc gccaccgtcc tgtacctctc catgtgctac 180
ttcggcccga agatcatggc caagagggag gcgttcgagc cgaaggggtt catgctggtg 240
tacaacgcgt accagaccgt gttcaacatc atcaccgtcg ccatcttcat cgctgagctc 300
aaccggctgg gcgtgaaggc gtggggcggc cgcctgtcgt ggtccgatcc caacagcttc 360
tacatctgcc tcgccatctg gctccactac aacaacaagt acctggagct cctcgacacc 420
gtcttcatgg tgctgcgcaa gaagaacaac cagctcagct cctccacat ctaccaccac 480
tgcctcctca tctgggcgtg gtggatggtg tgcttcgtca tcaagaacaa cgactgcatc 540
gacgcgtact ttggcgcctg catgaacgct ggaattcacg tcatcatgta ctcctattac 600
ctcatggccg cgctgaagat caagtgcccg tggaagcagt acatcaccat ggcgcagatg 660
ctccagttcg ccatcgtctt tgcgcacagc tgctacgtca tctacgacgg cactgcccg 720
gcgattctgc cgtggtcgca gatgttcgtg atgaccaaca tgctggtgct gttcgggcag 780
ttctacgtgc agacgtacac gaagaagaag gtaaaggcca agtaa 825

SEQ ID NO: 2           moltype = AA   length = 274
FEATURE                Location/Qualifiers
source                 1..274
                       mol_type = protein
                       note = Strain CS-0170
                       organism = Micromonas sp.
SEQUENCE: 2
MAFPAVATAV FGIYAYVMYW YSVPGAGFLA EGKQDVVAWI GDLSVALPAT ATVLYLSMCY  60
FGPKIMAKRE AFEPKGFMLV YNAYQTVFNI ITVAIFIAEL NRLGVKAWGG RLSWSDPNSF 120
YICLAIWLHY NNKYLELLDT VFMVLRKKNN QLSFLHIYHH CLLIWAWWMV CFVIKNNDCI 180
DAYFGACMNA GIHVIMYSYY LMAALKIKCP WKQYITMAQM LQFAIVFAHS CYVIYDGHCP 240
AILPWSQMFV MTNMLVLFGQ FYVQTYTKKK VKAK                             274

SEQ ID NO: 3           moltype = DNA   length = 894
FEATURE                Location/Qualifiers
source                 1..894
                       mol_type = genomic DNA
                       organism = Pyramimonas sp.
                       strain = CS-0140
SEQUENCE: 3
atggagttcg ctcagcctct tgtggctatg gcacaggagc agtatgccgc aattgacgcg  60
gtggtagccc ctgcaatttt ctcagctacc gacagcatcg gttggggtct taagcccatt 120
agcagcgcga caaaggatct tcctctcgtt gagagtccga cgccgctcat actgagcctg 180
ttggcctatt ttgcgatcgt cggctctggg ctggtgatca gcaaagtatt ccctcgcaca 240
gtaaagggc aagacccctt cctgctgaag gcgctcatgc ttgcgcacaa cgtgttcctc 300
attggcctca gtctatacat gtgcttgaag cttgtctacg aggcttacgt caacaagtac 360
tccttctggg gaaacgccta caaccccgca cagaccgaga tggcgaaggt catctggatt 420
ttctacgtct ccaagatcta tgagttcatg gacacgttca tcatgctctt gaagggcaac 480
gtcaaccagg tctcttttcct gcatgtgtac catcatggcc ccatctctgg tatctggtgg 540
atgatcacct acgctgcccc tggcggtgac gcgtacttct cggcggcgct caactcgtgg 600
gtgcacgtgt gcatgtacac gtactacttc atggcggcgg tgctgcccaa ggacgagaag 660
accaagcaca agtacctgtg gtgggcgc tacctgaccc agatgcagt gttccagttc 720
ttcatgaacc tgctccaggc ggtctacctc tctactcct ctagccccta ccccaagttc 780
atcgcccagc tgctggtggt gtacatggtc acgctgctga tgctcttcgg caacttctac 840
tacatgaagc accacgcgag caagaagcag aagctggcca gcaagaagca gtag 894

SEQ ID NO: 4           moltype = AA   length = 297
FEATURE                Location/Qualifiers
source                 1..297
                       mol_type = protein
                       note = Strain CS-0140
                       organism = Pyramimonas sp.
SEQUENCE: 4
MEFAQPLVAM AQEQYAAIDA VVAPAIFSAT DSIGWGLKPI SSATKDLPLV ESPTPLILSL  60
LAYFAIVGSG LVYRKVFPRT VKGQDPFLLK ALMLAHNVFL IGLSLYMCLK LVYEAYVNKY 120
SFWGNAYNPA QTEMAKVIWI FYVSKIYEFM DTFIMLLKGN VNQVSFLHVY HHGSISGIWW 180
MITYAAPGGD AYFSAALNSW VHVCMYTYYF MAAVLPKDEK TKRKYLWWGR YLTQMQMFQF 240
FMNLLQAVYL LYSSSPYPKF IAQLLVVYMV TLLMLFGNFY YMKHHASKKQ KLASKKQ    297

SEQ ID NO: 5           moltype = DNA   length = 804
FEATURE                Location/Qualifiers
source                 1..804
                       mol_type = genomic DNA
                       organism = Pyramimonas sp.
                       strain = CS-0140
SEQUENCE: 5
atggcgtcta ttgcgattcc ggctgcgctg cagggactc ttggttatgt gacgtacaat  60
gtcgcaaacc cagatattcc tgcatccgag aaggtgcctg cttactttat gcaggtcgag 120
tattgggggc caacgattgg gaccatcggt tatcttctgt tcatctactt tggtaaacgg 180
attatgcaaa acaggagcca gccgtttggc ctgaagaacg ctatgctggt gtacaacttc 240
tatcagactt tcttcaactc gtactgcata tacctttttg tcacgtcgca ccgcgctcag 300
gggctgaaaa ttggggaaa catccccgat atgactgcca acagctgggg gatctcacag 360
gtgatctggc tgcactacaa caacaagtac gttgagctgc tggacacgtt cttcatggtc 420
atgcgcaaga agttttgacca gctttcgttc ctgcacattt accatcatac cctgttgatc 480
```

```
tggtcttggt tcgtggtgat gaaattggag cccgttgggg actgctactt tggctctagc    540
gtcaacacgt ttgtgcacgt cattatgtac tcgtactatg gccttgccgc gctcggggtg    600
aattgcttct ggaagaagta cattacgcag attcagatgc tgcagttctg tatctgcgct    660
tcgcactcga tttataccgc ctatgtgcag aacaccgcgt tctggttgcc ttacttgcag    720
ctgtgggtga tggtgaacat gttcgtgttg ttcgccaact tctatcgcaa gcgctacaag    780
agcaagggtg ccaagaagca gtaa                                           804

SEQ ID NO: 6           moltype = AA  length = 267
FEATURE                Location/Qualifiers
source                 1..267
                       mol_type = protein
                       note = CS-0140
                       organism = Pyramimonas sp.
SEQUENCE: 6
MASIAIPAAL AGTLGYVTYN VANPDIPASE KVPAYFMQVE YWGPTIGTIG YLLFIYFGKR     60
IMQNRSQPFG LKNAMLVYNF YQTFFNSYCI YLFVTSHRAQ GLKVWGNIPD MTANSWGISQ    120
VIWLHYNNKY VELLDTFFMV MRKKFDQLSF LHIYHHTLLI WSWFVVMKLE PVGDCYFGSS    180
VNTFVHVIMY SYYGLAALGV NCFWKKYITQ IQMLQFCICA SHSIYTAYVQ NTAFWLPYLQ    240
LWVMVNMFVL FANFYRKRYK SKGAKKQ                                        267

SEQ ID NO: 7           moltype = DNA  length = 1392
FEATURE                Location/Qualifiers
source                 1..1392
                       mol_type = genomic DNA
                       organism = Micromonas sp.
                       strain = CCMP1545
SEQUENCE: 7
atgtgtcctc ctaagaccga tggaagatct tctcctagat ctcctctcac caggtctaag     60
tcatctgctg aggctcttga tgctaaggat gcttctaccg ctcctgttga tcttaagacc    120
cttgagcctc atgaacttgc tgctaccttc gagactagat gggttagggt tgaggatgtt    180
gagtacgacg tgaccaactt caaacatcct ggtggaagcg tgatcttcta catgcttgct    240
aacactggtg ctgatgctac tgaggctttc aaagaatttc acatgcgtag cctcaaggct    300
tggaagatgc ttagagcttt gccttctaga cctgctgaga tcaagagatc tgagtctgag    360
gatgctccta tgcttgagga tttcgctagg tggagagctg aacttgagag ggacggattc    420
ttcaagcctt ctatcaccca tgttgcttac cgtcttttgg agcttcttgc tactttcgct    480
cttggaaccg ctcttatgta cgctggatac cctatcattg ctagcgttgt gtacggtgct    540
ttcttcggag ctagatgtgg atgggttcaa catgagggtg gacacaactc tcttaccgga    600
tctgtgtacg tggataagag acttcaggct atgacttgcg gattcggact ttctaccagc    660
ggagagatgt ggaaccagat gcataacaag caccatgcta cccctcagaa agttagacac    720
gacatggatc ttgataccac tcctgctgtg gctttcttca acaccgctgt ggaggataat    780
agacctaggg gattctctag agctgggct agacttcaag cttggacctt cgttcctgtt    840
acttctggac ttctcgttca ggctttctgg atctacgttc tccatcctag acaggtgctc    900
aggaagaaga actacgagga agcttcttgg atgctcgttt ctcacgttgt tagaaccgct    960
gttatcaagc ttgctaccgg atactcttgg cctgttgctt actggtggtt cactttcgga   1020
aactggatcg cttacatgta cctcttcgct cacttctcta cttctcacac tcacctccct   1080
gttgttccat ctgacaagca ccttagctgg gttaactacg ctgttgatca caccgttgac   1140
atcgatcctt ctcgtggata cgttaactgg cttatgggct tccaggttat caccgttgac   1200
caccatctct tccctgatat gcctcaattc agacagcctg aggtgtcaag aagattcgtc   1260
cctttcgcta agaagtgggg actcaactac aaggtgctct cttactacgg tgctttggaag 1320
gctactttca gcaacctcga caaagttgga cagcactact acgttaacgg aaaggctgag   1380
aaggctcact ga                                                       1392

SEQ ID NO: 8           moltype = AA  length = 463
FEATURE                Location/Qualifiers
source                 1..463
                       mol_type = protein
                       note = Strain CCMP1545
                       organism = Micromonas sp.
SEQUENCE: 8
MCPPKTDGRS SPRSPLTRSK SSAEALDAKD ASTAPVDLKT LEPHELAATF ETRWVRVEDV     60
EYDVTNFKHP GGSVIFYMLA NTGADATEAF KEFHMRSLKA WKMLRALPSR PAEIKRSESE    120
DAPMLEDFAR WRAELERDGF FKPSITHVAY RLLELLATFA LGTALMYAGY PIIASVVYGA    180
FFGARCGWVQ HEGGHNSLTG SVYVDKRLQA MTCGFGLSTS GEMWNQMHNK HHATPQKVRH    240
DMDLDTTPAV AFFNTAVEDN RPRGFSRAWA RLQAWTFVPV TSGLLVQAFW IYVLHPRQVL    300
RKKNYEEASW MLVSHVVRTA VIKLATGYSW PVAYWWFTFG NWIAYMYLFA HFSTSHTHLP    360
VVPSDKHLSW VNYAVDHTVD IDPSRGYVNW LMGYLNCQVI HHLFPDMPQF RQPEVSRRFV    420
PFAKKWGLNY KVLSYYGAWK ATFSNLDKVG QHYYVNGKAE KAH                      463

SEQ ID NO: 9           moltype = DNA  length = 1449
FEATURE                Location/Qualifiers
source                 1..1449
                       mol_type = genomic DNA
                       organism = Ostreococcus lucimarinus
SEQUENCE: 9
atgtgcgtcg aaacgaccga aggcacatcg cgaacgatgg cgaacgaacg cacgagctcg     60
tcgtcgtcgc tgagcgaagg cggaacgccg acggtgacgg tcgggatggg aagcgaagac    120
gcggggaaga agactcgaaa cgcgagcgtc acggcgtgga cgaaagagtt ggagccgcac    180
gcgatcgcga agacgttcga acggcggtac gtgacgatcg aaggcgtgga atacgatgtg    240
acggatttta agcatcccgg aggatcggtt atttattaca tgctgtcgaa cacggagagcg   300
```

```
gacgcgacgg aggcttttaa agagtttcat tatcggtcga aaaaggcgcg caaggcgttg   360
gcggcgttgc cgcataagcc agtggacgcg gcgacgcggg aaccgatcga agatgaggcg   420
atgctgaagg atttcgcgca gtggcgcaag gaattggagc gtgagggatt ttttaagccc   480
tcgccggcgc acgtggcgta tcgattcgcc gagctcgcgg cgatgttcgc gctcggcacg   540
gcgttgatgc acgcgcgttg gcacgtcgct tccgtgatcg tgtactcgtg tttcttcggc   600
gcgcgatgcg gttgggtgca gcacgagggt gggcacaatt cgttgactgg aaacatttgg   660
tgggacaagc gaatccaagc cttcgccgcg gggttcggct tggcgtcgag tggcgacatg   720
tggaacaaca tgcacaacaa gcatcacgcg acgccccaaa aggtgcgaca cgatatggat   780
ctcgacacca ctcccacggt ggcgttcttc aactccgcgg ttgaagaaaa tcgcccgcgg   840
ggattcagta agttgtggtt gcgccttcaa gcgtggacct tcgtgcccgt gacgtccggt   900
atggttttgt tcttctggat gttcgtcttg cacccgcgta acgcgctgcg acgcaaaagc   960
ttcgaagaag cggcttggat gttttccgcg cacgtcattc gcacggcggt tatcaaagcc  1020
gtcaccggct actcctggat cgcctcgtac ggcttgttcg cggcgacgat gtgggcgagc  1080
ggatgttact tgttcgcgca cttttccacg tctcacacgc tcgatgtgtc cgtgccgagc  1140
gataaacacc tctcgtgggt gcgatacgcc gtcgatcaca cgatcgacat caatccgaac  1200
aacagcgtcg tcaactggtt gatgggctac ttgaactgcc aagtcatcca tcacctgttc  1260
ccggatatgc ctcagttccg ccaacccgaa gtctcccgcc gattcgtccc gtttgcgaag  1320
aagtgaact taaactacaa ggtcttgacg tattatgggg cctggaaggc gacgttcggc  1380
aacttgaacg acgtcgggaa gcactattac gtgcacggat ctcagcgcgt caaatcaaag  1440
tcggcgtga                                                          1449

SEQ ID NO: 10         moltype = AA  length = 482
FEATURE               Location/Qualifiers
source                1..482
                      mol_type = protein
                      organism = Ostreococcus lucimarinus
SEQUENCE: 10
MCVETTEGTS RTMANERTSS SSSLSEGGTP TVTVGMGSED AGKKTRNASV TAWTKELEPH    60
AIAKTFERRY VTIEGVEYDV TDFKHPGGSV IYYMLSNTGA DATEAFKEFH YRSKKARKAL   120
AALPHKPVDA ATREPIEDEA MLKDFAQWRK ELEREGFFKP SPAHVAYRFA ELAAMFALGT   180
ALMHARWHVA SVIVYSCFFG ARCGWVQHEG GHNSLTGNIW WDKRIQAFAA GFGLASSGDM   240
WNNMHNKHHA TPQKVRHDMD LDTTPTVAFF NSAVEENRPR GFSKLWLRLQ AWTFVPVTSG   300
MVLFFWMFVL HPRNALRRKS FEEAAWMFSA HVIRTAVIKA VTGYSWIASY GLFAATMWAS   360
GCYLFAHFST SHTHLDVVPS DKHLSWVRYA VDHTIDINPN NSVVNWLMGY LNCQVIHHLF   420
PDMPQFRQPE VSRRFVPFAK KWNLNYKVLT YYGAWKATFG NLNDVGKHYY VHGSQRVKSK   480
SA                                                                 482

SEQ ID NO: 11         moltype = DNA  length = 1449
FEATURE               Location/Qualifiers
misc_feature          1..1449
                      note = Codon-optimized nucleotide sequence for production
                      in plants of SEQ ID NO:10
source                1..1449
                      mol_type = other DNA
                      organism = synthetic construct
SEQUENCE: 11
atgtgtgttg agactactga gggaaccctct agaactatgg ctaacgagag gacctcttct    60
tcttcttcac tctctgaggg tggaactcct actgttactg tgggaatggg atctgaggat   120
gctggaaaga aaaccagaaa cgcttctgtt actgcttgga ccaaagagct tgagcctcac   180
gctatcgcta agaccttcga gagaagatac gttaccatcg agggtgttga gtacgatgtg   240
accgatttca aacaccctgg tggatctgtg atctactaca tgctctctaa cactggtgct   300
gatgctactg aggctttcaa agagttccac taccgttcta agaaggctag aaaggctctt   360
gctgctcttc ctcacaagcc tgttgatgct gctactagag agcctattga ggacgaggct   420
atgcttaagg atttcgctca gtggagaaaa gagttggaga gaggatt cttcaagcct   480
tctcctgctc atgttgctta ccgtttcgct gaactcgctg ctatgttcgc tcttggaacc   540
gctcttatgc atgctagatg gcacgttgct agcgttatcg tgtactcctg tttcttcgga   600
gctagatgtg gatgggttca acatgagggt ggacacaact ctcttaccgg aaacatctgg   660
tgggataaga gaatccaagc tttcgctgct ggattcggac ttgcttcttc tggtgacatg   720
tggaacaaca tgcacaacaa gcaccatgct actcctcaga agtgagacga cgatatggat   780
cttgatacca ccccctaccgt tgctttcttc aactctgctg tggaggaaaa cagacctagg   840
ggattctcta agctttggct cagacttcaa gcttggacct tcgttcctgt tacctctgga   900
atggtgctct tcttctggat gttcgttctc atcctagaa acgctctccg tcgtaagtct   960
ttcgaagagg ctgcttggat gttctctgct cacgttatca gaaccgctgt tatcaaggct  1020
gttaccggat actcttggat cgctagctac ggacttttcg ctgctactat gtgggcttct  1080
ggatgctacc ttttcgctca cttctctact tctcacaccc acctcgatgt tgttccatct  1140
gataagcacc ttagctgggt taggtacgct gttgatcaca ccatcgacat caaccctaac  1200
aactctgttg tgaactggct tatgggatac cttaactgcc aggttatcca ccatctcttc  1260
cctgatatgc ctcaattcag acagcctgag gttgtcaagaa gattcgtccc tttcgctaag  1320
aagtggaacc tcaactacaa ggtgctcact tactacggtg cttggaaggc tactttcgga  1380
aacctcaacg atgttggaaa gcactactac gttcacggat ctcagagagt gaagagcaag  1440
agcgcttga                                                          1449

SEQ ID NO: 12         moltype = DNA  length = 1329
FEATURE               Location/Qualifiers
source                1..1329
                      mol_type = genomic DNA
                      organism = Pyramimonas sp.
                      strain = CS-0140
SEQUENCE: 12
```

```
atgggaaagg gaggcaatgc tagcgctcct actgcgaaga aggaggtgtt gatcgagggg    60
aagttttacg atgtcaccga cttcaggcac cccggtggtt cgatcatcaa gtttctctcg   120
ggttctggtg ctgacgccac cgcttcctac cgcgagttcc acgttaggtc agcgaaggca   180
gacaagttct tgaagacgct gccctcccgc gaagccactc cccaggagct gaagcaggcg   240
gttgagttct ccaagctcaa cccgccctcc gcggagagtg cctctgctcc cctgaccgac   300
cttgccaagg tggaagcgct gaacaaggac ttcgaggctt tccgtgagca gctcattcag   360
gagggcttct ttaagcccaa tatcccgcat gtggtcaagc gcatcacgga agtcgtggcg   420
atgatggccg tagcctcctg gatgatggtg cagaccaacg ctcttgttgt gaccctcgga   480
gttctgatcc gcggcattgc acagggccgg tgcggttggc ttatgcacga gggcggccac   540
tatagtctta ctgggaagat ctccattgat aggcgtctgc aggagtcaat ttacggattc   600
ggctgtggaa tgtccggcgc ctggtggcgc aaccagcaca acaagcacca cgcaacccca   660
cagaagctgc agcatgacgt cgacctggag acccttcctc tgatggcttt caacaacgct   720
gttaccgata gacgcaaggt gaagcctggt agtctccagg ctctgtggct caagtaccag   780
gccttcctct tcttcccgt gacctccctt ctggtcggac tcggttggac caccgtcctc   840
caccccaggc acagcttgcg caccaagcac tatttcgagc tgctctgcat ggctgctcgt   900
tacgcgagtt tcgctgctct tttcgctccc aagtacggac ttgcaggagc tgccgggctc   960
tacctcgcca ccttcgctgt cgggtgcaac tatattttca tcaacttctc ggtctctcac  1020
actcacctgc ccgtgagcgg tgcgagcgag tacctgcatt ggtgggttgt gtatggccatc 1080
cacaccacta acatcaaatc cagcatgctg tgcgattggt ggatgtcatt cctcaacttc  1140
cagatcgagc atcacctgtt cccttcaatg cccagttcc gccacaagat tatctccccg   1200
cgtgtaaagg ccttgtttga aagcacggt cttgtgtatg atgtgcgccc ctattggggg   1260
gccatggctg acaccttcaa gaacttgaat gacgttggca ctcacgcatc tcactccaag  1320
gcgcactag                                                           1329

SEQ ID NO: 13          moltype = AA   length = 442
FEATURE                Location/Qualifiers
source                 1..442
                       mol_type = protein
                       note = Strain CS-0140
                       organism = Pyramimonas sp.
SEQUENCE: 13
MGKGGNASAP TAKKEVLIEG KFYDVTDFRH PGGSIIKFLS GSGADATASY REFHVRSAKA    60
DKFLKTLPSR EATPQELKQA VEFSKLNPPS AESASAPLTD LAKVEALNKD FEAFREQLIQ   120
EGFFKPNIPH VVKRITEVVA MMAVASWMMV QTNALVVTLG VLIRGIAQGR CGWLMHEGGH   180
YSLTGKISID RRLQESIYGF GCGMSGAWWR NQHNKHHATP QKLQHDVDLE TLPLMAFNNA   240
VTDRRKVKPG SLQALWLKYQ AFLFFPVTSL LVGLGWTTVL HPRHSLRTKH YFELLCMAAR   300
YASFAALFAP KYGLAGAAGL YLATFAVGCN YIFINFSVSH THLPVSGASE YLHWVVYSAI   360
HTTNIKSSML CDWWMSFLNF QIEHHLFPSM PQFRHKIISP RVKALFEKHG LVYDVRPYWG   420
AMADTFKNLN DVGTHASHSK AH                                           442

SEQ ID NO: 14          moltype = DNA   length = 528
FEATURE                Location/Qualifiers
source                 1..528
                       mol_type = genomic DNA
                       organism = Micromonas sp.
                       strain = CS-0170
SEQUENCE: 14
tgtggtgcat cggccatgat tgggggcacg gatccttctc caaaaacgcc ctcgtcaacg    60
gcgtcgtcgg acacctcacg cactcgccgc tgctcgtgcc cttttacccg tgggcgtact   120
cgcacaagca gcaccacagg tttcacaacc acgaggtacg gacatgtcg cacccgtgga   180
tgtccaagga ggagtacgcg gacgtgaacc cgtcgtcgag ggcgctggcg ctggacggtg   240
ggtggggaac cttcctcggc tttcccgggt acctcctcct ggaaccgcag tgggccggga   300
cggacggtgt ccacttcaac ccgaactcca ggctcttcga cagggcgccc aaggatgagc   360
gggtgaagtg cgcggtttcc accgtggcgt gcgcggcgtt tctcggcgcg tccttcgtcg   420
cgtgcgactc gaacccccgtt cactggttcg ctcagtactt ggcgccgtac ttgtgcttct   480
cgtggtggct cttcaccgtg acatacttac agcacaacga cgaggaca              528

SEQ ID NO: 15          moltype = AA   length = 175
FEATURE                Location/Qualifiers
source                 1..175
                       mol_type = protein
                       note = Strain CS-0170
                       organism = Micromonas sp.
SEQUENCE: 15
WCIGHDWGHG SFSKNALVNG VVGHLTHSPL LVPFYPWAYS HKQHHRFHNH EVRDMSHPWM    60
SKEEYADVNP VVRALALDGW WGTFLGFPGY LLLEPQWAGT DGCHFNPNSR LFDRAPKDER   120
VKCAVSTVAC AAFLGASFVA CDSNPVHWFA QYLAPYLCFS WWLFTVTYLQ HNDED        175

SEQ ID NO: 16          moltype = DNA   length = 1461
FEATURE                Location/Qualifiers
source                 1..1461
                       mol_type = genomic DNA
                       organism = Micromonas sp.
                       strain = RCC299
SEQUENCE: 16
atgaccgccg tcggcggcgg gcgtcgacac tcccgcgccg cgcgtccgga gcggactcga    60
gaccgtcgga agcgctcgtc ggattccaca gagtcggatt ccgtcgtctc ccggacaccc   120
ggcgacgtac ctcccgccgc gctcgttcac gcgatgcccg cgatgatgac ctcatccacc   180
tgtctgcggg ccacgtcgcc ccggatggaa tcgacacgcc gcggctccct ccgcgtcgtc   240
```

```
gacgccgcgg cgcccgcacg caccggcgca tccaagacgg gtcggtccgt cccgcgtcaa    300
ctcccccgcg ccatttccgc gccgacgacg aacctcggaa ccgcggacgc gccaactccc    360
gccgccggtc ccgtgccgtc cctccgagag ctgcgcgcat ccatcccgaa ggagtgcttc    420
gagcccgacc tggggagtc gctcaagtac gccgcgtacg atctcgccgc gctcgccgcg    480
tgcttcggcg tcatctcccc gcacgtggtg gaccaccgt ggctgttagt gctgtacgcg    540
ccctcacgg gcaccgtcat gtggatgaac ttcgtcgtcg gccacgactg cgggcacggc    600
tccttctcca atcctccgt cgtcaacggc gtcgtcggcc acctcacgca ctcgccgctg    660
ctcgtgccct tctacccgtg ggcgtactcg cacaagcagc accacaggtt tcacaaccac    720
caggtaaagg acatgtcgca cccgtggatg actgcagagg agtacgccga ggtgaacctc    780
atcgtccggg ctctggcgct tgacgggtgg tggggaacct tcctcggctt tcccgggtac    840
ctcctcctgg aaccgcggtg ggccgggacg gacgggtgcc acttcaaccc acaatccagg    900
ctcttcgaca gggcgcccaa ggacgagcgg gtgaagtgcg cggtttccac cgtggcgtgc    960
gcggcgtttc tcggcgcgtc cttcgtcgcg tgcgactcga accggcgca ctggttcgct   1020
cagtacttgg cgccgtactt tgtcttctcg tggtggctct tcaccgtgac ctacctccag   1080
caccacgact acgacacaac gacgtacgaa gagggccagt gggagtacgt gctgggggt   1140
ttggagacga tcgaccgcga gtttgggcac ggcgtggacg agctgacgca tcacatcacc   1200
gactgccacg tcgcgcacca catgttccg gacatgcccc actaccgcct gcccgcggcg   1260
accgccgggg tgcgatcggt gctggagccc cgtgggttgt acaagcgacg ggacacgcgg   1320
gatttcgtga cgaaggtgtt cgagttgcac ggggacgtcg gcactgcgt ggagagcgag   1380
gcggggggtga ggccgagggc gacgcgcgac gagtgcgcgg cggcgttcaa cggcgaggag   1440
tggcgcgagg ttcgcaagta g                                               1461

SEQ ID NO: 17          moltype = AA   length = 486
FEATURE                Location/Qualifiers
source                 1..486
                       mol_type = protein
                       note = Strain RCC299
                       organism = Micromonas sp.
SEQUENCE: 17
MTAVGGGRRH SRAARPERTR DRRKRSSDST ESDSVVSRTP GDVPPAALVH AMPAMMTSST    60
CLRATSPRME STRRGSLRVV DAAAPARTGA SKTGRSVPRQ LPRAISAPTT NLGTADAPTP   120
AAGPVPSLRE LRASIPKECF EPDLGESLKY AAYDLAALAA CFGVISPHVV DHPWLLPLYA   180
PLTGTVMWMN FVVGHDCGHG SFSKSSVVNG VVGHLTHSPL LVPFYPWAYS HKQHHRFHNH   240
QVKDMSHPWM TAEEYAEVNP IVRALALDGW WGTFLGFPGY LLLEPRWAGT DGCHFNPQSR   300
LFDRAPKDER VKCAVSTVAC AAFLGASFVA CDSNPAHWFA QYLAPYLCFS WWLFTVTYLQ   360
HHDYDTTTYE EGQWEYVLGG LETIDREFGH GVDELTHHIT DCHVAHHMFS DMPHYRLPAA   420
TAGVRSVLEP RGLYKRRDTR DFVTKVFELH GDVGHCVESE AGVRPRATRD ECAAAFNGEE   480
WREVRK                                                             486

SEQ ID NO: 18          moltype = DNA   length = 1461
FEATURE                Location/Qualifiers
misc_feature           1..1461
                       note = Codon-optimized nucleotide sequence for production
                        in plants of SEQ ID NO:17
source                 1..1461
                       mol_type = other DNA
                       organism = synthetic construct
SEQUENCE: 18
atgactgctg ttggaggtgg aagaaggcat tctagagctg ctagacctga gagaaccagg    60
gatcgtagaa agagatcttc tgactctacc gagtctgatt ctgtggtttc taggacccct   120
ggtgatgttc ctcctgctgc tcttgttcat gctatgcctg ctatgatgac ctcttctact   180
tgccttagag ctacttctcc taggatggaa tctaccagaa gggatctct cagagttgtt   240
gacgctgctg ctccagctag aactggtgct tctaagaccg gaagatctgt tcctagacag   300
ctccctagag ctatctctgc tcctactact aaccttggaa ccgctgatgc tcctactcct   360
gctgctggac ctgttcctc tcttagagag cttagggcta gcatccctaa agagtgcttc   420
gagcctgatc ttggagagtc tctcaagtac gctgcttacg atcttgctgc tctcgctgct   480
tgtttcggag ttatctctcc tcacgttgtt gatcatcctt ggcttctccc actttacgct   540
cctcttaccg gaactgtgat gtggatgaac ttcgttgttg gacatgattg cggacacgga   600
tcttctctca agtctagcgt ggttaacggt gttgttggac accttacca ctctcctctt   660
ctcgttcctt tctacccttg ggcttactct cataagcagc accacagatt ccataaccac   720
caggtgaagg atatgtctca cccttggatg actgctgagg aatacgctga ggttaaccct   780
attgtgaggg ctcttgctct tgatggatgg tggggaactt tccttggatt ccctggatac   840
cttcttcttg agcctagatg ggctggaact gatggatgtc acttcaaccc tcagtctaga   900
cttttcgaca gggctcctaa ggatgaacgt gttaagtgcg ctgtttctac tgttgcttgc   960
gctgctttcc ttggagcttc tttcgttgct tgcgattcta accctgctca ttggttcgct  1020
cagtaccttg ctccttacct tgcttctct tggtggctct tcactgttac ttacctccag  1080
caccacgatt acgataccac tacctacgag gaaggacagt gggaatacgt tcttggagga  1140
ctcgagacta tcgatagaga atttggacac ggtgttgatg agcttactca ccacatcact  1200
gattgtcacg tggctcacca catgttctct gacatgcctc attacagact tccagctgct  1260
actgctggtg ttagatctgt tctcgagcct agaggactct acaagagaag agacaccagg  1320
gatttcgtta ccaaggtgtt cgagcttcat ggtgatgttg gacactgcgt tgagtctgaa  1380
gctggtgtta ggcctagagc tactagagat gagtgcgctg ctgcttttaa tggtgaagag  1440
tggagggaag ttaggaagtg a                                             1461

SEQ ID NO: 19          moltype = DNA   length = 1389
FEATURE                Location/Qualifiers
source                 1..1389
                       mol_type = genomic DNA
                       organism = Micromonas sp.
```

```
                        strain = CS-0140
SEQUENCE: 19
atgacggcgg cgacgacgct ctcgcgcgcg tcctccgtcg tcggcgtcgg cgcaggcgcc   60
acgtcgaggc gtccggtcga tcgcgccgtc tccgccgtcg cgacgtcctc ctcgtattcg  120
cgccgcgcgc gccgcgtcgc gaccgtccgc gcggcgtcca gccgcacgtc gtcctccgcg  180
acgacgacga cgacgacgac gacgcgctcc gctctggcca tggagacccc gtccacgacg  240
acgacggacg cggacgacga cgacgacaag accggcgtcg tcccgtcgct ccgagagctc  300
cgagccgcga tccccgcgga gtgcttcgtc ccgtgcctga gggagtcgat gaagtacgcc  360
gcgatcgacc tcggtctcct cgccgcctgc ttcggtctgt ggtctccgct cgtggtggat  420
aacccgtgga tgctcccgct gtacgccccc gtcaccggga cgatcatgtg gatgtgcttc  480
gtcgtcgggc acgactgcgg gcacggcagt ttcaggtgcg tcagttctac aaacgtcgag  540
aacaagtgga tcaacggcgt cgtcggtcac gcgacgcact cgccgctgct cgtgccgttc  600
tacccgtggg cgtactcgca caagcagcac accggtttc ataaccacga ggagaaggac  660
atgtcgcacc cgtggatgag cgcggagcgg tacaaggaca cgaacgcgat cgttcggtgc  720
gcggcgggcg gctcggtttc tggttttttgg ttcctcgcgc tcgatcaccc atggggcgcg  780
tttctcggct tccccgggta tctcctcctc gagccaaagt ggagcagcac ggacggctcg  840
cacttcaacc cggccggtcg tctgttcgac cgcgcccca aggacgaacg tctcaagtgc  900
gcggtcgtca cggtcgtcgtg cgcggcgttc ctcctcgtca cgttcgccgc gtgcgacggc  960
cccgcgcagt gggcgacgca gtacctcgcg ccgtatctgt gcttctcgtg gtggctcttc 1020
acggtgacct acctccagca ccacgaccac gacacgaaga cgtacaagga aggcgagtgg 1080
gagtacgtct tgggggggatt agagacgatc gatcgcgagt tcgggtacgg cgtggacgag 1140
gcgacgcatc acatcacgga ctgccacgtc gcgcaccaca tgttttcgga catgccgcac 1200
tacaacttgg agaaggccac cgcggggggtg cggggcgtgc tcgagcccag gggactgtat 1260
aagaagaggg acacgaggga tttcgcgacg aagattttg ggttgcacaa agacgtcggg 1320
cactgcgtcg agccggaccg gccgcgggcg acgaaggagg agctcgtgaa ggcgttgggg 1380
cgggagtga                                                        1389

SEQ ID NO: 20            moltype = AA   length = 462
FEATURE                  Location/Qualifiers
source                   1..462
                         mol_type = protein
                         note = Strain CCMP1545
                         organism = Micromonas sp.
SEQUENCE: 20
MTAATTLSRA SSVVGVGAGA TSRRPVDRAV SAVATSSSYS RRARRVATVR AASSRTSSSA   60
TTTTTTTTRS ALAMETPSTT TTDADDDDDK TGVVPSLREL RAAIPAECFV PCLRESMKYA  120
AIDLGLLAAC FGLWSPLVVD NPWMLPLYAP VTGTIMWMCF VVGHDCGHGS FRCVSSTNVE  180
NKWINGVVGH ATHSPLLVPF YPWAYSHKQH HRFHNHEEKD MSHPWMSAER YKDTNAIVRC  240
AAGGSVSGFW FLALDHPWGA FLGFPGYLLL EPKWSSTDGS HFNPAGRLFD RAPKDERLKC  300
AVSTVACAAF LLATFAACDG PAQWATQYLA PYLCFSWWLF TVTYLQHHDH DTKTYKEGEW  360
EYVLGGLETI DREFGYGVDE ATHHITDCHV AHHMFSDMPH YNLEKATAGV RGVLEPRGLY  420
KKRDTRDFAT KIFGLHKDVG HCVEPDRPRA TKEELVKALG RE                    462

SEQ ID NO: 21            moltype = DNA   length = 792
FEATURE                  Location/Qualifiers
source                   1..792
                         mol_type = genomic DNA
                         organism = Isochrysis galbana
SEQUENCE: 21
atggcccctcg caaacgacgc gggagagcgc atctgggcgg ctgtgaccga cccggaaatc   60
ctcattggca ccttctcgta cttgctactc aaaccgctgc tccgcaattc cgggctggtg  120
gatgagaaga agggcgcata caggacgtcc atgatctggt acaacgttct gctggcgctc  180
ttctctcgcg tgagcttcta cgtgacggcg accgccctcg gctgggacta tggtacgggc  240
gcgtggctgc gcaggcaaac cggcgacaca ccgcagccgc tcttccagtg cccgtccccg  300
gtttgggact cgaagctctt cacatggacc gccaaggcat tctattactc caagtacgtg  360
gagtacctcg acacggcctg gctggtgctc aagggcaaga gggtctcctt ctctccaggc  420
ttccaccact ttggcgcgcc gtgggatgtg taccctcggca ttcggctgca caacgagggc  480
gtatggatct tcatgttttt caactcgttc attcacacca tcatgtacac ctactacggc  540
ctcaccgccg ccgggtataa gttcaaggcc aagcgcgtca tcaccgcgat gcagatctgc  600
cagttcgtgg gcgcgcttcct gttggtctgg gactacatca acgtccctg cttcaactcg  660
gacaaaggga gttgttcag ctgggcttc aactatgcat acgtcggctc ggtcttcttg  720
ctcttctgcc acttttttcta ccaggacaac ttggcaacga gaaatcggc caaggcgggc  780
aagcagctct ag                                                      792

SEQ ID NO: 22            moltype = AA   length = 263
FEATURE                  Location/Qualifiers
source                   1..263
                         mol_type = protein
                         organism = Isochrysis galbana
SEQUENCE: 22
MALANDAGER IWAAVTDPEI LIGTFSYLLL KPLLRNSGLV DEKKGAYRTS MIWYNVLLAL   60
FSALSFYVTA TALGWDYGTG AWLRRQTGDT PQPLFQCPSP VWDSKLFTWT AKAFYYSKYV  120
EYLDTAWLVL KGKRVSFLQA FHHFGAPWDV YLGIRLHNEG VWIFMFFNSF IHTIMYTYYG  180
LTAAGYKFKA KPLITAMQIC QFVGGFLLVW DYINVPCFNS DKGKLFSWAF NYAYVGSVFL  240
LFCHFFYQDN LATKKSAKAG KQL                                          263

SEQ ID NO: 23            moltype = DNA   length = 1284
FEATURE                  Location/Qualifiers
source                   1..1284
```

```
                        mol_type = genomic DNA
                        organism = Pavlova salina
SEQUENCE: 23
atgggacgcg gcggagacag cagtgggcag gcgcatccgg cggcggagct ggcggtcccg    60
agccgaccgcg cggaggtgag caacgctgac agcaaagcgc tgcacatcgt gctgtatggc   120
aagcgcgtgg atgtgaccaa gttccaacgc acgcacccgg tggtagcaa ggtcttccgg    180
atcttccagg accgcgatgc gacggagcag ttcgagtcct accactcgaa gcgcgcgatc   240
aagatgatgg agggcatgct caagaagtct gaggatgctc cgccgacac gcccttgccc    300
tcccagtcac cgatggggaa ggacttcaag gcgatgatcg agcggcacgt tgcagcgggt   360
tactacgatc catgcccgct cgatgagctg ttcaagctca gcctcgtgct cctcccgacc   420
tttgcgggca tgtacatgct caaggcgggc gtcggctccc cgctctgcgg cgccctcatg   480
gtgagctttg gctggtacct cgatggctgg ctcgcgcacg actatctgca ccactccgtc   540
ttcaaggggg ccgtcgcacg caccgtcggg tggaacaacg cggcgggcta cttcctcggc   600
ttcgtgcagg ggtatgcggt cgagtggtgg cgcgcgcgga ataacacgca ccacgtgtgc   660
accaatgagg acggctcgga ccccgacatc aaaacggcgc cgctgctcat atacgtgcgc   720
aacaagccga gcatcgccaa gcgcctgaac gccttccagc gctaccagca gtactactat   780
gtgccggtga tggcaatcct cgacctgtac tggcggctcg agtcgatcgc ctacgtcgcg   840
atgcgcctgc cgaagatgct gccgcaggcc ctcgcactcg tcgcgcacta cgccatcgtc   900
gcgtgggtct ttgcgggcaa ctaccacctg ctcccgctcg tgacggttct gcgcgggttt   960
ggcactggga tcaccgttt cgcgacgcac tacggtgagg acattctcga cgcggaccag  1020
gtgcgtcaca tgacgctcgt cgagcagacg gcactcacct cgcgcaacat ctcgggcggc  1080
tggctcgtga acgtgctcac ggcttcatc tcactgacga cggagcacca cctgttcccg  1140
atgatgccaa ccggcaacct catgactatc cagcccgagg tgcgcgcctt cttcaagaag  1200
cacggacttg agtaccgcga gggcaaccte attgagtgcg tgcggcagaa catccgtgcg  1260
cttgcattcg agcacctgct ttga                                         1284

SEQ ID NO: 24            moltype = AA   length = 427
FEATURE                  Location/Qualifiers
source                   1..427
                         mol_type = protein
                         organism = Pavlova salina
SEQUENCE: 24
MGRGGDSSGQ AHPAAELAVP SDRAEVSNAD SKALHIVLYG KRVDVTKFQR THPGGSKVFR    60
IFQDRDATEQ FESYHSKRAI KMMEGMLKKS EDAPADTPLP SQSPMGKDFK AMIERHVAAG  120
YYDPCPLDEL FKLSLVLLPT FAGMYMLKAG VGSPLCGALM VSFGWYLDGW LAHDYLHHSV  180
FKGSVARTVG WNNAAGYFLG FVQGYAVEWW RARHNTHHVC TNEDGSDPDI KTAPLLIYVR  240
NKPSIAKRLN AFQRYQQYYY VPVMAILDLY WRLESIAYVA MRLPKMLPQA LALVAHYAIV  300
AWVFAGNYHL LPLVTVLRGF GTGITVFATH YGEDILDADQ VRHMTLVEQT ALTSRNISGG  360
WLVNVLTGFI SLQTEHHLFP MMPTGNLMTI QPEVRAFFKK HGLEYREGNL IECVRQNIRA  420
LAFEHLL                                                            427

SEQ ID NO: 25            moltype = DNA   length = 1278
FEATURE                  Location/Qualifiers
source                   1..1278
                         mol_type = genomic DNA
                         organism = Pavlova salina
SEQUENCE: 25
atgccgccgc gcgatagcta ctcgtacgcc gccccgccgt cggcccagct gcacgaggtc    60
gataccccgc aggagcatga taagaaggag ctcgtcatcg gtgaccgcgc gtacgacgtg   120
accaactttg tgaagcgcca cccgggtggc aagatcatcg cataccaggt tggcacagat   180
gcgacggacg cgtacaagca gttccatgtg cggtctgcca aggcggacaa gatgctcaag   240
tcgctgcctt cgcgcccggt gcacaagggc tactcgcccc gccgcgctga cctcattgcc   300
gacttccagg agttccacca gcagctggag cggagggca tgtttgagcc gtcgctgccg   360
cacgtggcat accgcctggc ggaggtgatc gcgatgcacg tggccggcgc cgcgctcatc   420
tggcacgggt acaccttcgc gggcattgcc atgctcggcg ttgtgcaggg ccgctgcggc   480
tggctcatgc acgagggcgg ccactactcg ctcacgggca acattgcttt tgaccgtgcg   540
atccaagtcg cgtgctacgg ccttggctgc ggcatgtcgg cgcgtggtg gcgcaaccag   600
cacaacaagc accacgcgac gccgcagaag ttgcagcacg acgtcgacct cgacaccctc   660
ccgctcgtcg ccttccacga gcggatagcc gccaaggtga gagccccgc gatgaaggcg   720
tggcttagta tgcaggcgaa gctcttccgg ccagtgacca cgctgctggt cgcgctgggc   780
tggcagctgt acctgcaccc gcgccatatg ctgcgcacca gcactacga cgagctcgcg   840
atgctcggca ttcgctacgg ccttgtcggc tacctcgcgg cgaactacgg cgcggggtac   900
gtgctcgcgt gctacctgct gtacgtgcag ctcggcgcca tgtacatctt ctgcaacttt   960
gccgtgtcgc acacacacct gccggttgtc gagcctaacg gcacgcaac atggtgtgag  1020
tacgccgcga accacacgac caactgctcg ccctcgtggt ggtcgactg gtggatgtcg  1080
tacctcaact accagatcga gcaccactc taccgtcca tgccgcagtt ccgccacccg  1140
aagattgcgc gcgggtgaa gcagctcttc gagaagcacg gcctgcacta cgacgtgcgt  1200
ggctacttcg aggccatggc ggacacgttt gccaaccttg acaacgtcgc gcacgcgccg  1260
gagaagaaga tgcagtga                                                1278

SEQ ID NO: 26            moltype = AA   length = 425
FEATURE                  Location/Qualifiers
source                   1..425
                         mol_type = protein
                         organism = Pavlova salina
SEQUENCE: 26
MPPRDSYSYA APPSAQLHEV DTPQEHDKKE LVIGDRAYDV TNFVKRHPGG KIIAYQVGTD    60
ATDAYKQFHV RSAKADKMLK SLPSRPVHKG YSPRRADLIA DFQEFTKQLE AEGMFEPSLP  120
HVAYRLAEVI AMHVAGAALI WHGYTFAGIA MLGVVQGRCG WLMHEGGHYS LTGNIAFDRA  180
```

```
IQVACYGLGC GMSGAWWRNQ HNKHHATPQK LQHDVDLDTL PLVAFHERIA AKVKSPAMKA    240
WLSMQAKLFA PVTTLLVALG WQLYLHPRHM LRTKHYDELA MLGIRYGLVG YLAANYGAGY    300
VLACYLLYVQ LGAMYIFCNF AVSHTHLPVV EPNEHATWVE YAANHTTNCS PSWWCDWWMS    360
YLNYQIEHHL YPSMPQFRHP KIAPRVKQLF EKHGLHYDVR GYFEAMADTF ANLDNVAHAP    420
EKKMQ                                                                425

SEQ ID NO: 27            moltype = DNA   length = 801
FEATURE                  Location/Qualifiers
source                   1..801
                         mol_type = genomic DNA
                         organism = Emiliania huxleyi
                         strain = CCMP1516
SEQUENCE: 27
atgctcgatc gcgcctcgtc cgacgcggcc atctggtctg cggtgtccga tccggaaatc    60
ctgatcggca ctttctccta cctgctgctc aagccgctgc tacgcaactc agggctcgtg    120
gacgagcgga aaggcgccta ccggacctcg atgatctggt acaacgtggt gctcgcgctc    180
ttctccgcga cgagcttcta cgtgactgcg accgcgctcg gtgggacaa gggcaccggc    240
gagtggctcc gcagtctcac gggcgacagc ccgcagcagc tgtggcaatg cccgtcgagg    300
gtatgggact ccaagctgtt cctgtggacg gccaaggcct tctactactc aaagtacgtg    360
gagtacctcg acacgcgtg gctcgtcctc aaggggaaga aggtctcctt cctgcagggc    420
ttccaccact tggcgcgcc gtgggacgtg tacctgggca ttcggctgaa gaacgagggc    480
gtgtggatct tcatgttctt caactcgttc atccacacgg tcatgtacac gtactacggc    540
ctcaccgccg cgggctacaa gatccgcggc aagccgatca tcaccgcgat gcaaataagc    600
cagttcgtcg gcggctttgt cctagtgtgg gactacatca acgtgccgtg cttccacgcc    660
gacgccgggc aggtcttcag ctgggtctt aactatgctt acgtcggctc cgtctttctg    720
ctgttctgcc acttcttcta catggacaac atcgcgaagg ccaaggccaa gaaggccgtc    780
gctacccgca aggcgctgtg a                                              801

SEQ ID NO: 28            moltype = AA   length = 266
FEATURE                  Location/Qualifiers
source                   1..266
                         mol_type = protein
                         note = Strain CCMP1516
                         organism = Emiliania huxleyi
SEQUENCE: 28
MLDRASSDAA IWSAVSDPEI LIGTFSYLLL KPLLRNSGLV DERKGAYRTS MIWYNVVLAL    60
FSATSFYVTA TALGWDKGTG EWLRSLTGDS PQQLWQCPSR VWDSKLFLWT AKAFYYSKYV    120
EYLDTAWLVL KGKKVSFLQG FHHFGAPWDV YLGIRLKNEG VWIFMFFNSF IHTVMYTYYG    180
LTAAGYKIRG KPIITAMQIS QFVGGFVLVW DYINVPCFHA DAGQVFSWVF NYAYVGSVFL    240
LFCHFFYMDN IAKAKAKKAV ATRKAL                                         266

SEQ ID NO: 29            moltype = DNA   length = 801
FEATURE                  Location/Qualifiers
misc_feature             1..801
                         note = Codon-optimized nucleotide sequence for production
                          in plants of SEQ ID NO:28
source                   1..801
                         mol_type = other DNA
                         organism = synthetic construct
SEQUENCE: 29
atgcttgata gagcttcatc tgatgctgct atttggagcg ctgtttctga tcctgagatc    60
cttatcggaa cctttctta ccttttgctt aagcctctcc tcagaaactc tggacttgtg    120
gatgagagaa agggagctta ccgtacttct atgatctggt acaacgttgt tcttgctctt    180
ttctctgcta cctcttctta cgttactgct actgctcttg gatgggataa gggaactggt    240
gagtggctta gatctcttac tggtgattct ctcaacaac tttggcagtg cccttctaga    300
gtttgggaca gcaaactctt cttgtggact gctaaagcct tctactactc caagtacgtt    360
gagtaccttg atactgcttg gcttgttctc aagggaaaga aggtttcatt cctccaggga    420
ttccatcatt tcggtgctcc atgggatgtt taccttggaa tcaggcttaa gaacgaggga    480
gtttggatct tcatgttctt caacagcttc atccacactg ttatgtacac ttactacgga    540
cttactgctg ctggatacaa gatcagagga aagccatca tcaccgctat gcaaatctcc    600
caattcgttg gtggattcgt tcttgtgtgg gactacatca acgttccttg tttccatgct    660
gatgctggac aagtttctc ttgggtgttc aactacgctt atgtgggatc tgttttcctt    720
cttttctgcc acttcttcta catggacaac attgctaagg ctaaggctaa aaaggctgtt    780
gctaccagaa aggctctttg a                                              801

SEQ ID NO: 30            moltype = AA   length = 456
FEATURE                  Location/Qualifiers
source                   1..456
                         mol_type = protein
                         organism = Ostreococcus tauri
SEQUENCE: 30
MCVETENNDG IPTVEIAFDG ERERAEANVK LSAEKMEPAA LAKTFARRYV VIEGVEYDVT    60
DFKHPGGTVI FYALSNTGAD ATEAFKEFHH RSRKARKALA ALPSRPAKTA KVDDAEMLQD    120
FAKWRKELER DGFFKPSPAH VAYRFAELAA MYALGTYLMY ARYVVSSVLV YACFFGARCG    180
WVQHEGGHSS LTGNIWWDKR IQAFTAGFGL AGSGDMWNSM HNKHHATPQK VRHDMDLDTT    240
PAVAFFNTAV EDNRPRGFSK YWLRLQAWTF IPVTSGLVLL FWMFFLHPSK ALKGGKYEEL    300
VWMLAAHVIR TWTIKAVTGF TAMQSYGLFL ATSWVSGCYL FAHFSTSHTH LDVVPADEHL    360
SWVRYAVDHT IDIDPSQGWV NWLMGYLNCQ VIHHLFPSMP QFRQPEVSRR FVAFAKKWNL    420
NYKVMTYAGA WKATLGNLDN VGKHYYVHGQ HSGKTA                              456
```

```
SEQ ID NO: 31          moltype =    length =
SEQUENCE: 31
000

SEQ ID NO: 32          moltype = AA   length = 5
FEATURE                Location/Qualifiers
REGION                 1..5
                       note = Elongase consensus domain 2
SITE                   3
                       note = MISC_FEATURE - X = any amino acid
source                 1..5
                       mol_type = protein
                       organism = synthetic construct
SEQUENCE: 32
MYXYY                                                                  5

SEQ ID NO: 33          moltype = AA   length = 8
FEATURE                Location/Qualifiers
REGION                 1..8
                       note = Elongase consensus domain 3
source                 1..8
                       mol_type = protein
                       organism = synthetic construct
SEQUENCE: 33
KIYEFVDT                                                               8

SEQ ID NO: 34          moltype = AA   length = 7
FEATURE                Location/Qualifiers
REGION                 1..7
                       note = Elongase consensus domain 4
source                 1..7
                       mol_type = protein
                       organism = synthetic construct
SEQUENCE: 34
VHVCMYT                                                                7

SEQ ID NO: 35          moltype = AA   length = 7
FEATURE                Location/Qualifiers
REGION                 1..7
                       note = Elongase consensus domain 5
source                 1..7
                       mol_type = protein
                       organism = synthetic construct
SEQUENCE: 35
YLELLDT                                                                7

SEQ ID NO: 36          moltype = AA   length = 5
FEATURE                Location/Qualifiers
REGION                 1..5
                       note = Elongase consensus domain 6
source                 1..5
                       mol_type = protein
                       organism = synthetic construct
SEQUENCE: 36
MYSYY                                                                  5

SEQ ID NO: 37          moltype = AA   length = 10
FEATURE                Location/Qualifiers
REGION                 1..10
                       note = Desaturase consensus domain 1
source                 1..10
                       mol_type = protein
                       organism = synthetic construct
SEQUENCE: 37
WKNMHNKHHA                                                             10

SEQ ID NO: 38          moltype = AA   length = 8
FEATURE                Location/Qualifiers
REGION                 1..8
                       note = Desaturase consensus domain 2
source                 1..8
                       mol_type = protein
                       organism = synthetic construct
SEQUENCE: 38
HHLFPSMP                                                               8

SEQ ID NO: 39          moltype = AA   length = 8
FEATURE                Location/Qualifiers
```

```
REGION                    1..8
                          note = Desaturase consensus domain 3
source                    1..8
                          mol_type = protein
                          organism = synthetic construct
SEQUENCE: 39
WCIGHDCG                                                                      8

SEQ ID NO: 40             moltype = AA   length = 10
FEATURE                   Location/Qualifiers
REGION                    1..10
                          note = Desaturase consensus domain 4
source                    1..10
                          mol_type = protein
                          organism = synthetic construct
SEQUENCE: 40
TFLQHHDEDM                                                                   10

SEQ ID NO: 41             moltype = DNA   length = 37
FEATURE                   Location/Qualifiers
misc_feature              1..37
                          note = Oligonucleotide primer
source                    1..37
                          mol_type = other DNA
                          organism = synthetic construct
SEQUENCE: 41
atttaggtga cactatagtt tttttttttt tttttv                                      37

SEQ ID NO: 42             moltype = DNA   length = 23
FEATURE                   Location/Qualifiers
misc_feature              1..23
                          note = Oligonucleotide primer
misc_feature              7
                          note = n= inosine
misc_feature              14
                          note = n= inosine
source                    1..23
                          mol_type = other DNA
                          organism = synthetic construct
SEQUENCE: 42
aagwwcnksg arynsytcga cac                                                    23

SEQ ID NO: 43             moltype = DNA   length = 20
FEATURE                   Location/Qualifiers
misc_feature              1..20
                          note = Oligonucleotide primer
misc_feature              1..20
                          note = n = inosine
misc_feature              2..3
                          note = n = inosine
misc_feature              5
                          note = n = inosine
source                    1..20
                          mol_type = other DNA
                          organism = synthetic construct
SEQUENCE: 43
annmnrtart asgtgtacat                                                        20

SEQ ID NO: 44             moltype = DNA   length = 21
FEATURE                   Location/Qualifiers
misc_feature              1..21
                          note = Oligonucleotide primer
source                    1..21
                          mol_type = other DNA
                          organism = synthetic construct
SEQUENCE: 44
gaacaacgac tgcatcgacg c                                                      21

SEQ ID NO: 45             moltype = DNA   length = 23
FEATURE                   Location/Qualifiers
misc_feature              1..23
                          note = Oligonucleotide primer
source                    1..23
                          mol_type = other DNA
                          organism = synthetic construct
SEQUENCE: 45
cgactggagc acgaggacac tga                                                    23

SEQ ID NO: 46             moltype = DNA   length = 23
```

```
FEATURE                 Location/Qualifiers
misc_feature            1..23
                        note = Oligonucleotide primer
source                  1..23
                        mol_type = other DNA
                        organism = synthetic construct
SEQUENCE: 46
ttgcgcagca ccataaagac ggt                                              23

SEQ ID NO: 47           moltype = DNA  length = 26
FEATURE                 Location/Qualifiers
misc_feature            1..26
                        note = Oligonucleotide primer
source                  1..26
                        mol_type = other DNA
                        organism = synthetic construct
SEQUENCE: 47
ggacactgac atggactgaa ggagta                                           26

SEQ ID NO: 48           moltype = DNA  length = 22
FEATURE                 Location/Qualifiers
misc_feature            1..22
                        note = Oligonucleotide primer
source                  1..22
                        mol_type = other DNA
                        organism = synthetic construct
SEQUENCE: 48
caggcgacgc gcgccagagt cc                                               22

SEQ ID NO: 49           moltype = DNA  length = 26
FEATURE                 Location/Qualifiers
misc_feature            1..26
                        note = Oligonucleotide primer
source                  1..26
                        mol_type = other DNA
                        organism = synthetic construct
SEQUENCE: 49
ttattagtta cttggccttt accttc                                           26

SEQ ID NO: 50           moltype = DNA  length = 23
FEATURE                 Location/Qualifiers
misc_feature            1..23
                        note = Oligonucleotide primer
misc_feature            18
                        note = n = inosine
source                  1..23
                        mol_type = other DNA
                        organism = synthetic construct
SEQUENCE: 50
aaratmtayg agttygtnga tac                                              23

SEQ ID NO: 51           moltype = DNA  length = 25
FEATURE                 Location/Qualifiers
misc_feature            1..25
                        note = Oligonucleotide primer
misc_feature            3
                        note = n = inosine
source                  1..25
                        mol_type = other DNA
                        organism = synthetic construct
SEQUENCE: 51
tangtgtaca tgcacacrtg waccc                                            25

SEQ ID NO: 52           moltype = DNA  length = 22
FEATURE                 Location/Qualifiers
misc_feature            1..22
                        note = Oligonucleotide primer
source                  1..22
                        mol_type = other DNA
                        organism = synthetic construct
SEQUENCE: 52
ttcgtggata cgttcatcat gc                                               22

SEQ ID NO: 53           moltype = DNA  length = 23
FEATURE                 Location/Qualifiers
misc_feature            1..23
                        note = Oligonucleotide primer
source                  1..23
                        mol_type = other DNA
```

```
                        organism = synthetic construct
SEQUENCE: 53
agttgagcgc cgccgagaag tac                                        23

SEQ ID NO: 54           moltype = DNA   length = 22
FEATURE                 Location/Qualifiers
misc_feature            1..22
                        note = Oligonucleotide primer
source                  1..22
                        mol_type = other DNA
                        organism = synthetic construct
SEQUENCE: 54
acctggttga cgttgccctt ca                                         22

SEQ ID NO: 55           moltype = DNA   length = 21
FEATURE                 Location/Qualifiers
misc_feature            1..21
                        note = Oligonucleotide primer
source                  1..21
                        mol_type = other DNA
                        organism = synthetic construct
SEQUENCE: 55
gctatggagt tcgctcagcc t                                          21

SEQ ID NO: 56           moltype = DNA   length = 26
FEATURE                 Location/Qualifiers
misc_feature            1..26
                        note = Oligonucleotide primer
source                  1..26
                        mol_type = other DNA
                        organism = synthetic construct
SEQUENCE: 56
ttactactgc ttcttgctgg ccagct                                     26

SEQ ID NO: 57           moltype = DNA   length = 22
FEATURE                 Location/Qualifiers
misc_feature            1..22
                        note = Oligonucleotide primer
source                  1..22
                        mol_type = other DNA
                        organism = synthetic construct
SEQUENCE: 57
artayytsga rytrytggay ac                                         22

SEQ ID NO: 58           moltype = DNA   length = 21
FEATURE                 Location/Qualifiers
misc_feature            1..21
                        note = Oligonucleotide primer
source                  1..21
                        mol_type = other DNA
                        organism = synthetic construct
SEQUENCE: 58
catkarrtar tasgagtaca t                                          21

SEQ ID NO: 59           moltype = DNA   length = 22
FEATURE                 Location/Qualifiers
misc_feature            1..22
                        note = Oligonucleotide primer
source                  1..22
                        mol_type = other DNA
                        organism = synthetic construct
SEQUENCE: 59
catcatccct gttgatctgg tc                                         22

SEQ ID NO: 60           moltype = DNA   length = 23
FEATURE                 Location/Qualifiers
misc_feature            1..23
                        note = Oligonucleotide primer
source                  1..23
                        mol_type = other DNA
                        organism = synthetic construct
SEQUENCE: 60
ccagatcaac agggtatgat ggt                                        23

SEQ ID NO: 61           moltype = DNA   length = 27
FEATURE                 Location/Qualifiers
misc_feature            1..27
                        note = Oligonucleotide primer
source                  1..27
```

```
                            mol_type = other DNA
                            organism = synthetic construct
SEQUENCE: 61
cgaaagctgg tcaaacttct tgcgcat                                              27

SEQ ID NO: 62           moltype = DNA  length = 27
FEATURE                 Location/Qualifiers
misc_feature            1..27
                        note = Oligonucleotide primer
source                  1..27
                        mol_type = other DNA
                        organism = synthetic construct
SEQUENCE: 62
aacatggcgt ctattgcgat tccggct                                              27

SEQ ID NO: 63           moltype = DNA  length = 27
FEATURE                 Location/Qualifiers
misc_feature            1..27
                        note = Oligonucleotide primer
source                  1..27
                        mol_type = other DNA
                        organism = synthetic construct
SEQUENCE: 63
ttattactgc ttcttggcac ccttgct                                              27

SEQ ID NO: 64           moltype = DNA  length = 31
FEATURE                 Location/Qualifiers
misc_feature            1..31
                        note = Oligonucleotide primer
misc_feature            23
                        note = n = inosine
source                  1..31
                        mol_type = other DNA
                        organism = synthetic construct
SEQUENCE: 64
ggtggaagaa caagcacaac rdncaycayg c                                         31

SEQ ID NO: 65           moltype = DNA  length = 24
FEATURE                 Location/Qualifiers
misc_feature            1..24
                        note = Oligonucleotide primer
misc_feature            16
                        note = n = inosine
source                  1..24
                        mol_type = other DNA
                        organism = synthetic construct
SEQUENCE: 65
gggcatcgtg gggwanarrt grtg                                                 24

SEQ ID NO: 66           moltype = DNA  length = 20
FEATURE                 Location/Qualifiers
misc_feature            1..20
                        note = Oligonucleotide primer
source                  1..20
                        mol_type = other DNA
                        organism = synthetic construct
SEQUENCE: 66
agcgagtacc tgcattgggt                                                      20

SEQ ID NO: 67           moltype = DNA  length = 27
FEATURE                 Location/Qualifiers
misc_feature            1..27
                        note = Oligonucleotide primer
source                  1..27
                        mol_type = other DNA
                        organism = synthetic construct
SEQUENCE: 67
atagtgcttg gtgcgcaagc tgtgcct                                              27

SEQ ID NO: 68           moltype = DNA  length = 25
FEATURE                 Location/Qualifiers
misc_feature            1..25
                        note = Oligonucleotide primer
source                  1..25
                        mol_type = other DNA
                        organism = synthetic construct
SEQUENCE: 68
caccatggga aagggaggca atgct                                                25
```

```
SEQ ID NO: 69            moltype = DNA  length = 25
FEATURE                  Location/Qualifiers
misc_feature             1..25
                         note = Oligonucleotide primer
source                   1..25
                         mol_type = other DNA
                         organism = synthetic construct
SEQUENCE: 69
ttactagtgc gccttggagt gagat                                          25

SEQ ID NO: 70            moltype = DNA  length = 25
FEATURE                  Location/Qualifiers
misc_feature             1..25
                         note = Oligonucleotide primer
misc_feature             20
                         note = n = inosine
misc_feature             23
                         note = n = inosine
source                   1..25
                         mol_type = other DNA
                         organism = synthetic construct
SEQUENCE: 70
tgtggtgcat cggccaygan ksngg                                          25

SEQ ID NO: 71            moltype = DNA  length = 28
FEATURE                  Location/Qualifiers
misc_feature             1..28
                         note = Oligonucleotide primer
misc_feature             20
                         note = n = inosine
misc_feature             26
                         note = n = inosine
source                   1..28
                         mol_type = other DNA
                         organism = synthetic construct
SEQUENCE: 71
tgtcctcgtc gttgtgctgn arrwangt                                       28

SEQ ID NO: 72            moltype = DNA  length = 1344
FEATURE                  Location/Qualifiers
source                   1..1344
                         mol_type = genomic DNA
                         organism = Pavlova salina
SEQUENCE: 72
atgcctccga gcgcggcgaa gcagatgggc gcgagcacgg gcgtgcatgc gggcgtcaca    60
gattcgtcgg ccttcacgcg caaggatgtc gccgacaggc cggacctcac gatcgtgggt   120
gacagcgtgt acgatgcgaa ggcgttccgc tccgagccgg cgggtggcgc cactttgtg   180
tcgctgttcg gcgggcgcga tgccacggag gcgttcatgg agtaccaccg gcgcgcctgc   240
cccaagtcgc gcatgtcgcg cttccacgtc ggctctctgg catcgaccga ggagcccgtc   300
gccgccgatg agggctacct ccagctgtgc gctcgcatcg ccaagatggt gccgtcggtc   360
agcagcgggt tcgcgccggc gtcgtactgg gtgaaggccg ggctgatcct cggctccgcg   420
atcgcgctcg aggcgtacat gctgtacgcg ggcaagcgcc tgctcccgtc gatcgtgctc   480
gggtggctgt tgcgctgat tggcctgaac atccagcacg atgccaacca cggcgcgctc   540
tccaagtcgg cctcggtcaa cctggcgctc gggttgtgcc aggactggat cggcggggagc   600
atgatcctct ggctgcagga gcacgttgtc atgcaccact tgcacaccaa cgacgttgac   660
aaggacccgg accagaaggc gcacggcgcc ctgcggctca gccgaccga cgcgtggagc    720
ccgatgcact ggctgcagca cctctacctg ctgcctgggg agacgatgta cgccttcaag   780
ctgctgtttc tcgacatcag cgagctggtg atgtggcgt gggagggcga gcccatcagc   840
aagctggccg ggtacctctt catgccctcg ctgctcctca agctccactt ctgggcgcgc   900
tttgtcgcgc tgccgctgta cctcgcgccc acgtgcaca cggcggtgtg catcgcggcg   960
acggtaatga cggggagctt ctacctcgcc ttcttcttct tcatctcgca caacttcgag  1020
ggcgtggcga gcgtcggacc ggacggcagc atcaccagca tgacgcgcgg cgcatccttc  1080
ctcaagcggg aggccgagac ctcgtccaac gtgggcggcc gcctgctcgc cacgctcaac  1140
ggcggcctca actaccaaat cgagcaccac ctcttcccca gggtgcacca cggcttctac  1200
cctcgcctcg cgccgttggt caaggcgag ctcgaggcgc gcggcattga gtacaagcac  1260
taccccacca tatggagcaa cctggcatcc acgctgaggc acatgtacgc gctcggccgc  1320
aggccgcgca gcaaggcgga gtga                                         1344

SEQ ID NO: 73            moltype = AA  length = 447
FEATURE                  Location/Qualifiers
source                   1..447
                         mol_type = protein
                         organism = Pavlova salina
SEQUENCE: 73
MPPSAAKQMG ASTGVHAGVT DSSAFTRKDV ADRPDLTIVG DSVYDAKAFR SEHPGGAHFV    60
SLFGGRDATE AFMEYHRRAW PKSRMSRFHV GSLASTEEPV AADEGYLQLC ARIAKMVPSV   120
SSGFAPASYW VKAGLILGSA IALEAYMLYA GKRLLPSIVL GWLFALIGLN IQHDANHGAL   180
SKSASVNLAL GLCQDWIGGS MILWLQEHVV MHHLHTNDVD KDPDQKAHGA LRLKPTDAWS   240
PMHWLQHLYL LPGETMYAFK LLFLDISELV MWREGEPIS KLAGYLFMPS LLLKLTFWAR   300
```

```
FVALPLYLAP SVHTAVCIAA TVMTGSFYLA FFFFISHNFE GVASVGPDGS ITSMTRGASF   360
LKRQAETSSN VGGPLLATLN GGLNYQIEHH LFPRVHHGFY PRLAPLVKAE LEARGIEYKH   420
YPTIWSNLAS TLRHMYALGR RPRSKAE                                      447

SEQ ID NO: 74            moltype = DNA   length = 1563
FEATURE                  Location/Qualifiers
source                   1..1563
                         mol_type = genomic DNA
                         organism = Arabidopsis thaliana
SEQUENCE: 74
atggcgattt tggattctgc tggcgttact acggtgacgg agaacggtgg cggagagttc    60
gtcgatcttg ataggcttcg tcgacggaaa tcgagatcgg attcttctaa cggacttctt   120
ctctctggtt ccgataataa ttctccttcg gatgatgttg gagctcccgc cgacgttagg   180
gatcggattg attccgttgt taacgatgac gctcagggaa cagccaattt ggccggagat   240
aataacggtg gtgccgataa taacggtggt ggaagaggcg gcggagaagg aagaggaaac   300
gccgatgcta cgtttacgta tcgaccgtcg gttccagctc atcggagggc gagagagagt   360
ccacttagct ccgacgcaat cttcaaacag agccatgccg gattattcaa cctctgtgta   420
gtagttctta ttgctgtaaa cagtagactc atcatcgaaa atcttatgaa gtatggttgg   480
ttgatcagaa cggatttctg gtttagttca agatcgctgc gagattggcc gcttttcatg   540
tgttgtatat ccctttcgat cttttccttt gctgccttta cggttgagaa attggtactt   600
cagaaataca tatcagaacc tgttgtcatc tttcttcata ttattatcac catgacagag   660
gttttgtatc cagtttacgt caccctaagg tgtgattcgt cttttttatc aggtgtcact   720
ttgatgctcc tcacttgcat tgtgtggcta aagttggttt cttatgctca tactagctat   780
gacataagat ccctagccaa tgcagctgat aaggccaatc ctgaagtctc ctactacgtt   840
agcttgaaga gcttggcata tttcatggtc gctcccacat tgtgttatca gccaagttat   900
ccacgttctg catgtatacg gaagggttgg gtggctcgtc aatttgcaaa actggtcata   960
ttcaccggat tcatgggatt tataatagaa caatatataa atcctattgt caggaactca  1020
aagcatcctt tgaaaggcga tcttctatat gctattgaaa gagtgttgaa gctttcagtt  1080
ccaaatttat atgtgtggct ctgcatgttc tactgcttct tccaccttcg gttaaacata  1140
ttggcagagc ttctctgctt cggggatcgt gaattctaca agattggtg gaatgcaaaa  1200
agtgtgggag attactggag aatgtggaat atgcctgttc ataaatggat ggttcgacat  1260
atatacttcc cgtgcttgcg cagcaagata ccaaagacac tcgccattat cattgctttc  1320
ctagtctctg cagtctttca tgagctatgc atcgcagttc cttgtcgtct cttcaagcta  1380
tgggcttttc ttgggattat gtttcaggtg cctttggtct tcatcacaaa ctatcttcag  1440
gaaaggtttg gctcaacggt ggggaacatg atcttctggt tcatcttctg cattttcgga  1500
caaccgatgt gtgtgcttct ttattaccac gacctgatga accgaaaagg atcgatgtca  1560
tga                                                               1563

SEQ ID NO: 75            moltype = AA   length = 520
FEATURE                  Location/Qualifiers
source                   1..520
                         mol_type = protein
                         organism = Arabidopsis thaliana
SEQUENCE: 75
MAILDSAGVT TVTENGGGEF VDLDRLRRRK SRSDSSNGLL LSGSDNNSPS DDVGAPADVR    60
DRIDSVVNDD AQGTANLAGD NNGGGDNNGG GRGGGEGRGN ADATFTYRPS VPAHRRARES   120
PLSSDAIFKQ SHAGLFNLCV VVLIAVNSRL IIENLMKYGW LIRTDFWFSS RSLRDWPLFM   180
CCISLSIFPL AAFTVEKLVL QKYISEPVVI FLHIIITMTE VLYPVYVTLR CDSAFLSGVT   240
LMLLTCIVWL KLVSYAHTSY DIRSLANAAD KANPEVSYYV SLKSLAYFMV APTLCYQPSY   300
PRSACIRKGW VARQFAKLVI FTGFMGFIIE QYINPIVRNS KHPLKGDLLY AIERVLKLSV   360
PNLYVWLCMF YCFFHLWLNI LAELLCFGDR EFYKDWWNAK SVGDYWRMWN MPVHKWMVRH   420
IYFPCLRSKI PKTLAIIIAF LVSAVFHELC IAVPCRLFKL WAFLGIMFQV PLVFITNYLQ   480
ERFGSTVGNM IFWFIFCIFG QPMCVLLYYH DLMNRKGSMS                         520

SEQ ID NO: 76            moltype = AA   length = 9
FEATURE                  Location/Qualifiers
REGION                   1..9
                         note = Elongase consensus domain 7
source                   1..9
                         mol_type = protein
                         organism = synthetic construct
SEQUENCE: 76
VDTRKGAYR                                                             9

SEQ ID NO: 77            moltype = AA   length = 9
FEATURE                  Location/Qualifiers
REGION                   1..9
                         note = Elongase consensus domain 8
source                   1..9
                         mol_type = protein
                         organism = synthetic construct
SEQUENCE: 77
FIHTIMYTY                                                             9

SEQ ID NO: 78            moltype = DNA   length = 28
FEATURE                  Location/Qualifiers
misc_feature             1..28
                         note = Oligonucleotide primer
misc_feature             20
```

```
                        note = n is a, c, g, or t
misc_feature            23
                        note = n is a, c, g, or t
source                  1..28
                        mol_type = other DNA
                        organism = synthetic construct
SEQUENCE: 78
tggtggacac aaggaagggn gcntaymg                                          28

SEQ ID NO: 79           moltype = DNA  length = 27
FEATURE                 Location/Qualifiers
misc_feature            1..27
                        note = Oligonucleotide primer
source                  1..27
                        mol_type = other DNA
                        organism = synthetic construct
SEQUENCE: 79
gtaggtgtac atgatggtrt gdatraa                                           27

SEQ ID NO: 80           moltype = DNA  length = 24
FEATURE                 Location/Qualifiers
misc_feature            1..24
                        note = Oligonucleotide primer
source                  1..24
                        mol_type = other DNA
                        organism = synthetic construct
SEQUENCE: 80
gtccttgctc cagggcttcc acca                                              24

SEQ ID NO: 81           moltype = DNA  length = 36
FEATURE                 Location/Qualifiers
misc_feature            1..36
                        note = Oligonucleotide primer
source                  1..36
                        mol_type = other DNA
                        organism = synthetic construct
SEQUENCE: 81
atttaggtga cactatagtt tttttttttt tttttt                                 36

SEQ ID NO: 82           moltype = DNA  length = 23
FEATURE                 Location/Qualifiers
misc_feature            1..23
                        note = Oligonucleotide primer
source                  1..23
                        mol_type = other DNA
                        organism = synthetic construct
SEQUENCE: 82
ttccagaacg agggcatcta cgt                                               23

SEQ ID NO: 83           moltype = DNA  length = 25
FEATURE                 Location/Qualifiers
misc_feature            1..25
                        note = Oligonucleotide primer
source                  1..25
                        mol_type = other DNA
                        organism = synthetic construct
SEQUENCE: 83
ttgggtgatc tgcatgagcg tgatg                                             25

SEQ ID NO: 84           moltype = DNA  length = 26
FEATURE                 Location/Qualifiers
misc_feature            1..26
                        note = Oligonucleotide primer
source                  1..26
                        mol_type = other DNA
                        organism = synthetic construct
SEQUENCE: 84
cgaatacttg aagagcttgt tggaga                                            26

SEQ ID NO: 85           moltype = DNA  length = 25
FEATURE                 Location/Qualifiers
misc_feature            1..25
                        note = Oligonucleotide primer
source                  1..25
                        mol_type = other DNA
                        organism = synthetic construct
SEQUENCE: 85
gggctacgag ctggcagatg aagca                                             25
```

```
SEQ ID NO: 86          moltype = DNA  length = 25
FEATURE                Location/Qualifiers
misc_feature           1..25
                       note = Oligonucleotide primer
source                 1..25
                       mol_type = other DNA
                       organism = synthetic construct
SEQUENCE: 86
gaaaaaatgg ttgcgccacc catca                                         25

SEQ ID NO: 87          moltype = DNA  length = 27
FEATURE                Location/Qualifiers
misc_feature           1..27
                       note = Oligonucleotide primer
source                 1..27
                       mol_type = other DNA
                       organism = synthetic construct
SEQUENCE: 87
tcactacttc ttcttcttgc ccgcggc                                       27

SEQ ID NO: 88          moltype = DNA  length = 21
FEATURE                Location/Qualifiers
misc_feature           1..21
                       note = Oligonucleotide primer
source                 1..21
                       mol_type = other DNA
                       organism = synthetic construct
SEQUENCE: 88
ttccggtact cagcggtggc g                                             21

SEQ ID NO: 89          moltype = DNA  length = 17
FEATURE                Location/Qualifiers
misc_feature           1..17
                       note = Oligonucleotide primer
source                 1..17
                       mol_type = other DNA
                       organism = synthetic construct
SEQUENCE: 89
caggaaacag ctatgac                                                  17

SEQ ID NO: 90          moltype = DNA  length = 20
FEATURE                Location/Qualifiers
misc_feature           1..20
                       note = Oligonucleotide primer
source                 1..20
                       mol_type = other DNA
                       organism = synthetic construct
SEQUENCE: 90
acgtagatgc cctcgttctg                                               20

SEQ ID NO: 91          moltype = DNA  length = 26
FEATURE                Location/Qualifiers
misc_feature           1..26
                       note = Oligonucleotide primer
source                 1..26
                       mol_type = other DNA
                       organism = synthetic construct
SEQUENCE: 91
caccgaatgg cgactgaagg gatgcc                                        26

SEQ ID NO: 92          moltype = DNA  length = 27
FEATURE                Location/Qualifiers
misc_feature           1..27
                       note = Oligonucleotide primer
source                 1..27
                       mol_type = other DNA
                       organism = synthetic construct
SEQUENCE: 92
ctactcggtt ttcatgcggt tgctgga                                       27

SEQ ID NO: 93          moltype = DNA  length = 819
FEATURE                Location/Qualifiers
source                 1..819
                       mol_type = genomic DNA
                       organism = Pavlova pinguis
SEQUENCE: 93
atggttgcgc cacccatcac gctcgagtgg ctgctttcgc cgaagctcaa ggatgcagtg   60
ttcggtgggg aggtgctcta cttctccatt ggctacctgt ttcttgcgcc cattttgaag   120
cgcacccccgt tggtggacac gcggaagggc gcgtataaga gtggtatgat cgcgtacaac   180
```

```
gtgatcatgt gcgtgttctc gctggtgtgc ttcatctgcc agctcgcagc cctgggctat    240
gacatgggct acttgcagtg ggtgcgtgac ctcacagggg acgagattgt cccctctac    300
caggacgtgt ccccgtcccc cgccttctcc aacaagctct tcaagtattc gtctattgcc    360
ttccactact ccaagtatgt tgagtacatg gacaccgcat ggctggtgat gaagggcaag    420
cccgtgtcct tgctccaggg cttccaccac tttggcgtcg cctgggacac ctactttggc    480
atcaccttcc agaacgaggg catctacgtg ttcgtggtgc tcaacgcctt catccacacg    540
atcatgtacg catactacgc ggccactgcg gcgggtctca agttctcact gaagttcgtc    600
atcacgctca tgcagatcac ccaattcaac gtgggcttcg taatggtgta tcactacatc    660
accctggagt acttccgcaa ctcaccggag ctcgtcttct cctacctttt caactatgcg    720
tacgtctgca cggttctcct cctcttcatg cagttcttct acatggacaa ctttggcaag    780
aagaaggccg ctgccgccgc gggcaagaag aagaagtag                            819

SEQ ID NO: 94          moltype = AA  length = 272
FEATURE                Location/Qualifiers
source                 1..272
                       mol_type = protein
                       organism = Pavlova pinguis
SEQUENCE: 94
MVAPPITLEW LLSPKLKDAV FGGEVLYFSI AYLFLAPILK RTPLVDTRKG AYKSGMIAYN     60
VIMCVFSLVC FICQLAALGY DMGYLQWVRD LTGDEIVPLY QDVSPSPAFS NKLFKYSSIA   120
FHYSKYVEYM DTAWLVMKGK PVSLLQGFHH FGAAWDTYFG ITFQNEGIYV FVVLNAFIHT   180
IMYAYYAATA AGLKFSLKFV ITLMQITQFN VGFVMVYHYI TLEYFRNSPE LVFSYLFNYA   240
YVCTVLLLFM QFFYMDNFGK KKAAAAAGKK KK                                  272

SEQ ID NO: 95          moltype = DNA  length = 840
FEATURE                Location/Qualifiers
source                 1..840
                       mol_type = genomic DNA
                       organism = Pavlova salina
SEQUENCE: 95
atggcgactg aagggatgcc ggcgataacg ctggactggc tgctctcgcc cgggctgaag     60
gatgccgtaa ttggcgggga ggtgctctac ttttcgcttg ggtatctgct gctcgagccc   120
atcctcaagc gctcaccgtt tgtggacaag cgcaagggcg catatcgcaa cggcatgatc   180
gcgtacaaca tcctcatgtg cggtttctcg ctggtatgct tcgtgtgcca gatggcggcg   240
ctcggccttg atcgcggcca cctgcagttt gtccgcgacc tcacgggcga cagcgtggtg   300
cagctctacc aggacgtgag cccatcccct gcattcgcga acaagctctt ccggtactca   360
gcggtggcgt tccactactc aaagtacgtg gagtacatgg acacagcgtg gcttgtgctg   420
aagggcaagc ccgtctcgtt cctgcagggc ttccaccact cggcgccgc gtgggacacc   480
tactttggca tcacgtttca gaacgagggc acctacgtct ttgtgctgct caacgcattc   540
atccacacaa tcatgtacac ctactacggc gcgacggca cgggcatcaa atctctgatg   600
aagccgctga tcaccctcat gcagatcacg cagttcctgc tgggcttcgc gctcgtctac   660
ccgtacattg acctcggcta cttccgtgcg tcgcccgagc tcgtgtggag ctacctgttc   720
aactatgcgt acgtactcat ggtgctcttc ctcttcatgc gcttcttcta ccacgacaac   780
tttagcaagc acaagccaat ctcgcgcatc gactccagca ccgcatgaa aaccgagtag    840

SEQ ID NO: 96          moltype = AA  length = 279
FEATURE                Location/Qualifiers
source                 1..279
                       mol_type = protein
                       organism = Pavlova salina
SEQUENCE: 96
MATEGMPAIT LDWLLSPGLK DAVIGGEVLY FSLGYLLLEP ILKRSPFVDK RKGAYRNGMI     60
AYNILMCGFS LVCFVCQMAA LGLDRGHLQF VRDLTGDSVV QLYQDVSPSP AFANKLFRYS   120
AVAFHYSKYV EYMDTAWLVL KGKPVSFLQG FHHFGAAWDT YFGITFQNEG TYVFVLLNAF   180
IHTIMYTYYG ATAAGIKISM KPLITLMQIT QFLLGFALVY PYIDLGYFRA SPELVWSYLF   240
NYAYVLMVLF LFMRFFYHDN FSKHKPISRI DSSNRMKTE                           279

SEQ ID NO: 97          moltype = AA  length = 172
FEATURE                Location/Qualifiers
source                 1..172
                       mol_type = protein
                       organism = Tomato bushy stunt virus
SEQUENCE: 97
MERAIQGNDA REQANSERWD GGSGGTTSPF KLPDESPSWT EWRLHNDETN SNQDNPLGFK     60
ESWGFGKVVF KRYLRYDRTE ASLHRVLGSW TGDSVNYAAS RFFGFDQIGC TYSIRFRGVS   120
ITVSGGSRTL QHLCEMAIRS KQELLQLAPI EVESNVSRGC PEGTETFEKE SE            172

SEQ ID NO: 98          moltype = AA  length = 116
FEATURE                Location/Qualifiers
source                 1..116
                       mol_type = protein
                       organism = Tomato yellow leaf curl virus
SEQUENCE: 98
MWDPLLNEFP ESVHGFRCML AIKYLQSVEE TYEPNTLGHD LIRDLISVVR ARDYVEATRR     60
YNHFHARLEG SPKAELRQPI QQPCCCPHCP RHKQATIMDV QAHVPEAQNI QNVSKP       116

SEQ ID NO: 99          moltype = AA  length = 351
FEATURE                Location/Qualifiers
source                 1..351
```

```
                        mol_type = protein
                        organism = Turnip crinkle virus
SEQUENCE: 99
MENDPRVRKF ASEGAQWAIK WQKKGWSSLT SRQKQTARAA MGIKLSPVAQ PVQKVTRLSA    60
PVALAYREVS TQPRVSTARD GITRSGSELI TTLKKNTDTE PKYTTAVLNP SEPGTFNQLI   120
KEAAQYEKYR FTSLRFRYSP MSPSTTGGKV ALAFDRDAAK PPPNDLASLY NIEGCVSSVP   180
WTGFILTVPT DSTDRFVADG ISDPKLVNFG KLIMATYGQG ANDAAQLGEV RVEYTVQLKN   240
RTGSTSDAQI GDFAGVKDGP RLVSWSKTKG TAGWEHDCHF LGTGNFSLTL FYEKAPVSGL   300
ENADASDFSV LGEAAAGSVQ WAGVKVAERG QSVKMVTTEE QPRGKWQALR I            351

SEQ ID NO: 100          moltype = AA   length = 303
FEATURE                 Location/Qualifiers
source                  1..303
                        mol_type = protein
                        organism = Pea mosaic virus
SEQUENCE: 100
MHGIEQPQLP LDYVHRCAST SFLLASLDGL LSEARELSGP LALITSSYYL LVSIALCWAI    60
PGSFWYRPGC WLQPVSGRNL IFCGPTEALQ RFRLYAARLG LVLSENCPRH GQSAAITLQS   120
YWALPNNIWM DMAQLDLLTF SMPIANTFAY LADCEARFPP IVEGVGSAYY VPTLLGLTHQ   180
DPRLYLALRR RNLDLSGEPH RVRPGVLESM ALLCSSVRST SRSRQIPPLY GSVLHHVLGL   240
AERDCILFDT DSNYSSYTHR VLEQDRNRAD QSLFSIDLEY VHDLELIALG YSDEDDEDLD   300
NFF                                                                 303

SEQ ID NO: 101          moltype = AA   length = 256
FEATURE                 Location/Qualifiers
source                  1..256
                        mol_type = protein
                        organism = Cereal yellow dwarf virus
SEQUENCE: 101
MFIAQPCGRV LVFDVASRTP SFFTRYSVEL SLRVLDPFFT RAVTDFRYTQ NEIDLFCVSL    60
GFLLPILLTG ESYSWRGHLN LPLSYTELLV RWGLAVGYFP TFSTDGDIRQ NPELRIDLST   120
MSTRSFYEQF LLRYNTSGLA KAIVGQQECF QSGMESFKRF LHYRLTCFES CLPRPRWESP   180
LAPGPYLDRA FEATLLGRMV GHNQLLFTGL SSDITRYYNE LVVEGVPVAF WDAAGITLHH   240
AGEEYFSNSY IQKILQ                                                   256

SEQ ID NO: 102          moltype = DNA   length = 519
FEATURE                 Location/Qualifiers
source                  1..519
                        mol_type = genomic DNA
                        organism = Tomato bushy stunt virus
SEQUENCE: 102
atggaacgag ctatacaagg aaacgacgct agggaacaag ctaacagtga acgttgggat    60
ggaggatcag gaggtaccac ttctcccttc aaacttcctg acgaaagtcc gagttggact   120
gagtggcggc tacataacga tgagacgaat tcgaatcaag ataatcccct tggtttcaag   180
gaaagctggg gtttcgggaa agttgtattt aagagatatc tcagatacga caggacggaa   240
gcttcactgc acagagtcct tggatcttgg acgggagatt cggttaacta tgcagcatct   300
cgattttcg gtttcgacca gatcggatgt acctatagta ttcggtttcg aggagttagt   360
atcaccgttt ctggagggtc gcgaactctt cagcatctct gtgagatggc aattcggtct   420
aagcaagaac tgctacagct tgccccaatc gaagtggaaa gtaatgtatc aagaggatgc   480
cctgaaggta ctgagacctt cgaaaaagaa agcgagtaa                          519

SEQ ID NO: 103          moltype = DNA   length = 351
FEATURE                 Location/Qualifiers
source                  1..351
                        mol_type = genomic DNA
                        organism = Tomato yellow leaf curl virus
SEQUENCE: 103
atgtgggatc cacttctaaa tgaatttcct gaatctgttc acggatttcg ttgtatgtta    60
gctattaaat atttgcagtc cgttgaggaa acttacgagc ccaatacatt gggccacgat   120
ttaattaggg atcttatatc tgttgtaagg gcccgtgact atgtcgaagc gaccaggcga   180
tataatcatt tccacgcccg cctcgaaggt tcgccgaagg ctgaacttcg acagcccata   240
cagcagccgt gctgctgtcc ccattgtcca aggcacaaac aagcgacgat catggacgta   300
caggcccatg taccggaagc ccagaatata cagaatgtat cgaagccctg a            351

SEQ ID NO: 104          moltype = DNA   length = 1056
FEATURE                 Location/Qualifiers
source                  1..1056
                        mol_type = genomic DNA
                        organism = Turnip crinkle virus
SEQUENCE: 104
atggaaaatg atcctagagt ccgaaagttc gcatccgagg gcgcccaatg ggcgataaag    60
tggcagaaga agggctggtc atccctaacc agcagacaga aacagaccgc ccgcgcagcg   120
atggggatca agctctcccc tgtggcgcaa cctgtgcaga aagtgactcg actgagtgct   180
ccggtggctc tcgcctaccg cgaggttttcc acccagcctg ggtttctac tgccagggag   240
ggcataacca gaagcggttc tgaactgatc acaaccctga agaagaacac tgacactgaa   300
cctaagtaca ccacagctgt gcttaaccca agcgaaccg gaacattcaa ccaactcatc   360
aaggaggcg cccagtatga aaaataccga ttcacgtcac tcagatttag gtactctccc   420
atgagcccct caaccaccgg gggcaaggtg gctctggcat cgaccgaga cgctgccaaa   480
cctccgccca acgacctcgc ttccctctac aacatagagg ttgtgtatc tagcgtgccc   540
```

```
tggacagggt ttattttgac cgtcccaaca gattctactg accgctttgt ggcggatggt    600
atcagcgatc caaagcttgt caatttcggc aagctcatca tggccaccta tggccaagga    660
gccaatgatg ccgcccaact cggtgaagtg cgagtcgagt acaccgtgca gctcaagaac    720
agaactggct caaccagcga cgcccagatt ggggacttcg cgggtgttaa ggacggaccc    780
aggttggtct cgtggtccaa gaccaaggga acagctgggt gggagcacga ttgtcatttt    840
ctcggaaccg gaaacttctc gttgacactg ttctacgaga aggcgcccgt ttcgggctta    900
gaaaacgcag acgcctctga cttctccggtc ctgggagaag ccgcagcagg tagtgtccaa    960
tgggctggag tgaaggtagc agaaagggga caaagcgtga aaatggtcac aactgaggag   1020
cagccaaggg gaaaatggca agcactcagg atttag                             1056

SEQ ID NO: 105         moltype = DNA   length = 912
FEATURE                Location/Qualifiers
source                 1..912
                       mol_type = genomic DNA
                       organism = Pea mosaic virus
SEQUENCE: 105
atgcacggaa ttgagcagcc tcaactaccg ctagattacg ttcaccgttg cgcatcaacc     60
tccttccttgc tcgcatcact agatggcctc ctttctgaag ccgtgaact tcagggcct    120
ctggctctca ttacttctag ctattactta cttgtttcta ttgccctctg ctgggcaatc    180
cctggatcct tctggtatag gccttggctgc tggttcagc cagtctcagg gcggaatctc    240
atcttttgcg ccctaccga ggccttgcaa cgattccgtc tgtacgctgc cagacttggg    300
ttggtcctgt cagagaactg cccaagacac ggccaatcag cagcaatcac ccttcaatca    360
tactgggcac ttcctaacaa catctgatg gacatggccc aattggactt gctcaccttc    420
tcaatgccaa ttgctaatac attgcctac ttggcagatt gtgaagcaag atttcctcct    480
attgttgaag gagtgggatc tgcttactat gtgccaacgc tgctcggact tactcaccaa    540
gacccaggcc tttatcttgc gcttcgcagg agaaaacctg atcttagtgg cgaacctcat    600
agagttcgtc ctggtgtcct ggagtctatg gctttgctct gttctagtgt acgtagcaca    660
agccgttcca ggcaaattcc tcctttatat ggcagcgttt tgcaccacgt tttgggcctg    720
gccgagagag actgcatcct cttgatacg gatagtaact actcctctta cactcatcgg    780
gttcttgaac aagaccggaa tcgggctgat cagtcattgt ttagcattga cttggaatat    840
gttcatgacc tggagcttat tgccctgggt tactctgatg aagatgatga agatcttgat    900
aacttcttct ag                                                       912

SEQ ID NO: 106         moltype = DNA   length = 771
FEATURE                Location/Qualifiers
source                 1..771
                       mol_type = genomic DNA
                       organism = Cereal yellow dwarf virus
SEQUENCE: 106
atgttcatcg cccaaccttg cgggcgagtt cttgtgttcg acgtcgcctc ccgcacgcca     60
tcgttcttca ctcgttatag tgttgaactc tcgctccgtg ttctagaccc attcttcacg    120
cgagcagtaa cagatttccg atacacccaa aatgaaatcg atttatttg tgtgtctctt    180
ggctttctgt tgccaattct cctcacagga gaatcttact cttggcgcgg tcaccctcaac    240
ctcccccttt cttacaccga attacttgtt cgatgggggc tcgcagtggg gtacttccct    300
accttctcca ctgatggtga cattcgacag aacccagaac tccgcatcga cctgtccacc    360
atgtcaaccc gctctttcta cgagcagttc ctactcgat ataacacgag tgggttggca    420
aaagctatcg tcggacagca agagtgcttt caaagcgtca tggagtcttt taaaagatc    480
ctacactacc gcctcacgtg ctttgaaagc tgccttccac gacctcgttg ggaaagtcct    540
ttggctcctg gtccttatct ggacagggct tttgaggcaa ctcttctcgg ccgtatggtc    600
ggtcataacc aactactctt taccggtttg tcttctgata tcactaggta ttataacgag    660
ttggttgtgg aaggcgtgcc ggtggctttt tgggacgctg ccggcattac tttgcatcac    720
gctggtgaag aatattttc gaattcttac attcaaaga ttcttcaatg a               771

SEQ ID NO: 107         moltype = DNA   length = 1005
FEATURE                Location/Qualifiers
source                 1..1005
                       mol_type = genomic DNA
                       organism = Micromonas sp.
                       strain = CCMP1545
SEQUENCE: 107
atgaccgctg ctccagcttc tgctagagat cctgctcttg ctactggatc tggatctctt     60
tacaaccacc tcatgatgtt cgcttggctt ggagttgttc atgctgttgt tgctcttgtt    120
gctgttgctt gctacttcct tcctcatcct gttgctactt gtgctatcgc tctcgttgct    180
cttgctgctc ttactcctgt tactactcct catcctgctc ggggacttgc tatcgctaga    240
gctatcacta aggctgctgt gagatacttc cctcttacta tggaatggga ggatgagaga    300
gcttaccttg acgctgctgc taagggtgtt cctgctgtta tcgacttga gcctcattct    360
gttctcccctt tgtctatcgt tgctttcgga aactacttct tcttcaccga atctacacct    420
gagtgcgtga gaaactctag agctttggct actggaacca tcttcgttat cctcgttctt    480
aagcaccttt ggtcttggct tggaatggat gctatctcta gcgtgctat gaagactctt    540
ctcgatgatg aagatctgt tctcatcatc cctggtggag ttgctgagtg ccttcaaatg    600
aggcctggtg ttgagactat ctacctcaag aagaggttcg gattcgttaa gcttgctatc    660
caaaccggtc cttctcttgt tcctgctttc acttcggac agaccagatc ttactcttac    720
tggcgtcttg gacctcctct tgttcctcat gttgttgctg aggttttcgc tagagcttgt    780
agagttcgtc ctatggtttt ctggggaaag tgggatctc ctatccctaa catgtccaca    840
atgcacactg ttgttggaaa gcctatccct gttaagaagc agtctgagcc ttctaacgag    900
tacgttcaag agaagctcaa cgagtcgttc gctgctatgg aatctcttta cgctagacac    960
aagggaaagc acggatacgc tgagtctact ctcgttgttc tttga                   1005

SEQ ID NO: 108         moltype = AA   length = 334
```

| FEATURE | Location/Qualifiers |
|---|---|
| source | 1..334<br>mol_type = protein<br>note = Strain CCMP1545<br>organism = Micromonas sp. |

SEQUENCE: 108
```
MTAAPASARD PALATGSGSL YNHLMMFAWL GVVHAVVALV AVACYFLPHP VATCAIALVA   60
LAALTPVTTP HPAWGLAIAR AITKAAVRYF PLTMEWEDER AYLDAAAKGV PAVIGLEPHS  120
VLPLSIVAFG NYFFFTESTP ECVRNSRALA TGTIFVIPVL KHLWSWLGMD AISRRAMKTL  180
LDDGRSVLII PGGVAECLQM RPGVETIYLK KRFGFVKLAI QTGASLVPAF TFGQTRSYSY  240
WRLGPPLVPH VVAEVPARAC RVAPMVFWGK WGSPIPNMVP MHTVVGKPIP VKKQSEPSNE  300
YVQEKLNEFV AAMESLYARH KGKHGYAEST LVVL                              334
```

SEQ ID NO: 109     moltype =    length =
SEQUENCE: 109
000

| SEQ ID NO: 110 | moltype = DNA   length = 25 |
|---|---|
| FEATURE | Location/Qualifiers |
| misc_feature | 1..25<br>note = Transfer nucleic acid border sequence |
| source | 1..25<br>mol_type = other DNA<br>organism = synthetic construct |

SEQUENCE: 110
tgacaggata tattggcggg taaac                                         25

| SEQ ID NO: 111 | moltype = DNA   length = 25 |
|---|---|
| FEATURE | Location/Qualifiers |
| misc_feature | 1..25<br>note = Transfer nucleic acid border sequence |
| source | 1..25<br>mol_type = other DNA<br>organism = synthetic construct |

SEQUENCE: 111
tggcaggata tattgtggtg taaac                                         25

| SEQ ID NO: 112 | moltype = DNA   length = 25 |
|---|---|
| FEATURE | Location/Qualifiers |
| misc_feature | 1..25<br>note = Transfer nucleic acid border sequence |
| source | 1..25<br>mol_type = other DNA<br>organism = synthetic construct |

SEQUENCE: 112
tggcaggata taccgttg taatt                                           25

| SEQ ID NO: 113 | moltype = DNA   length = 25 |
|---|---|
| FEATURE | Location/Qualifiers |
| misc_feature | 1..25<br>note = Transfer nucleic acid border sequence |
| source | 1..25<br>mol_type = other DNA<br>organism = synthetic construct |

SEQUENCE: 113
cggcaggata tattcaattg taatt                                         25

| SEQ ID NO: 114 | moltype = DNA   length = 25 |
|---|---|
| FEATURE | Location/Qualifiers |
| misc_feature | 1..25<br>note = Transfer nucleic acid border sequence |
| source | 1..25<br>mol_type = other DNA<br>organism = synthetic construct |

SEQUENCE: 114
tggtaggata taccgttg taatt                                           25

| SEQ ID NO: 115 | moltype = DNA   length = 25 |
|---|---|
| FEATURE | Location/Qualifiers |
| misc_feature | 1..25<br>note = Transfer nucleic acid border sequence |
| source | 1..25<br>mol_type = other DNA<br>organism = synthetic construct |

SEQUENCE: 115
tggcaggata tatggtactg taatt                                         25

| SEQ ID NO: 116 | moltype = DNA   length = 25 |
|---|---|
| FEATURE | Location/Qualifiers |

```
misc_feature          1..25
                      note = Transfer nucleic acid border sequence
misc_feature          1
                      note = y = c or t
misc_feature          3
                      note = r = a or g
misc_feature          4
                      note = y = c or t
misc_feature          14
                      note = w = a or t
misc_feature          15
                      note = s = c or g
misc_feature          16
                      note = n is a, c, g, or t
misc_feature          17
                      note = v = a, c or g
misc_feature          18
                      note = b = c, g or t
misc_feature          19
                      note = k = g or t
misc_feature          24
                      note = w = a or t
misc_feature          25
                      note = y = c or t
source                1..25
                      mol_type = other DNA
                      organism = synthetic construct
SEQUENCE: 116
ygryaggata tatwsnvbkg taawy                                         25

SEQ ID NO: 117        moltype = DNA   length = 25
FEATURE               Location/Qualifiers
misc_feature          1..25
                      note = Transfer nucleic acid border sequence
source                1..25
                      mol_type = other DNA
                      organism = synthetic construct
SEQUENCE: 117
cggcaggata tatcctgatg taaat                                         25

SEQ ID NO: 118        moltype = DNA   length = 25
FEATURE               Location/Qualifiers
misc_feature          1..25
                      note = Transfer nucleic acid border sequence
source                1..25
                      mol_type = other DNA
                      organism = synthetic construct
SEQUENCE: 118
tggcaggagt tattcgaggg taaac                                         25

SEQ ID NO: 119        moltype = DNA   length = 25
FEATURE               Location/Qualifiers
misc_feature          1..25
                      note = Transfer nucleic acid border sequence
source                1..25
                      mol_type = other DNA
                      organism = synthetic construct
SEQUENCE: 119
tgacaggata tatcgtgatg tcaac                                         25

SEQ ID NO: 120        moltype = DNA   length = 25
FEATURE               Location/Qualifiers
misc_feature          1..25
                      note = Transfer nucleic acid border sequence
source                1..25
                      mol_type = other DNA
                      organism = synthetic construct
SEQUENCE: 120
gggaagtaca tattggcggg taaac                                         25

SEQ ID NO: 121        moltype = DNA   length = 25
FEATURE               Location/Qualifiers
misc_feature          1..25
                      note = Transfer nucleic acid border sequence
source                1..25
                      mol_type = other DNA
                      organism = synthetic construct
SEQUENCE: 121
ttacaggata tattaatatg tatga                                         25
```

```
SEQ ID NO: 122          moltype = DNA  length = 25
FEATURE                 Location/Qualifiers
misc_feature            1..25
                        note = Transfer nucleic acid border sequence
source                  1..25
                        mol_type = other DNA
                        organism = synthetic construct
SEQUENCE: 122
taacatgata tattcccttg taaat                                         25

SEQ ID NO: 123          moltype = DNA  length = 25
FEATURE                 Location/Qualifiers
misc_feature            1..25
                        note = Transfer nucleic acid border sequence
source                  1..25
                        mol_type = other DNA
                        organism = synthetic construct
SEQUENCE: 123
tgacaggata tatggtaatg taaac                                         25

SEQ ID NO: 124          moltype = DNA  length = 25
FEATURE                 Location/Qualifiers
misc_feature            1..25
                        note = Transfer nucleic acid border sequence
source                  1..25
                        mol_type = other DNA
                        organism = synthetic construct
SEQUENCE: 124
tggcaggata tataccgatg taaac                                         25

SEQ ID NO: 125          moltype = DNA  length = 1395
FEATURE                 Location/Qualifiers
misc_feature            1..1395
                        note = Codon-optimized nucleotide sequence for production
                         in plants of SEQ ID NO:7
source                  1..1395
                        mol_type = other DNA
                        organism = synthetic construct
SEQUENCE: 125
atgtgtcctc ctaagaccga tggaagatct tctcctagat ctcctctcac caggtctaag   60
tcatctgctc aggctcttga tgctaaggat gcttctaccg ctcctgttga tcttaagacc  120
cttgagcctc atgaacttgc tgctaccttc gagactagat gggttagggt tgaggatgtt  180
gagtacgacg tgaccaactt caaacatcct ggtggaagcg tgatcttcta catgcttgct  240
aacactggtg ctgatgctac tgaggctttc aaagaatttc acatgcgtag cctcaaggct  300
tggaagatgc ttagagcttt gccttctaga cctgctgaga tcaagagatc tgagtctgag  360
gatgctccta tgcttgagga tttcgctagg tggagagctg aacttgagag ggacggattc  420
ttcaagcctt ctatcaccca tgttgcttac cgtctttttgg agcttcttgc tactttcgct  480
cttggaaccg ctcttatgta cgctggatac cctatcattg ctagcgttgt gtacggtgct  540
ttcttcggag ctagatgtgg atgggttcaa catgagggtg gacacaactc tcttaccgga  600
tctgtgtacg tggataagag acttcaggct atgacttgcg gattcggact ttctaccagc  660
ggagagatgt ggaaccagat gcataacaag caccatgcta cccctcagaa agttagacac  720
gacatggatc ttgataccac tcctgctgtg gcttttcttca acaccgctgt ggaggataat  780
agacctaggg gattctctag agcttgggct agacttcaag cttggacctt cgttcctgtt  840
acttctggac ttctcgttca ggcttttctgg atctacgttc tccatcctag acaggtgctc  900
aggaagaaga actacgagga agcttcttgg atgctcgttt ctcacgttgt tagaaccgct  960
gttatcaagc ttgctaccgg atactcttgg cctgttgctt actggtggtt cactttcgga 1020
aactggatcg cttacatgta cctcttcgct cacttctcta cttctcacac tcacctccct 1080
gttgttccat ctgacaagca ccttagctgg gttaactacg ctgttgatca caccgttgac 1140
atcgatcctt ctcgtggata cgttaactgc cttatgggat accttaactg ccaggttatc 1200
caccatctct tccctgatat gcctcaattc agacagcctg aggtgtcaag aagattcgtc 1260
cctttcgcta agaagtgggg actcaactac aaggtgctct cttactacgg tgcttggaag 1320
gctactttca gcaacctcga caaagttgga cagcactact acgttaacgg aaaggctgag 1380
aaggctcact gatga                                                  1395

SEQ ID NO: 126          moltype = DNA  length = 870
FEATURE                 Location/Qualifiers
misc_feature            1..870
                        note = Codon-optimized nucleotide sequence for production
                         in plants of SEQ ID NO:3
source                  1..870
                        mol_type = other DNA
                        organism = synthetic construct
SEQUENCE: 126
atggaatttg ctcaacctct cgttgctatg gctcaagagc agtacgctgc tatcgatgct   60
gttgttgctc ctgctatctt ctctgctacc gactctattg gatggggact caagcctatc  120
tcttctgcta ctaaggatct ccctctcgtt gaatctccta cccctcttat cctttctctc  180
ctcgcttact cgctatcgt tggttctgga ctcgtttacc gtaaagtgtt ccctagaacc  240
gttaagggac aggatccttt ccttctcaag gctcttatgc tcgctcacaa cgttttcctt  300
```

```
atcggactca gcctttacat gtgcctcaag ctcgtttacg aggcttacgt gaacaagtac   360
tccttctggg gaaacgctta caaccctgct caaaccgaga tggctaaggt gatctggatc   420
ttctacgtgt ccaagatcta cgagttcatg acaccttca tcatgcttct caagggaaac   480
gttaaccagg tttccttcct ccatgtttac caccacggat ctatctctgg aatctggtgg   540
atgatcactt atgctgctcc aggtggagat gcttacttct ctgctgtct caactcttgg   600
gttcatgtgt gcatgtacac ctactacttc atggctgctg ttcttcctaa ggacgaaaag   660
accaagagaa agtaccttg gtggggaaga taccttaccc agatgcaaat gttccagttc   720
ttcatgaacc ttctccaggc tgtttacctc ctctactctt cttctcctta ccctaagttc   780
attgctcaac tcctcgttgt ttacatggtt accctcctca tgcttttcgg aaacttctac   840
tacatgaagc accacgcttc taagtgataa                                    870

SEQ ID NO: 127           moltype = DNA  length = 1281
FEATURE                  Location/Qualifiers
misc_feature             1..1281
                         note = Codon-optimized nucleotide sequence for production
                         in plants of SEQ ID NO:25
source                   1..1281
                         mol_type = other DNA
                         organism = synthetic construct
SEQUENCE: 127
atgcctccta gggactctta ctcttacgct gctcctcctt ctgctcaact tcacgaggtt    60
gacactcctc aagagcacga caagaaagag cttgttatcg gagatgagc ttacgatgtg   120
accaacttcg ttaagagaca ccctggtgga aagatcattg cttaccaagt gggaactgat   180
gctaccgatg cttacaagca gttccatgtg agatctgcta aggctgacaa gatgctcaag   240
tctctcccct ctagacctgt tcacaaggga tactctccta aagagctga tcttatcgct   300
gacttccaag agttcactaa gcaacttgga gctgagggaa tgttcgaacc ttctctccct   360
catgttgctt accgtcttgc tgaggttatc gctatgcatg ttgctggtgc tgctcttatc   420
tggcacggat acactttcgc tggaatcgct atgcttggac ttgttcaggg aagatgcgga   480
tggcttatgc atgagggtgg acactactct cttaccggaa acattgcttt cgataggct   540
atccaagttg cttgttacgg acttggatgc ggaatgtctg gtgcttggtg gagaaaccag   600
cataacaagc accatgctac tcctcaaaag ctccagcacg atgttgatct tgatacccc   660
cctctcgttg ctttccatga gaatcgctg ctaaggtta agtctcctgc tatgaaggct   720
tggctctcca tgcaagctaa actcttgct cctgttacca ctcttcttgt tgctcttgga   780
tggcagcttt accttcaccc tagacacatg tcagaacta agcactacga cgagcttgct   840
atgcttggta tcagatacgg acttgtggga taccttgctg ctaactacgg tgctggatac   900
gttcttgctt gctaccttct ctacgttcag cttggagcta tgtacatctt ctgcaacttc   960
gctgtttctc acactcatct ccctgttgtt gagcctaacg agcatgctac ttgggttgag  1020
tacgctgcta accacactac taactgctct ccatcttggt ggtgtgattg gtggatgagc  1080
tacctcaact accagatcga gcatcacctt tacccttcct gcttccagtt caggcatcct  1140
aagatcgctc ctagagtgaa gcaactcttc gagaagcacg gacttcacta cgatgtgcgt  1200
ggatacttcg aggctatggc tgatactttc gctaacctcg ataacgttgc tcatgctcct  1260
gagaagaaaa tgcaatgatg a                                            1281

SEQ ID NO: 128           moltype = DNA  length = 807
FEATURE                  Location/Qualifiers
misc_feature             1..807
                         note = Codon-optimized nucleotide sequence for production
                         in plants of SEQ ID NO:5
source                   1..807
                         mol_type = other DNA
                         organism = synthetic construct
SEQUENCE: 128
atggcttcta tcgctatccc tgctgctctt gctggaactc ttggatacgt gacctacaac    60
gtggctaacc ctgatattcc tgcttctgag aaggttccag cttacttcat gcaagtggag   120
tactggggac ctactatcgg aactatcggt tacctcctct tcatctactt cggaaagcgt   180
atcatgcaaa acagaagcca gcctttcgga cttaagaacg ctatgctcgt gtacaacttc   240
taccagacct tcttcaacag ctactgcatc tacctcttcg ttacctctca tagggctcag   300
ggacttaaag tttggggaaa catccctgat atgaccgcta actcttgggg aatctctcag   360
gttatctggc tccactacaa caacaagtac gtggagcttc tcgatacctt cttcatggtg   420
atgaggaaga agttcgacca gctttctttc cttcacatct accaccacac tcttctcatc   480
tggtcatggt tcgtggttat gaagctcgag cctgttggag attgctactt cggatctagc   540
gttaacacct tcgtggcacgt gatcatgtac tcttactacg acttgctgc tcttggagtt   600
aactgcttct ggaagaagta catcacccag atccagatgc ttcagttctg tatctgcgct   660
tctcactcta tctacaccgc ttacgttcag aacactgctt tctggcttcc ttaccttcag   720
ctctgggtga tggttaacat gttcgtgctc ttcgctaact tctaccgtaa aggtacaag   780
agcaagggtg ctaagaagca gtgataa                                      807

SEQ ID NO: 129           moltype = DNA  length = 1347
FEATURE                  Location/Qualifiers
misc_feature             1..1347
                         note = Codon-optimized nucleotide sequence for production
                         in plants of SEQ ID NO:72
source                   1..1347
                         mol_type = other DNA
                         organism = synthetic construct
SEQUENCE: 129
atgcctccat ctgctgctaa acagatggga gcttctactg tgttcacgc tggtgttacc    60
gattcttctg ctttccaccag aaaggatgtg gctgatagac tgatcttac catcgttggt   120
gactctgtgt acgatgctaa ggctttcaga tctgagcatc ctggtggtgc tcatttcgtt   180
```

-continued

```
tcactcttcg gaggaagaga tgctactgag gctttcatgg aataccacag aagagcttgg    240
cctaagtcta ggatgtctag gttccatgtt ggatctcttg cttctaccga ggaacctgtt    300
gctgctgatg agggatacct tcagctttgt gctaggatcg ctaagatggt gccttctgtg    360
tcatctggat tcgctccagc ttcttactgg gttaaggctg gacttatcct cggatctgct    420
atcgctcttg aggcttacat gctctacgct ggaaagagac ttctcccttc tatcgttctt    480
ggatggctct tcgctcttat cggacttaac atccagcatg acgctaacca tggtgctttg    540
tctaagtctg ctagcgttaa ccttgctctt ggactttgtc aggattggat cggaggatct    600
atgatccttt ggctccaaga gcatgttgtt atgcaccacc tccacaccaa cgatgttgat    660
aaggaccctg atcaaaaggc tcatgtgct cttagactca agcctaccga tgcttggtca    720
cctatgcatt ggcttcagca cctttacctt ctccctggtg aaactatgta cgcttttcaag   780
ctcctcttcc tcgatatctc tgagcttgtg atgtggagat gggagggtga acctatctct    840
aagctcgctg gatacctctt catgccttct cttctcctca agcttacctt ctgggctaga    900
ttcgttgctc ttcctcttta cctcgctcct tctgttcata ctgctgtgtg tatcgctgct    960
actgttatga ccggaagctt ctaccttgct ttcttcttct tcatcagcca caacttcgag   1020
ggtgttgctt ctgttggacc tgatggatct atcacctcta tgaccagggg agcttctttc   1080
cttaagaggc aggctgagac ttcttctaat gtgggaggac ctcttcttgc tactcttaac   1140
ggtggactca actaccaaat cgagcaccac cttttcccta gagttcacca cggattctac   1200
cctagacttg ctcctcttgt gaaggctgaa cttgaggcta gaggaatcga gtacaagcac   1260
taccctacca tctggtctaa cctcgcttct accctcagac atatgtacgc tcttggaaga   1320
aggcctagat ctaaggctga gtgatga                                        1347
```